(12) United States Patent
Holliger et al.

(10) Patent No.: US 9,914,914 B2
(45) Date of Patent: Mar. 13, 2018

(54) POLYMERASE CAPABLE OF PRODUCING NON-DNA NUCLEOTIDE POLYMERS

(71) Applicant: Medical Research Council, Swindon (GB)

(72) Inventors: Philipp Holliger, Cambridge (GB); Chris Cozens, Cambridge (GB); Vitor Pinheiro, Cambridge (GB)

(73) Assignee: Medical Research Council, Swindon (GB)

( * ) Notice: Subject to any disclaimer, the term of this patent is extended or adjusted under 35 U.S.C. 154(b) by 188 days.

(21) Appl. No.: 14/395,429

(22) PCT Filed: Apr. 19, 2013

(86) PCT No.: PCT/GB2013/050991
§ 371 (c)(1),
(2) Date: Oct. 17, 2014

(87) PCT Pub. No.: WO2013/156786
PCT Pub. Date: Oct. 24, 2013

(65) Prior Publication Data
US 2015/0275192 A1 Oct. 1, 2015

(30) Foreign Application Priority Data
Apr. 19, 2012 (GB) .................................. 1207018.1

(51) Int. Cl.
*C12N 9/12* (2006.01)
*C12Q 1/68* (2018.01)
*C12P 19/34* (2006.01)

(52) U.S. Cl.
CPC ............ *C12N 9/1241* (2013.01); *C12P 19/34* (2013.01); *C12Q 1/686* (2013.01)

(58) Field of Classification Search
CPC .. C12N 9/1241; C12N 9/1247; C12N 9/1252; C12P 19/34; C12Q 1/686
See application file for complete search history.

(56) References Cited

U.S. PATENT DOCUMENTS 9,169,471 B2 * 10/2015 Holliger ................ C12N 9/1241

FOREIGN PATENT DOCUMENTS

WO 2011/135280 A2 11/2011

OTHER PUBLICATIONS

Peng et al., Polymerase-Directed Synthesis of 2'-Deoxy-2'-fluoro-β-D-arabinonucleic Acids, J. Am. Chem. Soc., (2007), vol. 129 (17), pp. 5310-5311.*
Peng et al., Probing DNA polymerase activity with stereoisomeric 2'-fluoro-β-D-arabinose (2'F-araNTPs) and 2'-fluoro-β-D-ribose (2'F-rNTPs) nucleoside 5'-triphosphates, Canadian Journal of Chemistry (2008), vol. 86(9), pp. 881-891.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Cozens, C. et al., "A short adaptive path from DNA to RNA polymerases," Proceedings of the National Acadmy of Sciences of the United States of America, vol. 109, No. 21, May 22, 2012, pp. 8067-8072, XP-002712428.
Pinheiro, V. B. et al., "Synthetic Genetic Polymers Capable of Heredity and Evolution," Science (Washington, D.C.), vol. 336, No. 6079, Apr. 2012, pp. 341-344, XP002712426.
Steele, F. R. et al., "The sweet allure of XNA," Nature Biotechnology, vol. 30, No. 7, Jul. 2012, pp. 624-625, XP002712427.
The International Search Report and Written Opinion dated Sep. 20, 2013, in related International Application No. PCT/GB2013/050991, filed Apr. 19, 2013.

* cited by examiner

*Primary Examiner* — Suzanne M Noakes
*Assistant Examiner* — Jae W Lee
(74) *Attorney, Agent, or Firm* — Wiley Rein LLP

(57) ABSTRACT

The invention relates to a nucleic acid polymerase capable of producing a non-DNA nucleotide polymer from a DNA nucleotide polymer template, the polymerase comprising amino acid sequence having at least 36% identity to the amino acid sequence of SEQ ID NO: 1, wherein the amino acid sequence is mutated relative to the amino acid sequence of SEQ ID NO: 1, wherein the amino acid sequence comprises the mutations P657T, E658Q, K659H, Y663H, D669A, K671N, and T676I; wherein the amino acid sequence is further mutated relative to the amino acid sequence of SEQ ID NO: 1 at residue: E664 and wherein the amino acid sequence comprises the mutation E664K. The invention also relates to methods of making nucleotide polymers comprising use of this polymerase. Suitably the nucleotides are arabino nucleotides such as ARA or FANA nucleotides.

11 Claims, 34 Drawing Sheets

A

```
              588   608   653                                      703        729
        402 404   591   611                                       682        710  731
TgoT    YLD..FVT..LEIV..YEVPPEKLVIYEQITRDLKDYKATGPHVAV..VLKGSGRI..AEY
Pol6G12 YLD..FAT..LKMV..YEVPPEQLVIYQPITKQLHDYRARGPHVSV..VPKGSGRI..AGY
PolC7   YLD..FVT..LEIV..YQVPPQQLAIYQPITRALQDYKAKGPHVAV..VLKGSGKI..AEY
PolD4K  YPD..FVT..LEIV..YEVPTQHLVIHKQITRALNDYKAIGPHVAV..VLKGSGRI..AEY
```

FIG. 3
A
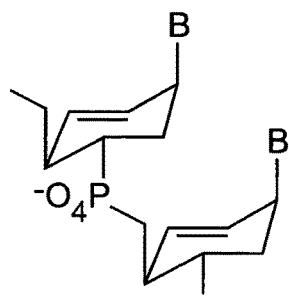
CeNA
B
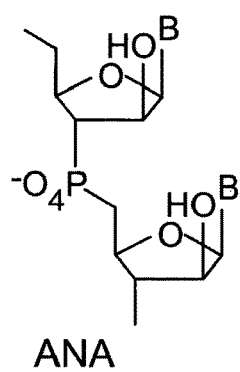
ANA
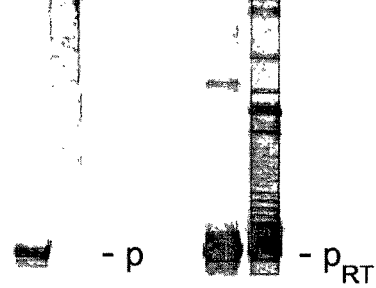
C
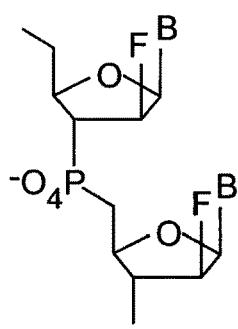
FANA
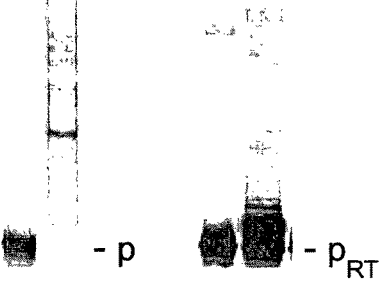

FIG. 3 continued
D 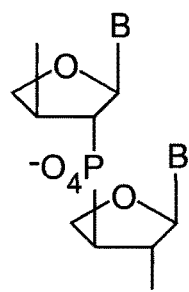 TNA 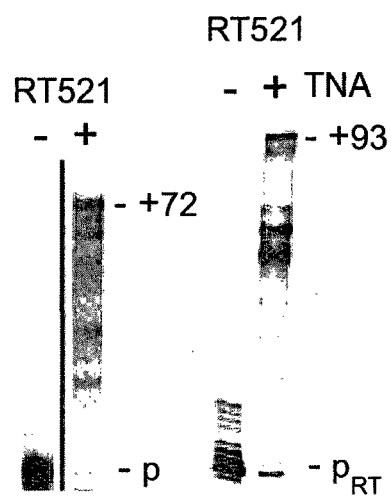
E 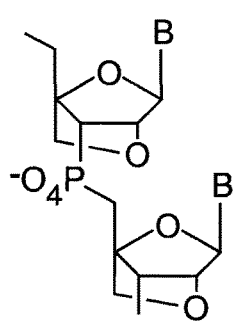 LNA 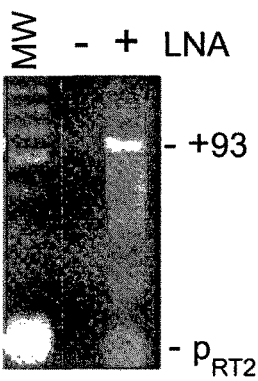
F 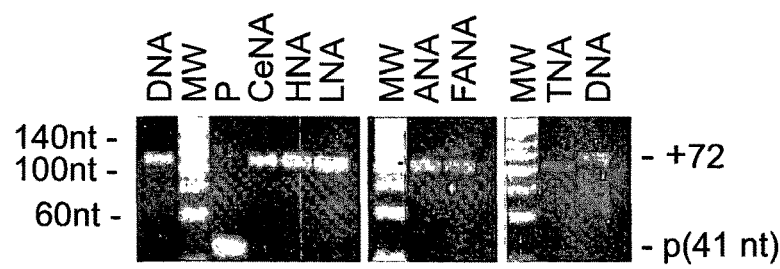
G 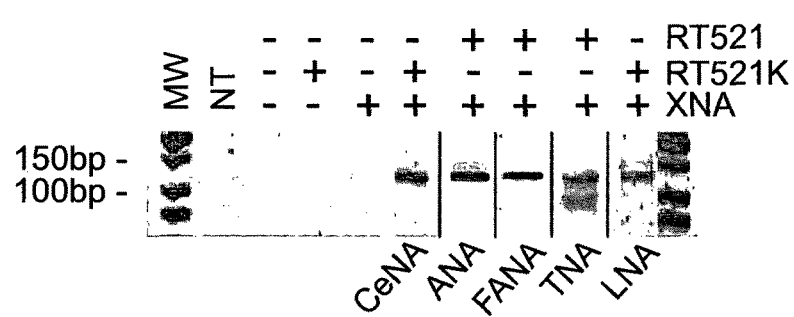

FIG. 6A
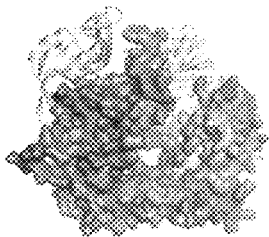
1TGO

FIG. 6B
4AIL

FIG. 6C
3MAQ

FIG. 6D

```
MILDTDYITE DGKPVIRIFK KENGEFKIDY DRNFEPYIYA LLKDDSAIED VKKITAERHG   60

TTVRVVRAEK VKKKFLGRPI EVWKLYFTHP QDQPAIRDKI KEHPAVVDIY EYDIPFAKRY  120

LIDKGLIPME GDEELKMLAF AIATLYHEGE EFAEGPILMI SYADEEGARV ITWKNIDLPY  180

VDVVSTEKEM IKRFLKVVKE KDPDVLITYN GDNFDFAYLK KRSEKLGVKF ILGREGSEPK  240
                                                         Motif 1
IQRMGDRFAV EVKGRIHFDL YPVIRRTINL PTYTLEAVYE AIFGQPKEKV YAEEIAQAWE  300
                     Motif 2
TGEGLERVAR YSMEDAKVTY ELGKEFFPME AQLSRLVGQS LWDVSRSSTG NLVEWFLLRK  360
                                          Motif 3                Motif 4
AYERNELAPN KPDERELARR RESYAGGYVK EPERGLWENI VYLDFRSLYP SIIITHNVSP  420
     Motif A-           Motif A        Motif A+
DTLNREGCEE YDVAPQVGHK FCKDFPGFIP SILGDLLEER QKVKKKMKAT IDPIEKKLLD  480
                                  Motif 5                    Motif B-
YRQRLIKILA NSFYGYYGYA KARWYCKECA ESVTAWGRQY IETTIREIEE KFGFKVLYAD  540
  Motif B        Motif 6-      Motif 6+                       Motif C
TDGFFATIPG ADAETVKKKA KEFLDYINAK LPGLLELEYE GFYKRGFFVT KKKYAVIDEE  600
  Motif C+              Motif 7                Motif 8          Motif 9
DKITTRGLEI VRRDWSEIAK ETQARVLEAI LKHGDVEEAV RIVKEVTEKL SKYEVPPEKI  660
                                                       Motif 10A
VIYEQITRDL KDYKATGPHV AVAKRLAARG IKIRPGTVIS YIVLKGSGRI GDRAIPFDEF  720
   Motif 10B                                                Motif 11
DPAKHKYDAE YYIENQVLPA VERILRAFGY RKEDLRYQKT RQVGLGAWLK PKT         773
  Motif 12
```

Forward synthesis PAGE – individual channels

Forward synthesis PAGE - overlaid

Gel-purified forward synthesis PAGE - overlaid

1TGO

4AIL

3MAQ $kT^* = 1.96$ (3σ cut-off from log-normal fit to covariation distribution)

FIG. 11A
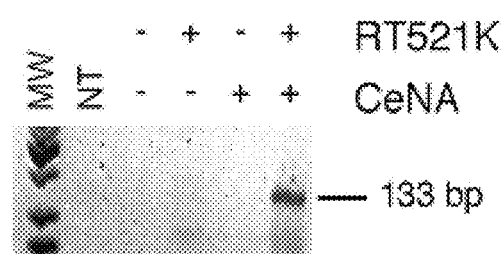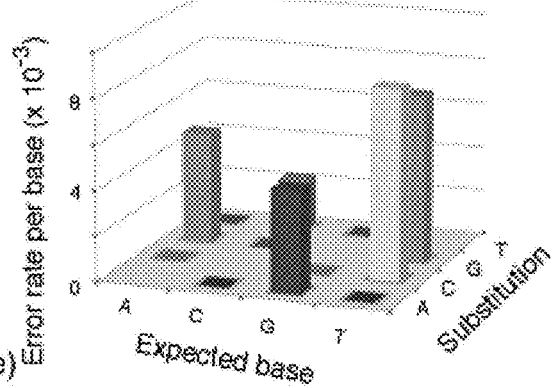
FIG. 11B
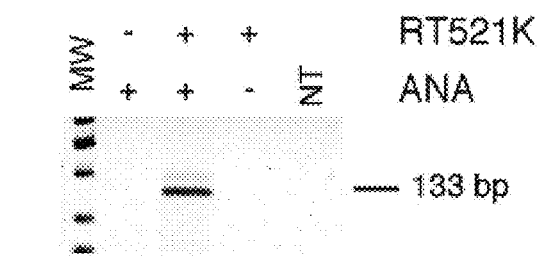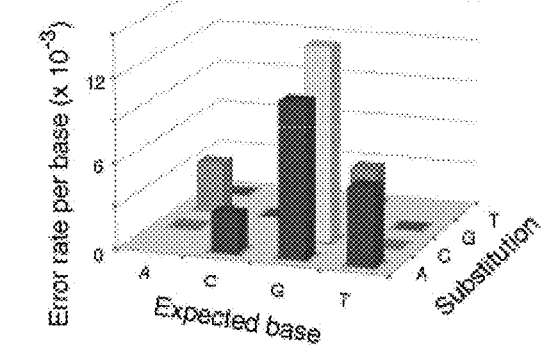
FIG. 11C
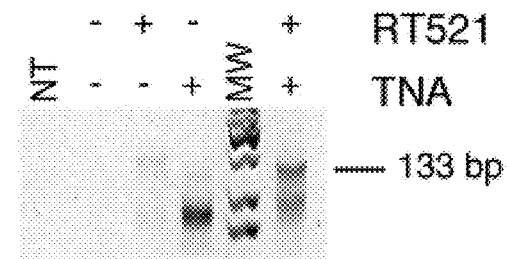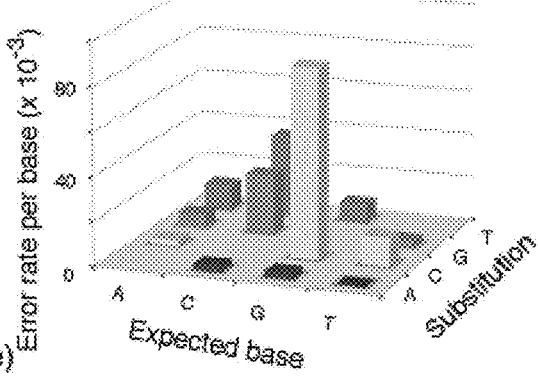

FIG. 11D
FANA
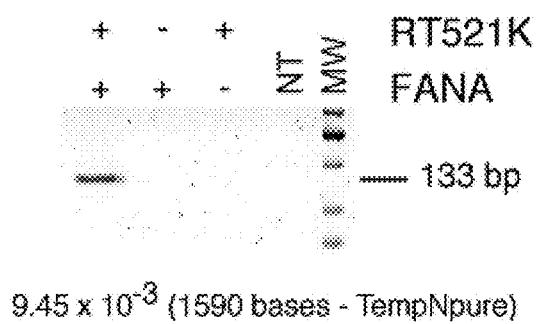
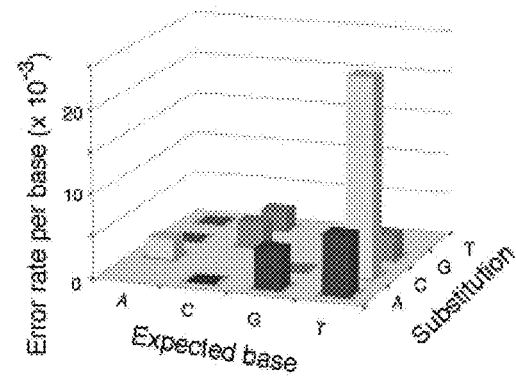
9.45 × 10⁻³ (1590 bases - TempNpure)
FIG. 11E
LNA
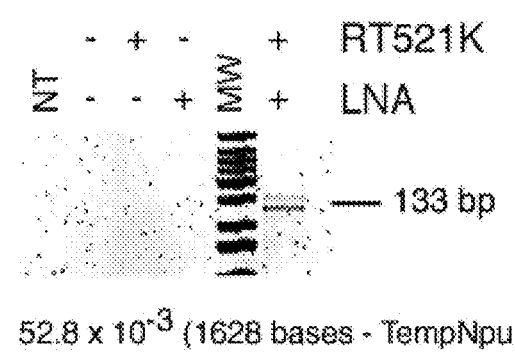
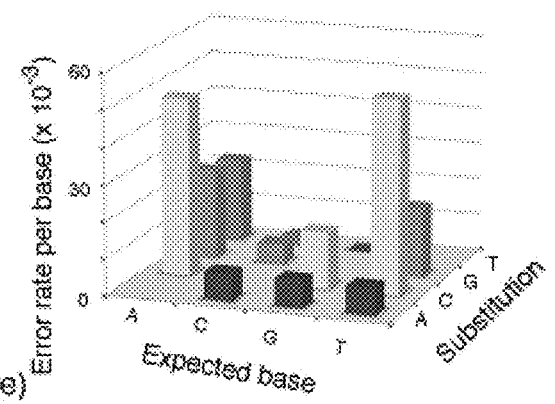
52.8 × 10⁻³ (1628 bases - TempNpure)

f

```
TestBind1 3'-GGTCCTCCACTTTTCCCATTGTTCTGCCTTTCTCTTTCCCTGAGATT-5'
    Test1  5'-CCAGGAGGTGAAAA-3'
    Test2                 5'-GGGTAACAAGACGGAAA-3'
    Test3                                 5'-AAGAGAAAGGGACTCTAA-3'

TestBind3 3'-CTAGGCAAAGGAGGAGGGATCAAGAAGGAGAAGGGAGAGAAGGGAAG-5'
    Test6                                 5'-TCCCTCTCTTCCCTTC-3'
    Test7                 5'-CCCTAGTTCTTCCTCTTCCC-3'
    Test8  5'-GATCCGTTTCCTCCTCCC-3'
```

FIG. 19
a
ANA
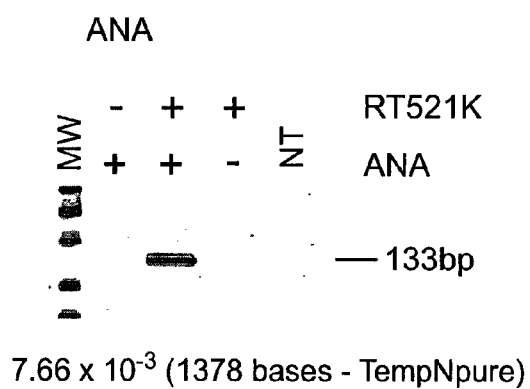
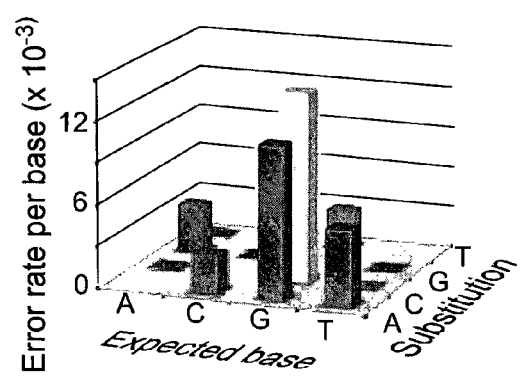
$7.66 \times 10^{-3}$ (1378 bases - TempNpure)
b
FANA
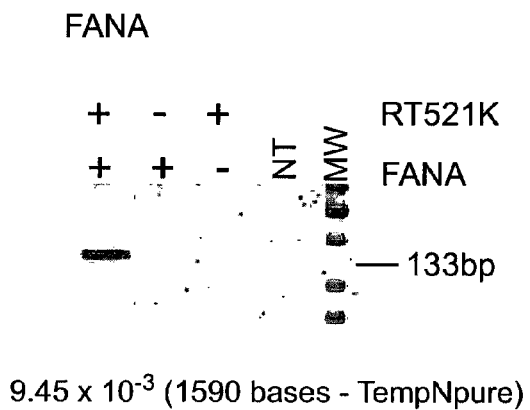
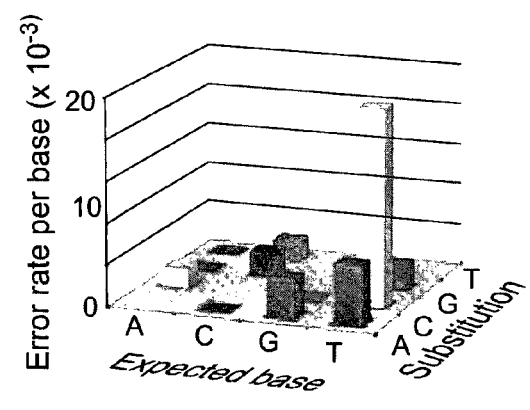
$9.45 \times 10^{-3}$ (1590 bases - TempNpure)

FIG. 20
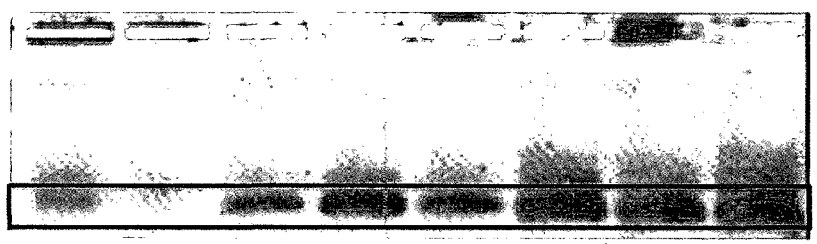
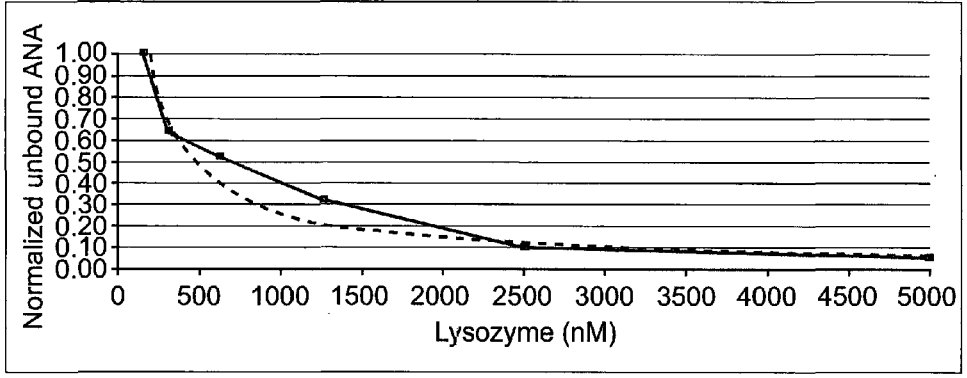
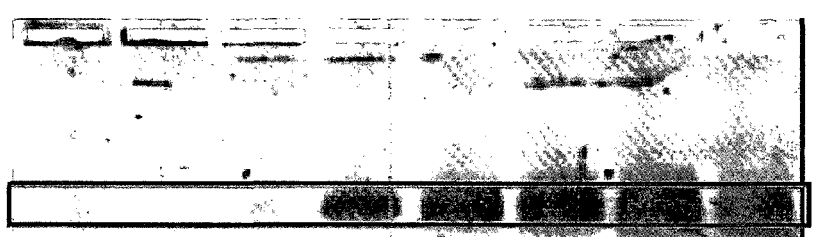
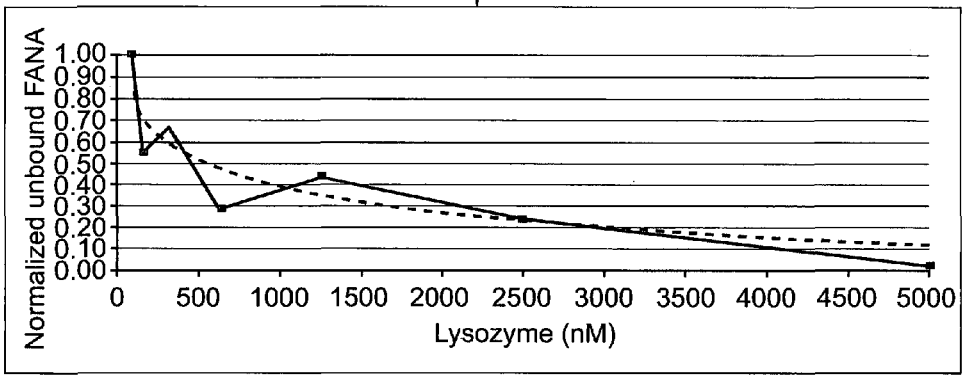

FIG. 26
a)
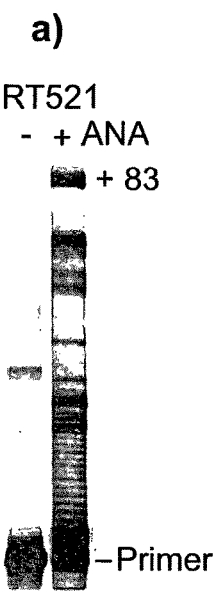
b) ANA
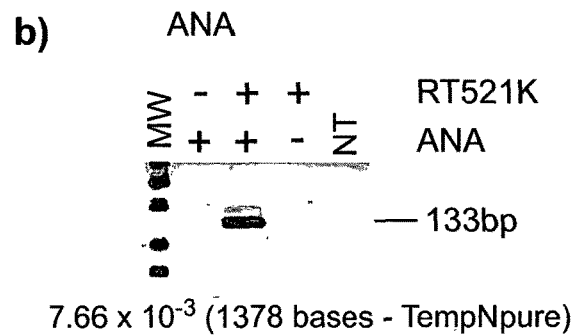
7.66 x 10$^{-3}$ (1378 bases - TempNpure)
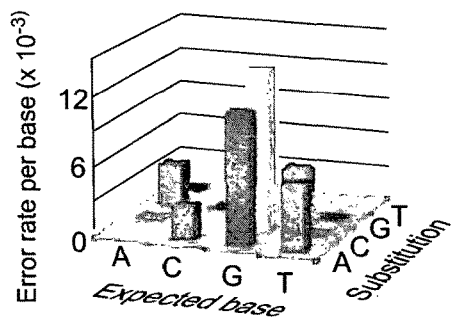
c)
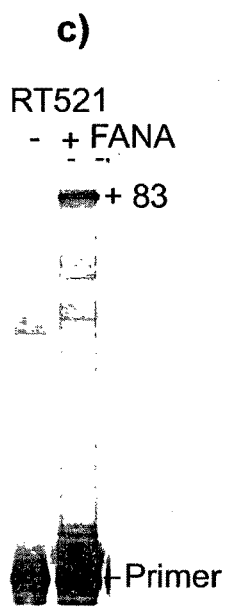
d) FANA
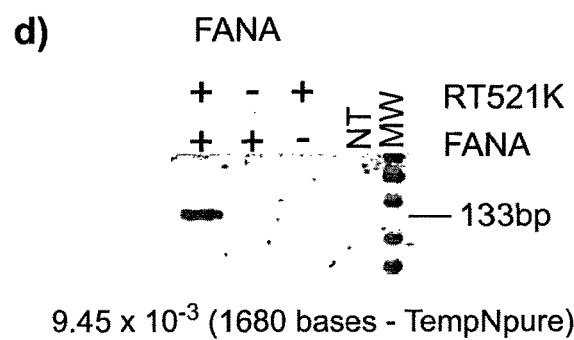
9.45 x 10$^{-3}$ (1680 bases - TempNpure)
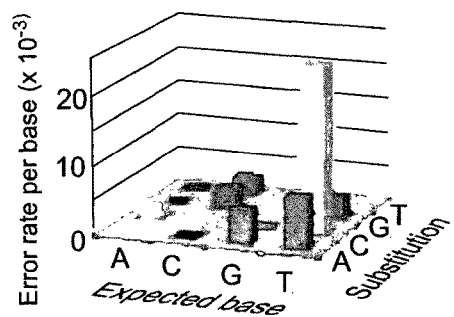

Red = ANA (A) or FANA (F) template. Green = synthesis using aNTPs

Red = ANA (A) or FANA (F) template. Green = synthesis using aNTPs

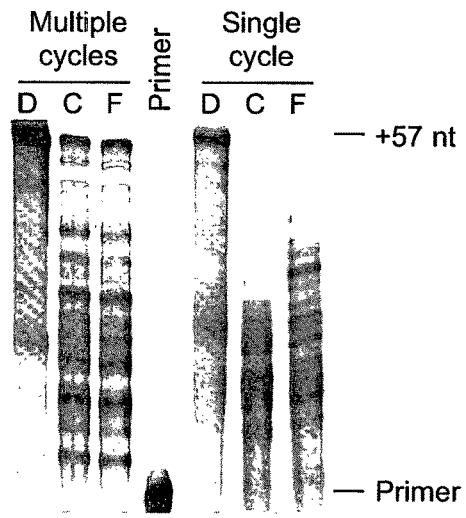
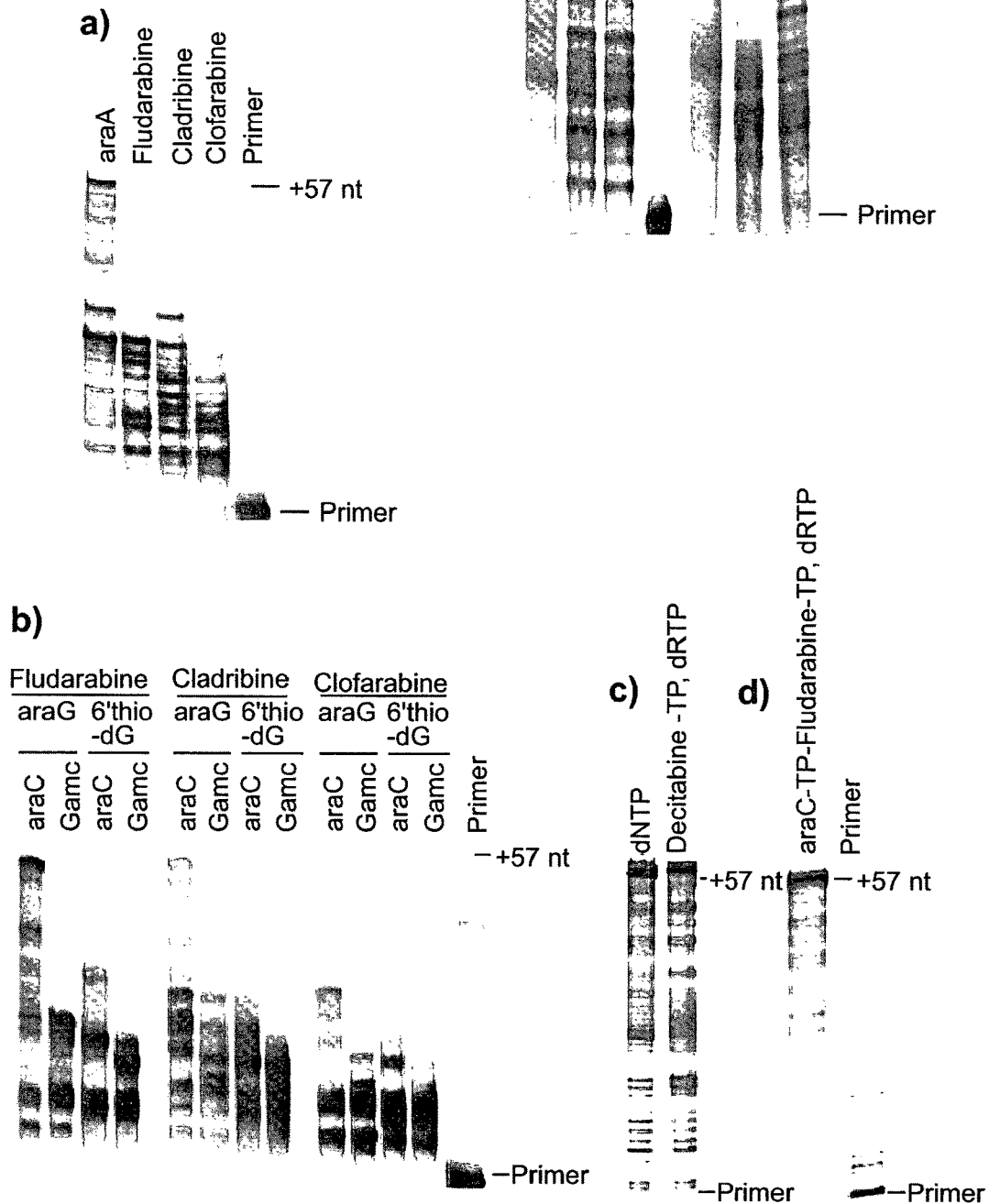

FIG. 33
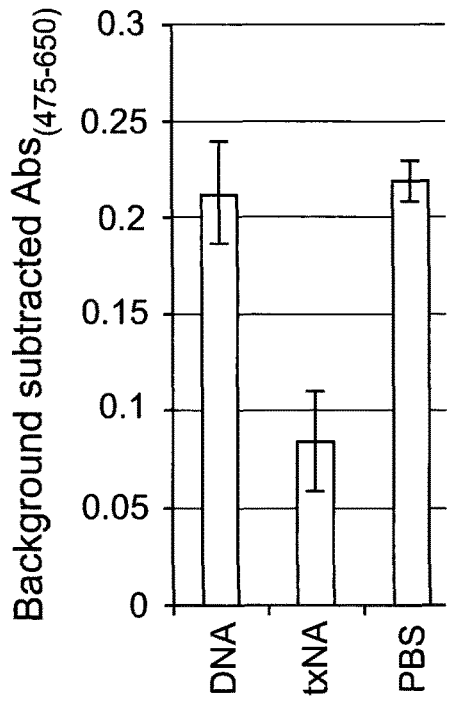
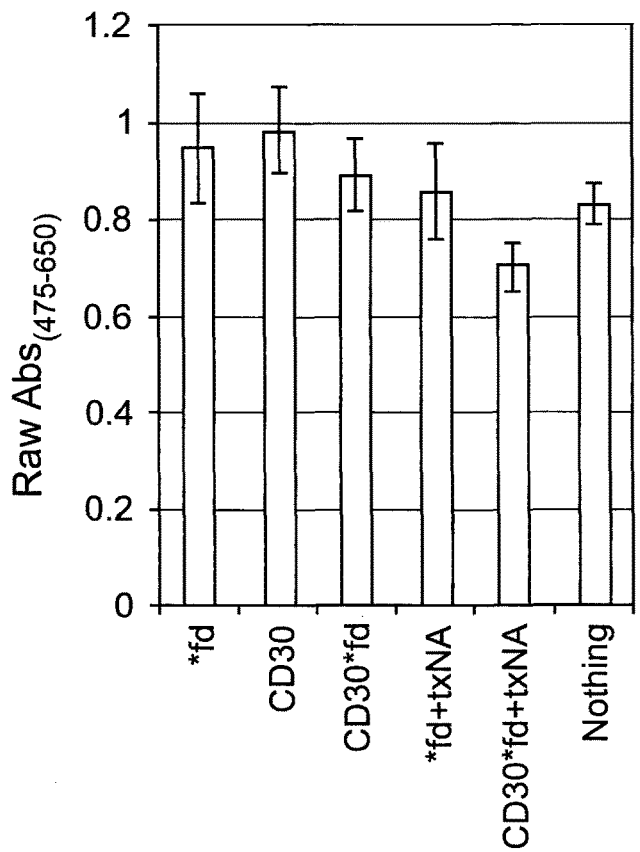

a)

SEQUENCE LISTING

```
<160> NUMBER OF SEQ ID NOS: 151

<210> SEQ ID NO 1
<211> LENGTH: 773
<212> TYPE: PRT
<213> ORGANISM: Thermococcus gorgonarius

<400> SEQUENCE: 1

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60
```

-continued

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
            85                  90                  95

Arg Asp Lys Ile Lys Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
            165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
            195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
            290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
            325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Arg Glu Ser Tyr
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
            450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr

```
                485                 490                 495
Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 2
<211> LENGTH: 773
<212> TYPE: PRT
<213> ORGANISM: Artificial Sequence
<220> FEATURE:
<223> OTHER INFORMATION: T. gorganarius-derived polymerase TgoT,
      mutations: uracil read-ahead V93Q, 2xexo D141A and E143A, and
      terminator A485L

<400> SEQUENCE: 2

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60
```

-continued

```
Val Val Arg Ala Glu Lys Val Lys Lys Phe Leu Gly Arg Pro Ile
 65                  70                  75                  80

Glu Val Trp Lys Leu Tyr Phe Thr His Pro Gln Asp Gln Pro Ala Ile
                 85                  90                  95

Arg Asp Lys Ile Lys Glu His Pro Ala Val Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Met Leu Ala Phe Ala Ile Ala Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
                180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
        450                 455                 460

Lys Lys Met Lys Ala Thr Ile Asp Pro Ile Glu Lys Lys Leu Leu Asp
465                 470                 475                 480
```

```
Tyr Arg Gln Arg Leu Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
        500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 3
<211> LENGTH: 773
<212> TYPE: PRT
<213> ORGANISM: Artificial Sequence
<220> FEATURE:
<223> OTHER INFORMATION: Prior art T. gorgonarius (Tgo) derived
      polymerase D4 with mutated patch 10 region

<400> SEQUENCE: 3

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60
```

```
Val Val Arg Ala Glu Lys Val Lys Lys Lys Phe Leu Gly Arg Pro Ile
 65                  70                  75                  80

Glu Val Trp Lys Leu Tyr Phe Thr His Pro Gln Asp Gln Pro Ala Ile
                 85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Ala Ile Ala Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480
```

```
Tyr Arg Gln Arg Leu Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
        500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
        530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Thr Gln His Leu Val Ile His Gln Gln Ile Thr Arg Ala Leu Asn Asp
            660                 665                 670

Tyr Lys Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
        770

<210> SEQ ID NO 4
<211> LENGTH: 2322
<212> TYPE: DNA
<213> ORGANISM: Artificial Sequence
<220> FEATURE:
<223> OTHER INFORMATION: DNA encoding polymerase D4 derived from T.
      gorgonarious

<400> SEQUENCE: 4
atgatcctcg atacagacta cataactgag gatggaaagc ccgtcatcag gatcttcaag     60
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga gttcctagg caggccgata    240 gaggtctgga agctctactt cactcacccc caggaccagc cgcaatcag ggacaagata    300 aaggagcatc ctgccgttgt ggacatctac gagtacgaca tcccttcgc gaagcgctac    360
```

-continued

```
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg aaggattca cttcgacctc     780 tacccgtca ttaggagaac gattaacctc cccacttaca cccttgaggc agtatatgaa     840
gccatctttg acagccgaa ggagaaggtc tacgctgagg agatagcgca ggcctgggaa     900
acgggcgagg gattagaaag ggtggcccgc tactcgatgg aggacgcaaa ggtaacctat    960
gaactcggaa agaattctt ccctatggaa gcccagctct cgcgcctcgt aggccagagc    1020
ctctgggatt tatctcgctc gagtaccgga acctcgtcg agtggttttt gctgaggaag    1080
gcctacgaga ggaatgaact tgcaccaaac aagccggacg agggagct ggcaagaaga    1140 agggagagct acgcgggtgg atacgtcaag gagcccgaaa ggggactgtg ggagaacatc    1200
gtgtatctgg acttccgctc cctgtatcct tcgataataa tcacccataa cgtctcccct    1260
gatacactca cagggagg ttgtgaggag tacgacgtgg ctcctcaggt aggccataag    1320
ttctgcaagg acttccccgg cttcatccca gcctcctcg gtgacctctt ggaggagaga    1380
cagaaggtaa agaagaagat gaaggccact atagacccaa tcgagaagaa actcctcgat    1440
tacaggcaac gactgatcaa atccttgct aatagcttct acggttacta cggctatgca    1500
aaggcccgct ggtactgcaa ggagtgcgcc gagagcgtta ccgcttgggg caggcagtac    1560
atcgagacta cgataaggga aatagaggag aaatttggct ttaaagtcct ctacgcggac    1620
acagatggat ttttcgcaac aatacctgga gcggacgccg aaaccgtcaa aagaaggca    1680 aaggagttcc tggactacat caacgccaaa ctgcccggcc tgctcgaact cgaatacgag    1740
ggcttctaca gcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga gaagcggta    1920 aggattgtca aagaggttac ggagaagctg agcaagtacg aggttccaac gcagcacctg    1980
gtcatccacc agcagataac cagagccctg aacgactaca aggccatcgg ccgcatgtg    2040 gctgttgcaa aacgcctcgc cgcaaggggg ataaaaatcc ggcccggaac ggtcataagc    2100
tacatcgtgc tcaaaggctc gggaaggat ggggacaggg ctataccctt tgacgaattt    2160
gacccggcaa agcacaagta cgatgcagaa tactacatcg agaaccaggt tcttccagct    2220
gtggagagga ttctgagggc ctttggttac cgtaaagaag atttaaggta tcagaaaacg    2280
cggcaggttg gcttgggggc gtggctaaaa cctaagacat aa                       2322
```

<210> SEQ ID NO 5
<211> LENGTH: 773
<212> TYPE: PRT
<213> ORGANISM: Artificial Sequence
<220> FEATURE:
<223> OTHER INFORMATION: Polymerase D4YK derived from T. gorgonarius

<400> SEQUENCE: 5

```
Met Ile Leu Asp Thr Asp Tyr Ile Thr Glu Asp Gly Lys Pro Val Ile
1               5                   10                  15
```

```
Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Ser Ala Ile
        35                  40                  45

Glu Asp Val Lys Lys Ile Thr Ala Glu Arg His Gly Thr Thr Val Arg
 50                  55                  60

Val Val Arg Ala Glu Lys Val Lys Lys Phe Leu Gly Arg Pro Ile
 65                  70                  75              80

Glu Val Trp Lys Leu Tyr Phe Thr His Pro Gln Asp Gln Pro Ala Ile
            85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
 130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
 210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
 290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
 370                 375                 380

Ala Gly Gly Tyr Val Lys Glu Pro Glu Arg Gly Leu Trp Glu Asn Ile
385                 390                 395                 400

Val Tyr Pro Asp Phe Arg Ser Leu Tyr Pro Ser Ile Ile Thr His
                405                 410                 415

Asn Val Ser Pro Asp Thr Leu Asn Arg Glu Gly Cys Glu Tyr Asp
            420                 425                 430
```

| | | | | | | | | | | | | |
|---|---|---|---|---|---|---|---|---|---|---|---|---|
| Val | Ala | Pro | Gln | Val | Gly | His | Lys | Phe | Cys | Lys | Asp | Phe | Pro | Gly | Phe |
| | | | 435 | | | | 440 | | | | 445 | |

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Thr Gln His Leu Val Ile His Lys Gln Ile Thr Arg Ala Leu Asn Asp
            660                 665                 670

Tyr Lys Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
770

<210> SEQ ID NO 6
<211> LENGTH: 2322
<212> TYPE: DNA
<213> ORGANISM: Artificial Sequence
<220> FEATURE:
<223> OTHER INFORMATION: DNA encoding polymerase D4YK derived from T.
      gorgonarius

<400> SEQUENCE: 6
atgatcctcg atacagacta cataactgag gatggaaagc ccgtcatcag gatcttcaag       60

```
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga aaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780 tacccgtca ttaggagaac gattaacctc cccacttaca cccttgaggc agtatatgaa    840
gccatctttg acagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc    1020
ctctgggatg tatctcgctc gagtaccgga aacctcgtcg agtggttttt gctgaggaag    1080
gcctacgaga ggaatgaact tgcaccaaac aagccggacg agagggagct ggcaagaaga    1140
agggagagct acgcgggtgg atacgtcaag gagcccgaaa ggggactgtg ggagaacatc    1200
gtgtatccgg acttccgctc cctgtatcct tcgataataa tcacccataa cgtctcccct    1260
gatacactca acagggaggg ttgtgaggag tacgacgtgg ctcctcaggt aggccataag    1320
ttctgcaagg acttccccgg cttcatccca agcctcctcg gtgacctctt ggaggagaga    1380
cagaaggtaa agaagaagat gaaggccact atagacccaa tcgagaagaa actcctcgat    1440
tacaggcaac gactgatcaa gatccttgct aatagcttct acggttacta cggctatgca    1500
aaggcccgct ggtactgcaa ggagtgcgcc gagagcgtta ccgcttgggg caggcagtac    1560
atcgagacta cgataaggga aatagaggag aaatttggct ttaaagtcct ctacgcggac    1620
acagatggat ttttcgcaac aatacctgga gcggacgccg aaaccgtcaa aaagaaggca    1680
aaggagttcc tggactacat caacgccaaa ctgcccggcc tgctcgaact cgaatacgag    1740
ggcttctaca agcgcggctt cttcgtgacg aagaagaagt acgcggttat agacgaggag    1800
gacaagataa cgacgcgcgg gcttgaaata gttaggcgtg actggagcga gatagcgaag    1860
gagacgcagg cgagggttct tgaggcgata ctaaagcacg gtgacgttga agaagcggta    1920
aggattgtca agaggttac ggagaagctg agcaagtacg aggttccaac gcagcacctg    1980
gtcatccaca gcagataac cagagccctg aacgactaca aggccatcgg gccgcatgtg    2040
gctgttgcaa aacgcctcgc cgcaaggggg ataaaaatcc ggcccggaac ggtcataagc    2100
tacatcgtgc tcaaaggctc gggaaggatt ggggacaggg ctatacccctt tgacgaattt    2160 gacccggcaa agcacaagta cgatgcagaa tactacatcg agaaccaggt tcttccagct    2220
gtggagagga ttctgagggc cttttggttac cgtaaagaag atttaaggta tcagaaaacg    2280
cggcaggttg gcttgggggc gtggctaaaa cctaagacat aa                      2322
```

<210> SEQ ID NO 7
<211> LENGTH: 773

<212> TYPE: PRT
<213> ORGANISM: Artificial Sequence
<220> FEATURE:
<223> OTHER INFORMATION: Mutant polymerase D4YK with I521L mutation, derived from T. gorgonarius

<400> SEQUENCE: 7

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
    370                 375                 380
```

```
Ala Gly Gly Tyr Val Lys Glu Pro Glu Arg Gly Leu Trp Glu Asn Ile
385                 390                 395                 400

Val Tyr Pro Asp Phe Arg Ser Leu Tyr Pro Ser Ile Ile Ile Thr His
            405                 410                 415

Asn Val Ser Pro Asp Thr Leu Asn Arg Glu Gly Cys Glu Glu Tyr Asp
        420                 425                 430

Val Ala Pro Gln Val Gly His Lys Phe Cys Lys Asp Phe Pro Gly Phe
    435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Leu Glu Thr Thr Ile Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Thr Gln His Leu Val Ile His Lys Gln Ile Thr Arg Ala Leu Asn Asp
            660                 665                 670

Tyr Lys Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
770

<210> SEQ ID NO 8
<211> LENGTH: 773
```

```
<212> TYPE: PRT
<213> ORGANISM: Artificial Sequence
<220> FEATURE:
<223> OTHER INFORMATION: T. go. derived polymerase RT521L mutated at
      V93Q, D141A, E143A, and A485L

<400> SEQUENCE: 8
```

| | | | | | | | | | | | | | | | |
|---|---|---|---|---|---|---|---|---|---|---|---|---|---|---|---|
| Met | Ile | Leu | Asp | Thr | Asp | Tyr | Ile | Thr | Glu | Asp | Gly | Lys | Pro | Val | Ile |
| 1 | | | | 5 | | | | | 10 | | | | | 15 | |
| Arg | Ile | Phe | Lys | Lys | Glu | Asn | Gly | Glu | Phe | Lys | Ile | Asp | Tyr | Asp | Arg |
| | | | 20 | | | | | 25 | | | | | 30 | | |
| Asn | Phe | Glu | Pro | Tyr | Ile | Tyr | Ala | Leu | Leu | Lys | Asp | Asp | Ser | Ala | Ile |
| | | | | 35 | | | | | 40 | | | | | 45 | |
| Glu | Asp | Val | Lys | Lys | Ile | Thr | Ala | Glu | Arg | His | Gly | Thr | Thr | Val | Arg |
| 50 | | | | | 55 | | | | | 60 | | | | | |
| Val | Val | Arg | Ala | Glu | Lys | Val | Lys | Lys | Phe | Leu | Gly | Arg | Pro | Ile | |
| 65 | | | | | 70 | | | | | 75 | | | | 80 | |
| Glu | Val | Trp | Lys | Leu | Tyr | Phe | Thr | His | Pro | Gln | Asp | Gln | Pro | Ala | Ile |
| | | | | 85 | | | | | 90 | | | | | 95 | |
| Arg | Asp | Lys | Ile | Lys | Glu | His | Pro | Ala | Val | Val | Asp | Ile | Tyr | Glu | Tyr |
| | | | 100 | | | | | 105 | | | | | 110 | | |
| Asp | Ile | Pro | Phe | Ala | Lys | Arg | Tyr | Leu | Ile | Asp | Lys | Gly | Leu | Ile | Pro |
| | | | | 115 | | | | | 120 | | | | | 125 | |
| Met | Glu | Gly | Asp | Glu | Glu | Leu | Lys | Met | Leu | Ala | Phe | Ala | Ile | Ala | Thr |
| 130 | | | | | 135 | | | | | 140 | | | | | |
| Leu | Tyr | His | Glu | Gly | Glu | Glu | Phe | Ala | Glu | Gly | Pro | Ile | Leu | Met | Ile |
| 145 | | | | | 150 | | | | | 155 | | | | | 160 |
| Ser | Tyr | Ala | Asp | Glu | Glu | Gly | Ala | Arg | Val | Ile | Thr | Trp | Lys | Asn | Ile |
| | | | | 165 | | | | | 170 | | | | | 175 | |
| Asp | Leu | Pro | Tyr | Val | Asp | Val | Ser | Thr | Glu | Lys | Glu | Met | Ile | Lys | |
| | | | 180 | | | | | 185 | | | | | 190 | | |
| Arg | Phe | Leu | Lys | Val | Val | Lys | Glu | Lys | Asp | Pro | Asp | Val | Leu | Ile | Thr |
| | | | 195 | | | | | 200 | | | | | 205 | | |
| Tyr | Asn | Gly | Asp | Asn | Phe | Asp | Phe | Ala | Tyr | Leu | Lys | Lys | Arg | Ser | Glu |
| 210 | | | | | 215 | | | | | 220 | | | | | |
| Lys | Leu | Gly | Val | Lys | Phe | Ile | Leu | Gly | Arg | Glu | Gly | Ser | Glu | Pro | Lys |
| 225 | | | | | 230 | | | | | 235 | | | | | 240 |
| Ile | Gln | Arg | Met | Gly | Asp | Arg | Phe | Ala | Val | Glu | Val | Lys | Gly | Arg | Ile |
| | | | | 245 | | | | | 250 | | | | | 255 | |
| His | Phe | Asp | Leu | Tyr | Pro | Val | Ile | Arg | Arg | Thr | Ile | Asn | Leu | Pro | Thr |
| | | | 260 | | | | | 265 | | | | | 270 | | |
| Tyr | Thr | Leu | Glu | Ala | Val | Tyr | Glu | Ala | Ile | Phe | Gly | Gln | Pro | Lys | Glu |
| | | | 275 | | | | | 280 | | | | | 285 | | |
| Lys | Val | Tyr | Ala | Glu | Glu | Ile | Ala | Gln | Ala | Trp | Glu | Thr | Gly | Glu | Gly |
| | | | 290 | | | | | 295 | | | | | 300 | | |
| Leu | Glu | Arg | Val | Ala | Arg | Tyr | Ser | Met | Glu | Asp | Ala | Lys | Val | Thr | Tyr |
| 305 | | | | | 310 | | | | | 315 | | | | | 320 |
| Glu | Leu | Gly | Lys | Glu | Phe | Phe | Pro | Met | Glu | Ala | Gln | Leu | Ser | Arg | Leu |
| | | | | 325 | | | | | 330 | | | | | 335 | |
| Val | Gly | Gln | Ser | Leu | Trp | Asp | Val | Ser | Arg | Ser | Ser | Thr | Gly | Asn | Leu |
| | | | 340 | | | | | 345 | | | | | 350 | | |
| Val | Glu | Trp | Phe | Leu | Leu | Arg | Lys | Ala | Tyr | Glu | Arg | Asn | Glu | Leu | Ala |
| | | | 355 | | | | | 360 | | | | | 365 | | |
| Pro | Asn | Lys | Pro | Asp | Glu | Arg | Glu | Leu | Ala | Arg | Arg | Arg | Glu | Ser | Tyr |
| | | | 370 | | | | | 375 | | | | | 380 | | |

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Glu Glu Tyr Asp
        420                 425                 430

Val Ala Pro Gln Val Gly His Lys Phe Cys Lys Asp Phe Pro Gly Phe
    435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Leu Glu Thr Thr Ile Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
            755                 760                 765

Leu Lys Pro Lys Thr
770

<210> SEQ ID NO 9
<211> LENGTH: 2322

<212> TYPE: DNA
<213> ORGANISM: Artificial Sequence
<220> FEATURE:
<223> OTHER INFORMATION: DNA sequence encoding T. gorgonarius derived
      polymerase RT521K mutated at V93Q, D141A, E143A, A485L, and E664K

<400> SEQUENCE: 9

```
atgatcctcg atacagacta cataactgag gatggaaagc ccgtcatcag gatcttcaag    60
aaggagaacg gcgagttcaa aatagactac gacagaaact ttgagccata catctacgcg   120
ctcttgaagg acgactctgc gattgaggac gtcaagaaga taactgccga gaggcacggc   180
actaccgtta gggttgtcag ggccgagaaa gtgaagaaga agttcctagg caggccgata   240
gaggtctgga agctctactt cactcacccc caggaccagc ccgcaatcag ggacaagata   300
aaggagcatc ctgccgttgt ggacatctac gagtacgaca tcccctttcgc gaagcgctac   360
ctcatagaca aaggcttaat cccgatggag ggcgacgagg aacttaagat gctcgccttc   420
gcgatcgcga cgctctatca cgagggcgag gagttcgccg aagggcctat cctgatgata   480
agctacgccg acgaggaagg ggcgcgcgtt attacctgga agaatatcga ccttccctat   540
gttgacgtcg tttccaccga aggagagatg ataaagcgct tcctcaaggt cgtcaaggaa   600
aaggatcccg acgtcctcat aacctacaac ggcgacaact tcgacttcgc ctacctcaag   660
aagcgctccg agaagctcgg agtcaagttc atcctcggaa gggaagggag cgagccgaaa   720
atccagcgca tgggcgatcg cttttgcggtg gaggtcaagg gaaggattca cttcgacctc   780
taccccgtca ttaggagaac gattaacctc cccacttaca cccttgaggc agtatatgaa   840
gccatctttg gacagccgaa ggagaaggtc tacgctgagg agatagcgca ggcctgggaa   900
acgggcgagg gattagaaag ggtggcccgc tactcgatgg aggacgcaaa ggtaacctat   960
gaactcggaa agaattcttc cctatggaa gcccagctct cgcgcctcgt aggccagagc  1020
ctctgggatg tatctcgctc gagtaccgga aacctcgtcg agtggttttt gctgaggaag  1080
gcctacgaga ggaatgaact tgcaccaaac aagccggacg agagggagct ggcaagaaga  1140
agggagagct acgcgggtgg atacgtcaag gagcccgaaa ggggactgtg ggagaacatc  1200
gtgtatctgg acttccgctc cctgtatcct tcgataataa tcacccataa cgtctcccct  1260
gatacactca acagggaggg ttgtgaggag tacgacgtgg ctcctcaggt aggccataag  1320
ttctgcaagg acttccccgg cttcatccca agcctcctcg gtgacctctt ggaggagaga  1380
cagaaggtaa agaagaagat gaaggccact atagacccaa tcgagaagaa actcctcgat  1440
tacaggcaac gactgatcaa aatccttgct aatagcttct acggttacta cggctatgca  1500
aaggcccgct ggtactgcaa ggagtgcgcc gagagcgtta ccgcttgggg caggcagtac  1560
ctcgagacta cgataaggga aatagaggag aaatttggct ttaaagtcct ctacgcggac  1620
acagatggat tttcgcaac aatacctgga gcggacgccg aaaccgtcaa aaagaaggca  1680
aaggagttcc tggactacat caacgccaaa ctgcccggcc tgctcgaact cgaatacgag  1740
ggcttctaca gcgcggctt cttcgtgacg aagaagaagt acgcggttat agacgaggag  1800
gacaagataa cgacgcgcgg gcttgaaata gttaggcgtg actggagcga gatagcgaag  1860
gagacgcagg cgagggttct tgaggcgata ctaaagcacg gtgacgttga agaagcggta  1920
aggattgtca aagaggttac ggagaagctg agcaagtacg aggttccacc ggagaagctg  1980
gtcatctaca gcagataac ccgcgacctg aaggactaca aggccaccgg ccgcatgtg   2040
gctgttgcaa aacgcctcgc cgcaaggggg ataaaaatcc ggcccggaac ggtcataagc  2100
tacatcgtgc tcaaaggctc gggaaggatt ggggacaggg ctataccctt tgacgaattt  2160
```

-continued

```
gacccggcaa agcacaagta cgatgcagaa tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagacat aa                     2322
```

<210> SEQ ID NO 10
<211> LENGTH: 773
<212> TYPE: PRT
<213> ORGANISM: Artificial Sequence
<220> FEATURE:
<223> OTHER INFORMATION: T. go derived polymerase RT521K mutated at
      V93Q, D141A, E143A, A485L, and E664K

<400> SEQUENCE: 10

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
```

```
                    325                 330                 335
Val Gly Gln Ser Leu Trp Asp Val Ser Arg Ser Thr Gly Asn Leu
                340                 345                 350
Val Glu Trp Phe Leu Leu Arg Lys Ala Tyr Glu Arg Asn Glu Leu Ala
            355                 360                 365
Pro Asn Lys Pro Asp Glu Arg Glu Leu Ala Arg Arg Glu Ser Tyr
        370                 375                 380
Ala Gly Gly Tyr Val Lys Glu Pro Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Glu Tyr Asp
                420                 425                 430
Val Ala Pro Gln Val Gly His Lys Phe Cys Lys Asp Phe Pro Gly Phe
            435                 440                 445
Ile Pro Ser Leu Leu Gly Asp Leu Leu Glu Glu Arg Gln Lys Val Lys
        450                 455                 460
Lys Met Lys Ala Thr Ile Asp Pro Ile Glu Lys Lys Leu Leu Asp
465                 470                 475                 480
Tyr Arg Gln Arg Leu Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Gln Tyr Leu Glu Thr Thr Ile Arg Glu Ile
        515                 520                 525
Glu Glu Lys Phe Gly Phe Lys Val Leu Tyr Ala Asp Thr Asp Gly Phe
            530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Lys Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Ile Lys Ile Arg Pro Gly Thr Val Ile Ser Tyr Ile Val Leu
        690                 695                 700
Lys Gly Ser Gly Arg Ile Gly Asp Arg Ala Ile Pro Phe Asp Glu Phe
705                 710                 715                 720
Asp Pro Ala Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
```

-continued

```
Glu Asp Leu Arg Tyr Gln Lys Thr Arg Gln Val Gly Leu Gly Ala Trp
        755                 760                 765

Leu Lys Pro Lys Thr
    770

<210> SEQ ID NO 11
<211> LENGTH: 1097
<212> TYPE: PRT
<213> ORGANISM: Saccharomyces cerevisiae

<400> SEQUENCE: 11

Met Ser Glu Lys Arg Ser Leu Pro Met Val Asp Val Lys Ile Asp Asp
1               5                   10                  15

Glu Asp Thr Pro Gln Leu Glu Lys Lys Ile Lys Arg Gln Ser Ile Asp
            20                  25                  30

His Gly Val Gly Ser Glu Pro Val Ser Thr Ile Glu Ile Ile Pro Ser
        35                  40                  45

Asp Ser Phe Arg Lys Tyr Asn Ser Gln Gly Phe Lys Ala Lys Asp Thr
    50                  55                  60

Asp Leu Met Gly Thr Gln Leu Glu Ser Thr Phe Glu Gln Glu Leu Ser
65                  70                  75                  80

Gln Met Glu His Asp Met Ala Asp Gln Glu Glu His Asp Leu Ser Ser
                85                  90                  95

Phe Glu Arg Lys Lys Leu Pro Thr Asp Phe Asp Pro Ser Leu Tyr Asp
            100                 105                 110

Ile Ser Phe Gln Gln Ile Asp Ala Glu Gln Ser Val Leu Asn Gly Ile
        115                 120                 125

Lys Asp Glu Asn Thr Ser Thr Val Val Arg Phe Phe Gly Val Thr Ser
    130                 135                 140

Glu Gly His Ser Val Leu Cys Asn Val Thr Gly Phe Lys Asn Tyr Leu
145                 150                 155                 160

Tyr Val Pro Ala Pro Asn Ser Ser Asp Ala Asn Asp Gln Glu Gln Ile
                165                 170                 175

Asn Lys Phe Val His Tyr Leu Asn Glu Thr Phe Asp His Ala Ile Asp
            180                 185                 190

Ser Ile Glu Val Val Ser Lys Gln Ser Ile Trp Gly Tyr Ser Gly Asp
        195                 200                 205

Thr Lys Leu Pro Phe Trp Lys Ile Tyr Val Thr Tyr Pro His Met Val
    210                 215                 220

Asn Lys Leu Arg Thr Ala Phe Glu Arg Gly His Leu Ser Phe Asn Ser
225                 230                 235                 240

Trp Phe Ser Asn Gly Thr Thr Thr Tyr Asp Asn Ile Ala Tyr Thr Leu
                245                 250                 255

Arg Leu Met Val Asp Cys Gly Ile Val Gly Met Ser Trp Ile Thr Leu
            260                 265                 270

Pro Lys Gly Lys Tyr Ser Met Ile Glu Pro Asn Asn Arg Val Ser Ser
        275                 280                 285

Cys Gln Leu Glu Val Ser Ile Asn Tyr Arg Asn Leu Ile Ala His Pro
    290                 295                 300

Ala Glu Gly Asp Trp Ser His Thr Ala Pro Leu Arg Ile Met Ser Phe
305                 310                 315                 320

Asp Ile Glu Cys Ala Gly Arg Ile Gly Val Phe Pro Glu Pro Glu Tyr
                325                 330                 335

Asp Pro Val Ile Gln Ile Ala Asn Val Val Ser Ile Ala Gly Ala Lys
```

-continued

```
                340                 345                 350
Lys Pro Phe Ile Arg Asn Val Phe Thr Leu Asn Thr Cys Ser Pro Ile
            355                 360                 365
Thr Gly Ser Met Ile Phe Ser His Ala Thr Glu Glu Met Leu Ser
        370                 375                 380
Asn Trp Arg Asn Phe Ile Ile Lys Val Asp Pro Asp Val Ile Ile Gly
385                 390                 395                 400
Tyr Asn Thr Thr Asn Phe Asp Ile Pro Tyr Leu Leu Asn Arg Ala Lys
                405                 410                 415
Ala Leu Lys Val Asn Asp Phe Pro Tyr Phe Gly Arg Leu Lys Thr Val
            420                 425                 430
Lys Gln Glu Ile Lys Glu Ser Val Phe Ser Ser Lys Ala Tyr Gly Thr
        435                 440                 445
Arg Glu Thr Lys Asn Val Asn Ile Asp Gly Arg Leu Gln Leu Asp Leu
        450                 455                 460
Leu Gln Phe Ile Gln Arg Glu Tyr Lys Leu Arg Ser Tyr Thr Leu Asn
465                 470                 475                 480
Ala Val Ser Ala His Phe Leu Gly Glu Gln Lys Glu Asp Val His Tyr
            485                 490                 495
Ser Ile Ile Ser Asp Leu Gln Asn Gly Asp Ser Glu Thr Arg Arg Arg
            500                 505                 510
Leu Ala Val Tyr Cys Leu Lys Asp Ala Tyr Leu Pro Leu Arg Leu Met
            515                 520                 525
Glu Lys Leu Met Ala Leu Val Asn Tyr Thr Glu Met Ala Arg Val Thr
        530                 535                 540
Gly Val Pro Phe Ser Tyr Leu Leu Ala Arg Gly Gln Gln Ile Lys Val
545                 550                 555                 560
Val Ser Gln Leu Phe Arg Lys Cys Leu Glu Ile Asp Thr Val Ile Pro
                565                 570                 575
Asn Met Gln Ser Gln Ala Ser Asp Asp Gln Tyr Glu Gly Ala Thr Val
            580                 585                 590
Ile Glu Pro Ile Arg Gly Tyr Tyr Asp Val Pro Ile Ala Thr Leu Asp
            595                 600                 605
Phe Asn Ser Leu Tyr Pro Ser Ile Met Met Ala His Asn Leu Cys Tyr
        610                 615                 620
Thr Thr Leu Cys Asn Lys Ala Thr Val Glu Arg Leu Asn Leu Lys Ile
625                 630                 635                 640
Asp Glu Asp Tyr Val Ile Thr Pro Asn Gly Asp Tyr Phe Val Thr Thr
                645                 650                 655
Lys Arg Arg Arg Gly Ile Leu Pro Ile Ile Leu Asp Glu Leu Ile Ser
                660                 665                 670
Ala Arg Lys Arg Ala Lys Lys Asp Leu Arg Asp Glu Lys Asp Pro Phe
            675                 680                 685
Lys Arg Asp Val Leu Asn Gly Arg Gln Leu Ala Leu Lys Ile Ser Ala
            690                 695                 700
Asn Ser Val Tyr Gly Phe Thr Gly Ala Thr Val Gly Lys Leu Pro Cys
705                 710                 715                 720
Leu Ala Ile Ser Ser Ser Val Thr Ala Tyr Gly Arg Thr Met Ile Leu
                725                 730                 735
Lys Thr Lys Thr Ala Val Gln Glu Lys Tyr Cys Ile Lys Asn Gly Tyr
            740                 745                 750
Lys His Asp Ala Val Val Val Tyr Gly Asp Thr Asp Ser Val Met Val
        755                 760                 765
```

```
Lys Phe Gly Thr Thr Asp Leu Lys Glu Ala Met Asp Leu Gly Thr Glu
    770                 775                 780
Ala Ala Lys Tyr Val Ser Thr Leu Phe Lys His Pro Ile Asn Leu Glu
785                 790                 795                 800
Phe Glu Lys Ala Tyr Phe Pro Tyr Leu Leu Ile Asn Lys Lys Arg Tyr
                805                 810                 815
Ala Gly Leu Phe Trp Thr Asn Pro Asp Lys Phe Asp Lys Leu Asp Gln
                820                 825                 830
Lys Gly Leu Ala Ser Val Arg Arg Asp Ser Cys Ser Leu Val Ser Ile
                835                 840                 845
Val Met Asn Lys Val Leu Lys Lys Ile Leu Ile Glu Arg Asn Val Asp
                850                 855                 860
Gly Ala Leu Ala Phe Val Arg Glu Thr Ile Asn Asp Ile Leu His Asn
865                 870                 875                 880
Arg Val Asp Ile Ser Lys Leu Ile Ile Ser Lys Thr Leu Ala Pro Asn
                885                 890                 895
Tyr Thr Asn Pro Gln Pro His Ala Val Leu Ala Glu Arg Met Lys Arg
                900                 905                 910
Arg Glu Gly Val Gly Pro Asn Val Gly Asp Arg Val Asp Tyr Val Ile
                915                 920                 925
Ile Gly Gly Asn Asp Lys Leu Tyr Asn Arg Ala Glu Asp Pro Leu Phe
930                 935                 940
Val Leu Glu Asn Asn Ile Gln Val Asp Ser Arg Tyr Tyr Leu Thr Asn
945                 950                 955                 960
Gln Leu Gln Asn Pro Ile Ile Ser Ile Val Ala Pro Ile Ile Gly Asp
                965                 970                 975
Lys Gln Ala Asn Gly Met Phe Val Val Lys Ser Ile Lys Ile Asn Thr
                980                 985                 990
Gly Ser Gln Lys Gly Gly Leu Met Ser Phe Ile Lys Lys Val Glu Ala
                995                1000                1005
Cys Lys Ser Cys Lys Gly Pro Leu Arg Lys Gly Glu Gly Pro Leu
    1010                1015                1020
Cys Ser Asn Cys Leu Ala Arg Ser Gly Glu Leu Tyr Ile Lys Ala
    1025                1030                1035
Leu Tyr Asp Val Arg Asp Leu Glu Glu Lys Tyr Ser Arg Leu Trp
    1040                1045                1050
Thr Gln Cys Gln Arg Cys Ala Gly Asn Leu His Ser Glu Val Leu
    1055                1060                1065
Cys Ser Asn Lys Asn Cys Asp Ile Phe Tyr Met Arg Val Lys Val
    1070                1075                1080
Lys Lys Glu Leu Gln Glu Lys Val Glu Gln Leu Ser Lys Trp
    1085                1090                1095

<210> SEQ ID NO 12
<211> LENGTH: 773
<212> TYPE: PRT
<213> ORGANISM: Artificial Sequence
<220> FEATURE:
<223> OTHER INFORMATION: T. go derived RT-521 polymerase

<400> SEQUENCE: 12

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Asp Tyr Asp Arg
                20                  25                  30
```

```
Asn Phe Glu Pro Tyr Ile Tyr Ala Leu Leu Lys Asp Asp Ser Ala Ile
         35                  40                  45

Glu Asp Val Lys Lys Ile Thr Ala Glu Arg His Gly Thr Thr Val Arg
 50                  55                  60

Val Val Arg Ala Glu Lys Val Lys Lys Phe Leu Gly Arg Pro Ile
 65                  70                  75                  80

Glu Val Trp Lys Leu Tyr Phe Thr His Pro Gln Asp Gln Pro Ala Ile
                 85                  90                  95

Arg Asp Lys Ile Lys Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Ala Ile Ala Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Ser Thr Glu Lys Glu Met Ile Lys
                180                 185                 190

Arg Phe Leu Lys Val Val Lys Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
            275                 280                 285

Lys Val Tyr Ala Glu Glu Ile Ala Gln Ala Trp Glu Thr Gly Glu Gly
        290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Glu Ser Tyr
        370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Gly Glu Tyr Asp
                420                 425                 430

Val Ala Pro Gln Val Gly His Lys Phe Cys Lys Asp Phe Pro Gly Phe
            435                 440                 445
```

```
Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Leu Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770

<210> SEQ ID NO 13
<211> LENGTH: 2322
<212> TYPE: DNA
<213> ORGANISM: Artificial Sequence
<220> FEATURE:
<223> OTHER INFORMATION: DNA encoding T. go derived RT-521 polymerase

<400> SEQUENCE: 13
atgatcctcg atacagacta cataactgag gatggaaagc ccgtcatcag gatcttcaag      60
aaggagaacg gcgagttcaa aatagactac gacagaaact ttgagccata catctacgcg     120
ctcttgaagg acgactctgc gattgaggac gtcaagaaga taactgccga gaggcacggc     180
```

```
actaccgtta gggttgtcag ggccgagaaa gtgaagaaga agttcctagg caggccgata    240
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga aaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtggggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa gatccttgct aatagcttct acggttacta cggctatgca   1500
aaggcccgct ggtactgcaa ggagtgcgcc gagagcgtta ccgcttgggg caggcagtac   1560
ctcgagacta cgataaggga aatagaggag aaatttggct ttaaagtcct ctacgcggac   1620
acagatggat ttttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca agaggttac ggagaagctg agcaagtacg aggttccacc ggagaagctg   1980
gtcatctacg agcagataac ccgcgacctg aaggactaca aggccaccgg gccgcatgtg   2040
gctgttgcaa aacgcctcgc cgcaaggggg ataaaaatcc ggcccggaac ggtcataagc   2100
tacatcgtgc tcaaaggctc gggaaggatt ggggacaggg ctatacccct tgacgaattt   2160
gacccggcaa agcacaggta cgatgcagaa tactacatcg agaaccaggt tcttccagct   2220
gtggagagga ttctgagggc cttttggttac cgtaaagaag atttaaggta tcagaaaacg   2280
cggcaggttg gcttggggc gtggctaaaa cctaagacat aa                       2322
```

<210> SEQ ID NO 14
<211> LENGTH: 773
<212> TYPE: PRT
<213> ORGANISM: Artificial Sequence
<220> FEATURE:
<223> OTHER INFORMATION: T. go derived polymerase designated RT-521K

<400> SEQUENCE: 14

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
    370                 375                 380

Val Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
```

```
                405                 410                 415
Asn Val Ser Pro Asp Thr Leu Asn Arg Glu Gly Cys Gly Glu Tyr Asp
            420                 425                 430
Val Ala Pro Gln Val Gly His Lys Phe Cys Lys Asp Leu Pro Gly Phe
        435                 440                 445
Ile Pro Ser Leu Leu Gly Asp Leu Leu Glu Glu Arg Gln Lys Val Lys
    450                 455                 460
Lys Lys Met Lys Ala Thr Ile Asp Pro Ile Glu Lys Lys Leu Leu Asp
465                 470                 475                 480
Tyr Arg Gln Arg Leu Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Gln Tyr Leu Glu Thr Ile Arg Glu Ile
        515                 520                 525
Glu Glu Lys Phe Gly Phe Lys Val Leu Tyr Ala Asp Thr Asp Gly Phe
    530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Lys Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Ile Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Ala Lys His Arg Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Gly Ala Trp
        755                 760                 765
Leu Lys Pro Lys Thr
    770

<210> SEQ ID NO 15
<211> LENGTH: 2322
<212> TYPE: DNA
<213> ORGANISM: Artificial Sequence
<220> FEATURE:
<223> OTHER INFORMATION: DNA encoding T. go derived mutant polymerase
      RT-521K
```

<400> SEQUENCE: 15

```
atgatcctcg atacagacta cataactgag gatggaaagc ccgtcatcag gatcttcaag        60
aaggagaatg gcgagttcaa aatagactac gacagaaact tgagccata catctacgcg       120
ctcttgaagg acgactctgc gattgaggac gtcaagaaga taactgccga gaggcacggc       180
actaccgtta gggttgtcag ggccgagaaa gtgaagaaga agttcctagg caggccgata       240
gaggtctgga agctctactt cactcacccc caggaccagc ccgcaatcag ggacaagata       300
aaggagcatc ctgccgttgt ggacatctac gagtacgaca tccccttcgc gaagcgctac       360
ctcatagaca aaggcttaat cccgatggag ggcgacgagg aacttaagat gctcgccttc       420
gcgatcgcga cgctctatca cgagggcgag gagttcgccg aagggcctat cctgatgata       480
agctacgccg acgaggaagg ggcgcgcgtt attacctgga gaatatcga ccttcccta t      540
gttgacgtcg tttccaccga gaaggagatg ataaagcgct tcctcaaggt cgtcaaggaa       600
aaggatcccg acgtcctcat aacctacaac ggcgacaact tcgacttcgc ctacctcaag       660
aagcgctccg agaagctcgg agtcaagttc atcctcggaa gggaagggag cgagccgaaa       720
atccagcgca tgggcgatcg ctttgcggtg gaggtcaagg gaaggattca cttcgacctc       780
taccccgtca ttaggagaac gattaacctc cccacttaca cccttgaggc agtatatgaa       840
gccatctttg gacagccgaa ggagaaggtc tacgctgagg agatagcgca ggcctgggaa       900
acgggcgagg gattagaaag ggtggcccgc tactcgatgg aggacgcaaa ggtaacctat       960
gaactcggaa aagaattctt ccctatggaa gcccagctct cgcgcctcgt aggccagagc      1020
ctctgggatg tatctcgctc gagtaccgga acctcgtcg agtggttttt gctgaggaag      1080
gcctacgaga ggaatgaact tgcaccaaac aagccggacg agagggagct ggcaagaaga      1140
agggagagct acgtgggtgg atacgtcaag gagcccgaaa ggggactgtg ggagaacatc      1200
gtgtatctgg acttccgctc cctgtatcct tcgataataa tcacccataa cgtctcccct      1260
gatacactca acagggaggg ttgtggggag tacgacgtgg ctcctcaggt aggccataag      1320
ttctgcaagg acctccccgg cttcatccca agcctcctcg gtgacctctt ggaggagaga      1380
cagaaggtaa agaagaagat gaaggccact atagacccaa tcgagaagaa actcctcgat      1440
tacaggcaac gactgatcaa gatccttgct aatagcttct acggttacta cggctatgca      1500
aaggcccgct ggtactgcaa ggagtgcgcc gagagcgtta ccgcttgggg caggcagtac      1560
ctcgagacta cgataaggga aatagaggag aaatttggct ttaaagtcct ctacgcggac      1620
acagatggat ttttcgcaac aatacctgga gcggacgccg aaaccgtcaa aaagaaggca      1680
aaggagttcc tggactacat caacgccaaa ctgcccggcc tgctcgaact cgaatacgag      1740
ggcttctaca gcgcggctt cttcgtgacg aagaagaagt acgcggttat agacgaggag      1800
gacaagataa cgacgcgcgg gcttgaaata gttaggcgtg actggagcga gatagcgaag      1860
gagacgcagg cgagggttct tgaggcgata ctaaagcacg gtgacgttga agaagcggta      1920
aggattgtca agaggttac ggagaagctg agcaagtacg aggttccacc ggagaagctg      1980
gtcatctaca gcagataac ccgcgacctg aaggactaca aggccaccgg gccgcatgtg      2040
gctgttgcaa aacgcctcgc cgcaagggg ataaaaatcc ggcccggaac ggtcataagc      2100
tacatcgtgc tcaaaggctc gggaaggatt ggggacaggg ctataccctt tgacgaattt      2160
gacccggcaa agcacaggta cgatgcagaa tactacatcg agaaccaggt tcttccagct      2220
gtggagagga ttctgagggc ctttggttac cgtaaagaag atttaaggta tcagaaaacg      2280
```

```
cggcaggttg gcttgggggc gtggctaaaa cctaagacat aa                              2322
```

<210> SEQ ID NO 16
<211> LENGTH: 48
<212> TYPE: DNA
<213> ORGANISM: Artificial Sequence
<220> FEATURE:
<223> OTHER INFORMATION: HNA aptamer T5-S8-7 targets HIV TAR
<220> FEATURE:
<221> NAME/KEY: misc_feature
<222> LOCATION: (1)..(48)
<223> OTHER INFORMATION: entire oligonucleotide is 1,5-anhydrohexitol
      nucleic acid (HNA) presented 6' to 4'

<400> SEQUENCE: 16

```
aggtagtgct gttcgttcat ctcaaatcta gttcgctatc cagttggc                         48
```

<210> SEQ ID NO 17
<211> LENGTH: 50
<212> TYPE: DNA
<213> ORGANISM: Artificial Sequence
<220> FEATURE:
<223> OTHER INFORMATION: HNA aptamer LYS-S8-19 targets HEL
<220> FEATURE:
<221> NAME/KEY: misc_feature
<222> LOCATION: (1)..(50)
<223> OTHER INFORMATION: Aptamer is 1,5-anhydrohexitol nucleic acid
      (HNA) presented 6' to 4'

<400> SEQUENCE: 17

```
aggtagtgct gttcgtttaa atgtgtgtcg tcgttcgcta tccagttggc                       50
```

<210> SEQ ID NO 18
<211> LENGTH: 77
<212> TYPE: DNA
<213> ORGANISM: Artificial Sequence
<220> FEATURE:
<223> OTHER INFORMATION: Primer, partial TempN template

<400> SEQUENCE: 18

```
cccettatta gcgtttgcca gatcgattac cgaacagcac tacgtggcta agtgcttatc            60
tggtccagca tcgtgag                                                           77
```

<210> SEQ ID NO 19
<211> LENGTH: 77
<212> TYPE: DNA
<213> ORGANISM: Artificial Sequence
<220> FEATURE:
<223> OTHER INFORMATION: Primer, partial TempN template

<400> SEQUENCE: 19

```
ctcacgatgc tggaccagat aagcacttag ccacgtagtg ctgttcggta atcgatctgg            60
caaacgctaa taagggg                                                           77
```

<210> SEQ ID NO 20
<211> LENGTH: 46
<212> TYPE: DNA
<213> ORGANISM: Artificial Sequence
<220> FEATURE:
<223> OTHER INFORMATION: Aptamer CD30_I3 targets CD30

<400> SEQUENCE: 20

```
tagatgtggt agaagtcgtc atttggcgag aaagctcagt ctcagg                           46
```

<210> SEQ ID NO 21
<211> LENGTH: 46

-continued

```
<212> TYPE: DNA
<213> ORGANISM: Artificial Sequence
<220> FEATURE:
<223> OTHER INFORMATION: Aptamer CD30_I30 targets CD30

<400> SEQUENCE: 21
tttcatggta ttgataaagc tgttgccgat acttggaaca atttct           46

<210> SEQ ID NO 22
<211> LENGTH: 59
<212> TYPE: DNA
<213> ORGANISM: Artificial Sequence
<220> FEATURE:
<223> OTHER INFORMATION: Aptamer L1-CAM_I1 targets L1-CAM

<400> SEQUENCE: 22
gcgacgccgt tcaaccagat attgaagcag aacgcaaaaa gagagatgag attgaggct   59

<210> SEQ ID NO 23
<211> LENGTH: 46
<212> TYPE: DNA
<213> ORGANISM: Artificial Sequence
<220> FEATURE:
<223> OTHER INFORMATION: Aptamer L1-CAM_I6 targets L1-CAM

<400> SEQUENCE: 23
tagatgtggt agaagtcgtc atttggcgag aaagctcagt ctcagg           46

<210> SEQ ID NO 24
<211> LENGTH: 47
<212> TYPE: DNA
<213> ORGANISM: Artificial Sequence
<220> FEATURE:
<223> OTHER INFORMATION: Aptamer L1-CAM_Icore targets  L1-CAM

<400> SEQUENCE: 24
acgacgcgac gccgttcaac cagatattga agcagaacgc aaaaaga         47

<210> SEQ ID NO 25
<211> LENGTH: 66
<212> TYPE: DNA
<213> ORGANISM: Artificial Sequence
<220> FEATURE:
<223> OTHER INFORMATION: Primer Motif1 backward
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 25
gagtcaggtc tctccgagcc gaaaatccag cgcatgggcg atannttttgc ggtggaggtc   60 aaggga                                                               66

<210> SEQ ID NO 26
<211> LENGTH: 33
<212> TYPE: DNA
<213> ORGANISM: Artificial Sequence
<220> FEATURE:
<223> OTHER INFORMATION: Primer Motif1 forward

<400> SEQUENCE: 26
gagtcaggtc tcctcggatc cwtcccttcc gag                         33
```

<210> SEQ ID NO 27
<211> LENGTH: 63
<212> TYPE: DNA
<213> ORGANISM: Artificial Sequence
<220> FEATURE:
<223> OTHER INFORMATION: Primer Motif2 backward
<220> FEATURE:
<221> NAME/KEY: misc_feature
<222> LOCATION: (40)..(40)
<223> OTHER INFORMATION: n is a, c, g or t
<220> FEATURE:
<221> NAME/KEY: misc_feature
<222> LOCATION: (43)..(43)
<223> OTHER INFORMATION: n is a, c, g or t
<220> FEATURE:
<221> NAME/KEY: misc_feature
<222> LOCATION: (55)..(55)
<223> OTHER INFORMATION: n is a, c, g or t

<400> SEQUENCE: 27
gagtcaggtc tcacttacac ccttgaggca gtatatgaan ycntcttwgg amagncgaag   60
gag                                                                 63

<210> SEQ ID NO 28
<211> LENGTH: 72
<212> TYPE: DNA
<213> ORGANISM: Artificial Sequence
<220> FEATURE:
<223> OTHER INFORMATION: Primer Motif2 forward

<400> SEQUENCE: 28
gagtcaggtc tcgtaagtgg ggaggttaat cgttctccta atgacggggt agaggtcgaa   60
gtggatcctt cc                                                       72

<210> SEQ ID NO 29
<211> LENGTH: 61
<212> TYPE: DNA
<213> ORGANISM: Artificial Sequence
<220> FEATURE:
<223> OTHER INFORMATION: Primer Motif3 backward

<400> SEQUENCE: 29
gagtcaggtc tcggatgtat ctcgctctag taccggaaac ctcgtcgagt ggtwtttgct   60
g                                                                   61

<210> SEQ ID NO 30
<211> LENGTH: 58
<212> TYPE: DNA
<213> ORGANISM: Artificial Sequence
<220> FEATURE:
<223> OTHER INFORMATION: Primer Motif3 forward
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 30
gagtcaggtc tcacatccca aanagnctgg ccaabgagwy kcgmgagctb ggcttcca     58

<210> SEQ ID NO 31
<211> LENGTH: 59
<212> TYPE: DNA
<213> ORGANISM: Artificial Sequence

```
<220> FEATURE:
<223> OTHER INFORMATION: Primer Motif4 backward

<400> SEQUENCE: 31
gagtcaggtc tcaatgawct tgcaccaaac aagccggacg agcgtgagct ggcaagaag        59

<210> SEQ ID NO 32
<211> LENGTH: 42
<212> TYPE: DNA
<213> ORGANISM: Artificial Sequence
<220> FEATURE:
<223> OTHER INFORMATION: Primer Motif4 forward

<400> SEQUENCE: 32
gagtcaggtc tcttcattcc tctcgtaggc twycbtcagc aa                         42

<210> SEQ ID NO 33
<211> LENGTH: 51
<212> TYPE: DNA
<213> ORGANISM: Artificial Sequence
<220> FEATURE:
<223> OTHER INFORMATION: Primer MotifA- backward W

<400> SEQUENCE: 33
gagtcaggtc tcggtggata cgtcaaggag cccgaaaggg gactgtggga g                51

<210> SEQ ID NO 34
<211> LENGTH: 42
<212> TYPE: DNA
<213> ORGANISM: Artificial Sequence
<220> FEATURE:
<223> OTHER INFORMATION: Primer MotifA- forward

<400> SEQUENCE: 34
gagtcaggtc tctccaccsd bgtawsysbb tsytcttctt gc                         42

<210> SEQ ID NO 35
<211> LENGTH: 79
<212> TYPE: DNA
<213> ORGANISM: Artificial Sequence
<220> FEATURE:
<223> OTHER INFORMATION: Primer TgAmoba2

<400> SEQUENCE: 35
ggaaaggtct cagtggramr rcmtsryytm tctggacttc cgctccctgt atccttcgat        60
catartcacc cataacgtc                                                    79

<210> SEQ ID NO 36
<211> LENGTH: 37
<212> TYPE: DNA
<213> ORGANISM: Artificial Sequence
<220> FEATURE:
<223> OTHER INFORMATION: Primer TgAmo forward

<400> SEQUENCE: 36
gagtaggtct ctccacagtc ccctttcggg ctccttg                               37

<210> SEQ ID NO 37
<211> LENGTH: 56
<212> TYPE: DNA
<213> ORGANISM: Artificial Sequence
<220> FEATURE:
<223> OTHER INFORMATION: Primer MotifA+ backward
<220> FEATURE:
<221> NAME/KEY: misc_feature
<222> LOCATION: (22)..(22)
```

```
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 37
gagtcaggtc tccactcraw mnwgagggtt gtrnrrawta cgacrhrgct cctcag        56

<210> SEQ ID NO 38
<211> LENGTH: 46
<212> TYPE: DNA
<213> ORGANISM: Artificial Sequence
<220> FEATURE:
<223> OTHER INFORMATION: Primer MotifA+ forward

<400> SEQUENCE: 38
gagtcaggtc tctgagtgta tcaggggaga cgttatgggt gaytat                   46

<210> SEQ ID NO 39
<211> LENGTH: 60
<212> TYPE: DNA
<213> ORGANISM: Artificial Sequence
<220> FEATURE:
<223> OTHER INFORMATION: Primer Motif5 backward

<400> SEQUENCE: 39
gagtcaggtc tcgaggasag acagaaggta aagaagaaga tgaaggccac gatcgaccca    60

<210> SEQ ID NO 40
<211> LENGTH: 39
<212> TYPE: DNA
<213> ORGANISM: Artificial Sequence
<220> FEATURE:
<223> OTHER INFORMATION: Primer Motif5 forward
<220> FEATURE:
<221> NAME/KEY: misc_feature
<222> LOCATION: (21)..(21)
<223> OTHER INFORMATION: n is a, c, g or t
<220> FEATURE:
<221> NAME/KEY: misc_feature
<222> LOCATION: (33)..(33)
<223> OTHER INFORMATION: n is a, c, g or t

<400> SEQUENCE: 40
gagtcaggtc tcctcctcca ngagwbbtyy gangaggct                           39

<210> SEQ ID NO 41
<211> LENGTH: 55
<212> TYPE: DNA
<213> ORGANISM: Artificial Sequence
<220> FEATURE:
<223> OTHER INFORMATION: Primer MotifB- backward

<400> SEQUENCE: 41
gagtcaggtc tccgagaaga aactcctcga ttacaggcaa cgactgatca aaatc         55

<210> SEQ ID NO 42
<211> LENGTH: 26
<212> TYPE: DNA
<213> ORGANISM: Artificial Sequence
<220> FEATURE:
<223> OTHER INFORMATION: Primer MotifB- forward
<220> FEATURE:
<221> NAME/KEY: misc_feature
<222> LOCATION: (20)..(20)
<223> OTHER INFORMATION: n is a, c, g or t

<400> SEQUENCE: 42
```
gagtcaggtc tcttctcsan tgggtc                                              26

<210> SEQ ID NO 43
<211> LENGTH: 67
<212> TYPE: DNA
<213> ORGANISM: Artificial Sequence
<220> FEATURE:
<223> OTHER INFORMATION: Primer TgTBmo backwards 2

<400> SEQUENCE: 43
ggaaaggtct ctgatcaaga tccttgctaa tagcttctac ggttactacg gctatvcsaa         60
ggcccgc                                                                   67

<210> SEQ ID NO 44
<211> LENGTH: 39
<212> TYPE: DNA
<213> ORGANISM: Artificial Sequence
<220> FEATURE:
<223> OTHER INFORMATION: Primer TgTBmo forward

<400> SEQUENCE: 44
gagtaggtct ctgatcagtc gttgcctgta atcgaggag                                39

<210> SEQ ID NO 45
<211> LENGTH: 22
<212> TYPE: DNA
<213> ORGANISM: Artificial Sequence
<220> FEATURE:
<223> OTHER INFORMATION: Primer Motif6- backward

<400> SEQUENCE: 45
gagtcaggtc tcgccgagag cg                                                  22

<210> SEQ ID NO 46
<211> LENGTH: 51
<212> TYPE: DNA
<213> ORGANISM: Artificial Sequence
<220> FEATURE:
<223> OTHER INFORMATION: Primer Motif6- forward W
<220> FEATURE:
<221> NAME/KEY: misc_feature
<222> LOCATION: (18)..(18)
<223> OTHER INFORMATION: n is a, c, g or t
<220> FEATURE:
<221> NAME/KEY: misc_feature
<222> LOCATION: (48)..(48)
<223> OTHER INFORMATION: n is a, c, g or t

<400> SEQUENCE: 46
gagtcaggtc tcctcggngc actccttgca gtaccagcgg gcctttgnat a                  51

<210> SEQ ID NO 47
<211> LENGTH: 53
<212> TYPE: DNA
<213> ORGANISM: Artificial Sequence
<220> FEATURE:
<223> OTHER INFORMATION: Primer Motif6+ backward 2

<400> SEQUENCE: 47
gagtcaggtc tctacatcrm shysryswks arsgaamtag agrvsaaatt tgg                53

<210> SEQ ID NO 48
<211> LENGTH: 52
<212> TYPE: DNA
<213> ORGANISM: Artificial Sequence
<220> FEATURE:

<223> OTHER INFORMATION: Primer Motif6+ forward 2

<400> SEQUENCE: 48
gagtcaggtc tcgatgtact bccbgccccc agcggtaacg ctctbggcgc ac    52

<210> SEQ ID NO 49
<211> LENGTH: 65
<212> TYPE: DNA
<213> ORGANISM: Artificial Sequence
<220> FEATURE:
<223> OTHER INFORMATION: Primer TgCmo backward

<400> SEQUENCE: 49
ggaaaggtct caggctttaa agtcctctac gcggacacag atggaytyyw cgcaacgatc    60
cctgg    65

<210> SEQ ID NO 50
<211> LENGTH: 36
<212> TYPE: DNA
<213> ORGANISM: Artificial Sequence
<220> FEATURE:
<223> OTHER INFORMATION: Primer TgCmo forward

<400> SEQUENCE: 50
gagtaggtct ctagccaaat ttctcctcta tttccc    36

<210> SEQ ID NO 51
<211> LENGTH: 50
<212> TYPE: DNA
<213> ORGANISM: Artificial Sequence
<220> FEATURE:
<223> OTHER INFORMATION: Primer MotifC+ backward

<400> SEQUENCE: 51
gagtcaggtc tctcaaarrs arggcamdsr agttcctgra stacatcaac    50

<210> SEQ ID NO 52
<211> LENGTH: 49
<212> TYPE: DNA
<213> ORGANISM: Artificial Sequence
<220> FEATURE:
<223> OTHER INFORMATION: Primer MotifC+ forward
<220> FEATURE:
<221> NAME/KEY: misc_feature
<222> LOCATION: (19)..(19)
<223> OTHER INFORMATION: n is a, c, g or t

<400> SEQUENCE: 52
gagtcaggtc tcttttgang gtttcggcgt ccgctccagg tattgttgc    49

<210> SEQ ID NO 53
<211> LENGTH: 57
<212> TYPE: DNA
<213> ORGANISM: Artificial Sequence
<220> FEATURE:
<223> OTHER INFORMATION: Primer Motif7 backward 3
<220> FEATURE:
<221> NAME/KEY: misc_feature
<222> LOCATION: (47)..(47)
<223> OTHER INFORMATION: n is a, c, g or t

<400> SEQUENCE: 53
gagtcaggtc tcggcctgct cvaactcvaa tacvagggct tctacvnscg cggcttc    57

<210> SEQ ID NO 54
<211> LENGTH: 39

```
<212> TYPE: DNA
<213> ORGANISM: Artificial Sequence
<220> FEATURE:
<223> OTHER INFORMATION: Primer Motif7 forward 3
<220> FEATURE:
<221> NAME/KEY: misc_feature
<222> LOCATION: (20)..(20)
<223> OTHER INFORMATION: n is a, c, g or t
<220> FEATURE:
<221> NAME/KEY: misc_feature
<222> LOCATION: (23)..(23)
<223> OTHER INFORMATION: n is a, c, g or t
<220> FEATURE:
<221> NAME/KEY: misc_feature
<222> LOCATION: (30)..(30)
<223> OTHER INFORMATION: n is a, c, g or t

<400> SEQUENCE: 54
gagtcaggtc tccaggccgn gcnstyttgn gttgatgta                        39

<210> SEQ ID NO 55
<211> LENGTH: 36
<212> TYPE: DNA
<213> ORGANISM: Artificial Sequence
<220> FEATURE:
<223> OTHER INFORMATION: Primer Motif8 backward
<220> FEATURE:
<221> NAME/KEY: misc_feature
<222> LOCATION: (19)..(19)
<223> OTHER INFORMATION: n is a, c, g or t
<220> FEATURE:
<221> NAME/KEY: misc_feature
<222> LOCATION: (22)..(22)
<223> OTHER INFORMATION: n is a, c, g or t

<400> SEQUENCE: 55
gagtcaggtc tctacgcgnt sntsgacgag gaggac                          36

<210> SEQ ID NO 56
<211> LENGTH: 45
<212> TYPE: DNA
<213> ORGANISM: Artificial Sequence
<220> FEATURE:
<223> OTHER INFORMATION: Primer Motif8 forward

<400> SEQUENCE: 56
gagtcaggtc tccgcgtact bctbctbcgt cacgaagaag ccgcg                45

<210> SEQ ID NO 57
<211> LENGTH: 54
<212> TYPE: DNA
<213> ORGANISM: Artificial Sequence
<220> FEATURE:
<223> OTHER INFORMATION: Primer Motif9 backwards 2

<400> SEQUENCE: 57
gagtcaggtc tcagataaya acgcgcgggc ttvaaatagt tvggcgtgac tgga      54

<210> SEQ ID NO 58
<211> LENGTH: 31
<212> TYPE: DNA
<213> ORGANISM: Artificial Sequence
<220> FEATURE:
<223> OTHER INFORMATION: Primer Motif9 forward

<400> SEQUENCE: 58
gagtcaggtc tcttatcyts ycsyyctcgt c                               31

<210> SEQ ID NO 59
```

```
<211> LENGTH: 55
<212> TYPE: DNA
<213> ORGANISM: Artificial Sequence
<220> FEATURE:
<223> OTHER INFORMATION: Primer Motif10A backward
<220> FEATURE:
<221> NAME/KEY: misc_feature
<222> LOCATION: (44)..(44)
<223> OTHER INFORMATION: n is a, c, g ot t

<400> SEQUENCE: 59
gagtcaggtc tcataaccar asmsctgmrs gastacargg ccansgggcc gcatg          55

<210> SEQ ID NO 60
<211> LENGTH: 63
<212> TYPE: DNA
<213> ORGANISM: Artificial Sequence
<220> FEATURE:
<223> OTHER INFORMATION: Primer Motif10A forward

<400> SEQUENCE: 60
gagtcaggtc tcggttatct bctbgtagat gaccagctbc tbcggtggaa cctbgtactt     60
gct                                                                  63

<210> SEQ ID NO 61
<211> LENGTH: 49
<212> TYPE: DNA
<213> ORGANISM: Artificial Sequence
<220> FEATURE:
<223> OTHER INFORMATION: Primer Motif10B backward

<400> SEQUENCE: 61
gagtcaggtc tcctcgccgc aarsgggrta aaartcmrsc ccggaacgg                 49

<210> SEQ ID NO 62
<211> LENGTH: 51
<212> TYPE: DNA
<213> ORGANISM: Artificial Sequence
<220> FEATURE:
<223> OTHER INFORMATION: Primer Motif10B forward

<400> SEQUENCE: 62
gagtcaggtc tcggcgaggc gvtttgcaac agccacatgc ggcccggtgg c              51

<210> SEQ ID NO 63
<211> LENGTH: 47
<212> TYPE: DNA
<213> ORGANISM: Artificial Sequence
<220> FEATURE:
<223> OTHER INFORMATION: Primer Motif10C backward 2

<400> SEQUENCE: 63
gagtcaggtc tcatgctcvr gggctbgggg aggattrggg acagggc                   47

<210> SEQ ID NO 64
<211> LENGTH: 47
<212> TYPE: DNA
<213> ORGANISM: Artificial Sequence
<220> FEATURE:
<223> OTHER INFORMATION: Primer Motif10C forward 2a
<220> FEATURE:
<221> NAME/KEY: misc_feature
<222> LOCATION: (21)..(21)
<223> OTHER INFORMATION: n is a, c, g or t
<220> FEATURE:
<221> NAME/KEY: misc_feature
<222> LOCATION: (33)..(33)
<223> OTHER INFORMATION: n is a, c, g or t
```

<400> SEQUENCE: 64
gagtcaggtc tcgagcacgr ngtayyytat ganyrytcca ggccgga    47

<210> SEQ ID NO 65
<211> LENGTH: 58
<212> TYPE: DNA
<213> ORGANISM: Artificial Sequence
<220> FEATURE:
<223> OTHER INFORMATION: Primer Motif 11_ forward 3
<220> FEATURE:
<221> NAME/KEY: misc_feature
<222> LOCATION: (39)..(39)
<223> OTHER INFORMATION: n is a, c, g or t
<220> FEATURE:
<221> NAME/KEY: misc_feature
<222> LOCATION: (42)..(42)
<223> OTHER INFORMATION: n is a, c, g or t

<400> SEQUENCE: 65
gagtcaggtc tcgtgcttsb ytrsgtcawa ttcsbyarng rntatarycc tgtcccca    58

<210> SEQ ID NO 66
<211> LENGTH: 63
<212> TYPE: DNA
<213> ORGANISM: Artificial Sequence
<220> FEATURE:
<223> OTHER INFORMATION: Primer Motif 11 backward 3a

<400> SEQUENCE: 66
gagtcaggtc tcaagcacaa gtacgatgca vaatactaca tcvagaacva ggttcttcca    60
gct    63

<210> SEQ ID NO 67
<211> LENGTH: 63
<212> TYPE: DNA
<213> ORGANISM: Artificial Sequence
<220> FEATURE:
<223> OTHER INFORMATION: Primer Motif12_ forward

<400> SEQUENCE: 67
gagtcaggtc tcgtaaccaa aggccctcag aatcctctbc acagctggaa gaacctggtt    60
ctc    63

<210> SEQ ID NO 68
<211> LENGTH: 63
<212> TYPE: DNA
<213> ORGANISM: Artificial Sequence
<220> FEATURE:
<223> OTHER INFORMATION: Primer Motif12_ backward
<220> FEATURE:
<221> NAME/KEY: misc_feature
<222> LOCATION: (38)..(38)
<223> OTHER INFORMATION: n is a, c, g or t

<400> SEQUENCE: 68
gagtcaggtc tcggttacmr warwgrwgat ttaargtnsc agarsascmr wcagrysggc    60
ttg    63

<210> SEQ ID NO 69
<211> LENGTH: 32
<212> TYPE: DNA
<213> ORGANISM: Artificial Sequence
<220> FEATURE:
<223> OTHER INFORMATION: Primer Tgo 578Bsa backward

```
<400> SEQUENCE: 69
gagtcaggtc tcgcttcctc aaggtcgtca ag                              32

<210> SEQ ID NO 70
<211> LENGTH: 38
<212> TYPE: DNA
<213> ORGANISM: Artificial Sequence
<220> FEATURE:
<223> OTHER INFORMATION: Primer Tgo 578Bsa forward

<400> SEQUENCE: 70
gagtcaggtc tcggaagcgc tttatcatct ccttctcg                        38

<210> SEQ ID NO 71
<211> LENGTH: 32
<212> TYPE: DNA
<213> ORGANISM: Artificial Sequence
<220> FEATURE:
<223> OTHER INFORMATION: Primer pA 308Bsa forward

<400> SEQUENCE: 71
gagtcaggtc tccgccattt ttcacttcac ag                              32

<210> SEQ ID NO 72
<211> LENGTH: 47
<212> TYPE: DNA
<213> ORGANISM: Artificial Sequence
<220> FEATURE:
<223> OTHER INFORMATION: Primer pA 304Bsa backward

<400> SEQUENCE: 72
gagtcaggtc tcatggcgca cattgtgcga catttttttt gtctgcc              47

<210> SEQ ID NO 73
<211> LENGTH: 42
<212> TYPE: DNA
<213> ORGANISM: Artificial Sequence
<220> FEATURE:
<223> OTHER INFORMATION: Primer for biotin spacer

<400> SEQUENCE: 73
cccccccccc cccccccccc cccccccccc ccccccacc ta                    42

<210> SEQ ID NO 74
<211> LENGTH: 20
<212> TYPE: DNA
<213> ORGANISM: Artificial Sequence
<220> FEATURE:
<223> OTHER INFORMATION: FITC-labeled, biotin-labeled oligonucleotide
      2xB forward primer

<400> SEQUENCE: 74 cccctattata gcgtttgcca                                           20

<210> SEQ ID NO 75
<211> LENGTH: 20
<212> TYPE: DNA
<213> ORGANISM: Artificial Sequence
<220> FEATURE:
<223> OTHER INFORMATION: Unlabeled fd oligonucleotide

<400> SEQUENCE: 75 cccctattata gcgtttgcca                                           20

<210> SEQ ID NO 76
```

```
<211> LENGTH: 36
<212> TYPE: DNA
<213> ORGANISM: Artificial Sequence
<220> FEATURE:
<223> OTHER INFORMATION: Biotin-labeled, FITC-labeled oligonucleotide
      NAPfd

<400> SEQUENCE: 76
cagtatcgac aaaggacccc ttattagcgt ttgcca                                  36

<210> SEQ ID NO 77
<211> LENGTH: 20
<212> TYPE: DNA
<213> ORGANISM: Artificial Sequence
<220> FEATURE:
<223> OTHER INFORMATION: FITC-labled OMe oligonucleotide

<400> SEQUENCE: 77
ccccttatta gcgtttgcca                                                    20

<210> SEQ ID NO 78
<211> LENGTH: 77
<212> TYPE: DNA
<213> ORGANISM: Artificial Sequence
<220> FEATURE:
<223> OTHER INFORMATION: TempN oligonucleotide template

<400> SEQUENCE: 78
ctcacgatgc tggaccagat aagcacttag ccacgtagtg ctgttcggta atcgatctgg        60
caaacgctaa taagggg                                                       77

<210> SEQ ID NO 79
<211> LENGTH: 89
<212> TYPE: DNA
<213> ORGANISM: Artificial Sequence
<220> FEATURE:
<223> OTHER INFORMATION: TempNpurine oligonucleotide template

<400> SEQUENCE: 79
cctagttctt cctcttcccg atgctggacc agataagcac ttagccacgt agtgctgttc        60
ggtaatcgat ctggcaaacg ctaataagg                                          89

<210> SEQ ID NO 80
<211> LENGTH: 31
<212> TYPE: DNA
<213> ORGANISM: Artificial Sequence
<220> FEATURE:
<223> OTHER INFORMATION: RTtempHNA oligonucleotide template

<400> SEQUENCE: 80
gttcggtaat cgatctggca aacgctaata a                                       31

<210> SEQ ID NO 81
<211> LENGTH: 39
<212> TYPE: DNA
<213> ORGANISM: Artificial Sequence
<220> FEATURE:
<223> OTHER INFORMATION: Oligonucleotide template RTtempNLNA4

<400> SEQUENCE: 81
gtagtgctgt tcggtaatcg atctggcaaa cgctaataa                               39

<210> SEQ ID NO 82
<211> LENGTH: 55
<212> TYPE: DNA
```

-continued

<213> ORGANISM: Artificial Sequence
<220> FEATURE:
<223> OTHER INFORMATION: Oligonucleotide template RTtempNCeNA

<400> SEQUENCE: 82
agcactagcc acgtagtgct gctcggtaat cgatctggca aacgctaata agggg        55

<210> SEQ ID NO 83
<211> LENGTH: 17
<212> TYPE: DNA
<213> ORGANISM: Artificial Sequence
<220> FEATURE:
<223> OTHER INFORMATION: Digoxigenin-labled Nmin3 oligonucleotide

<400> SEQUENCE: 83
ttcggtaatc gatctgg                                                  17

<210> SEQ ID NO 84
<211> LENGTH: 15
<212> TYPE: DNA
<213> ORGANISM: Artificial Sequence
<220> FEATURE:
<223> OTHER INFORMATION: Digoxigenin-labeled N4 oligonucleotide

<400> SEQUENCE: 84
gctgttcggt aatcg                                                    15

<210> SEQ ID NO 85
<211> LENGTH: 13
<212> TYPE: DNA
<213> ORGANISM: Artificial Sequence
<220> FEATURE:
<223> OTHER INFORMATION: Digoxigenin-labeled N10 oligonucleotide

<400> SEQUENCE: 85
gtagtgctgt tcg                                                      13

<210> SEQ ID NO 86
<211> LENGTH: 15
<212> TYPE: DNA
<213> ORGANISM: Artificial Sequence
<220> FEATURE:
<223> OTHER INFORMATION: Digoxigenin-labeled oligonucleotide N25

<400> SEQUENCE: 86
gataagcact tagcc                                                    15

<210> SEQ ID NO 87
<211> LENGTH: 85
<212> TYPE: DNA
<213> ORGANISM: Artificial Sequence
<220> FEATURE:
<223> OTHER INFORMATION: Template YtRtemp

<400> SEQUENCE: 87
ggtggggttc ccgagcggcc aaagggagca gactctaaat ctgccgtcat cgacttcgaa   60
ggttcgaatc cttcccccac cacca                                         85

<210> SEQ ID NO 88
<211> LENGTH: 76
<212> TYPE: DNA
<213> ORGANISM: Artificial Sequence
<220> FEATURE:
<223> OTHER INFORMATION: Template AtRtemp

<400> SEQUENCE: 88

```
gggctatag ctcagctggg agagcgcctg ctttgcacgc aggaggtctg cggttcgatc    60
ccgcatagct ccacca                                                    76

<210> SEQ ID NO 89
<211> LENGTH: 76
<212> TYPE: DNA
<213> ORGANISM: Artificial Sequence
<220> FEATURE:
<223> OTHER INFORMATION: Template FtRtemp

<400> SEQUENCE: 89
gcggatttag ctcagttggg agagcgccag actgaagatc tggaggtcct gtgttcgatc    60
cacagaattc gcacca                                                    76

<210> SEQ ID NO 90
<211> LENGTH: 103
<212> TYPE: DNA
<213> ORGANISM: Artificial Sequence
<220> FEATURE:
<223> OTHER INFORMATION: Template YtR4temp

<400> SEQUENCE: 90
tggcaaacgc taataagggg tggggttccc gagcggccaa agggagcaga ctctaaatct    60
gccgtcatcg acttcgaagg ttcgaatcct tcccccacct cca                     103

<210> SEQ ID NO 91
<211> LENGTH: 135
<212> TYPE: DNA
<213> ORGANISM: Artificial Sequence
<220> FEATURE:
<223> OTHER INFORMATION: Template YtRtemp5

<400> SEQUENCE: 91
caaagtagtg ctgttcgtgg ggttcccgag cggccaaagg gagcagactc taaatctgcc    60
gtcatcgact tcgaaggttc gaatccttcc cccaccacca gatcgattac cgaaggtggc   120
aaacgctaat gaggg                                                   135

<210> SEQ ID NO 92
<211> LENGTH: 142
<212> TYPE: DNA
<213> ORGANISM: Artificial Sequence
<220> FEATURE:
<223> OTHER INFORMATION: Template YtRtemp7

<400> SEQUENCE: 92
caaagtagtg ctgttcgtgg ggttcccgag cggccaaagg gagcagactc taaatctgcc    60
gtcatcgact tcgaaggttc gaatccttcc cccaccacca gatcgattac cgaaggtggc   120
aaacgctaat gagggaaaaa aa                                           142

<210> SEQ ID NO 93
<211> LENGTH: 85
<212> TYPE: DNA
<213> ORGANISM: Artificial Sequence
<220> FEATURE:
<223> OTHER INFORMATION: Template TempNmis

<400> SEQUENCE: 93
ctcgcgatgc tggaccagat aagcacttag ccacgtagtg ctgttcggta atcgatctgg    60
caaacgctaa taagtggaaa aaaaa                                         85
```

```
<210> SEQ ID NO 94
<211> LENGTH: 95
<212> TYPE: DNA
<213> ORGANISM: Artificial Sequence
<220> FEATURE:
<223> OTHER INFORMATION: Template TempNpuremis(T1)

<400> SEQUENCE: 94
cctaattctt cctcttcccg atgctggacc agataagcac ttagccacgt agtgctgttc     60
ggtaatcgat ctggcaaacg ctaatatgga aaaaa                                95

<210> SEQ ID NO 95
<211> LENGTH: 57
<212> TYPE: DNA
<213> ORGANISM: Artificial Sequence
<220> FEATURE:
<223> OTHER INFORMATION: Nproduct

<400> SEQUENCE: 95
gatcgattac cgaacagcac tacgtggcta agtgcttatc tggtccagca tcgtgag        57

<210> SEQ ID NO 96
<211> LENGTH: 33
<212> TYPE: DNA
<213> ORGANISM: Artificial Sequence
<220> FEATURE:
<223> OTHER INFORMATION: Cy3-labeled AtRNA2HNA

<400> SEQUENCE: 96
caggaaacag ctatgacaaa tggtgggagct atg                                 33

<210> SEQ ID NO 97
<211> LENGTH: 31
<212> TYPE: DNA
<213> ORGANISM: Artificial Sequence
<220> FEATURE:
<223> OTHER INFORMATION: Cy3-labeled YtRNA2HNA

<400> SEQUENCE: 97
caggaaacag ctatgacaaa tggtggtggg g                                    31

<210> SEQ ID NO 98
<211> LENGTH: 37
<212> TYPE: DNA
<213> ORGANISM: Artificial Sequence
<220> FEATURE:
<223> OTHER INFORMATION: Cy3-labeled FtRNA2HNA

<400> SEQUENCE: 98
caggaaacag ctatgacaaa tggtgcgaat tctgtgg                              37

<210> SEQ ID NO 99
<211> LENGTH: 36
<212> TYPE: DNA
<213> ORGANISM: Artificial Sequence
<220> FEATURE:
<223> OTHER INFORMATION: FITC-labeled NAPfd

<400> SEQUENCE: 99
cagtatcgac aaaggacccc ttattagcgt ttgcca                               36

<210> SEQ ID NO 100
<211> LENGTH: 36
<212> TYPE: DNA
<213> ORGANISM: Artificial Sequence
```

```
<220> FEATURE:
<223> OTHER INFORMATION: Biotin-FITC-labeled bNAPfd

<400> SEQUENCE: 100
cagtatcgac aaaggacccc ttattagcgt ttgcca                              36

<210> SEQ ID NO 101
<211> LENGTH: 16
<212> TYPE: DNA
<213> ORGANISM: Artificial Sequence
<220> FEATURE:
<223> OTHER INFORMATION: Unlabeled NAP

<400> SEQUENCE: 101
cagtatcgac aaagga                                                    16

<210> SEQ ID NO 102
<211> LENGTH: 16
<212> TYPE: DNA
<213> ORGANISM: Artificial Sequence
<220> FEATURE:
<223> OTHER INFORMATION: Biotin-labeled NAPcapture

<400> SEQUENCE: 102
cagtatcgac aaagga                                                    16

<210> SEQ ID NO 103
<211> LENGTH: 21
<212> TYPE: DNA
<213> ORGANISM: Artificial Sequence
<220> FEATURE:
<223> OTHER INFORMATION: Primer Tag4

<400> SEQUENCE: 103
gtcggatccg tttaagctag g                                              21

<210> SEQ ID NO 104
<211> LENGTH: 41
<212> TYPE: DNA
<213> ORGANISM: Artificial Sequence
<220> FEATURE:
<223> OTHER INFORMATION: FITC-labeled primer Tag4fdOme

<400> SEQUENCE: 104
gtcggatccg tttaagctag gccccttatt agcgtttgcc a                        41

<210> SEQ ID NO 105
<211> LENGTH: 20
<212> TYPE: RNA
<213> ORGANISM: Artificial Sequence
<220> FEATURE:
<223> OTHER INFORMATION: FITC-labeled fitcRNAfd

<400> SEQUENCE: 105
ccccuuauua gcguuugcca                                                20

<210> SEQ ID NO 106
<211> LENGTH: 19
<212> TYPE: DNA
<213> ORGANISM: Artificial Sequence
<220> FEATURE:
<223> OTHER INFORMATION: Cy3-labeled Cy3fd

<400> SEQUENCE: 106 cccccttatta gcgtttgcc                                                19
```

<210> SEQ ID NO 107
<211> LENGTH: 42
<212> TYPE: DNA
<213> ORGANISM: Artificial Sequence
<220> FEATURE:
<223> OTHER INFORMATION: Cy5-labeled LMB3+tag3a

<400> SEQUENCE: 107
caggaaacag ctatgacaaa caaggtagtg ctgttcgtgg gg             42

<210> SEQ ID NO 108
<211> LENGTH: 37
<212> TYPE: DNA
<213> ORGANISM: Artificial Sequence
<220> FEATURE:
<223> OTHER INFORMATION: Cy5-labeled LMB3+N40

<400> SEQUENCE: 108
caggaaacag ctatgacaaa ctaacgatgc tggacca                   37

<210> SEQ ID NO 109
<211> LENGTH: 20
<212> TYPE: DNA
<213> ORGANISM: Artificial Sequence
<220> FEATURE:
<223> OTHER INFORMATION: LMB3+

<400> SEQUENCE: 109
caggaaacag ctatgacaaa                                      20

<210> SEQ ID NO 110
<211> LENGTH: 20
<212> TYPE: DNA
<213> ORGANISM: Artificial Sequence
<220> FEATURE:
<223> OTHER INFORMATION: Cy5-labeled pyrimidine-rich DNA for annealing
      with purine-rich ANA

<400> SEQUENCE: 110
ccctagttct tcctcttccc                                      20

<210> SEQ ID NO 111
<211> LENGTH: 40
<212> TYPE: DNA
<213> ORGANISM: Artificial Sequence
<220> FEATURE:
<223> OTHER INFORMATION: LMB3+test7 (P subRT)

<400> SEQUENCE: 111
caggaaacag ctatgacaaa ccctagttct tcctcttccc                40

<210> SEQ ID NO 112
<211> LENGTH: 40
<212> TYPE: DNA
<213> ORGANISM: Artificial Sequence
<220> FEATURE:
<223> OTHER INFORMATION: 5'-Cy5-labeled bLMB3+test7

<400> SEQUENCE: 112
caggaaacag ctatgacaaa ccctagttct tcctcttccc                40

<210> SEQ ID NO 113
<211> LENGTH: 19
<212> TYPE: DNA
<213> ORGANISM: Artificial Sequence
<220> FEATURE:

```
<223> OTHER INFORMATION: Cy5-labeled Revfd

<400> SEQUENCE: 113
tggcaaacgc taataaggg                                                    19

<210> SEQ ID NO 114
<211> LENGTH: 41
<212> TYPE: DNA
<213> ORGANISM: Artificial Sequence
<220> FEATURE:
<223> OTHER INFORMATION: Cy5-labeled-Cytag4fdOme

<400> SEQUENCE: 114
gtcggatccg tttaagctag gccccttatt agcgtttgcc a                           41

<210> SEQ ID NO 115
<211> LENGTH: 47
<212> TYPE: DNA
<213> ORGANISM: Artificial Sequence
<220> FEATURE:
<223> OTHER INFORMATION: TempNshort2(T2)

<400> SEQUENCE: 115
accagtagtg ctgttcggta atcgatctgg caaacgctaa taagggg                     47

<210> SEQ ID NO 116
<211> LENGTH: 39
<212> TYPE: DNA
<213> ORGANISM: Artificial Sequence
<220> FEATURE:
<223> OTHER INFORMATION: Primer RT405 backward

<400> SEQUENCE: 116
gagtcaggtc tccgctccct gtatccttcg ataataatc                              39

<210> SEQ ID NO 117
<211> LENGTH: 34
<212> TYPE: DNA
<213> ORGANISM: Artificial Sequence
<220> FEATURE:
<223> OTHER INFORMATION: Primer RT405 forward
<220> FEATURE:
<221> NAME/KEY: misc_feature
<222> LOCATION: (21)..(21)
<223> OTHER INFORMATION: n is a, c, g or t

<400> SEQUENCE: 117
gagtcaggtc tcggagcggs ngtccagata cacg                                   34

<210> SEQ ID NO 118
<211> LENGTH: 39
<212> TYPE: DNA
<213> ORGANISM: Artificial Sequence
<220> FEATURE:
<223> OTHER INFORMATION: Primer RT408 backward
<220> FEATURE:
<221> NAME/KEY: misc_feature
<222> LOCATION: (19)..(19)
<223> OTHER INFORMATION: n is a, c, g or t

<400> SEQUENCE: 118
gagtcaggtc tccgctccnw ctatccttcg ataataatc                              39

<210> SEQ ID NO 119
<211> LENGTH: 34
<212> TYPE: DNA
<213> ORGANISM: Artificial Sequence
```

```
<220> FEATURE:
<223> OTHER INFORMATION: Primer RT408 forward

<400> SEQUENCE: 119
gagtcaggtc tcggagcgga agtccagata cacg                                34

<210> SEQ ID NO 120
<211> LENGTH: 40
<212> TYPE: DNA
<213> ORGANISM: Artificial Sequence
<220> FEATURE:
<223> OTHER INFORMATION: Primer RT520 backward
<220> FEATURE:
<221> NAME/KEY: misc_feature
<222> LOCATION: (19)..(19)
<223> OTHER INFORMATION: n is a, c, g or t

<400> SEQUENCE: 120
gagtcaggtc tcaggcagnw catcgagact acgataaggg                          40

<210> SEQ ID NO 121
<211> LENGTH: 40
<212> TYPE: DNA
<213> ORGANISM: Artificial Sequence
<220> FEATURE:
<223> OTHER INFORMATION: Primer RT521 backward
<220> FEATURE:
<221> NAME/KEY: misc_feature
<222> LOCATION: (22)..(22)
<223> OTHER INFORMATION: n ia a, c, g or t

<400> SEQUENCE: 121
gagtcaggtc tcaggcagta cnwcgagact acgataaggg                          40

<210> SEQ ID NO 122
<211> LENGTH: 40
<212> TYPE: DNA
<213> ORGANISM: Artificial Sequence
<220> FEATURE:
<223> OTHER INFORMATION: Primer RT521 backward NNS
<220> FEATURE:
<221> NAME/KEY: misc_feature
<222> LOCATION: (22)..(22)
<223> OTHER INFORMATION: n is a, c, g or t
<220> FEATURE:
<221> NAME/KEY: misc_feature
<222> LOCATION: (23)..(23)
<223> OTHER INFORMATION: n is a, c, g or t

<400> SEQUENCE: 122
gagtcaggtc tcaggcagta cnnsgagact acgataaggg                          40

<210> SEQ ID NO 123
<211> LENGTH: 37
<212> TYPE: DNA
<213> ORGANISM: Artificial Sequence
<220> FEATURE:
<223> OTHER INFORMATION: Primer RT520 forward

<400> SEQUENCE: 123
gagtcaggtc tcctgcctgc cccaagcggt aacgctc                             37

<210> SEQ ID NO 124
<211> LENGTH: 39
<212> TYPE: DNA
<213> ORGANISM: Artificial Sequence
<220> FEATURE:
<223> OTHER INFORMATION: Primer RT575 backward
<220> FEATURE:
```

<221> NAME/KEY: misc_feature
<222> LOCATION: (19)..(19)
<223> OTHER INFORMATION: n is a, c, g or t

<400> SEQUENCE: 124
gagtcaggtc tcggcctgnw cgaactcgaa tacgagggc         39

<210> SEQ ID NO 125
<211> LENGTH: 40
<212> TYPE: DNA
<213> ORGANISM: Artificial Sequence
<220> FEATURE:
<223> OTHER INFORMATION: Primer RT575 forward

<400> SEQUENCE: 125
gagtcaggtc tccaggccgg gcagtttggc gttgatgtag         40

<210> SEQ ID NO 126
<211> LENGTH: 4
<212> TYPE: PRT
<213> ORGANISM: Artificial Sequence
<220> FEATURE:
<223> OTHER INFORMATION: PolG12 mutations E609K and I610M

<400> SEQUENCE: 126

Leu Lys Met Val
1

<210> SEQ ID NO 127
<211> LENGTH: 30
<212> TYPE: PRT
<213> ORGANISM: Artificial Sequence
<220> FEATURE:
<223> OTHER INFORMATION: Mutated Patch 10 region of Pol6G12

<400> SEQUENCE: 127

Tyr Glu Val Pro Pro Glu Gln Leu Val Ile Tyr Gln Pro Ile Thr Lys
1               5                   10                  15

Gln Leu His Asp Tyr Arg Ala Arg Gly Pro His Val Ser Val
            20                  25                  30

<210> SEQ ID NO 128
<211> LENGTH: 8
<212> TYPE: PRT
<213> ORGANISM: Artificial Sequence
<220> FEATURE:
<223> OTHER INFORMATION: Pol6G12 mutation L704P

<400> SEQUENCE: 128

Val Pro Lys Gly Ser Gly Arg Ile
1               5

<210> SEQ ID NO 129
<211> LENGTH: 30
<212> TYPE: PRT
<213> ORGANISM: Artificial Sequence
<220> FEATURE:
<223> OTHER INFORMATION: Mutations in patch 10 region of PolC7

<400> SEQUENCE: 129

Tyr Gln Val Pro Pro Gln Gln Leu Ala Ile Tyr Gln Pro Ile Thr Arg
1               5                   10                  15

Ala Leu Gln Asp Tyr Lys Ala Lys Gly Pro His Val Ala Val
            20                  25                  30

```
<210> SEQ ID NO 130
<211> LENGTH: 8
<212> TYPE: PRT
<213> ORGANISM: Artificial Sequence
<220> FEATURE:
<223> OTHER INFORMATION: Mutation R709K in PolC7

<400> SEQUENCE: 130

Val Leu Lys Gly Ser Gly Lys Ile
1               5

<210> SEQ ID NO 131
<211> LENGTH: 30
<212> TYPE: PRT
<213> ORGANISM: Artificial Sequence
<220> FEATURE:
<223> OTHER INFORMATION: PolD4k mutations in patch 10 region

<400> SEQUENCE: 131

Tyr Glu Val Pro Thr Gln His Leu Val Ile His Lys Gln Ile Thr Arg
1               5                  10                  15

Ala Leu Asn Asp Tyr Lys Ala Ile Gly Pro His Val Ala Val
            20                  25                  30

<210> SEQ ID NO 132
<211> LENGTH: 9
<212> TYPE: PRT
<213> ORGANISM: Artificial Sequence
<220> FEATURE:
<223> OTHER INFORMATION: Mutation in D4 and D4YK polymerases with L403P

<400> SEQUENCE: 132

Tyr Pro Asp Phe Arg Ser Leu Tyr Pro
1               5

<210> SEQ ID NO 133
<211> LENGTH: 24
<212> TYPE: PRT
<213> ORGANISM: Artificial Sequence
<220> FEATURE:
<223> OTHER INFORMATION: Mutations in patch 10 region of D4, D4A, D4G
      and D4S polymerases

<400> SEQUENCE: 133

Val Pro Thr Gln His Leu Val Ile His Gln Gln Ile Thr Arg Ala Leu
1               5                  10                  15

Asn Asp Tyr Lys Ala Asn Gly Pro
            20

<210> SEQ ID NO 134
<211> LENGTH: 9
<212> TYPE: PRT
<213> ORGANISM: Artificial Sequence
<220> FEATURE:
<223> OTHER INFORMATION: D4A mutant

<400> SEQUENCE: 134

Tyr Pro Asp Phe Arg Ser Leu Ala Pro
1               5

<210> SEQ ID NO 135
<211> LENGTH: 9
<212> TYPE: PRT
<213> ORGANISM: Artificial Sequence
<220> FEATURE:
<223> OTHER INFORMATION: Mutations in D4G
```

```
<400> SEQUENCE: 135

Thr Pro Asp Phe Arg Ser Leu Gly Pro
1               5

<210> SEQ ID NO 136
<211> LENGTH: 9
<212> TYPE: PRT
<213> ORGANISM: Artificial Sequence
<220> FEATURE:
<223> OTHER INFORMATION: D4S mutations

<400> SEQUENCE: 136

Tyr Pro Asp Phe Arg Ser Leu Ser Pro
1               5

<210> SEQ ID NO 137
<211> LENGTH: 24
<212> TYPE: PRT
<213> ORGANISM: Artificial Sequence
<220> FEATURE:
<223> OTHER INFORMATION: Mutations in patch 10 region of D4YK

<400> SEQUENCE: 137

Val Pro Thr Gln His Leu Val Ile His Lys Gln Ile Thr Arg Ala Leu
1               5                   10                  15

Asn Asp Tyr Lys Ala Asn Gly Pro
            20

<210> SEQ ID NO 138
<211> LENGTH: 24
<212> TYPE: PRT
<213> ORGANISM: Artificial Sequence
<220> FEATURE:
<223> OTHER INFORMATION: Mutations in patch 10 region of TYK and TSK
      polymerases

<400> SEQUENCE: 138

Val Pro Pro Glu Lys Leu Val Ile Tyr Lys Gln Ile Thr Arg Asp Leu
1               5                   10                  15

Lys Asp Tyr Lys Ala Thr Gly Pro
            20

<210> SEQ ID NO 139
<211> LENGTH: 9
<212> TYPE: PRT
<213> ORGANISM: Artificial Sequence
<220> FEATURE:
<223> OTHER INFORMATION: Mutation in TSK polymerase

<400> SEQUENCE: 139

Tyr Leu Asp Phe Arg Ser Leu Ser Pro
1               5

<210> SEQ ID NO 140
<211> LENGTH: 9
<212> TYPE: PRT
<213> ORGANISM: Artificial Sequence
<220> FEATURE:
<223> OTHER INFORMATION: L403P mutationTgo P403 and D4 P403 polymerases

<400> SEQUENCE: 140

Asn Ile Val Tyr Pro Asp Phe Arg Ser
1               5

<210> SEQ ID NO 141
```

```
<211> LENGTH: 24
<212> TYPE: PRT
<213> ORGANISM: Artificial Sequence
<220> FEATURE:
<223> OTHER INFORMATION: Mutations in patch 10 region of D4 L403, D4
      P403 and D4K10 polymerases

<400> SEQUENCE: 141

Val Pro Thr Gln His Leu Val Ile His Gln Gln Ile Thr Arg Ala Leu
1               5                   10                  15

Asn Asp Tyr Lys Ala Ile Gly Pro
            20

<210> SEQ ID NO 142
<211> LENGTH: 9
<212> TYPE: PRT
<213> ORGANISM: Artificial Sequence
<220> FEATURE:
<223> OTHER INFORMATION: Mutations in D4YK

<400> SEQUENCE: 142

Asn Ile Val Thr Pro Asp Phe Arg Ser
1               5

<210> SEQ ID NO 143
<211> LENGTH: 24
<212> TYPE: PRT
<213> ORGANISM: Artificial Sequence
<220> FEATURE:
<223> OTHER INFORMATION: Mutations in patch 10 region of D4YK polymerase

<400> SEQUENCE: 143

Val Pro Thr Gln His Leu Val Ile His Lys Gln Ile Thr Arg Ala Leu
1               5                   10                  15

Asn Asp Tyr Lys Ala Ile Gly Pro
            20

<210> SEQ ID NO 144
<211> LENGTH: 5
<212> TYPE: PRT
<213> ORGANISM: Artificial Sequence
<220> FEATURE:
<223> OTHER INFORMATION: Mutation in D4K10

<400> SEQUENCE: 144

Gln Arg Ala Ile Lys
1               5

<210> SEQ ID NO 145
<211> LENGTH: 47
<212> TYPE: DNA
<213> ORGANISM: Artificial Sequence
<220> FEATURE:
<223> OTHER INFORMATION: TestBlind1 pyrimidine-rich ANA
<220> FEATURE:
<221> NAME/KEY: misc_feature
<222> LOCATION: (1)..(47)
<223> OTHER INFORMATION: Arabino nucleic acid polymer (ANA)

<400> SEQUENCE: 145
ttagagtccc tttctctttc cgtcttgtta cccttttcac ctcctgg           47

<210> SEQ ID NO 146
<211> LENGTH: 14
<212> TYPE: DNA
<213> ORGANISM: Artificial Sequence
<220> FEATURE:
```

```
<223> OTHER INFORMATION: Purine-rich DNA for annealing with pyrimidine-
      rich ANA

<400> SEQUENCE: 146
ccaggaggtg aaaa                                                          14

<210> SEQ ID NO 147
<211> LENGTH: 17
<212> TYPE: DNA
<213> ORGANISM: Artificial Sequence
<220> FEATURE:
<223> OTHER INFORMATION: Purine-rich DNA for annealing with pyrimidine-
      rich ANA

<400> SEQUENCE: 147
gggtaacaag acggaaa                                                       17

<210> SEQ ID NO 148
<211> LENGTH: 18
<212> TYPE: DNA
<213> ORGANISM: Artificial Sequence
<220> FEATURE:
<223> OTHER INFORMATION: Purine-rich DNA for annealing with pyrimidine-
      rich ANA

<400> SEQUENCE: 148
aagagaaagg gactctaa                                                      18

<210> SEQ ID NO 149
<211> LENGTH: 47
<212> TYPE: DNA
<213> ORGANISM: Artificial Sequence
<220> FEATURE:
<223> OTHER INFORMATION: Pyrimidine-rich ANA
<220> FEATURE:
<221> NAME/KEY: misc_feature
<222> LOCATION: (1)..(47)
<223> OTHER INFORMATION: Arabino nuclein acid polymer (ANA)

<400> SEQUENCE: 149
gaagggaaga gagggaagag gaagaactag ggaggaggaa acggatc                      47

<210> SEQ ID NO 150
<211> LENGTH: 16
<212> TYPE: DNA
<213> ORGANISM: Artificial Sequence
<220> FEATURE:
<223> OTHER INFORMATION: Pyrimidine-rich DNA for annealing with purine-
      rich ANA

<400> SEQUENCE: 150
tccctctctt ccctcc                                                        16

<210> SEQ ID NO 151
<211> LENGTH: 18
<212> TYPE: DNA
<213> ORGANISM: Artificial Sequence
<220> FEATURE:
<223> OTHER INFORMATION: Pyrimidine-rich DNA for annealing with purine-
      rich ANA

<400> SEQUENCE: 151
gatccgtttc ctcctccc                                                      18
```

US 9,914,914 B2

POLYMERASE CAPABLE OF PRODUCING NON-DNA NUCLEOTIDE POLYMERS

BACKGROUND TO THE INVENTION

Genetic information storage and processing rely on just two polymers, DNA and RNA. Whether their role reflects evolutionary history or fundamental functional constraints is unknown. The nucleic acids DNA and RNA provide the molecular basis for all life through their unique ability to store and propagate information. To better understand these singular properties and discover relevant parameters for the chemical basis of molecular information encoding, nucleic acid structure has been dissected by systematic variation of nucleobase, sugar and backbone moieties.

Prior art studies have revealed the profound influence of backbone, sugar and base chemistry on nucleic acid properties and function. Crucially, only a small subset of chemistries allows information transfer through base pairing with DNA or RNA, a prerequisite for crosstalk with extant biology. However, base pairing alone cannot conclusively determine the capacity of a given chemistry to serve as a genetic system, as hybridization need not preserve information content. A more thorough examination of candidate genetic polymers' potential for information storage, propagation and evolution requires a system for replication which would allow a systematic exploration of the informational, evolutionary and functional potential of synthetic genetic polymers and open up applications ranging from biotechnology to material science.

In principle, informational polymers can be synthesized and replicated chemically with advances in the non-enzymatic polymerization of mononucleotides and short oligomers enabling model selection experiments. Nevertheless, chemical polymerization remains relatively inefficient, which is a problem in the art.

On the other hand, enzymatic polymerization has been hindered by the stringent substrate selectivity of polymerases. Despite progress in understanding the determinants of polymerase substrate specificity and in engineering polymerases with expanded substrate spectra, most unnatural nucleotide analogues are poor polymerase substrates at full substitution, both as nucleotides for polymer synthesis and as templates for reverse transcription. Notable exceptions are 2'OMe-DNA and TNA. 2'OMe-DNA is present in eukaryotic rRNAs, is well-tolerated by natural reverse transcriptases (RTs) and has been shown to support heredity and evolution at near full substitution. TNA allowed polymer synthesis and evolution in a three letter system but only limited reverse transcription. Thus, polymerase substrate specificity remains a significant drawback to progress in this area.

WO2011/135280 describes certain polymerases. This document describes a polymerase which is capable of making an RNA polymer from a DNA polymer template. This polymerase is termed TGK. This polymerase comprises mutations Y409G and E664K. The TGK polymerase is described as the first primer dependent thermostable RNA polymerase engineered from a DNA scaffold. The TGK polymerase can synthesise a tRNA gene in less than a minute and can synthesise a 1.7 kb luciferase gene in only one hour. Thus, the TGK polymerase is described as a very efficient RNA polymerase.

WO2011/135280 describes polymerase D4, which is a processive, high fidelity RNA polymerase. The D4 polymerase is based on the TgoT polymerase but with a number of mutations, in particular eight mutations in the region of the thumb domain (motif 10A). The amino acid and nucleotide sequences of the TgoT-derived polymerase D4 is shown in SEQ ID NO:3 and SEQ ID NO:4, respectively. In addition, the Y409N mutation is added to the D4 polymerase to make the polymerase D4N3. This D4N3 polymerase exhibits a striking ability to processively synthesize RNAs up to 87 nucleotides in length.

WO2011/135280 discusses mutation of the E664 residue of TgoT. It is mentioned that E664 may be mutated to E664K, or E664Q, or a small number of other resides as shown in the table at the top of page 51 of WO2011/135280. It was concluded in WO2011/135280 that the E664Q mutation is both necessary and sufficient for processive RNA synthesis (page 80 lines 21 to 22 of WO2011/135280).

The discovery that ANA and FANA in hybrid duplexes with RNA activate RNaseH led to interest in their use for siRNA and FANA in particularly effective at gene knockdown. Furthermore, FANA is stable to chemical (acid or base) hydrolysis, serum resistant, can improve the binding of DNA aptamers, stabilizes G-quadruplexes, hybridizes with RNA more tightly than RNA:RNA and can silence genes more effectively than native (RNA) siRNA. As a result FANA is of interest as a backbone for aptamer generation.

No polymerases are known in the art which are capable of producing arabino nucleotide polymers, such as ANA polymers or FANA polymers.

The present invention seeks to overcome problems associated with the prior art.

SUMMARY OF THE INVENTION

In the prior art, nucleotide polymerases have been described which are able to polymerise orthogonal nucleotides. Examples of these include polymerases capable of producing cyclohexenyl (CeNA) nucleotide polymers, anhydrohexitol (HNA) nucleotide polymers or other such orthogonal nucleic acids. However, no polymerase for arabino nucleotide polymerisation has been described. To date, arabino nucleotide polymers have only been synthesised chemically. Therefore, production of an arabino nucleotide polymer of biologically useful length has been very expensive and technically demanding.

The present inventors studied a range of polymerases, in particular the prior art D4 polymerase which is capable of producing RNA polymers. The inventors produced and studied further mutations of the prior art D4 polymerase. In the course of their studies they discovered the importance of the E664 residue, which is E664Q in the D4 polymerase. More importantly, the inventors found that if the E664 residue was mutated to E664K, that the polymerase acquired a range of new functions which were unknown in the art. These functions include the ability to polymerise arabino nucleic acids. In particular, the ability to polymerise ANA and/or FANA nucleotides is possessed by this new polymerase.

The present invention is based upon these surprising findings.

The inventors investigated the prior art D4 polymerase. This contains at least 13 separate mutations compared to the wild type polymerase TgoT from which D4 polymerase was derived. These mutations had all been aimed at and optimised for, the production of RNA polymers. Therefore, it was a great surprise to the inventors when they managed to engineer new activities into this polymerase by making the important E664K mutation. Study of this enzyme led to the unexpected finding that it had polymerase activity for arabino nucleotides, most suitably ANA and/or FANA nucleotides. Moreover, this polymerase is even able to produce a FANA polymer from FANA template (i.e. direct reproduction of a nucleic acid polymer made up of orthogonal fluoroarabino nucleotides). It is these unexpected properties and surprising activities upon which the invention is based.

Thus in one aspect the invention provides a nucleic acid polymerase capable of producing a non-DNA nucleotide polymer from a DNA nucleotide polymer template, said polymerase comprising amino acid sequence having at least 36% identity to the amino acid sequence of SEQ ID NO:1, wherein said amino acid sequence is mutated relative to the amino acid sequence of SEQ ID NO:1;
wherein said amino acid sequence comprises the mutations P657T, E658Q, K659H, Y663H, D669A, K671N, and T676I;
wherein said amino acid sequence is further mutated relative to the amino acid sequence of SEQ ID NO:1 at residue E664 and wherein said amino acid sequence comprises the mutation E664K.

The introduction of the E664K mutation transforms the activity of the polymerase. The polymerase having this mutation has new activities which do not exist in the prior art. These activities and the technical benefits of these activities are demonstrated herein.

In another aspect, the invention relates to a nucleic acid polymerase as described above wherein said polymerase further comprises the mutations D141A and E143A.

In another aspect, the invention relates to a nucleic acid polymerase as described above wherein said polymerase further comprises the mutation L403P.

In another aspect, the invention relates to a nucleic acid polymerase as described above wherein said polymerase further comprises the mutation V93Q.

In another aspect, the invention relates to a nucleic acid polymerase as described above wherein said polymerase further comprises the mutation A485L.

In another aspect, the invention relates to a nucleic acid polymerase as described above wherein said polymerase further comprises the mutations V93Q, D141A and E143A.

In another aspect, the invention relates to a nucleic acid polymerase as described above wherein said polymerase further comprises the mutations L403P, V93Q, A485L, D141A and E143A. This is an especially preferred combination of mutations. This particular combination of mutations is referred to as D4K polymerase ("D4K"). D4K polymerase is sometimes referred to as D4YK polymerase ("D4YK"). The nucleotide coding sequence for D4YK is shown in SEQ ID NO:6.

For the avoidance of doubt, the preferred D4K polymerase comprises (more suitably consists of) mutations relative to the Tgo wild type of SEQ ID NO:1 of V93Q, D141A, E143A, L403P, A485L, P657T, E658Q, K659H, Y663H, E664K, D669A, K671N, and I676T.

A polymerase having the sequence of SEQ ID NO:1 (wild type TgoT) wherein said amino acid sequence comprises the mutations P657T, E658Q, K659H, Y663H, D669A, K671N, T676I and E664K only relative to SEQ ID NO:1 is referred to as D4K10 polymerase.

Suitably the nucleic acid polymerase as described above is capable of producing an arabino nucleotide polymer, for example an ANA or FANA nucleotide polymer, from a DNA nucleotide polymer template. Suitably said polymerase comprises amino acid sequence corresponding to amino acids 651 to 679 (patch 10A) of SEQ ID NO:5.

More suitably said polymerase is capable of producing an ANA or FANA nucleotide polymer from a DNA nucleotide polymer template and said polymerase comprises amino acid sequence corresponding to SEQ ID NO:5.

Most suitably said polymerase is capable of producing an ANA or FANA nucleotide polymer from a DNA nucleotide polymer template and said polymerase consists of amino acid sequence corresponding to SEQ ID NO:5.

In another aspect, the invention relates to a nucleic acid polymerase as described above wherein said amino acid sequence is further mutated relative to the amino acid sequence of SEQ ID NO:1 at residue I521. Suitably said polymerase comprises the mutation I521L. This has the advantage of increased activity such as increased ANA polymerase activity.

Especially preferred is a polymerase which comprises (more suitably consists of) mutations relative to the Tgo wild type of SEQ ID NO:1 of V93Q, D141A, E143A, L403P, A485L, P657T, E658Q, K659H, Y663H, E664K, D669A, K671N, and I676T (ie. corresponding to the amino acid sequence of D4K), with the further mutation I521L. In a preferred embodiment this polymerase has the sequence of SEQ ID NO:7, and is referred to as D4K521.

Suitably said non-DNA nucleotide polymer is an arabino nucleotide polymer.

Suitably said non-DNA nucleotide polymer is an ANA or FANA nucleotide polymer.

Suitably said non-DNA nucleotide polymer is an ANA nucleotide polymer.

Suitably said non-DNA nucleotide polymer is a FANA nucleotide polymer.

In another aspect, the invention relates to a method for making an arabino nucleotide polymer, said method comprising contacting a DNA template with a nucleic acid polymerase as described above and incubating to allow polymerisation.

In another aspect, the invention relates to a method for making an ANA or FANA nucleotide polymer, said method comprising contacting a DNA template with a nucleic acid polymerase as described above and incubating to allow polymerisation.

Suitably synthesis (polymerisation) may be followed by suitable step(s) to either dissociate said polymer from the DNA template or remove the DNA template to free the polymer.

In another aspect, the invention relates to a method for making a FANA nucleotide polymer, said method comprising contacting a FANA template with a nucleic acid polymerase as described above and incubating to allow polymerisation. Suitably synthesis (polymerisation) may be followed by suitable step(s) to either dissociate said polymer from the FANA template or remove the FANA template to free the polymer.

In another aspect, the invention relates to a non-DNA nucleotide polymer which is an arabino nucleotide polymer which comprises at least 50 nucleotides. Suitably said arabino nucleotide polymer comprises ANA or FANA.

In another aspect, the invention relates to an arabino nucleotide polymer obtained by the method as described above.

In another aspect, the invention relates to use of a polymerase as described above in the manufacture of an arabino nucleotide polymer. Suitably said arabino nucleotide polymer is an ANA or FANA nucleotide polymer.

In another aspect, the invention relates to a nucleic acid encoding a polymerase as described above.

In another aspect, the invention relates to a host cell comprising a nucleic acid as described above.

In another aspect, the invention relates to a method of screening for an arabino nucleotide polymer having a particular predetermined characteristic, said method comprising preparing a candidate arabino nucleotide polymer as described above, and assaying said arabino nucleotide polymer for said characteristic.

Reverse Transcriptases

In another aspect, the invention relates to a nucleic acid polymerase capable of reverse transcribing an arabino nucleotide polymer into a DNA nucleotide polymer said polymerase comprising amino acid sequence having at least 36% identity to the amino acid sequence of SEQ ID NO:1, wherein said amino acid sequence is mutated relative to the amino acid sequence of SEQ ID NO:1 at residue I521, wherein said polymerase comprises the mutation I521L.

Suitably the polymerase is further mutated relative to the amino acid sequence of SEQ ID NO:1, wherein said polymerase comprises the mutations V93Q, D141A, E143A and A485L. This combination of mutations (i.e. including I521L) is referred to as RT521L_V93Q_D141A_E143A_A485L. An exemplary sequence of RT521L_V93Q_D141A_E143A_A485L is provided as SEQ ID NO:8. More suitably this polymerase also has the mutation K726R. More suitably this polymerase also has the mutation E429G. Most suitably this polymerase also has both the mutations K726R and E429G; this polymerase is particularly preferred and is referred to as RT-521; an exemplary sequence of RT-521 is provided as SEQ ID NO:12 with an example of a coding sequence provided as SEQ ID NO:13.

This polymerase may optionally also have the mutation A385V.

Suitably said polymerase further comprises the mutation E664K. This has the further advantage of ease of use. Suitably the polymerase is further mutated relative to the amino acid sequence of SEQ ID NO:1, wherein said polymerase comprises the mutations V93Q, D141A, E143A, A485L and E664K. This combination of mutations (i.e. including I521L) is referred to as RT521K_V93Q_D141A_E143A_A485L_E664K. An exemplary sequence of RT521K_V93Q_D141A_E143A_A485L_E664K is provided as SEQ ID NO:10, with an example of a coding sequence provided as SEQ ID NO:9. More suitably this polymerase also has the mutation K726R. More suitably this polymerase also has the mutation A385V. Most suitably this polymerase also has both the mutations K726R and A385V; this polymerase is particularly preferred and is referred to as RT-521K; an exemplary sequence of RT-521K is provided as SEQ ID NO:14 with an example of a coding sequence provided as SEQ ID NO:15.

This polymerase may optionally also have the mutation E429G.

Suitably the arabino nucleotide polymer is an ANA polymer.

Suitably the arabino nucleotide polymer is a FANA polymer.

In another aspect, the invention relates to use of a nucleic acid polymerase capable of reverse transcribing an arabino nucleotide polymer into a DNA nucleotide polymer as described above in the production of a DNA nucleotide polymer from an arabino nucleotide template.

In another aspect, the invention relates to use of a nucleic acid polymerase capable of reverse transcribing an arabino nucleotide polymer into a DNA nucleotide polymer as described above in the production of a DNA nucleotide polymer from an ANA nucleotide template.

In another aspect, the invention relates to use of a nucleic acid polymerase capable of reverse transcribing an arabino nucleotide polymer into a DNA nucleotide polymer as described above in the production of a DNA nucleotide polymer from a FANA nucleotide template.

In another aspect, the invention relates to a method for making a DNA nucleotide polymer, said method comprising contacting an arabino nucleotide template, suitably an ANA or FANA template, with a nucleic acid polymerase capable of reverse transcribing an arabino nucleotide polymer into a DNA nucleotide polymer as described above and incubating to allow polymerisation.

In another aspect, the invention relates to use of a nucleic acid polymerase capable of reverse transcribing an arabino nucleotide polymer into a DNA nucleotide polymer as described above in the manufacture of a DNA nucleotide polymer. Suitably said arabino nucleotide polymer is an ANA or FANA nucleotide polymer.

In another aspect, the invention relates to a nucleic acid encoding a nucleic acid polymerase capable of reverse transcribing an arabino nucleotide polymer into a DNA nucleotide polymer as described above. In another aspect, the invention relates to a host cell comprising said nucleic acid.

Systems

In another aspect, the invention relates to a system comprising:
(i) a nucleic acid polymerase capable of producing an arabino nucleotide polymer from a DNA nucleotide polymer template as described above; and
(ii) a nucleic acid polymerase capable of reverse transcribing an arabino nucleotide polymer into a DNA nucleotide polymer,
said polymerase comprising amino acid sequence having at least 36% identity to the amino acid sequence of SEQ ID NO:1,
wherein said amino acid sequence is mutated relative to the amino acid sequence of SEQ ID NO:1 at residue I521.

Suitably said polymerase of (ii) comprises the mutation I521L.

Suitably said polymerase of (ii) further comprises the mutations V93Q, D141A, E143A and A485L.

Suitably said polymerase of (ii) further comprises the mutation E664K.

DETAILED DESCRIPTION OF THE INVENTION

We describe a general strategy to enable enzymatic replication and evolution of a broad range of synthetic genetic polymers based on: 1) a chemical framework (XNA) capable of specific base-pairing with DNA, 2) the engineering of polymerases that can synthesize XNA from a DNA template, as well as 3) the engineering of polymerases that can reverse transcribe XNA back into DNA. We chose six different XNAs in which the canonical ribofuranose ring of DNA and RNA is replaced by five- or six-membered congeners comprising HNA (1,5 anhydrohexitol nucleic acids), CeNA (cyclohexenyl nucleic acids), LNA (2'-O,4'-C-methylene-β-D-ribonucleic acids; locked nucleic acids), ANA (arabinonucleic acids), FANA (2'-fluoro-arabinonucleic acid) and TNA (a-L-threofuranosyl nucleic acids) (4-6, 17, 18). In particular the invention is concerned with arabino nucleic acids such as ANA (arabinonucleic acids), and FANA (2'-fluoro-arabinonucleic acid) nucleic acids.

Our work establishes strategies for the replication and evolution of synthetic genetic polymers not found in nature, providing a route to novel sequence space. The capacity of synthetic polymers for both heredity and evolution also shows that DNA and RNA are not functionally unique as genetic materials. The methodologies developed herein are readily applied to other nucleic acid architectures and have the potential to enable the replication of genetic polymers of increasingly divergent chemistry, structural motifs and physicochemical properties, as shown here by the acid resistance of HNA aptamers (FIG. S17). Thus, aspects of the correlations between chemical structure, evolvability and phenotypic diversity may become amenable to systematic study. Such "synthetic genetics", i.e. the exploration of the informational, structural and catalytic potential of synthetic genetic polymers, should advance our understanding of the parameters of chemical information encoding, and provide a source of ligands, catalysts and nanostructures with tailor-made chemistries for applications in biotechnology and medicine.

Definitions

The term 'comprises' (comprise, comprising) should be understood to have its normal meaning in the art, i.e. that the stated feature or group of features is included, but that the term does not exclude any other stated feature or group of features from also being present.

A non DNA nucleotide means a nucleotide other than a deoxy ribonucleotide. For example, it may mean a conventional ribonucleotide which may be used to make an RNA polymer. Alternatively, it may mean any other kind of non DNA nucleotide, such as an arabino nucleotide, which may be used to make the corresponding polymers. Examples of arabino nucleotides include ANA (arabinonucleic acid) nucleotides such as arabinosyl nucleotide triphosphates, FANA (2'-fluoro-arabinonucleic acid) nucleotides such as fluoroarabinosyl nucleotide triphosphates or other such nucleotides.

Arabino Nucleic Acid Chemistry

Arabinonucleosides are structural analogues of deoxynucleosides and differ only by the presence of a β-hydroxyl at the 2' position of the sugar moiety. This is sufficient to render the arabinonuclesoide triphosphates (araNTPs) potent chain terminators to multiple DNA polymerases, telomerase and reverse transcriptases in vitro. Unlike ribonucleotide triphosphates (rNTPs), enantiomers of araNTPs which are excluded by the steric gate of DNA polymerases, araNTPs are efficiently incorporated by DNA polymerases, rendering them more efficient as chain terminators than ddNTPs in vitro. Structurally, arabinonucleic acid (ANA) is thought to be predominantly B-form owing to the bias towards the C2'-endo (Southern) ribose conformation promoted by an internal hydrogen-bond between the 2'OH and the 5'O of the sugar, although we are not aware of an ANA-ANA duplex structure. The sugar pucker of fluoro-arabinonucleic acid (FANA) is more varied as the 2'F does not interact with the 5'O. Another major consequence of the replacement of the 2'OH with F is on melting temperature (Tm), which can differ by up to 1.8° C./base pair as the 2'F appears able to form pseudohydrogen bonds with the H8 of a purine immediately 3' of a FANA-purine-MP. As a result, FANA-modified siRNA is more potent than native (RNA) siRNA. Arabinonucleosides, specifically araC, are used as therapeutics with particular efficacy against leukaemias. Despite their potent inhibition of pol alpha in vitro, the majority of the araNMP incorporated into DNA is found at internucleotide positions, not at the 3' as would be expected for a chain terminator. This is partly because ~60% is incorporated by repair mechanisms and partly as araNMPs are inefficient chain terminators in vivo and it is these incorporated araNMPs which appear to exert the greatest lethal effect. Single araNMPs in DNA induce substantial local structural distortions, inhibiting polymerase bypass and stimulating Topoisomerase I and II-induced cleavage, suggesting arabino drugs act via chain termination, replication inhibition and induced genome cleavage. Having evolved DNA polymerases with mutations in the thumb domain capable of synthesising anyhdrohexitol nucleic acids (HNA) and RNA, we decided to investigate the effect on polymerase activity when the 2'OH was flipped from a ("down", as in NTPs) to β ("up", as in araNTPs). One polymerase, D4 was particularly active, and this activity was enhanced by the optimisation of a key position, E664K. Furthermore, this polymerase is exceptionally active as a FANA-polymerase which, when coupled with the ability of RT-521 to reverse transcribe both ANA and FANA enables SELEX-based selections for aptamers.

Suitably the invention relates to the production of a complete new polymer i.e. orthogonal nucleic acid. The aim is to keep the information which is encoded in that polymer the same as the information encoded in a conventional DNA polymer. For example, it is not an aim of the invention to include a fifth base or to expand the genetic alphabet beyond the four conventional bases, although the invention could be applied in this manner by the skilled operator if desired. Suitably, the polymers of the invention reflect the same four bases as conventional DNA polymers in terms of their information content.

Orthogonal nucleic acids are non DNA nucleic acids. Examples include ANA or FANA as described herein. These non DNA nucleic acids are sometimes referred to as "3NA" or as "XNA" as will be apparent from the context. Suitably the orthogonal nucleic acid is an arabino nucleic acid such as ANA or FANA nucleic acid. Most suitably, the orthogonal nucleic acid is FANA. FANA is particularly advantageous since it is the most experimentally tractable of the orthogonal nucleic acids discussed herein, being able to support FANA-templated FANA polymer synthesis.

As used herein, the term reverse transcriptase or "reverse transcriptase activity" refers to the manufacture of a DNA polymer from a non DNA polymer template. Thus, when the non DNA template comprises RNA, then the term has its normal meaning in the art. As will be apparent from the context, in numerous aspects and embodiments the invention relates to reverse transcriptase activity in the sense of manufacturing a DNA polymer from a non DNA polymer template which may be, for example, RNA, ANA, FANA, or other such non DNA template. Thus, reverse transcriptase may be classically regarded as an RNA dependant DNA polymerase. For other non DNA nucleotide polymers the term "reverse transcriptase" has the same overall meaning, except that the template nucleic acid may of course vary. For example, a reverse transcriptase for ANA means an ANA dependant DNA polymerase; a reverse transcriptase for FANA means a FANA dependant DNA polymerase.

Nucleoside Antimetabolites

The polymerases of the invention such as D4YK, can synthesise XNA molecules from a variety of XNA nucleotides/phosphorylated nucleosides. Exemplary nucleotides which can be polymerised by the polymerases of the invention are discussed throughout the text, and more specifically are discussed in detail below.

The polymerases of the invention such as D4YK, can synthesise XNA molecules long enough for aptamer selection. Many XNAs are DNase sensitive. This means that an XNA aptamer such as a ANA aptamer, capable of binding an internalising cell surface receptor would be readily degraded by lysosomal nucleases resulting in the intracellular release of (eg) arabinosyl monophosphates and nucleosides. In this context, ANA may be thought of a "toxic nucleic acid" (txNA), and the aptamers may be thought of as txNA aptamers. By synthesizing aptamers from nucleotides that are established anti-cancer drugs the aptamer itself becomes a polymeric prodrug comprising a mixture of up to four anti-tumour compounds that are delivered in concert to the target cell such as cancer cell.

Such arabinosyl nucleosides (in particular araC) are profoundly cytotoxic and are widely used as anti-cancer drugs. However, their use is limited to certain cells, mostly lymphocytes, as they have to be actively taken up from the extracellular milieu and phosphorylated by target cells into monophosphates, diphosphates and triphosphates.

Nucleoside antimetabolites have been a cornerstone of chemotherapy ever since the FDA approved the first, 6-mercaptopurine, for use against leukaemia less than two years after it was first published. Over the last sixty years a large number of nucleoside analogues have been developed and characterised resulting in a range of drugs effective against not only haematological malignancies but also some solid tumours. Nucleoside drugs are activated by cellular enzymes to the active forms of mononucleotide di- and triphosphates and are potent inhibitors of DNA synthesis, DNA repair, genome stability, key enzymes of DNA and RNA metabolism such as ribonucleotide reductase (RNR) and thymidine synthetase (TS) and can even alter gene expression by inhibiting DNA methylation. However, as nucleoside antimetabolites are readily taken up and metabolised by lymphocytes, therapy results in prolonged and profound immumosupression.

Most arabinosyl nucleosides by themselves cannot be used as antimetabolites as they are either insufficiently toxic or instable in vivo. Extensive work has been carried out on modifications to arabinosyl nucleosides that has resulted in substantial increases in activity: for example modifying C2' of adenosine in araA resulted in Fludarabine (9-β-D-arabinofuranosyl-2'fluoroadensoine). Adenosine C2' modifications were originally investigated to stabilize araA against adenosine deaminase and so potentiate araA as an antiviral or anti-cancer drug. Fludarabine is in sensitive to adenosine deaminase and, more importantly, it is a potent RNR inhibitor. Further modifications resulted in Cladribine (2'deoxy, 2'chloroadenosine, Table 5.1) a more potent RNR inhibitor and Clofarabine (9-β-D-fluoroarabinosyl-2'chloroadenosine), which combined the potent DNA polymerase inhibition of Fludarabine and RNR inhibition of Cladribine.

While araC is a potent drug (Cytarabine), work has continued on modifications with a view to improving activity in solid tumours where cytidine deaminase renders araC non-toxic. One successful such second generation analogues is Gemcitabine (2'T-difluorodeoxycytidine). Gemcitabine inhibits DNA polymerases, albeit not as effectively as araC but is primarily a potent RNR inhibitor. AraG is not potently cytotoxic but is a telomerase inhibitor and so may contribute to tumour cell senescence in analogy to small-molecule telomerase inhibitors. AraU is not inherently cytotoxic and is actually the major degradation product of araC, but fluorinated pyrimidines, in particular 5'fluoro-uracil, have been known to have anti-tumour activity in mice since the 1950s. Floxuridine (2'deoxy, 5'flourouridine) is a potent and irreversible thymidylate synthetase inhibitor and is a most cytotoxic nucleoside.

Structures of nucleoside antimetabolites are shown in the table below (RNR=ribonucleotide reductase. PAP=poly(A) polymerase).

| Nucleoside | Common name | Structure |
| --- | --- | --- |
| 9-beta-D-arabinofuranosyl-2'fluoroadenosine | Fludarabine | 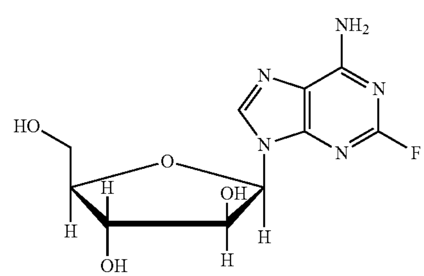 |
| 2'deoxy, 2'chloroadenosine | Cladribine | 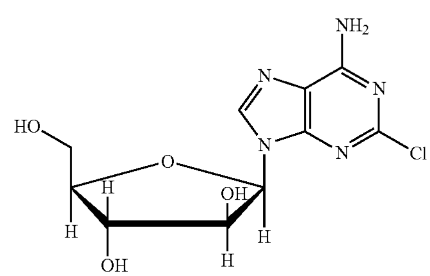 |

-continued

| Nucleoside | Common name | Structure |
|---|---|---|
| 9-beta-D-fluoroarabinosyl-2'chloroadenosine | Clofarabine, Clolar | 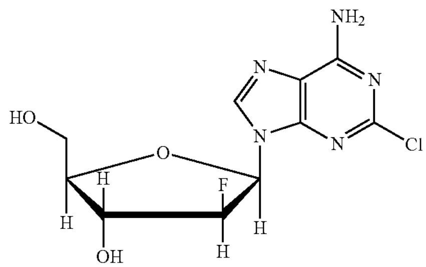 |
| 9-beta-D-arabinofuranosyl-cytidine | Cytarabine | 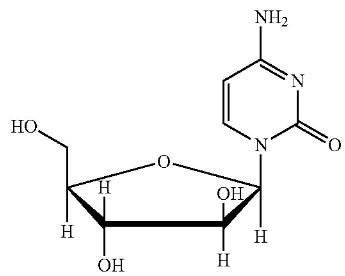 |
| 5'aza-deoxycytidine | Decitabine | 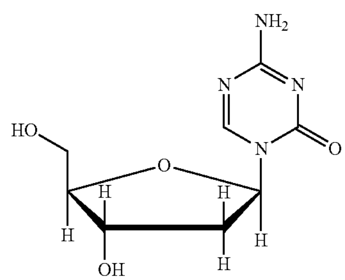 |
| 2'2'-difluorodeoxycytidine | Gemcitabine, Gemstar | 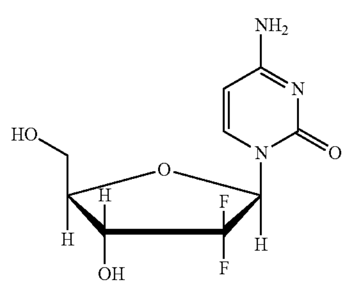 |
| 9-beta-D-arabinofuranosyl-guanosine | araG | 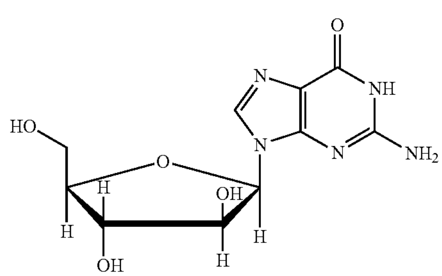 |

-continued

| Nucleoside | Common name | Structure |
|---|---|---|
| 2'deoxy, 6'thioguanosine | | 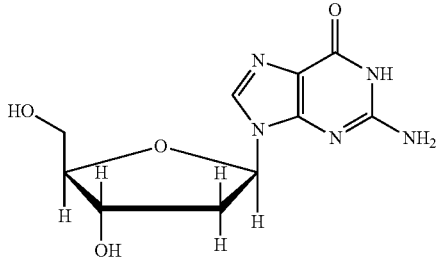 |
| 2'deoxy, 5'fluorouridine | Floxuridine | 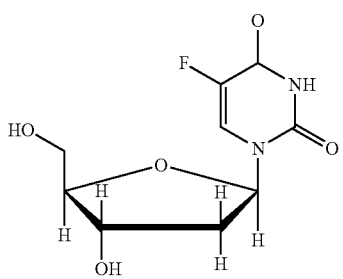 |

More suitably the polymerases of the invention may be used to polymerise (i.e. incorporate or synthesise polymers from) pharmaceutically active nucleotides wherein the nucleotides are linked via phosphodiester or phosphothiorate groups and may be free polymers or conjugated to targeting moieties (e.g. nucleic acid aptamers, peptide aptamers, antibodies). Such "polymeric prodrugs" or "toxic nucleic acids" (txNA) may be synthesised from the 5'-triphosphate forms of any mixture of natural nucleotides (e.g. DNA, RNA), and/or any of the aforementioned XNAs (e.g. HNA, CeNA, LNA, TNA, ANA, FANA).

More suitably the nucleotides are selected from any of the following:

Group A:

Vidarabine (araA), Fludarabine, Cladribine, Clofarabine, Cytarabine (araC), Gemcitabine, araG, 2'2'-difluorodeoxyguanosine, 5-azacytidine, doxifluridine (5-fluorodeoxyuridine), 5-nitro-deoxyuridine, enocitabine, floxuridine, pentostatin, brivudine, edoxudine, fiacitabine, fialuridine, ibacitabine, idoxuridine, ribavirin, trifluridine and Zebularine. Alternatively, nucleoside analogs such as acyclovir, valacyclovir, penciclovir, famciclovir, ganciclovir, cidofovir, adefovir, lobucavir and ribavirin may be incorporated.

Other suitable nucleoside analogs contemplated for use in the invention include both carbacylic nucleosides and L-nucleotides.

More suitably the nucleotides are selected from Group B:

Group B:
A: Fludarabine, Cladribine, Clofarabine,
C: Cytarabine (araC), Gemcitabine, Decitabine
G: araG, 6'thio-dG, 2'2'-difluorodeoxyguanosine
U: Floxuridine More suitably the nucleotides are selected from Group C:

Group C:
A: Clofarabine
C: Cytarabine or Gemcitabine
G: 2'2'-difluorodeoxyguanosine, FANA-G or phosphothiorate-G
U: Floxuridine More suitably nucleotides are selected from Group D:

Group D:
Clofarabine, Gemcitabine, 2'2-difluorodeoxyguanosine and Floxuridine.

Most suitably nucleotides are selected from Group E:

Group E:
A: Fludarabine
C: Cytarabine or Gemcitabine
G: FANA-G or phosphothiorate-G
U: Floxuridine Polymers The invention relates to polymers produced using a polymerase of the invention.

The invention also relates to polymers consisting of pharmaceutically active nucleotides as described herein wherein the nucleotides are linked via phosphodiester or phosphothiorate groups.

These may be free polymers or may be conjugated to targeting moieties (e.g. nucleic acid aptamers, peptide aptamers, antibodies). Such "polymeric prodrugs" or "toxic nucleic acids" (txNA) are suitably synthesised from the 5'-triphosphate forms of any mixture of natural nucleotides (e.g. DNA, RNA), any of the aforementioned XNAs (e.g. HNA, CeNA, LNA, TNA, ANA, FANA). More suitably said polymers consist of nucleotides selected from any one of the groups listed above. More suitably an individual polymer of the invention consists of nucleotides selected from an individual (i.e. single) group listed above. Most suitably an individual polymer of the invention is composed exclusively from nucleotides of an individual (i.e. single) group listed above.

Such polymers can be synthesised by chemical synthesis or by natural polymerases, or more suitably by engineered polymerases of the invention. Both D4K and preferentially D4K521 are capable of synthesising such "polymeric prodrugs" or "txNA" molecules. These txNA molecules can be reverse transcribed into DNA by RT-521 and RT-521K.

Further Advantages

D4K is further able to extend diverse non-DNA primers including non-ANA/non-FANA primers. For example, D4K can extend RNA primers and 2'OMe primers. In addition, D4K is able to extend DNA primers.

Polymer Lengths

To be considered a useful enzyme according to the invention (i.e. to be considered capable of having the specified functions), the polymerase or reverse transcriptase of the invention should be able to produce a polymer of at least 31 nucleotides in length, suitably at least 35 nucleotides in length; more suitably 40 nucleotides in length, most suitably at least 50 nucleotides in length.

If polymerases of the invention are discussed as being for or specific for a particular type of orthogonal nucleic acid, it should be understood that they are expected to be able to consistently produce a polymer of at least 40 nucleotides, suitably at least 50 nucleotides in length.

Suitably the polymerases of the invention are specific for arabino nucleic acids such as ANA or FANA nucleic acids. Suitably the polymerases of the invention are able to consistently produce a polymer of at least 40 arabino nucleotides, suitably at least 50 arabino nucleotides in length. Most suitably the arabino nucleotides are ANA or FANA nucleotides.

Typically the smallest aptamers or ribozymes need approximately 40 nucleotides of sequence in order to fold. More suitably, small aptamers or ribozymes also comprise a few extra nucleotides for polymerase binding, therefore suitably being at least about 50 nucleotides in length. For aptamer screening applications, a typical preferred minimum length is therefore 50 nucleotides.

Polymerase

In principle, polymerases of the invention may be made by introducing the specific mutations described herein into the corresponding site of a starting polymerase or 'polymerase backbone' of the operator's choice. In this way, the activity of that starting polymerase may be modified to provide the orthogonal activities as described herein.

The polymerase backbone may be any member of the well known polB enzyme family (including the pol delta variant which shows only 36% identity with the exemplary true wild type TgoT sequence of SEQ ID NO:1). More suitably the polymerase backbone may be any member of the well known polB enzyme family excluding viral polymerases. More suitably the polymerase backbone may be any member of the well known polB enzyme family having at least 36% identity to SEQ ID NO:1; suitably at least 50%; suitably at least 60%; suitably at least 70%; suitably at least 80%. At the 80% identity level, the invention suitably embraces polB enzymes from the Archaeal *Thermococcus* and/or *Pyrococcus* genera. In a preferred embodiment suitably the polymerase backbone has at least 90% identity to SEQ ID NO:1. In a further preferred embodiment suitably the polymerase backbone has at least 92% identity to SEQ ID NO:1. In a further preferred embodiment suitably the polymerase backbone has at least 94% identity to SEQ ID NO:1. In a further preferred embodiment suitably the polymerase backbone has at least 96% identity to SEQ ID NO:1. In a further preferred embodiment suitably the polymerase backbone has at least 98% identity to SEQ ID NO:1.

When using other polymerase backbones, mutations are transferred to the equivalent position as is well known in the art and as noted above. For example, with reference to the exemplary polymerase D4K, the following table illustrates how the transfer of mutations to alternate backbones may be carried out. The table shows D4K mutations and structural equivalent positions in other PolBs. The mutations found in D4K are shown against the underlying sequence of the wild-type Tgo. The structurally equivalent residue in other well-studied B-family polymerases is given. Residues that were not mapped to equivalent positions are shown as N.D.

| Tgo (1TGO) | | D4K | RB69 (1IG9) | E. coli (3MAQ) |
|---|---|---|---|---|
| L | 403 | P | 410 | 418 |
| P | 657 | T | 776 | N.D. |
| E | 658 | Q | 777 | 680 |
| K | 659 | H | 778 | 681 |
| Y | 663 | H | 782 | 685 |
| E | 664 | K | 783 | 686 |
| D | 669 | A | 789 | 691 |
| K | 671 | N | N.D. | 693 |
| T | 676 | I | 801 | 700 |

This table shows the transplant of the 8 important residues in the thumb domain (patch 10A). In addition the table show the transplant of the A-motif mutation (L403P). The same principles may be easily applied to the remaining D4K mutations such as the therminator mutation (A485L), the mutation to disabling uracil stalling (V93Q), and mutations to disable exonuclease activity (D141A and E143A) as desired.

Most suitably, the polymerase backbone is Archaeal *thermococcus* TgoT polB; the true wild type sequence is as shown in SEQ ID NO:1. This will serve as the reference sequence, and preferred embodiments of the invention are described with reference to this sequence.

Reference Sequence

When particular amino acid residues of polymerase are referred to using numeric addresses, the numbering is taken with reference to the true wild type TgoT polB amino acid sequence of SEQ ID NO:1 (or to the nucleic acid sequence encoding same).

This is to be used as is well understood in the art to locate the residue of interest. This is not always a strict counting exercise—attention must be paid to the context. For example, if the protein of interest is of a slightly different length, then location of the correct residue in that sequence corresponding to (for example) E664 may require the sequences to be aligned and the equivalent or corresponding residue picked, rather than simply taking the 664th residue of the sequence of interest. This is well within the ambit of the skilled reader.

Mutating may refer to the substitution or truncation or deletion of the residue, motif or domain referred to. Preferably mutation means substitution. Thus, unless otherwise indicated expressly or by context, 'mutation' may be taken to refer to substitution of the amino acid referred to herein.

The standard convention for describing mutations (substitution mutations) is used herein. For example, E664K means replacing the residue corresponding to E664 with K. A substitution does not alter the length of the resulting polypeptide, it simply replaces the mentioned amino acid residue with the stated substitute residue.

Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, as a default alanine (A) may be used. Suitably the mutations used at particular site(s) are as set out herein.

A fragment is suitably at least 10 amino acids in length, suitably at least 25 amino acids, suitably at least 50 amino acids, suitably at least 100 amino acids, or suitably the majority of the polymerase polypeptide of interest i.e. 387 amino acids or more, suitably at least 500 amino acids, suitably at least 600 amino acids, suitably at least 700 amino acids, suitably the entire 773 amino acids of the TgoT polB sequence.

Sequence Variation

The polymerase of the invention may comprise sequence changes relative to the wild type sequence in addition to the key mutations described in more detail herein. Specifically the polymerase of the invention may comprise sequence changes at sites which do not significantly compromise the function or operation of the polymerase as described herein.

Polymerase function may be easily tested by operating the polymerase as described, such as in the examples section, in order to verify that function has not been abrogated or significantly altered.

Thus, provided that the polymerase retains its function which can be easily tested as set out herein, sequence variations may be made in the polymerase molecule relative to the wild type reference sequence.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In considering what mutations, substitutions or other such changes might be made relative to the wild type sequence, retention of the function of the polymerase is paramount. Typically conservative amino acid substitutions would be less likely to adversely affect the function. Suitably the polymerase of the invention varies from the wild type sequence only by conservative amino acid substitutions except as discussed.

Sequence Homology/Identity

Although sequence homology can also be considered in terms of functional similarity (i.e., amino acid residues having similar chemical properties/functions), in the context of the present document it is preferred to express homology in terms of sequence identity.

Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example in an otherwise identical pair of sequences, one insertion or deletion will cause the following amino acid residues to be put out of alignment, thus potentially resulting in a large reduction in percent homology (percent identity) when a global alignment (an alignment across the whole sequence) is performed. Consequently, most sequence comparison methods are designed to produce optimal alignments that take into consideration possible insertions and deletions without penalising unduly the overall homology (identity) score. This is achieved by inserting "gaps" in the sequence alignment to try to maximise local homology/identity.

These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215: 403-410) and the GENEWORKS suite of comparison tools.

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Once the software has produced an optimal alignment, it is possible to calculate percent homology, preferably percent sequence identity. The software typically does this as part of the sequence comparison and generates a numerical result.

Suitably identity is assessed at the amino acid level over at least 400 or 500, preferably 600, 700, or even more amino acids with the relevant polypeptide sequence(s) disclosed herein, most suitably with the full length progenitor "true wild type" TgoT polB sequence of SEQ ID NO:1.

Suitably, homology should be considered with respect to one or more of those regions of the sequence known to be essential for protein function rather than non-essential neighbouring sequences. This is especially important when considering homologous sequences from distantly related organisms.

When considering conserved regions, suitably the 36% of residues common to both SEQ ID NO:1 and to the pol delta member of the polB enzyme family should be taken to be potentially important residues which are suitably not mutated in the polypeptide of the invention unless otherwise discussed. Thus, suitably substitutions made are at residues outside of (i.e. different from) those 36% of residues common to both SEQ ID NO:1 and to the pol delta member of the polB enzyme family. Thus suitably the polypeptide of the invention has at least 36% identity to SEQ ID NO:1 and suitably the amino acid residues making up said at least 36% identity comprise the amino acid residues corresponding to those which are identical between SEQ ID NO:1 and the pol delta member of the polB enzyme family. Suitably the polypeptide of the invention has at least 36% identity to SEQ ID NO:1 and has at least 36% identity to the pol delta member of the polB enzyme family.

The sequence of the pol delta member of the polB enzyme family is shown as SEQ ID NO:11.

The same considerations apply to nucleic acid nucleotide sequences.

In a preferred embodiment the polypeptide of the invention has 16 or fewer substitutions to SEQ ID NO:1; when the polypeptide of the invention comprises full length sequence corresponding to SEQ ID NO:1, this equates to 98% identity; suitably the polypeptide of the invention has 15 or fewer substitutions to SEQ ID NO:1; suitably the polypeptide of the invention has 14 or fewer substitutions to SEQ ID NO:1. Most suitably the polypeptide of the invention has 13 substitutions to SEQ ID NO:1; most suitably these 13 substitutions are those set out for D4K.

Polynucleotides of the Invention

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Protein Expression and Purification

Proteins of the invention are typically made by recombinant means, for example as described below and in the examples. However they may also be made by synthetic means using techniques well known to skilled persons such as solid phase synthesis. Proteins of the invention may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Clearly the fusion protein selected must not hinder the function of the polymerase of the invention.

Suitably the polymerase of the invention is not fused to any sequence for purification since the polymerase of the invention may be advantageously purified based on its thermostable properties and/or using simple well known purification schemes as noted herein.

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Polymerase Mutants

We have identified specific mutations within a region of the polymerase enzyme which may be varied in order to provide orthogonal polymerase functions. Referring to the conventional structural model of the polymerase enzyme, the mutations which have been identified are located in the "thumb" part of the enzyme. In the accepted model, the polymerase is thought of as a right "hand" extending around a DNA "rod" which passes through a central space defined by the structure of the enzyme. The region of the enzyme which we teach may be varied in order to provide the orthogonal polymerase functions described is in the "thumb" part of the enzyme. In more detail, it is that part of the thumb at the exit point where the DNA "rod" leaves the enzymatic "hand".

The region of the enzyme which we teach may be varied is in the "thumb" region. The thumb region represents a single three dimensional part of the enzyme. However, this single three dimensional thumb structure is represented by separate linear parts of the amino acid sequence. Within this linear parts two patches are identified that specify orthogonal polymerase function. These two patches are designated patch 10A and patch 12 and are discussed in more detail below.

Patch 10A

Patch 10A corresponds to amino acids 651 to 679 of SEQ ID NO: 1. Mutations in this patch can provide orthogonal polymerase activity for at arabino nucleic acids such as ANA and FANA. Patch 10A is considered the most important patch described herein.

Within patch 10A is a motif of special importance, which is the small beta-sheet region from aa 662 to 666. This region occupies a space near the nucleic acid backbone and is especially suitably mutated for polymerase(s) acting to produce RNA. In particular, residue E664 is especially suitable to mutate, for example E664K.

Thus suitably the orthogonal polymerase of the invention comprises an E664 mutation such as E664K. This is especially beneficial in combination with seven other mutations in patch 10A, as set out herein for the D4K polymerase.

Patch 12

Patch 12 comprises amino acids 734 to 765 of SEQ ID NO: 1. Patch 12 may be considered less important than Patch 10A.

Backbone Mutations

There are a number of mutations which may advantageously be made to the backbone polypeptide.

One such mutation is at position V93 of SEQ ID NO:1. Suitably the backbone has a V93 mutation such as V93Q. This has the advantage of disabling read-ahead stalling which can occur for example when the template comprises uracil.

One such mutation is at positions D141 and E143 of SEQ ID NO:1. Suitably the backbone has a D141 mutation such as D141A; suitably the backbone has an E143 mutation such as E143A; most suitably the backbone has both D141 and E143 mutations such as D141A and E143A. This has the advantage of disabling the exonuclease function of the enzyme. This further enhances incorporation of unnatural substrates.

One such mutation is the 'therminator' mutant (New England Bio Labs) at position A485 of SEQ ID NO:1. Suitably the backbone has an A485 mutation such as A485L. This has the advantage of enhancing incorporation of unnatural substrates.

The mutations mentioned are mutually compatible; in other words the polypeptide of the invention may have each of the backbone mutations in the same polypeptide. An example of this is in SEQ ID NO:2. This is sometimes referred to as the 'wild type' sequence and may be regarded as an excellent example of a starting polymerase backbone into which the mutations of the invention may be introduced. Thus suitably all four of the preferred backbone mutations V93Q, A485L, D141A and E143A are present in the polypeptides of the invention.

In a strict sense of course it will be noted that the sequence of SEQ ID NO:2 is not the true 'wild type' because it has these four mutations in the backbone already. For ease of reference the true wild type sequence is given as SEQ ID NO:1; this sequence is referred to as the "true wild type" herein for clarity.

A further useful mutation is in the A-motif of the polymerase, at position L403. Suitably the backbone has an L403 mutation such as L403P. This has the advantage of assisting polymerisation. This can help make longer polymers. This can improve polymerisation of arabino nucleotides by 3-4 fold, or even more. In some applications the improvement can be as high as 10 fold.

Other conventional mutations may be applied to the polymerase/reverse transcriptase. Moreover, other optimising mutations may be made as appropriate.

Further Mutations

Y409

Amino acid 409 is located outside patch 10A. Amino acid 409 is the steric gate; mutants of position 409 are referred to as steric gate mutants. Modification of the steric gate (Y409) of D4 allows better-than-wild-type incorporation of various substrates.

For example, substituting amino acid 409 (e.g. to N or G, suitably G) has the advantage of increasing RNA pol activity.

Suitably the amino acid sequence of the polymerase of the invention is not mutated relative to the amino acid sequence of SEQ ID NO:1 at residue Y409. Suitably the polymerase of the invention does not have a Y409G mutation. Suitably the polymerase of the invention has a residue other than G at position 409. Suitably the polymerase of the invention has a wild type residue at position 409. Suitably the polymerase of the invention has Y at position 409.

Truncations

Truncations of the overall full length polymerase enzyme of the invention may be made if desired. Suitably full length polymerase polypeptide is used as the backbone polypeptide, such as full length TgoT polymerase 1-773 as shown in the attached sequence listing. Any truncations used should be carefully checked for activity. This may be easily done by assaying the enzyme(s) as described herein.

Purification

Polymerases of the invention are advantageously thermostable. By expressing these polymerases in a conventional (non-thermostable) host strain, purification is advantageously simplified. For example, when the polymerases of the invention are expressed in a conventional non-thermostable host cell, approximately 90% purity may be obtained simply by heating the host cells to 99° C. followed by centrifugal removal of cellular debris. Higher purity levels may easily be obtained for example by subjecting the heat treated soluble fraction of the host cell to ion exchange and/or heparin column purifications.

Suitably the polymerase of the invention is not fused to any other polypeptide.

Suitably the polymerase of the invention is not tagged with any further polypeptides or fusions.

It is an advantage of the invention that mutations directed to the particular patches discussed may be substitutions to any of a wide range of amino acids without loss of function of the polymerase. The patches defined are extremely tolerant of amino acid changes.

Fidelity

It is clearly important that sufficient fidelity is maintained for accurate production (or reproduction) of the orthogonal nucleic acid polymers. Suitably polymerases of the invention retain at least 95% fidelity. Fidelity (error threshold) may be taken as the number of errors introduced divided by the number of nucleotides polymerised. In other words, an error rate of 1% equates to the introduction of one error for every 100 nucleotides polymerised. In fact, the polymerases of the invention attain a much better fidelity than this. An error rate of 5% or less is considered as the minimum useful fidelity level for the polymerases of the invention; suitably the polymerases of the invention have an error rate of 5% or less; suitably 4% or less; suitably 3% or less; suitably 2% or less; suitably 1% or less.

Unless otherwise stated, fidelity may be assessed as aggregate fidelity (e.g. DNA-3NA-DNA) which thus encompasses two conversion events (DNA-3NA and 3NA-DNA); the figures should be adjusted or interpreted accordingly.

Compartmentalised Self-Replication Technology

The techniques of directed evolution and compartmentalised self replication are detailed in GB 97143002 and GB 98063936 and GB 01275643. The specific application of this technique to engineered polymerases is described in WO2011/135280. These documents are herein incorporated by reference.

The methods of compartmentalised self tagging may be applied to optimise the DNA polymerases as herein defined.

(A) Sequence alignments showing mutations from Tgo consensus (corresponding to SEQ ID NO:1 as indicated by residue numbers) in polymerases Pol6G12 (SEQ ID NO:126), PolC7 (SEQ ID NO:127), and PolD4K (SEQ ID NO:128). (B) Mutations are mapped on the structure of Pfu (PDB: 4AIL). Template is shown in gray, primer in black. Mutations present in the parent polymerase TgoT are labeled.

Figure 2:
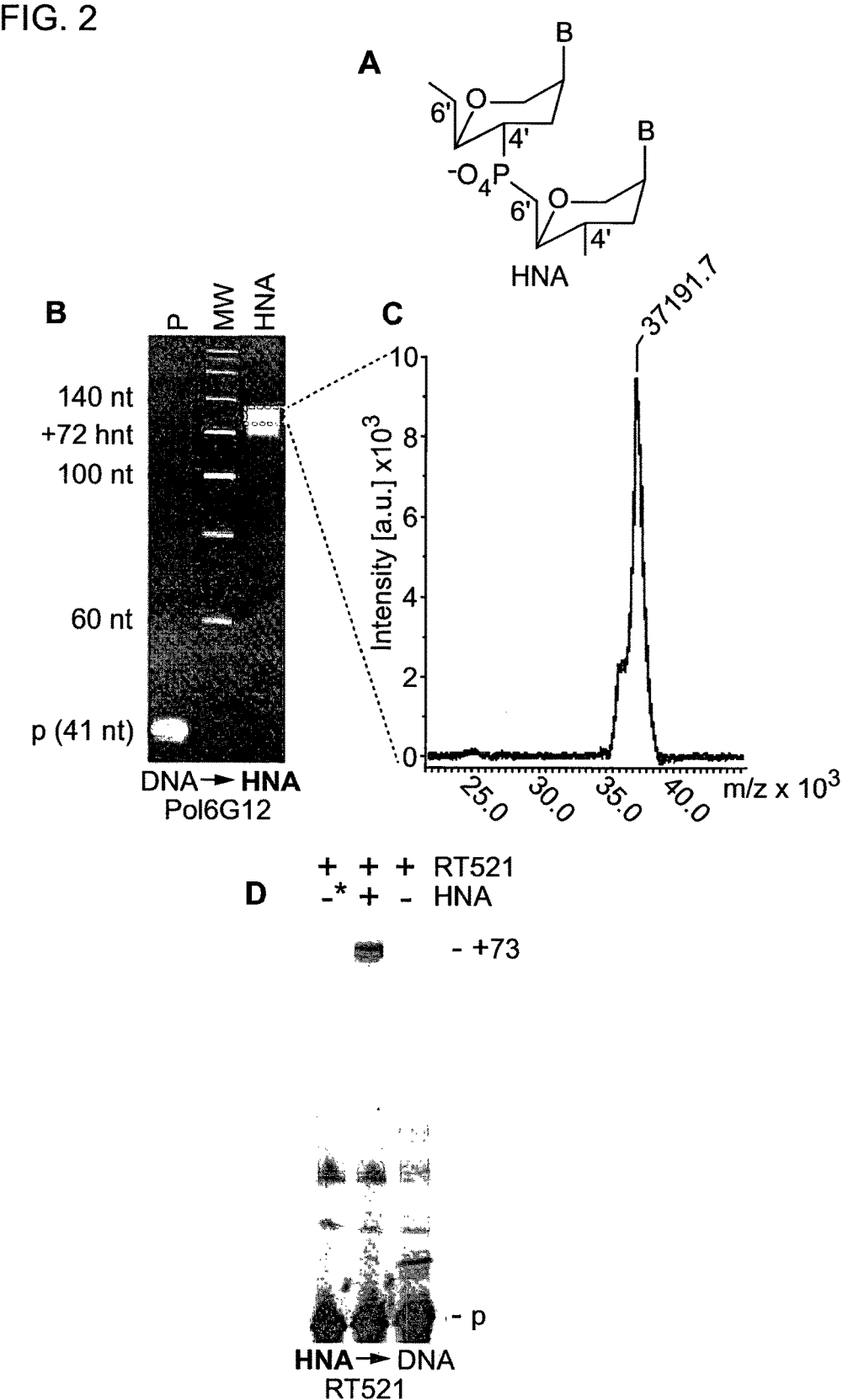

FIG. 2: HNA synthesis, mass spectrometry (MS) analysis and reverse transcription.

(A) Structure of 1,5-anhydrohexitol (HNA) nucleic acids (B: nucleobase). (B) Pol6G12 extends the primer (p) incorporating 72 hNTP against template T1 (Table S3) to generate a full-length hybrid molecule of 37,215 Da expected molecular mass (26). MW (ILS 600 molecular weight marker. (C) MALDI-ToF MS spectrum of full-length HNA molecule showing a measured HNA mass of 37,190±15 Da (n=3). (D) HNA reverse transcription (DNA synthesis from an HNA template). Polymerase-synthesised HNA (from template YtHNA4; Table S3) is used as template by RT521 for HNA-RT (-* denotes a no HNA synthesis control to rule out template contamination).

FIG. 3: XNA genetic polymers.

Structures (B: nucleobase), PAGE of synthesis (+72 xnt) and reverse transcription (+93 nt) of (A) CeNA, (B) ANA, (C) FANA, (D) and TNA. (E) PAGE of LNA synthesis (primer (41 nt)+72 lnt) and LNA RT (red) resolved by alkali agarose gel electrophoresis (AAGE). LNA synthesis (green) migrates at its expected size (113 nt) and co-migrates with reverse transcribed DNA (red) synthesized from primer $P_{RT2}$ (20 nt) (Table S3, FIG. S8). (F) AAGE of XNA and DNA polymers of identical sequence (PAGE: FIG. S5) (MW: ILS 600 molecular weight markers). (G) XNA RT-PCR (MW: NEB Low Molecular weight marker, NT: no template control). Amplification products of expected size (133 bp) are only obtained with both XNA forward synthesis and RT (RT521 or RT521K) (FIG. S12).

Figure 4:
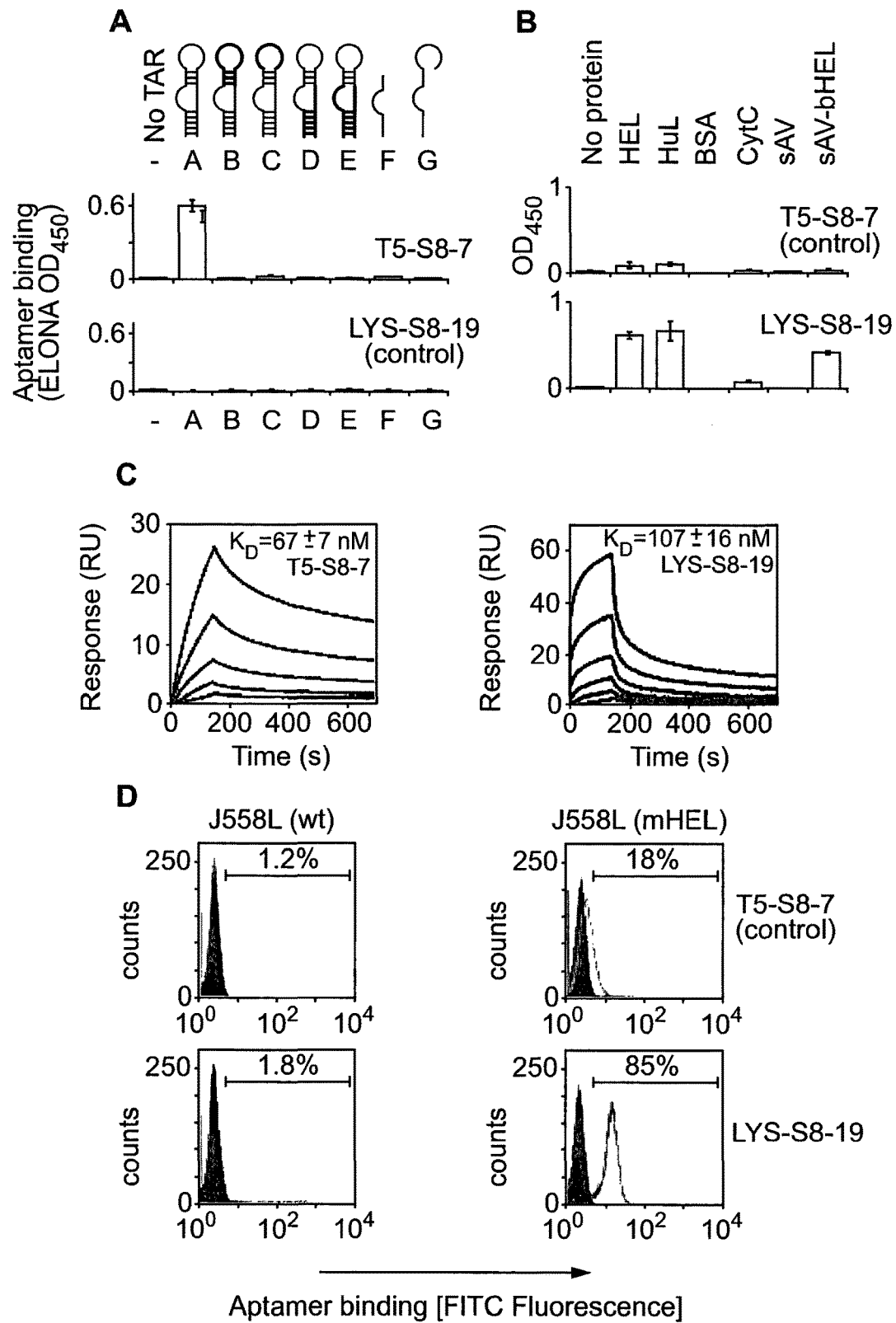

FIG. 4: Characterization of HNA aptamers.

Anti-TAR aptamer T5-S8-7 (HNA: 6'-AGGTAGTGCT-GTTCGTTCATCTCAAAT CTAGTTCGCTATCCAGT-TGGC-4') (SEQ ID NO:16) and anti-HEL aptamer LYS-S8-19 (HNA: 6'-AGGTAGTGCTGTTCGTTTAAATGTGTGTCGTCGT-TCGCTATCCAGTTGG C-4') (SEQ ID NO:17) were characterized by ELONA (26). (A and B) Aptamer binding specificity against TAR variants (sequence randomized but with base-pairing patterns maintained) and different protein antigens (hen egg lysozyme, HEL; human lysozyme, HuL; bovine serum albumin, BSA; cytochrome C, CytC; streptavidin, sAV; and biotinylated-HEL bound to streptavidin, sAV-bHEL). (C) Affinity measurements of aptamer binding by SPR. (D) FACS analysis of FITC-labeled aptamers binding to plasmacytoma line J558L with and without expression of membrane-bound HEL (mHEL) (26).

Figure 5A:
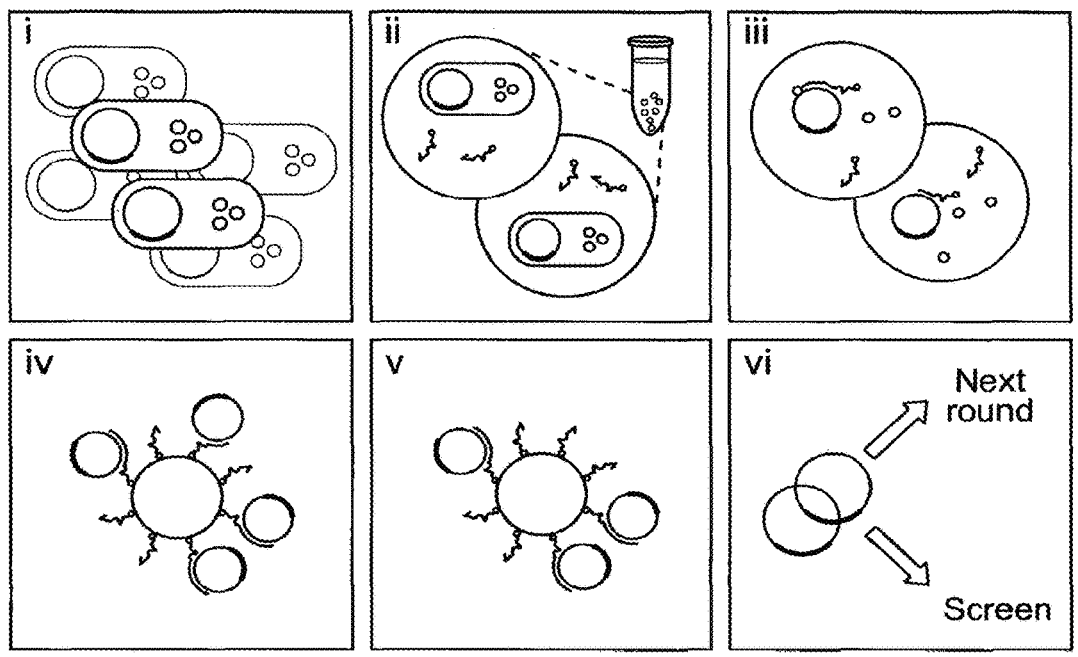
Figure 5B:
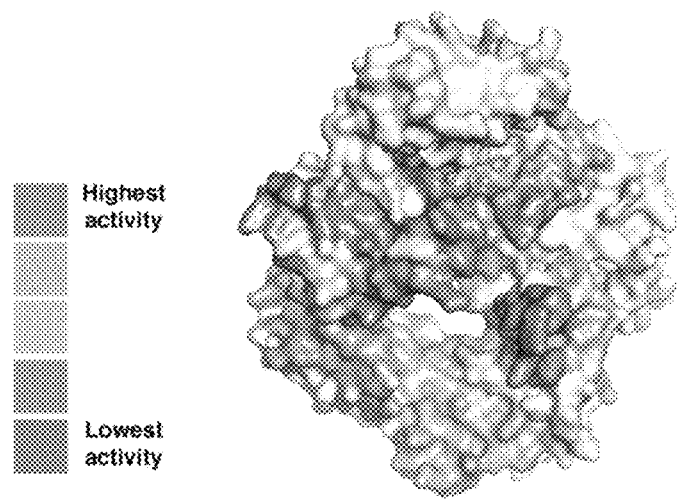

FIG. 5A-FIG. 5B: Compartmentalized Self-tagging (CST)

In CST (FIG. 5A), polymerase repertoires (i) are compartmentalized with primers and modified nucleotides in water-in-oil emulsions (ii) to ensure genotype-phenotype linkage (58). CST is based on a positive feedback loop whereby a polymerase tags the plasmid containing its gene by extending a biotinylated primer (iii). Primer extension stabilizes the metastable primer-plasmid complex allowing capture in proportion to its stability (iv). Selection can be further modulated through stringent washing of the beads (v). Recovered plasmid DNA is amplified and used to start a new round of selection or screening. (FIG. 5B) Heat map showing ranked library polyclonal activity mapped to the ternary complex (although the DNA has been omitted for clarity) of the related Pfu DNA polymerase (PDB: 4AIL). Sequence segment (10A) (TgoT: E654-T676), in red, showed the highest activity.

FIG. 6A-FIG. 6D: Mutagenesis libraries

Residues targeted for diversity are shown as blue surfaces on the Tgo (36) (FIG. 6A), Pfu (PDB: 4AIL) (FIG. 6B) and E. coli Pol II (44) (FIG. 6C) backbones in cartoon representation. Motif 10A is highlighted in orange. Individual libraries in alternating colors are shown against the TgoT sequence (FIG. 6D). Libraries targeted parts of the exonuclease domain (Motifs 1, 2) and the interhelical domain (Motifs 3, 4) as well as to the palm (Motifs 4, A-, A, A+, 6-, 6+, C, C+ and 7), finger (Motifs 5, B-, B) and thumb (Motifs 8, 9, 10A, 10B, 11 and 12) polymerase subdomains.

Figure 7A:
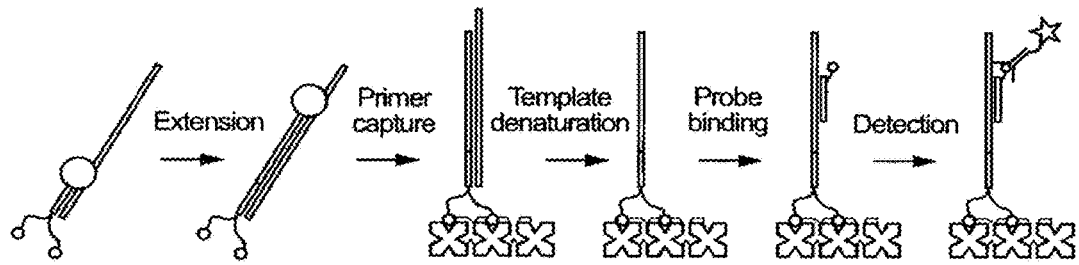
Figure 7B:
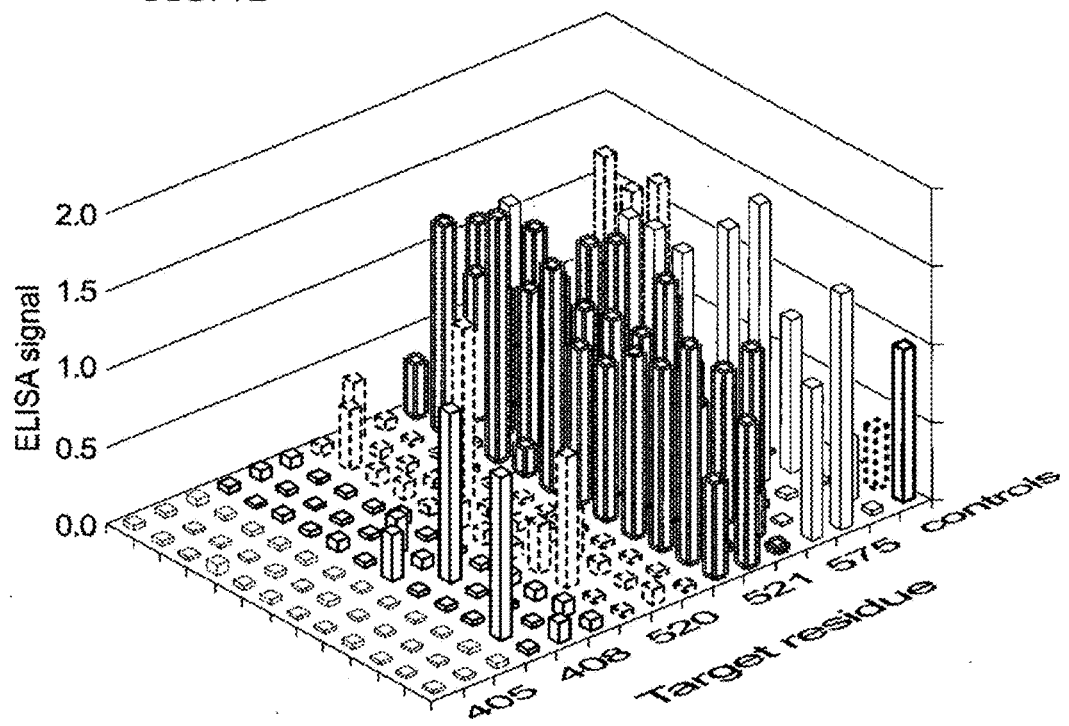

FIG. 7A-FIG. 7B: Polymerase activity assay (PAA)

(FIG. 7A) Principles of the PAA. A primer-extension reaction is carried out using a 5'-biotinylated primer that allows product immobilization onto a solid surface coated with streptavidin. The original template is removed by heat or alkali treatment and a digoxigenin (DIG)-labeled probe bound to the extended product, allowing immunodetection of the DIG label. (FIG. 7B) Individual isolates from small, single-residue, partial coverage libraries (encoded as NWC) were screened with PAA for DNA synthesis against a chemically synthesized HNA template. Residue 408 and significant SCA residues in its spatial vicinity (405, 520, 521 and 575) were initially investigated with significant activity identified in residues 521 and 575. Pre-extended controls are shown in magenta (+7) and green (+9) as well as the wild-type TgoT (red). Due to the high sensitivity of PAA, HNA RT activity is observed with all mutants except 405, but only mutations at residue 521 could successfully synthesize DNA against longer stretches of HNA.

Figure 8A:
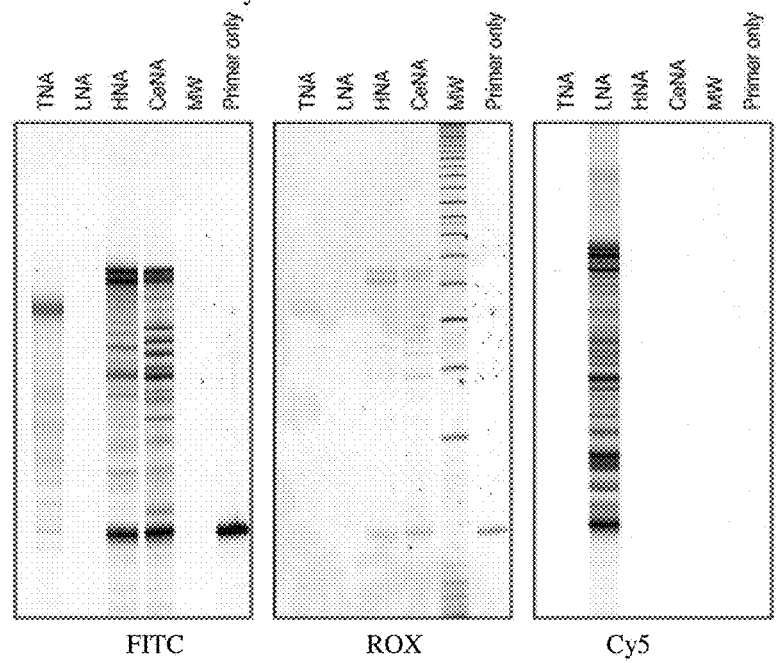
Figure 8B:
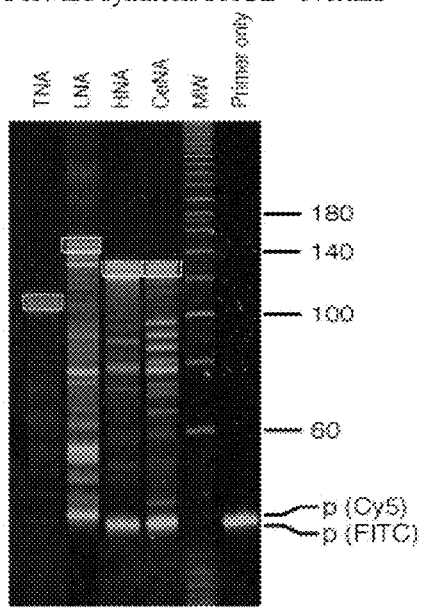
Figure 8C:
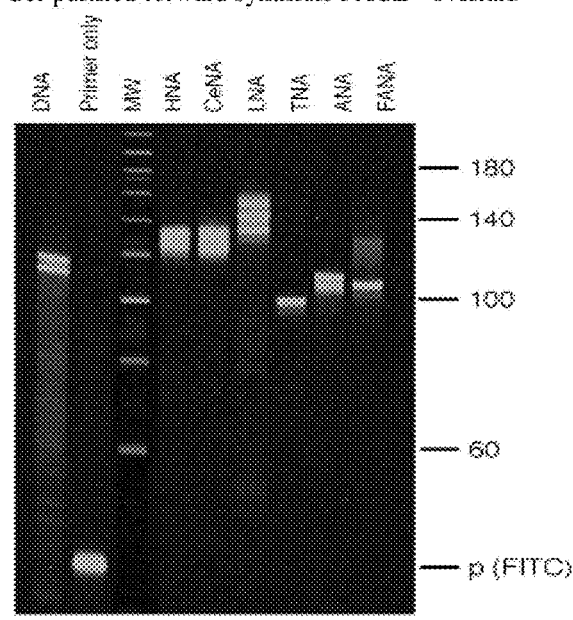
Figure 9A:
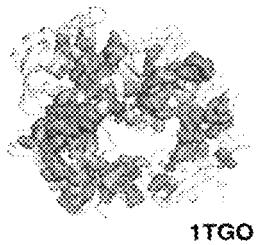
Figure 9B:
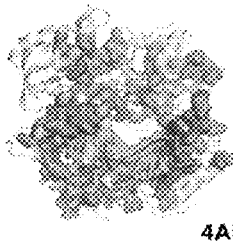
Figure 9C:
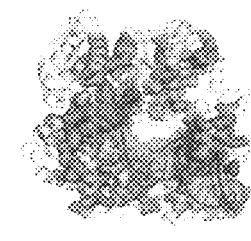
Figure 9D:
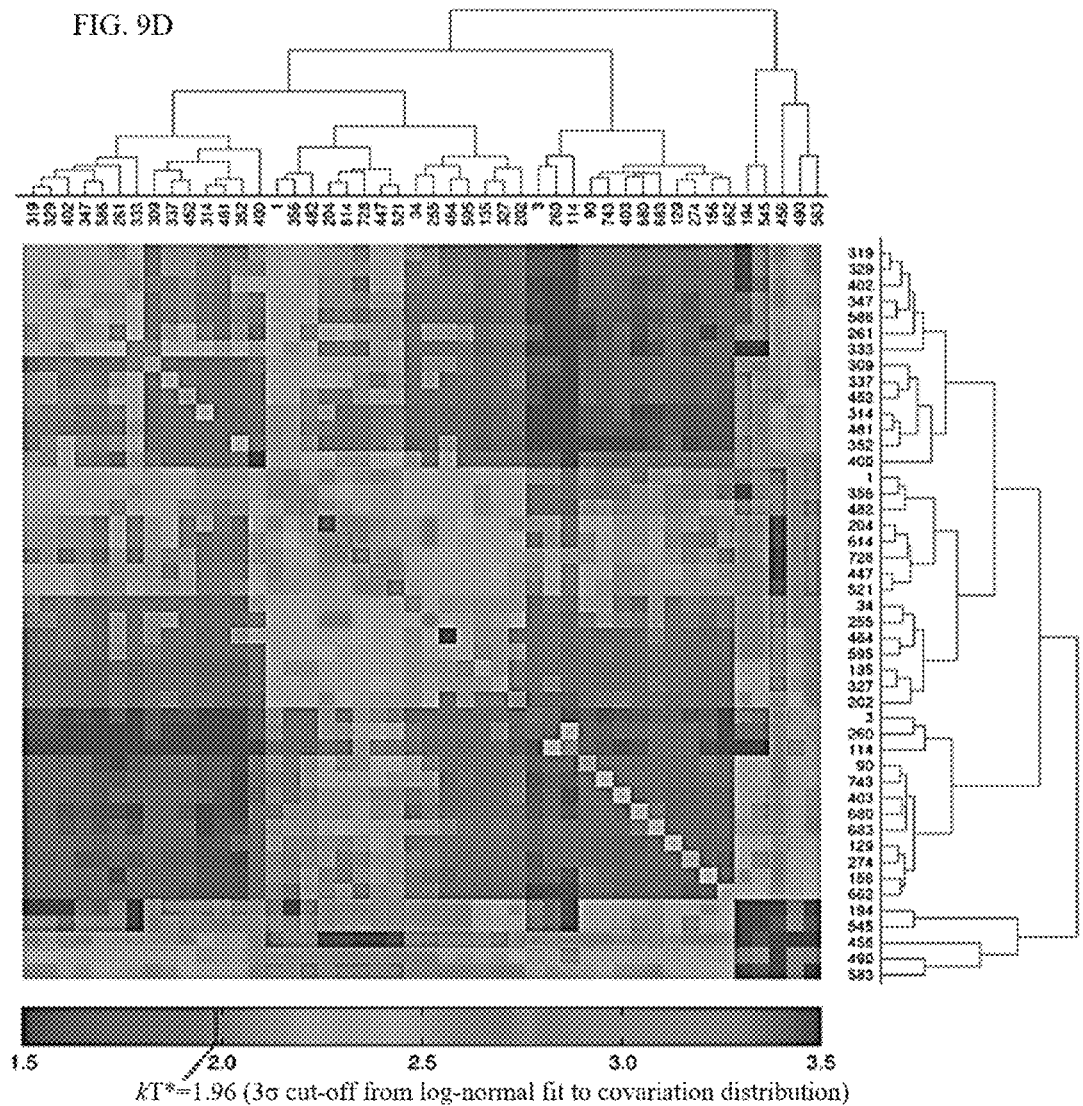

FIG. 8A-FIG. 8C: Gel electrophoresis of synthesized genetic polymers by PAGE

Forward synthesis of different genetic polymers and molecular weight marker are shown according to their individual fluorescent labels (FIG. 8A): PAGE gel showing synthesis of TNA (synthesized from 5'-FITC-bNAPfd), HNA and CeNA (synthesized from 5'FITC-tag4fdOMe) and LNA (synthesized from 5'-Cy5-Cytag4fdOMe) alongside ILS 600 molecular weight marker (ROX labeled), scanned in three separate channels (FITC, ROX and Cy5). Single wavelength scans are overlaid (FIG. 8B) and arbitrarily colored (FITC-red, ROX and Cy5-green). Full-length products are excised (grey boxes) and re-run on denaturing urea-PAGE (FIG. 8C) or AAGE (FIG. 3F).

FIG. 9A-FIG. 9D: Statistical coupling analysis (SCA) of PolB-family polymerases

A manually-curated sequence alignment of 671 non-redundant B-family polymerases was used in SCA. The distribution of covariation values obtained fitted a log-normal distribution (SI section (9.)) Highly significant residues (kT*>2.4) (orange) and highly conserved residues (cyan) are mapped onto (FIG. 9A) the apo structure of Tgo (1 TGO), (FIG. 9B) the ternary complex of the related Pfu DNA polymerase (PDB: 4AIL), and (FIG. 9C) the related *E. coli* pol 11 (3MAQ) (primer/template, green/purple). (FIG. 9D) Hierarchical clustering of the residues identified by SCA as covariant with I521.

Figure 10A:
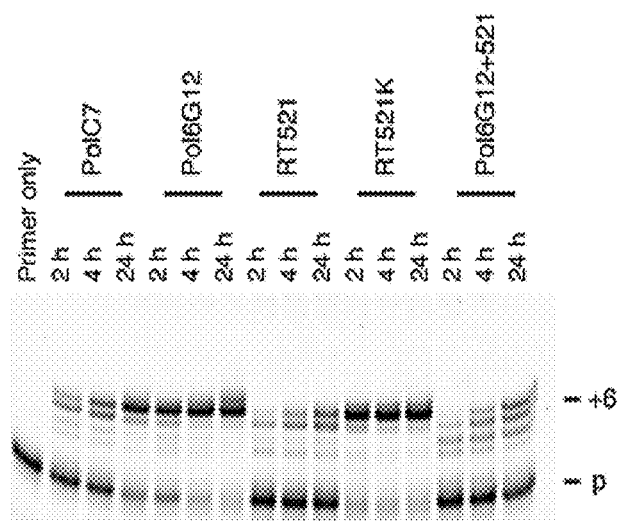
Figure 10B:
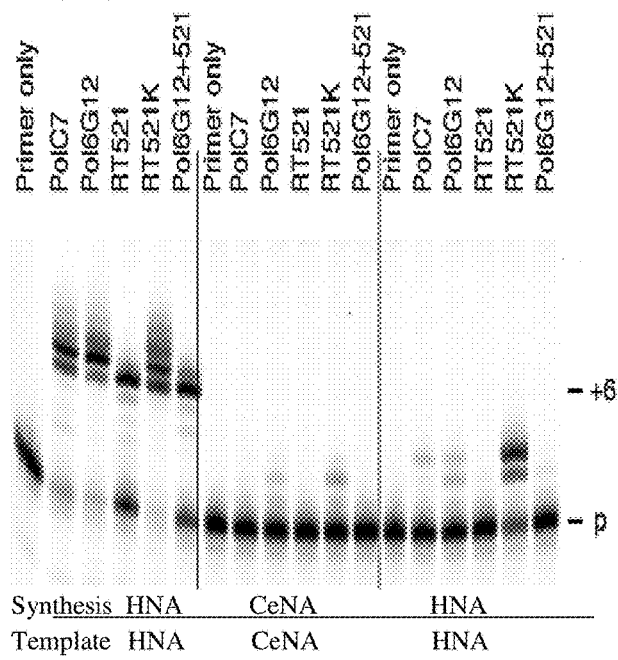
Figure 10C:
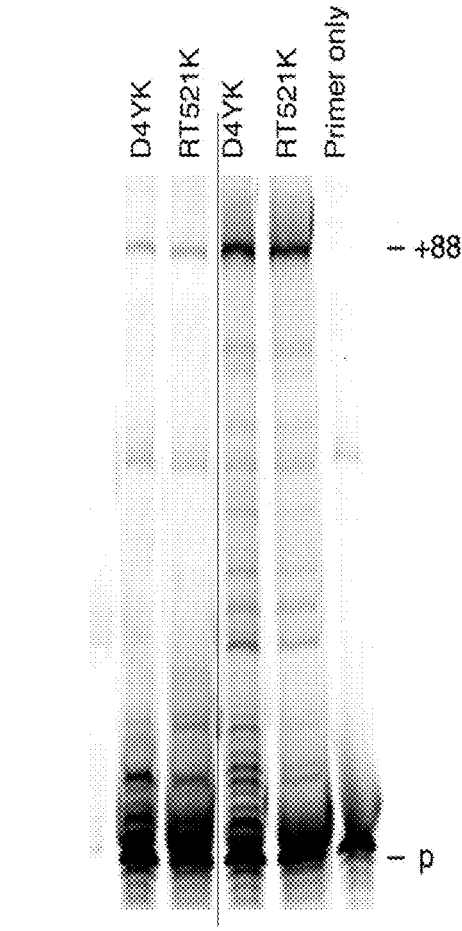

FIG. 10A-FIG. 10C: XNA-templated XNA synthesis.

(FIG. 10A, FIG. 10B) Polymerases PolC7, Pol6G12, RT521, RT521K and Pol6G12521 (Pol6G12:1521L) were screened for their ability to synthesize (FIG. 10A) CeNA on a CeNA template or (FIG. 10B) (from left to right) HNA on a CeNA template, CeNA on an HNA template or HNA on an HNA template. (FIG. 10C) FANA-templated FANA synthesis by D4K and RT521K (left) is shown compared to standard FANA reverse transcription (FANA-templated DNA synthesis) (right) (TempNpure, Table S3).

FIG. 11A-FIG. 11E: XNA synthesis and RT-PCR aggregate fidelities and error spectra RT-PCR, aggregate misincorporation rates and error spectra of CeNA (FIG. 11A), ANA (FIG. 11B), TNA (FIG. 11C), FANA (FIG. 11D) and LNA (FIG. 11E). NEB Low Molecular weight marker (MW) and no template controls (NT) are shown.

Figure 12:
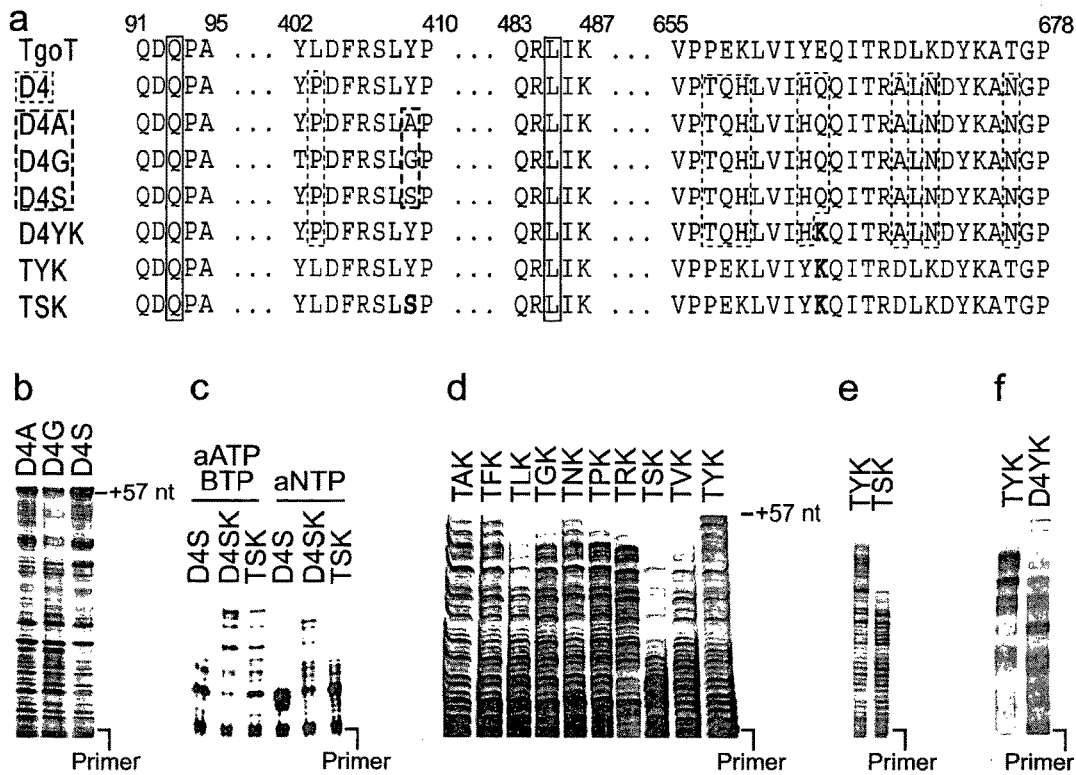

FIG. 12 Development of D4YK (a) Alignment of the polymerase mutant sequences in the subsequent primer extensions: TgoT (corresponding to SEQ ID NO:2 as indicated); D4 (SEQ ID NO:129); D4A (SEQ ID NO:130); D4G (SEQ ID NO:131); D4S (SEQ ID NO:132); D4YK (SEQ ID NO:133); TYK (SEQ ID NO:134); and TSK (SEQ ID NO:135). (b) Incorporation of aATP and BTP by small panel of D4 steric gate mutants. All show full-length extension but D4S appears best. (c) Optimisation of thumb subdomain mutations for ANA synthesis. D4SK is superior to D4 or TSK with either aATP/BTP or aNTP. (d) Screen of steric gate mutants for ANA synthesis, showing TYK generates the most full length product. (e) Comparison of TYK and TSK with aNTP to demonstrate Y409 is superior to S409. (f) Comparison of TYK and D4YK with aNTP, demonstrating that D4YK is the best ANA synthetase.

Figure 13:
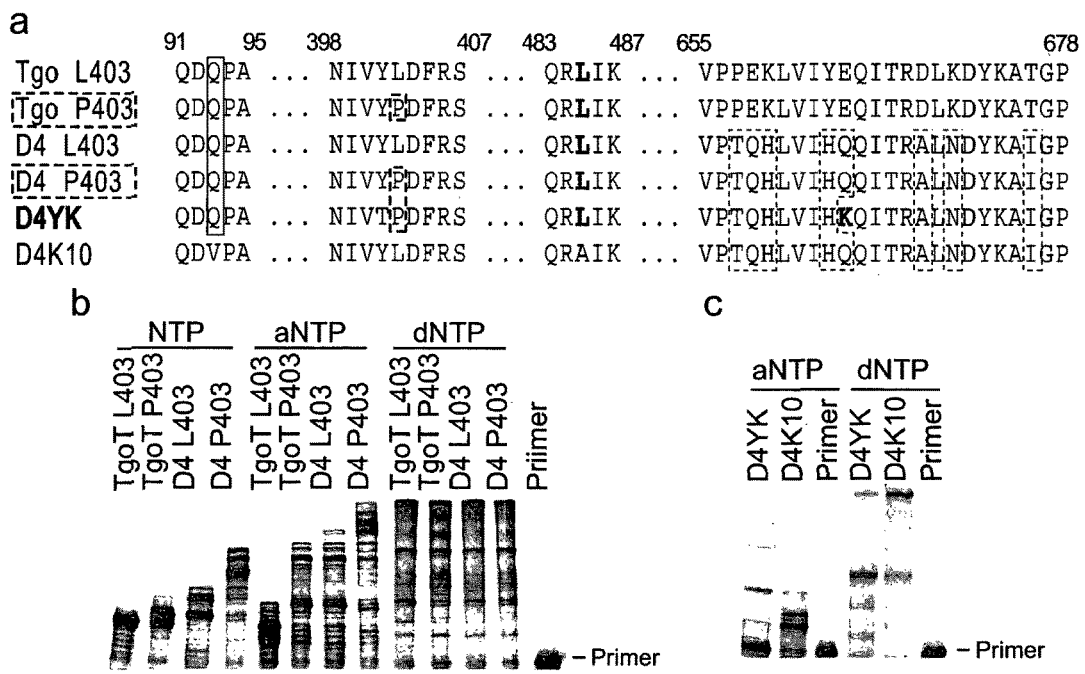

FIG. 13 D4 active site reversion analysis (a) Alignment of the polymerase mutant sequences in the subsequent primer extensions: Tgo L403 (SEQ ID NO:136); Tgo P403 (SEQ ID NO:137); D4 L403 (SEQ ID NO:138); D4 P403 (SEQ ID NO:139); D4YK (SEQ ID NO:140); and D4K10 (SEQ ID NO:141). (b) Reversion analysis of L403P mutation on ANA synthesis. For both RNA (NTP) and ANA (aNTP) synthesis the D4 mutation (P403) is more active than Tgo wild-type (L403). Similarly, D4 is more active than TgoT with both L403 and P403 for RNA and ANA synthesis. (c) D4K10 is D4 V93, L403, A485 (that is, reversion of the V93Q and A485L mutations present in TgoT and the D4 active site mutation L403P). Clearly, D4YK is substantially more active than D4K10 as an ANA synthetase.

Figure 14:
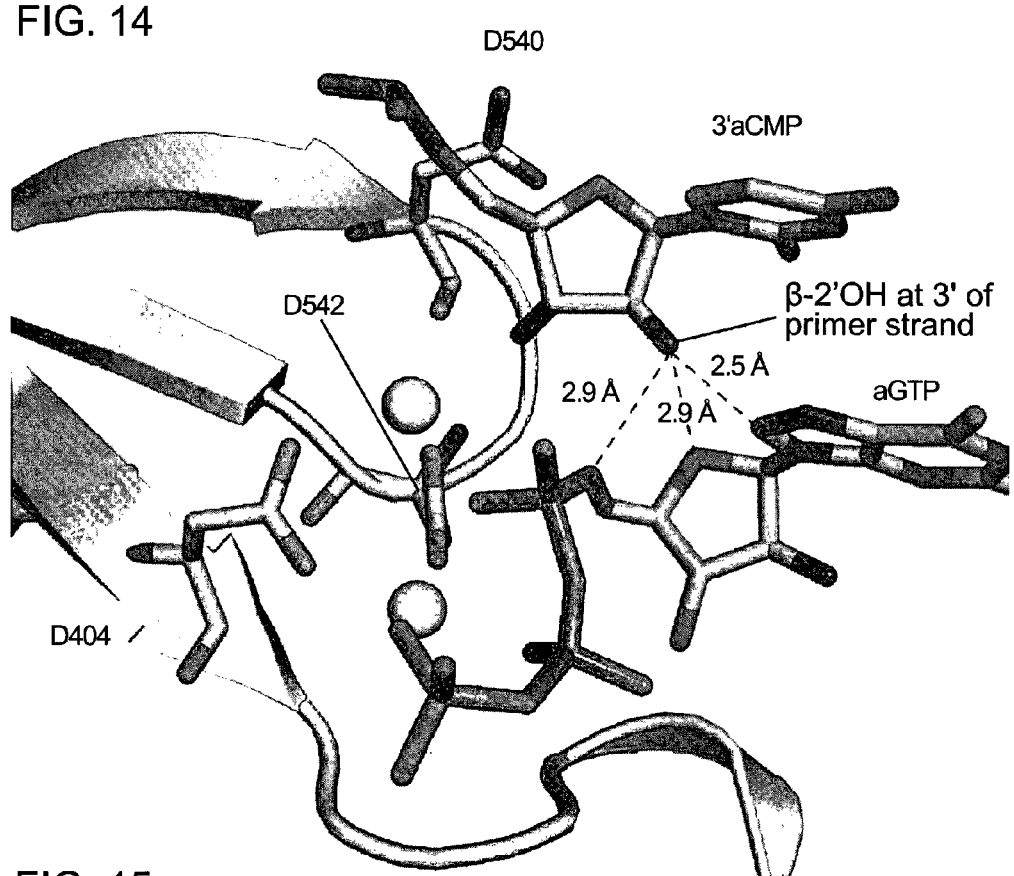

FIG. 14 Possible steric clash generated by 3'ANA during synthesis beta-2'OH (brown) modeled onto the dCMP at the 3' of the primer (nascent) strand (aCMP) and incoming dGTP (aGTP) of the DNA in *E. coli* pol II (PDB: 3MAQ). The three catalytic aspartates (D404, D540 and D542 using Tgo numbering) are shown as sticks and $Mg^{2+}$ as yellow spheres. This model suggests neither 3' nor incoming ANA nucleotide would directly affect $Mg^{2+}$ coordination, but rather that there may be a steric clash generated between the incoming dNTP and 3'aNMP. Mutations to L403, shown in orange adjacent to D404, may affect dNTP coordination and reduce any steric clash, possibly explaining the effect of L403P in D4

Figure 15:
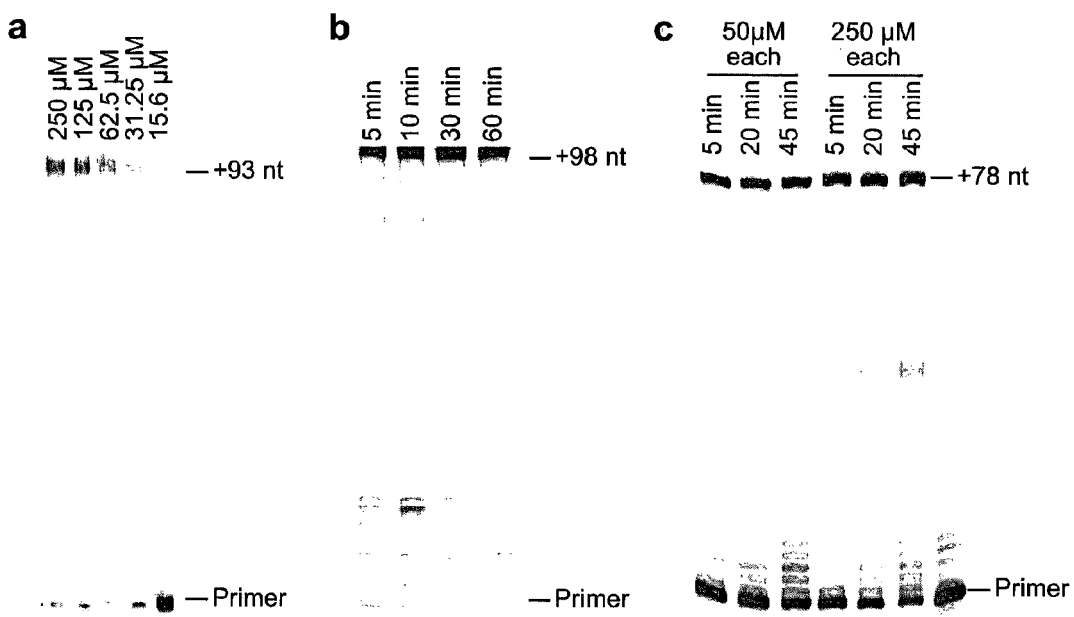

FIG. 15 FANA synthesis by D4YK (a) FANA synthesis at reduced faNTP concentrations. Synthesis of YtRtemp9 (encoding 93 nt incorporations) remains robust until it drops below 31.25 mM each faNTP. (b) Timecourse of YtRtemp8 (encoding 98 nt incorporations) synthesis by D4YK, showing substantial full-length synthesis in only 5 min. (c) Timecourse of ApLib5 (encoding 78 nt incorporations, of which 40 are random nucleotides) synthesis by D4YK, again showing substantial full length product in only 5 min.

Figure 16:
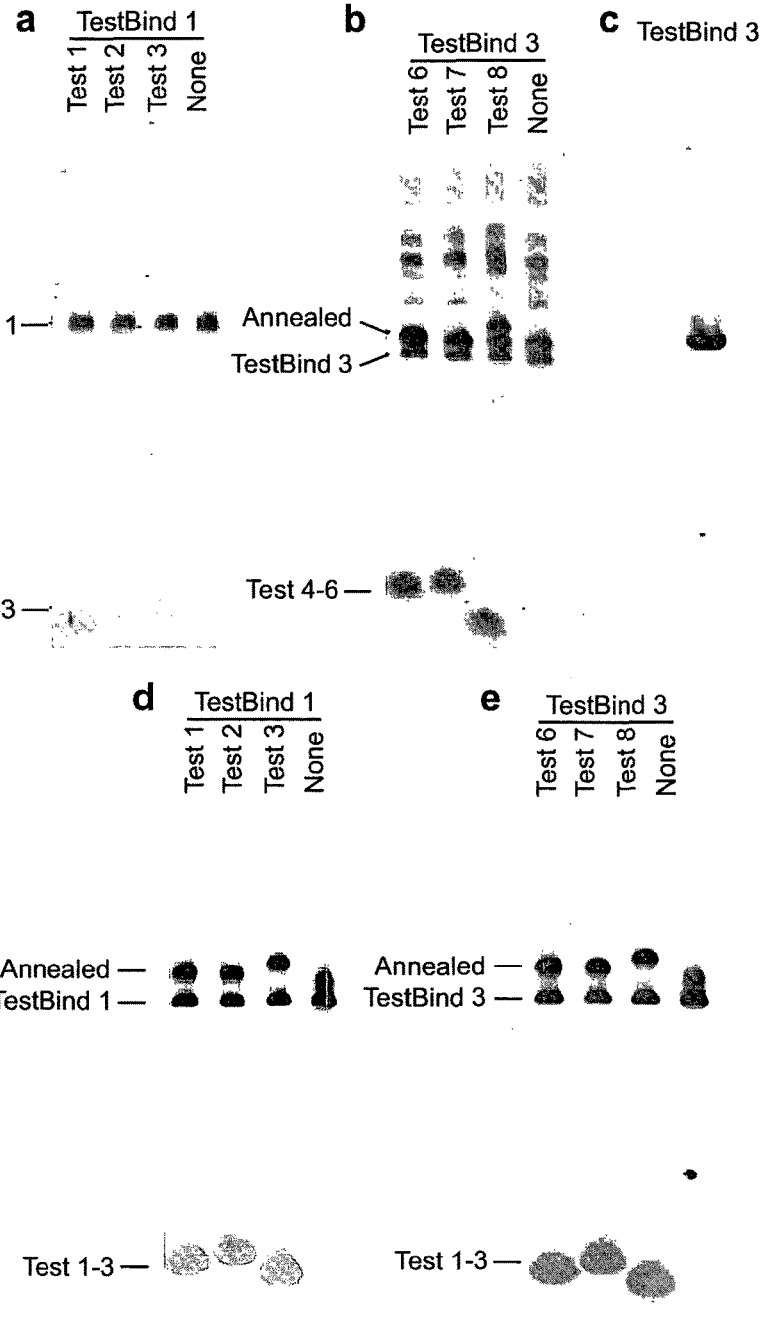

FIG. 16 Investigation of the base-pairing bias of ANA and FANA.

(a) Purine-rich DNA (Test1-3) anneals to pyrimidine-rich ANA (TestBind1) extremely poorly. (b) Pyrimidine-rich DNA (Test6-8) anneals well to purine-rich ANA (TestBind3). Pyrimidine-rich ANA also appears to form secondary structures as indicated by multiple bands on the gel, which are not present when pyrimidine-rich ANA are run on a denaturing (8 M urea) gel (c) implying the ANA is of a single length. In contrast to ANA, both purine-rich (d) and pyrimidine-rich (e) FANA bind to complementary DNA. (f) Sequences of the oligonucleotides used in this figure were: TestBind1 (SEQ ID NO:145); Test1 (SEQ ID NO:146); Test2 (SEQ ID NO:147); Test3 (SEQ ID NO:148); TestBind3 (SEQ ID NO:149); Test6 (SEQ ID NO:150); Test7 (SEQ ID NO:110); and Test8 (SEQ ID NO:151).

Figures 17, 18:
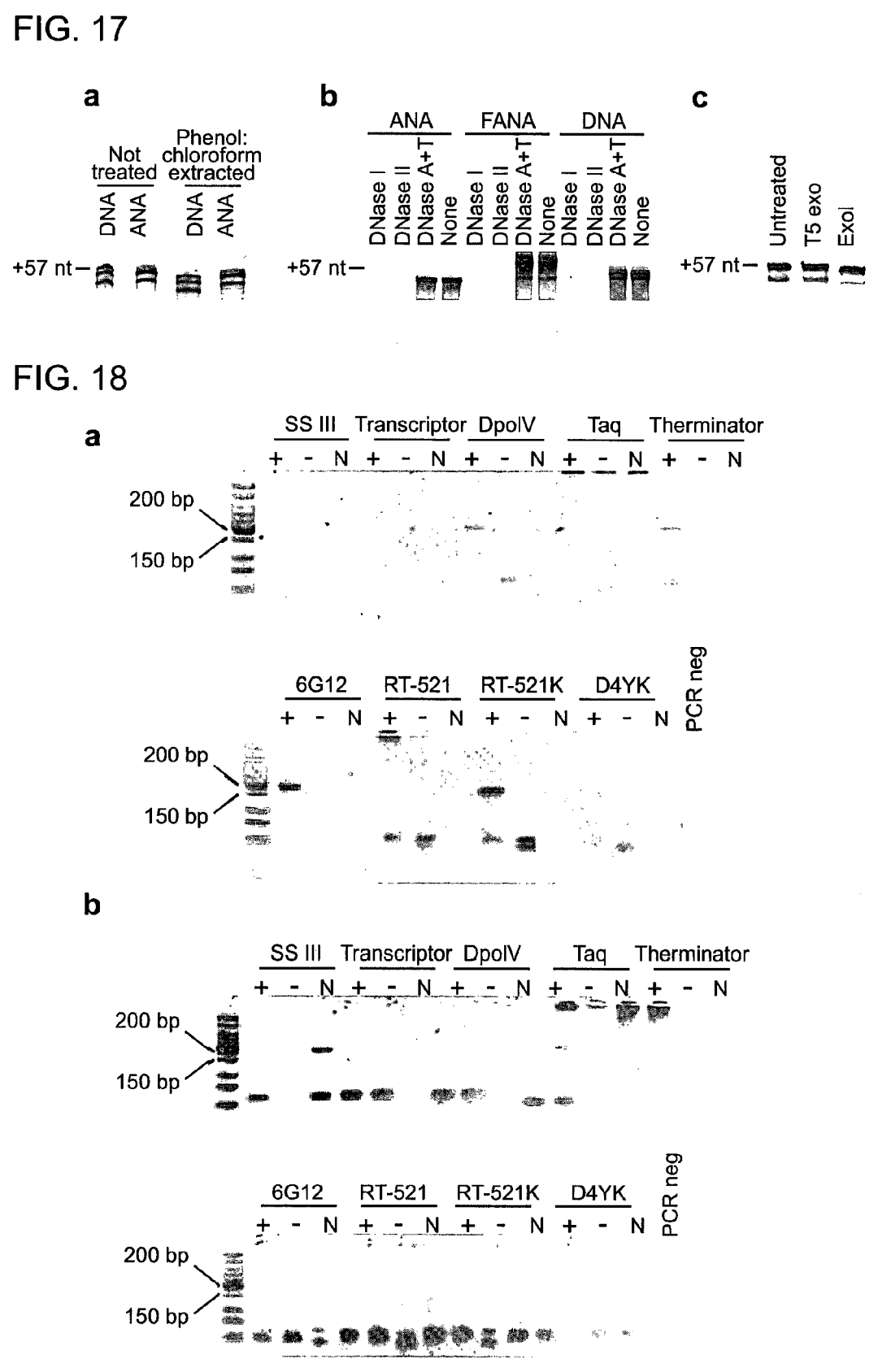

FIG. 17 Properties of ANA and FANA (a) ANA is efficiently recovered after phenol:chloroform extraction. (b) SYBR Gold-stained gel demonstrating that ANA and FANA, like DNA, are sensitive to DNaseI and DNaseII but resistant to RNases A/T. (c) ANA:DNA hybrid duplexes are resistant to T5 exonuclease (5'-3') and Exonuclease I (3'-5') treatment.

FIG. 18 FANA and ANA RT screens (a) PCR following RT using various enzymes as FANA reverse transcriptases demonstrates DpolV and Therminator have weak FANA RT activity and that Pol6G12 {Pinheiro, #1084} and RT-521K have robust FANA RT activity. RT-521 does have FANA RT activity but has to be removed prior to PCR, or the PCR fails, as seen here. b) PCR following RT using various enzymes as ANA reverse transcriptases implies no enzymes are effective as ANA RTs. This is not in fact the case and is likely due to the ineffective RT primer used I this study FIG. 19 RT-PCR and fidelity of synthesis RT-PCR of (a) ANA and (b) FANA showing a PCR band is only obtained when both ANA and RT-521K were present in the RT reaction and estimated fidelity of synthesis.

Figure 20:
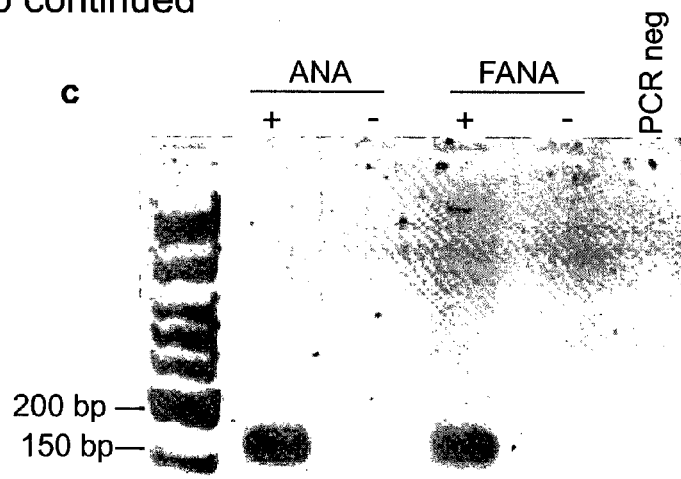

FIG. 20 Affinity determination of ANA and FANA N40 libraries for libraries.

EMSA and plot of unbound fraction of (a) ANA and (b) FANA used to estimate affinity of initial libraries for lysozyme. (c) RT-PCR of ANA and FANA recovered following SELEX Round 1 using the parameters suggested by EMSA analysis.

Figure 21:
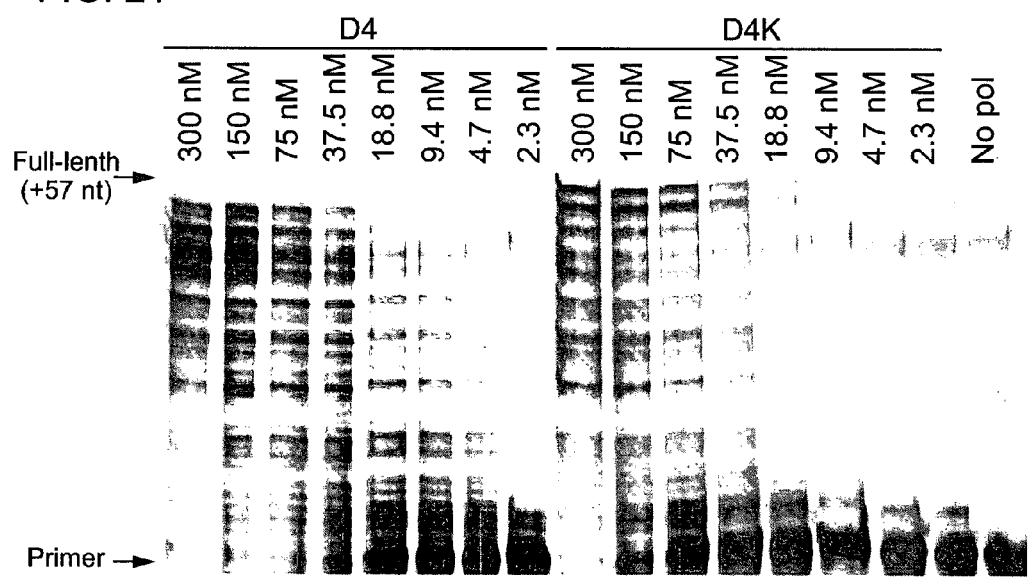

FIG. 21 shows comparative data demonstrating the superior qualities of the E664K mutation (D4K compared to prior art D4).

Figure 22:
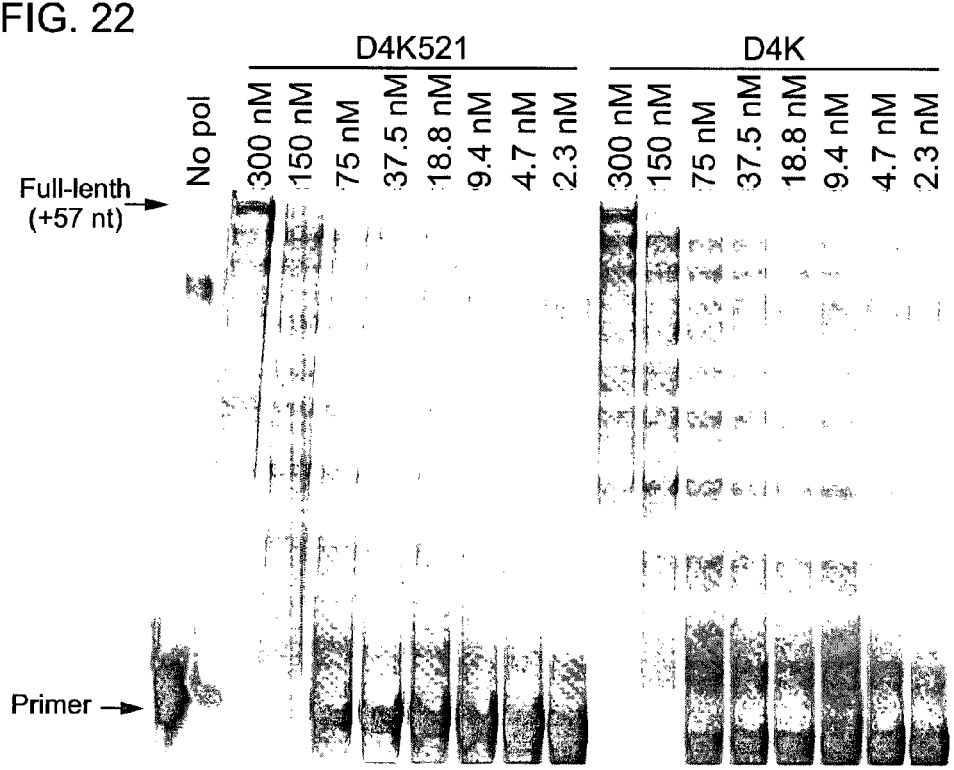

FIG. 22 shows comparative data demonstrating the superior qualities of the I521L mutation (D4K521 compared to D4K).

Figure 23:
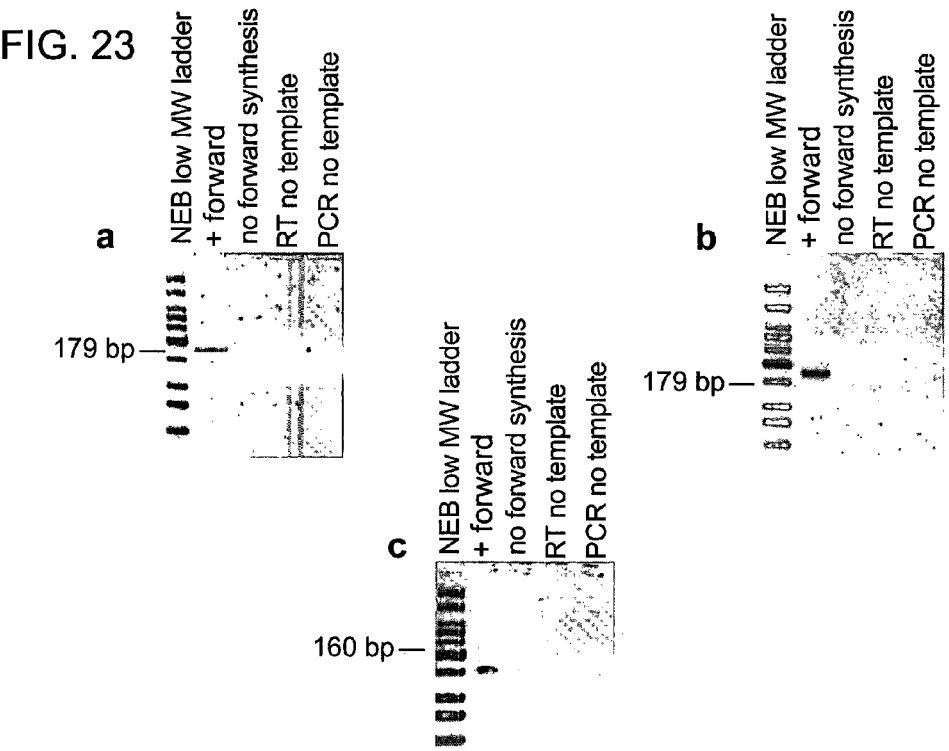

FIG. 23 shows RT-PCR of (a) arabino nucleic acid (ANA), (b) fluoroarabino nucleic acid (FANA) and (c) a "tetra-antimetabolite" polymer consisting Cladribine, araC, araG and 5-fluorodeoxyuracil (Floxuradine).

Figure 24:
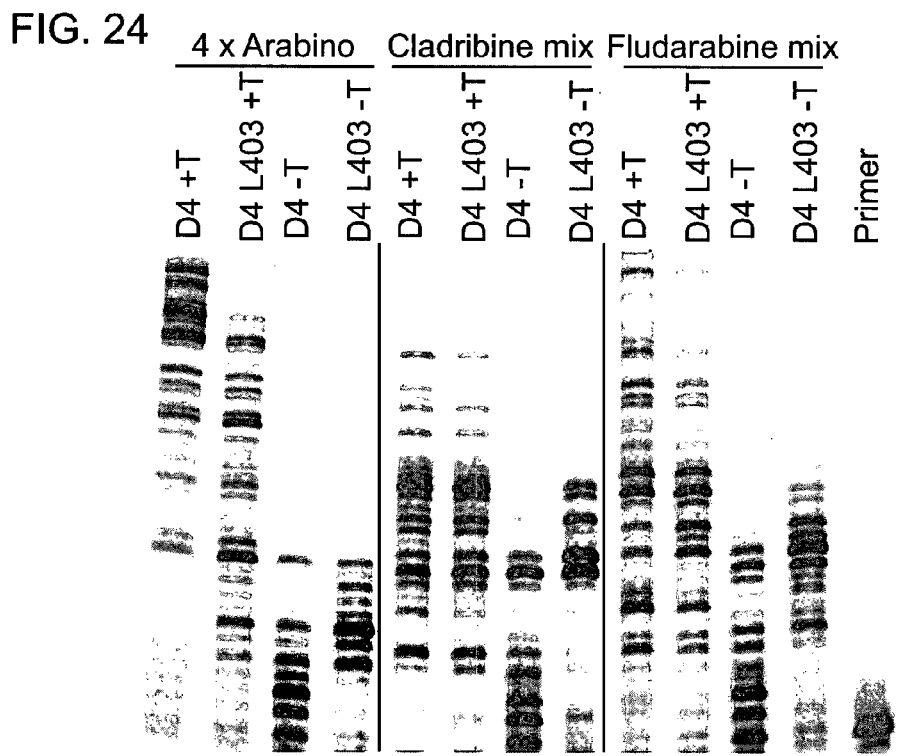

FIG. 24 shows analysis of the influence of 403 and 485 (Therminator) mutations on
ANA polymerase activity.
D4+T=D4 with Therminator mutation
D4 L403+T=D4 with L403P mutation reversed, and with Therminator mutation.
D4−T/D4K03−T=as above but with Therminator mutation reversed.

Reaction conditions: 1× ThermoPol buffer (NEB), 0.25 mM each araNTP, 1.2 pmol Cy5-labelled DNA primer (FD), 2.4 pmol DNA template (YtRtemp7), 300 nM D4K. Incubated for 4 cycles of: 10 sec 94° C., 5 min 50° C., 30 m 64° C. and analysed on 6% denaturing (8M urea) PAGE.

"4× Arabino": equimolar mix of each ANA-NTP
"Cladribine mix": equimolar mix of Cladribine (9-β-D-arabinofuranosyl-2-fluoroadenine), araC (9-β-D-arabino-furanosyl-cytosine), araG (9-β-Darabinofuranosyl-guanosine) and Floxuridine (5-fluoro-2'-deoxyuridine) 5' triphosphates.

"Fludarabine mix": equimolar mix of (2'-deoxy-β-2'-chloro-adenosine), araC (9-β-D-arabinofuranosyl-cytosine), araG (9-β-D-arabinofuranosyl-guanosine) and Floxuridine (5-fluoro-2'-deoxyuridine) 5'triphosphates.

Figure 25:
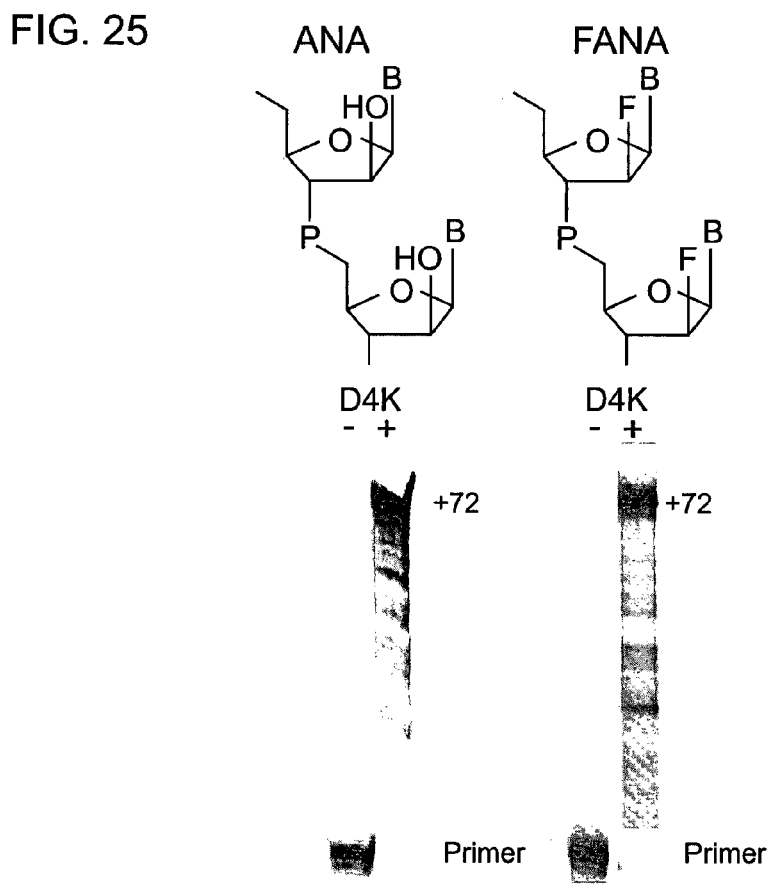

FIG. 25 shows structures and forward synthesis of arabinonucleic acid (ANA) and fluoroarabinonucleic acid (FANA) extension by D4K.

FIG. 26 shows (a) Reverse transcription, (b) PCR and aggregate fidelity of arabinonucleic acid (ANA) and (c) reverse transcription, (d) PCR and aggregate fidelity of fluoroarabinonucleic acid (FANA) synthesis by D4K.

Figure 27:
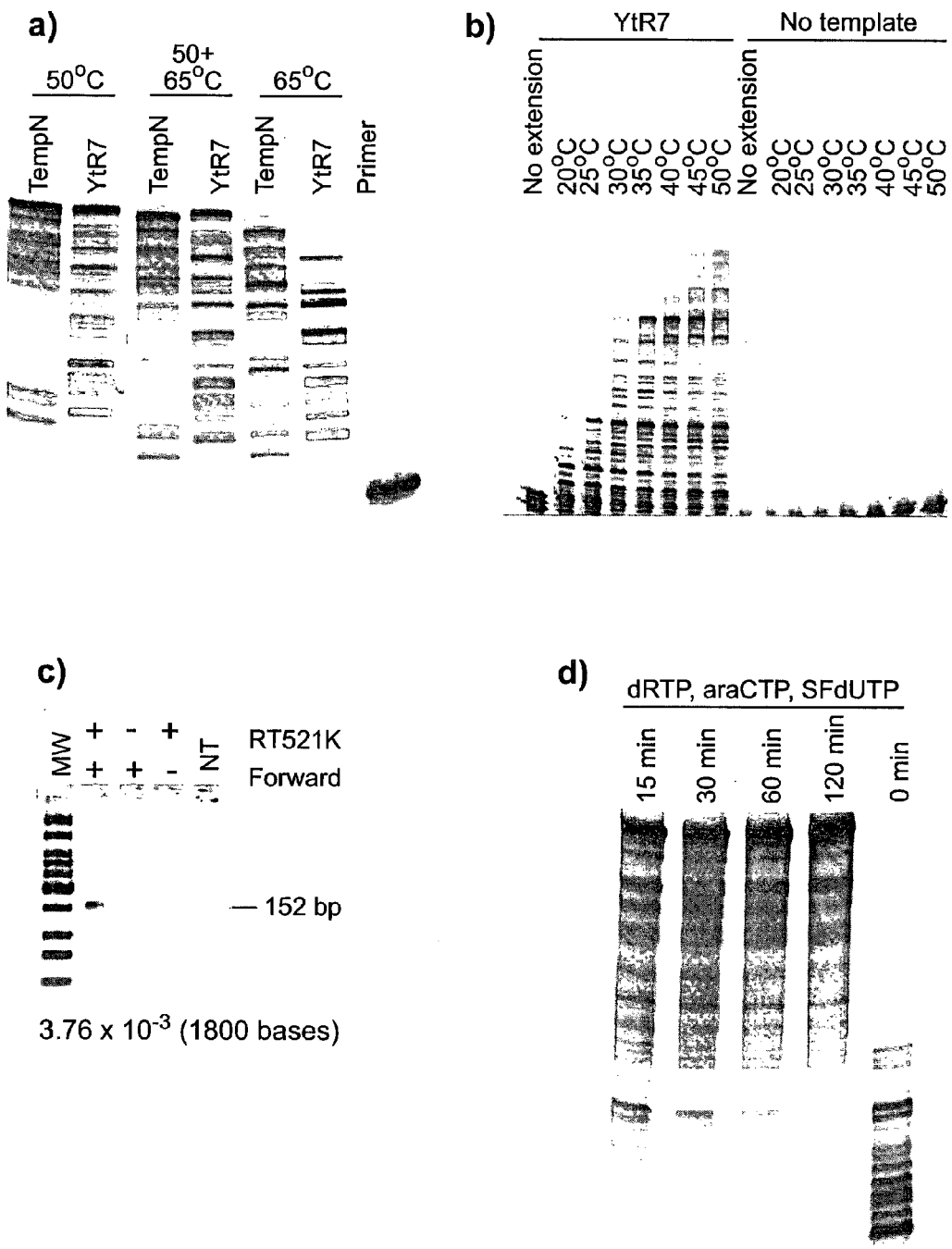

FIG. 27 shows (a) Forward synthesis of a polymer consisting of Fludarabine (9-β-Darabinofuranosyl-2-fluoroadenine), araC (9-β-D-arabinofuranosyl-cytosine), araG (9-β-D-arabinofuranosyl-guanosine) and Floxuridine (5-fluoro-2'-deoxyuridine), on two different templates for 30 min at 50° C., 15 min at 50° C. and 15 min at 65° C. or 30 min at 65° C. by D4K. (b) Synthesis of a longer template (YtR7) by D4K for 2 min at various temperatures. 50° C. was concluded to be the optimum temperature for this reaction. (c) PCR of reverse transcribed YtR7 (template used in (b)). Expected PCR product=152 bp, 1.8 kb of sequence data were analysed. (d) Timecourse showing synthesis with dRTP, araCTP and 5'fluoro-dCTP at 65° C. demonstrating the improvement when Fludarabine is not used.

Figure 28:
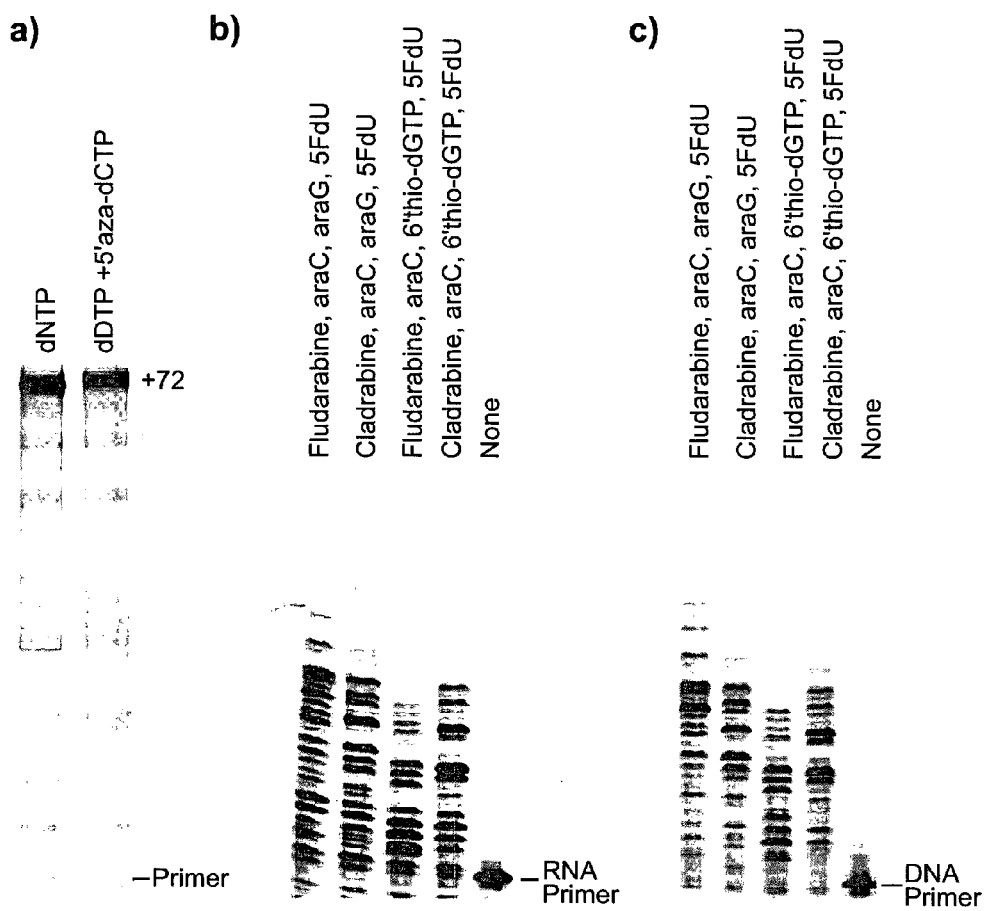

FIG. 28 shows (a) Polymer synthesis by D4K of all dNTP or with dCTP replaced by 5'aza-dCTP (Decitabine). (b) Short extensions demonstrating incorporation of Fludarabine, Cladribine, araC, araG, 6'thio-dGTP and 5'fluoro-dUTP (5FdUTP) in various combinations from RNA and (c) DNA primers.

Figure 29:
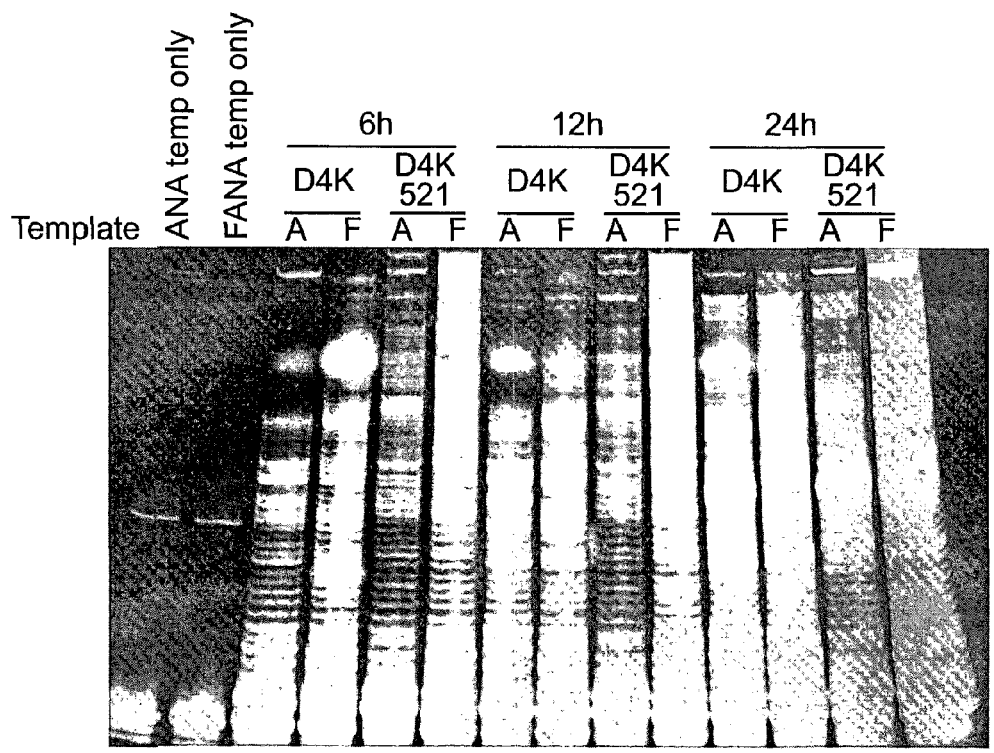

FIG. 29 shows synthesis of arabino nucleic acids from ANA and FANA templates.

Figure 30:
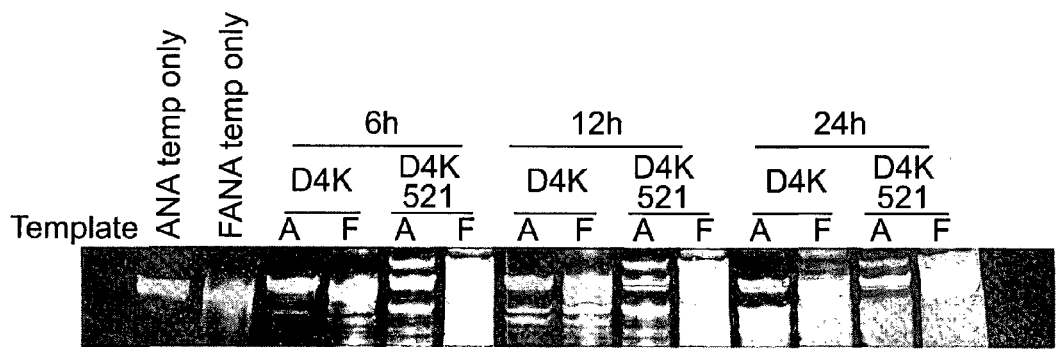

FIG. 30 shows synthesis of arabino nucleic acids from ANA and FANA templates in more detail.

FIG. 31 shows Synthesis of txNA by D4YK.

FIG. 32 shows Synthesis of txNAs of different compositions

Figure 34:
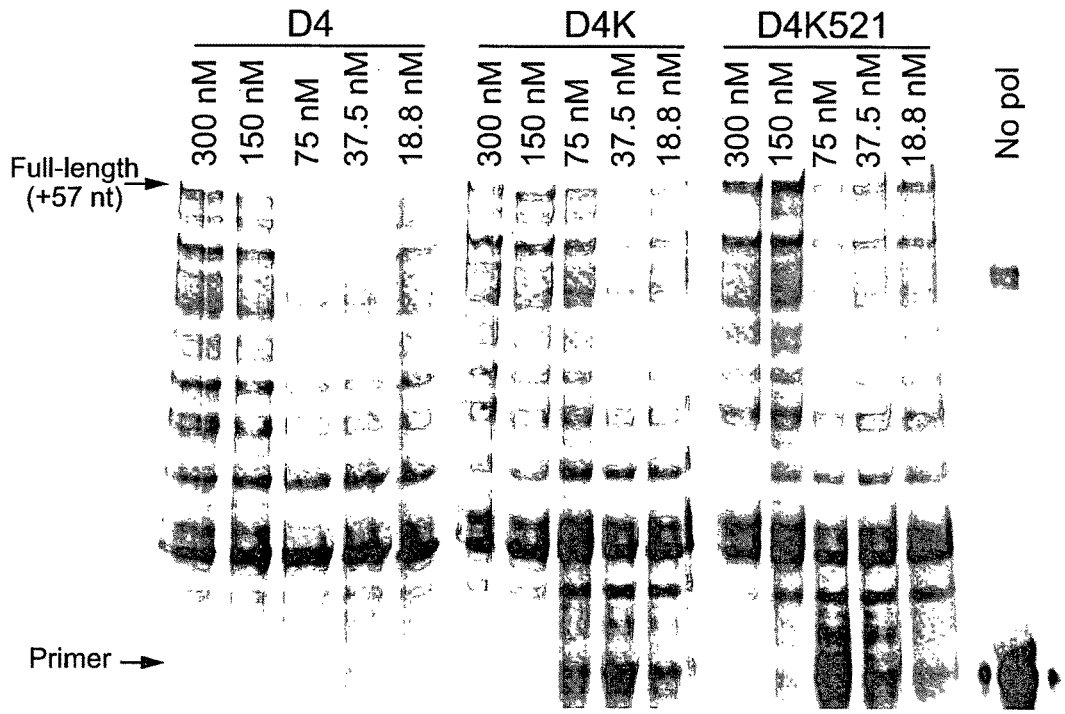
Figure 35:
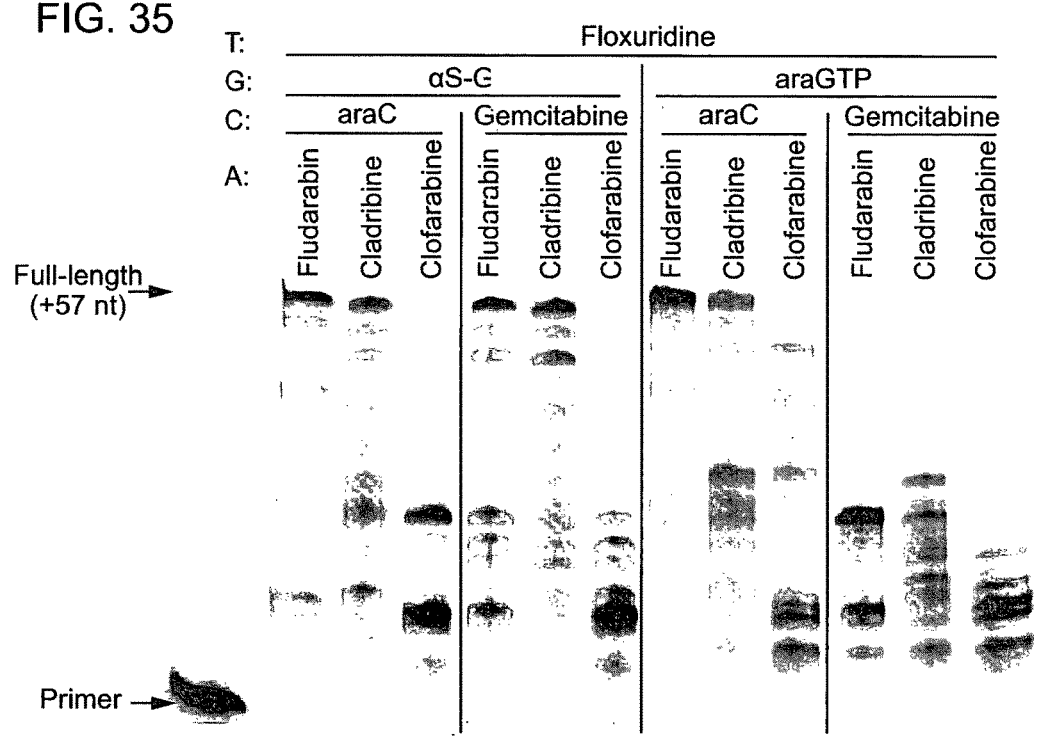
Figure 36:
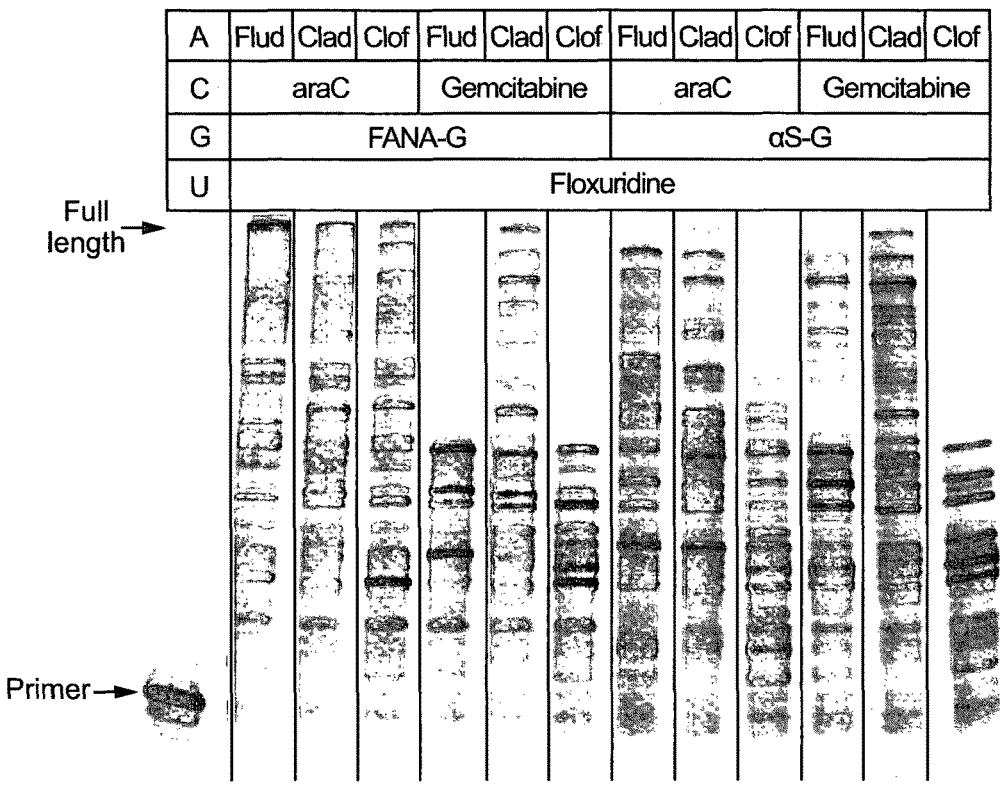
Figure 37:
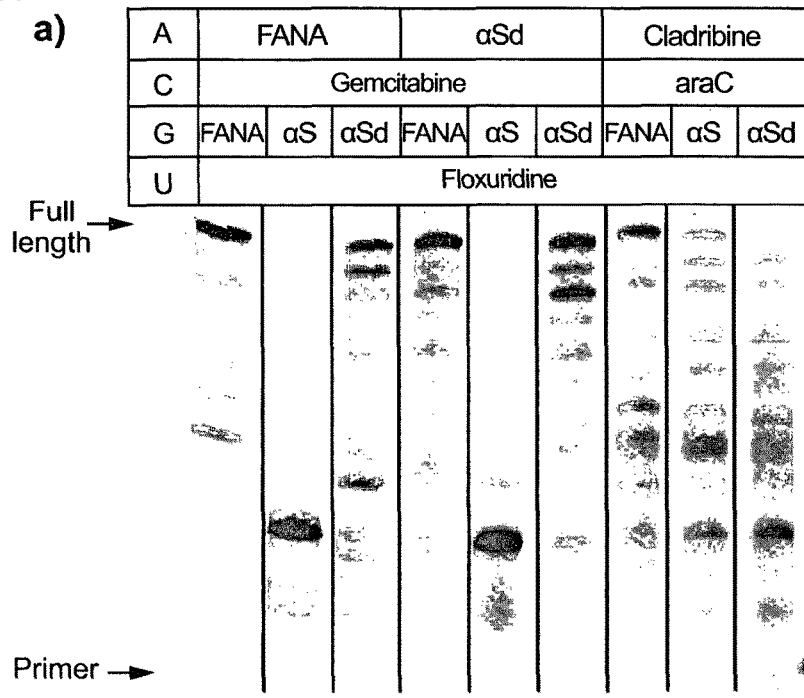
Figure 37:
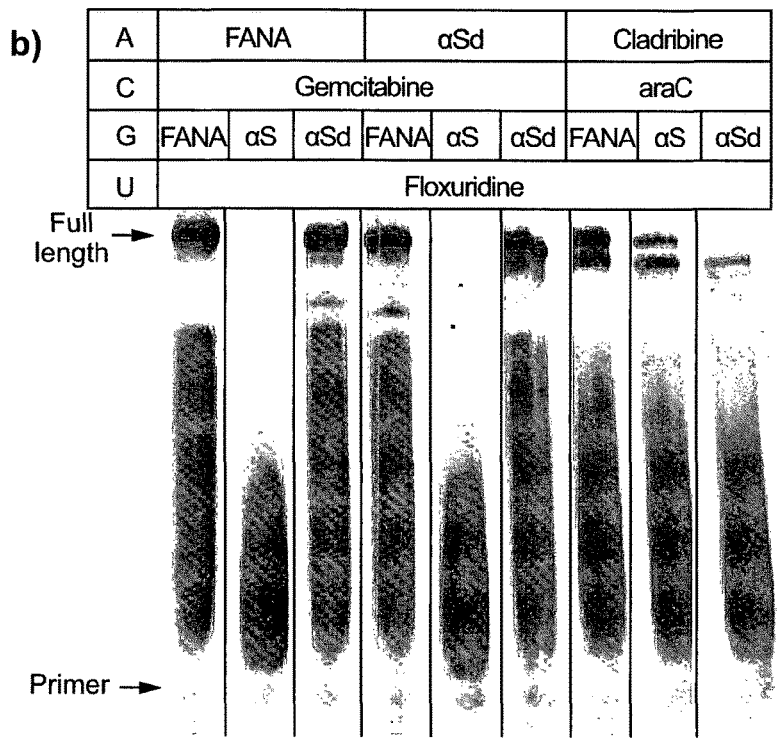
Figure 38:
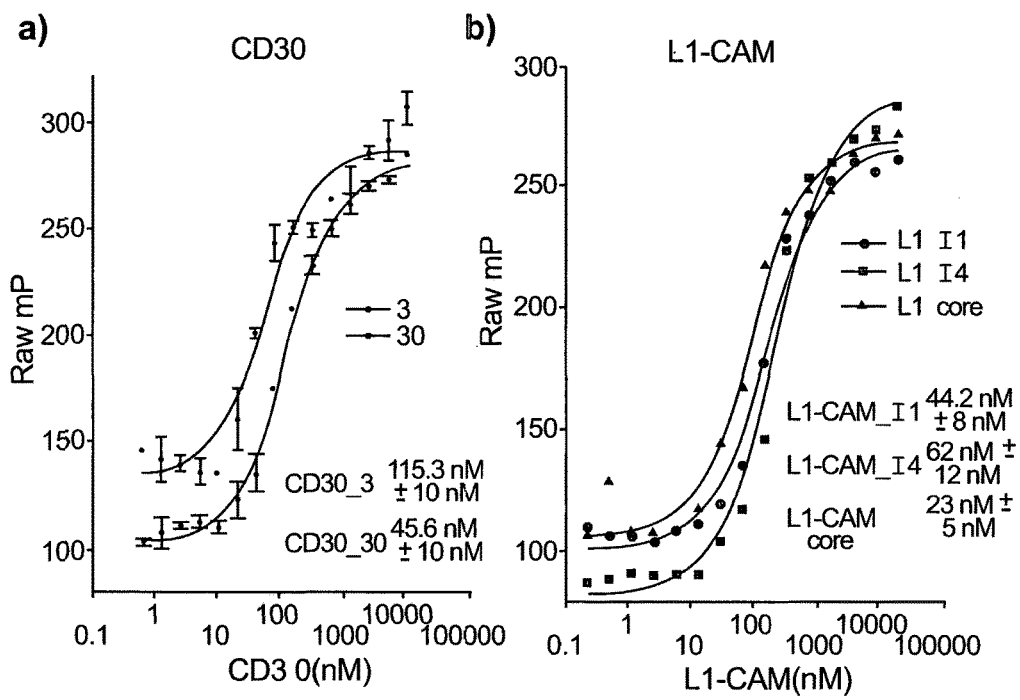
Figure 39:
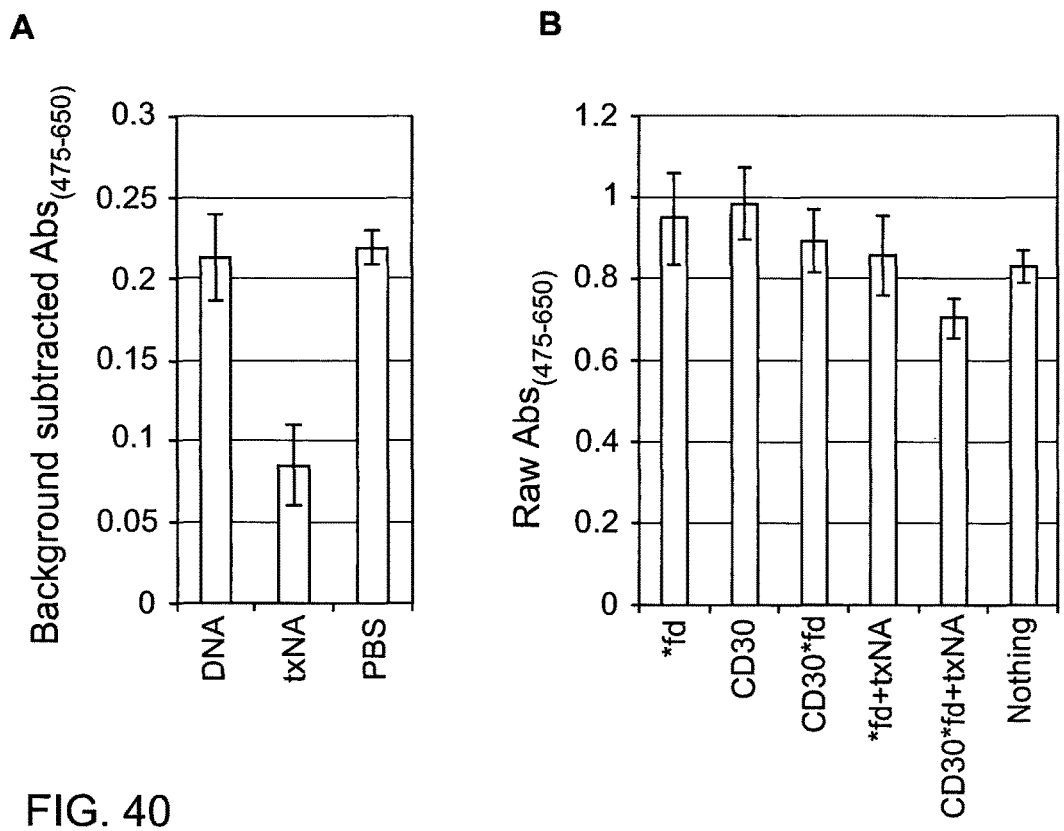
Figure 40:
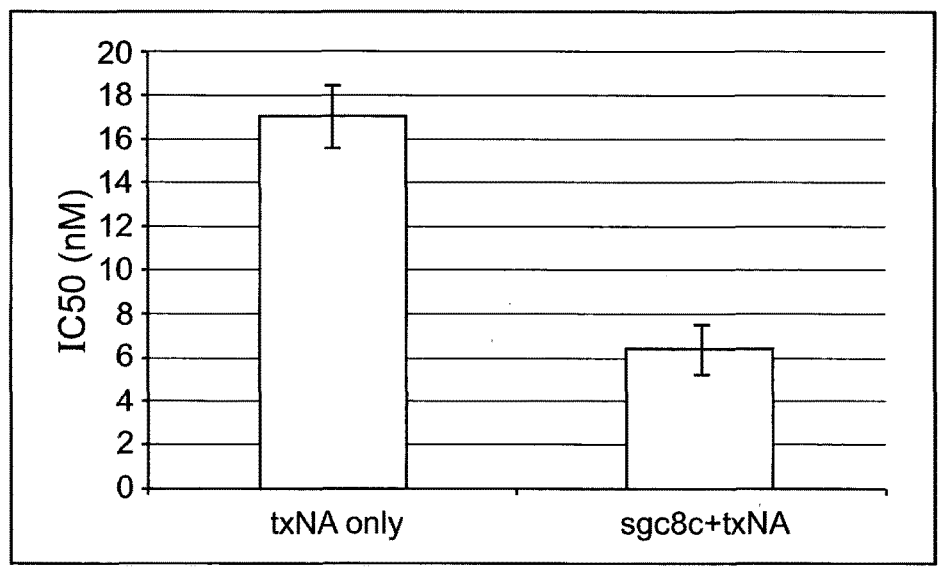
Figure 41:
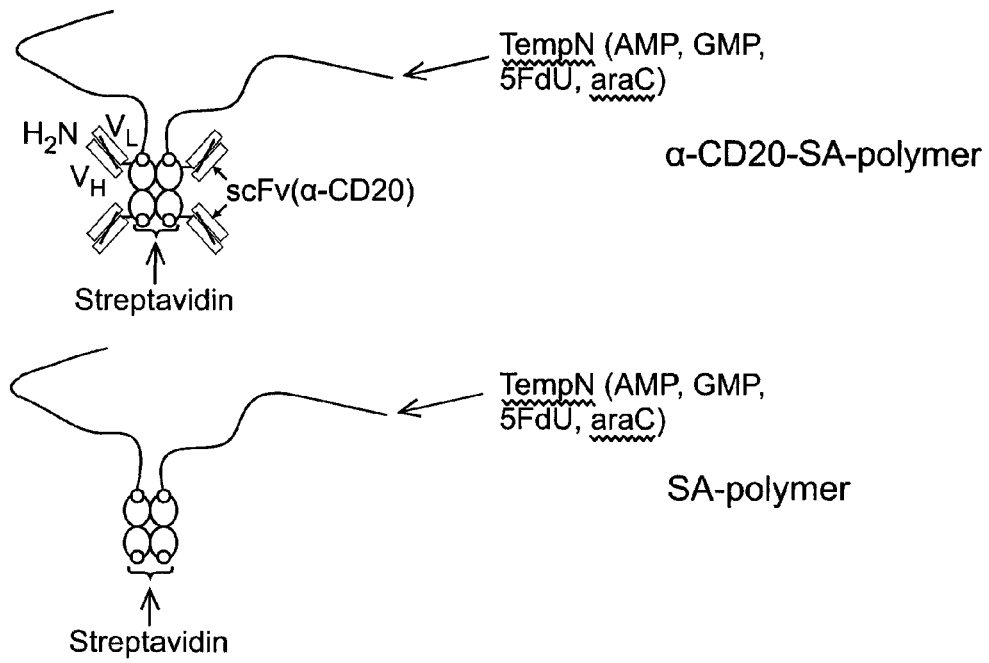
Figure 42:
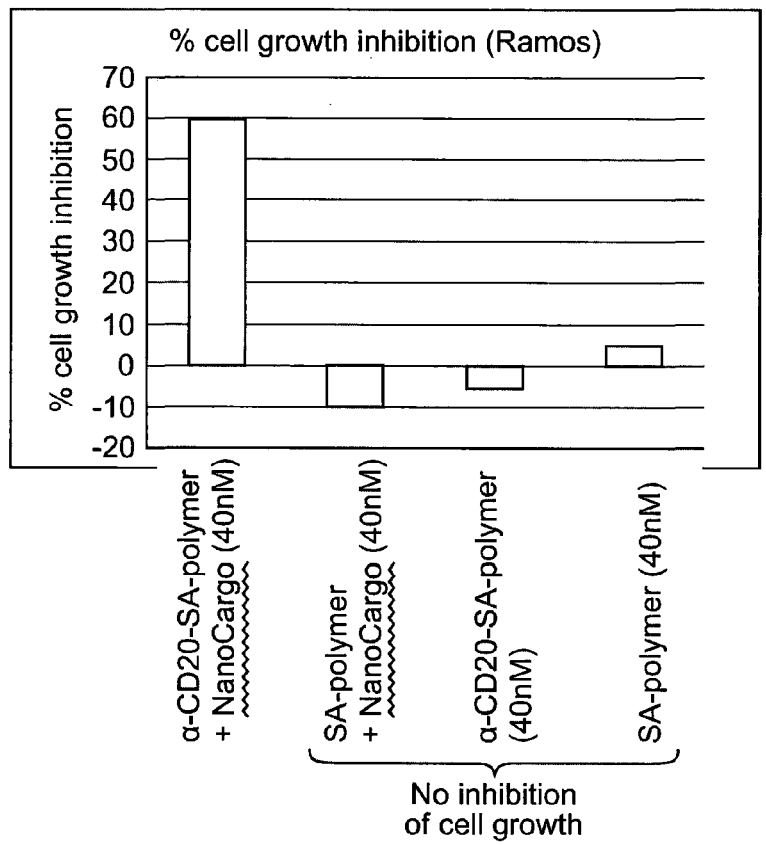
Figure 43:
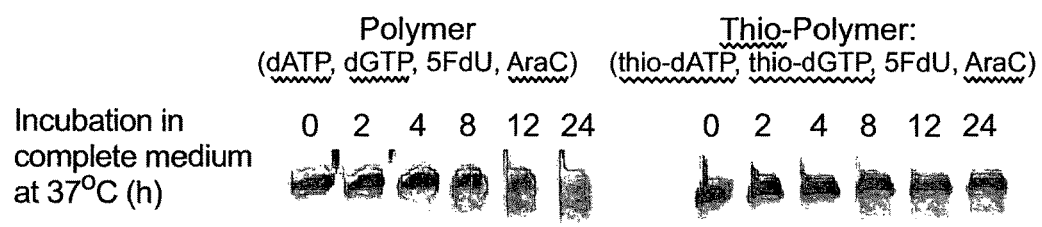

FIG. 33 shows Cytotxicity of txNA polymeric prodrugs
FIG. 34 shows synthesis of txNA
FIG. 35 shows synthesis of txNA polymers by D4K
FIG. 36 shows synthesis of txNA polymers by D4K
FIG. 37 shows syntheses of txNA polymers by D4K
FIG. 38 shows affinity of selected aptamers FIG. 39 shows cytotoxicity of txNA polymeric prodrugs
FIG. 40 shows increased toxicity by targeted polymer
FIG. 41 shows a schematic of the materials used
FIG. 42 shows that targeted polymer delivery gives specific cell death
FIG. 43 shows serum stability The invention is now described by way of example. These examples are intended to be illustrative, and are not intended to limit the appended claims.

EXAMPLES

Materials and Methods
1. Nucleotides and Oligonucleotides

Triphosphates of HNA (hNTPs), CeNA (ceNTPs), LNA (lNTPs) and TNA (tNTPS), were synthesized according to established protocols (27-30). Triphosphates of ANA (aNTPs) except aGTP were obtained from TriLink BioTechnologies (San Diego, Calif., USA) and FANA (faNTPs) were obtained from Metkinen Chemistry (Kuusisto, Finland). aGTP was synthesized as described (31)—$^{31}$P NMR (D20, ppm): −7.54 (d, J 19 Hz, 1P); −10.83 (d, J 19 Hz, 1P); −21.66 (t, J 19 Hz, 1P). High resolution mass spectrometry: Found [M-1] 521.9836. Calculated mass ($C_{10}H_{16}N_5O_{14}P_3$.) [M-1] 521.9828. Triphosphates of DNA (dNTPs) were GE Illumina series (GE Life Sciences UK Ltd, UK). RNA triphosphates (NTPs) were obtained from Roche (Roche Diagnostics GmbH, Germany). Oligonucleotides were from Sigma (Sigma-Aldrich Co., Missouri, USA) or IDT (Integrated DNA technologies BVBA, Leuven, Belgium) unless stated otherwise. The biotinylated ITAR RNA oligonucleotide was prepared from a dsDNA template (LongTART7temp3 and LongTART7temp4 annealed) using MEGAshortcript T7 transcription kit (Ambion Inc., Texas, USA) as per manufacturer's recommendations, but with 3.75 mM ATP, CTP and TTP, and 2 mM GTP supplemented with 2 mM 5'-biotin-AG dinucleotide (Dharmacon Inc, Illinois, USA). DNA and RNA oligonucleotides used in this study are shown in Supplementary Tables S1-S5.

2. DNA Manipulation, Protein Expression and Purification

All DNA manipulation and small-scale expression was carried out in *E. coli* NEB 10-β cells (New England Biolabs Inc., Massachusetts, USA). Expression for large-scale purification of polymerases was carried out in *E. coli* BL21 CodonPlus®-RIL (Agilent Technologies UK Ltd., UK). Cloning of amplified fragments for sequencing was carried out in *E. coli* TOP10 (Invitrogen Ltd., UK). All transformations were carried out according to manufacturers' guidelines.

*Thermococcus gorgonarius* (Tgo) DNA polymerase and all its variants used in this work were cloned and expressed in pASK75 (32). Large scale expression and purification were carried out as previously (33). Briefly, mid- to late-log cultures were induced with anhydrotetracycline (0.4 µg ml$^{-1}$ final concentration) for 2-4 h at 37° C. Cleared lysates were pre-cleaned on DE52 anion exchange resin (Whatman Inc, New Jersey, USA) prior to loading onto 6/10 Hi-Prep Heparin FF column (GE Life Sciences UK Ltd, UK). All polymerases eluted at 0.5-0.8 M NaCl, were filter dialyzed (Amicon Ultra Centrifugal Filters 50K; Millipore, Massachusetts, USA) into 2× Vent storage buffer (New England Biolabs Inc., Massachusetts, USA) and stored in 50% glycerol at −20° C. Small-scale expressions were similarly carried out, but were typically stored as 10× cleared lysate in 1× Thermopol buffer (New England Biolabs Inc., Massachusetts, USA) at 4° C.

3. TgoT Mutagenesis Library Design and Synthesis

A structural alignment between the ternary complex of RB69 DNA polymerase (1IG9 (34)), its apo structure (1WAJ (35)) and the apo structure of Tgo DNA polymerase (1TGO (36)) was produced in Pymol and used to identify the regions in Tgo likely to be within 10 Å of the primer-template duplex in a closed ternary complex. The identified residues were divided into 22 motifs targeted for mutagenesis (FIG. S2). Sequence diversity introduced by mutagenesis included positional phylogenetic variation (where that was present among archaeal polB-family polymerases) and targeted random spike mutagenesis (5-10%) of conserved residues. Overlapping primers harboring a BsaI site in their 5'-terminus, to allow seamless cloning, were designed to introduce such diversity through positional spike mutagenesis (e.g. retaining 95% dA, spiking 5% dG, dC, dT) and degeneracies (e.g. 50% A, 50% C) (see Table S1).

Libraries were generated by iPCR (37) from the Tgo variant TgoT (Tgo: V93Q, D141A, E143A, A485L) using Expand High Fidelity polymerase (Roche Diagnostics GmbH, Germany). Typical reactions were carried out as an initial incubation of 2 min at 95° C. followed by 25× of (30 s 95° C., 30 s 50° C., 18 min 68° C.,) followed by a final extension of 10 min 68° C. Amplified DNA was purified (QIAquick PCR purification kit, QIAGEN GmbH, Germany) according to the manufacturer's recommendations and restricted with BsaI and DpnI (New England Biolabs Inc., Massachusetts, USA). Reactions were again purified (QIAquick PCR purification kit) and ligated with T4 DNA ligase (New England Biolabs Inc., Massachusetts, USA). Ligated plasmids were transformed into *E. coli* NEB 10-β cells (New England Biolabs Inc., Massachusetts, USA), transformants were resuspended in 2×TY supplemented with 15% glycerol (v/v) and stored at −20° C. (after being flash frozen). Diversity of resulting libraries, shown in FIG. S2, was between $5 \times 10^7 - 3 \times 10^9$ cfu. Random clones from each library were sequenced to confirm correct assembly and tested for DNA synthesis activity, by PAA (see 5. below). Polyclonal polymerase activity of the libraries (with dNTPs) was typically a tenth of the wild-type TgoT polymerase.

4. Compartmentalized Self-Tagging (CST) Selection

Polymerases were expressed as previously described for CSR-based selections (33). Typical reactions (150 µl) contained $2 \times 10^8$ cells (expressing polymerase variants), 50 pmol of biotinylated primer (33.3 µM final concentration), 20 nmol of each hNTP (133.3 µM), in 1× ThermoPol Reaction Buffer (New England Biolabs Inc., Massachusetts, USA) supplemented with glycerol (10% v/v), 0.5 mM $MnCl_2$, 0.5 mM $MgCl_2$, formamide (2% v/v), DTT (1 mM), and BSA (0.1 mg $ml^{-1}$) and were emulsified as described (38). The resulting emulsion was divided into 0.5 ml PCR tubes (SARSTEDT Ltd.; UK) and the reaction carried out as a 5-cycle PCR with increasing annealing and extension temperatures (Cycle 1: 5.25 min 94° C., 15 min 37° C., 15 min 50° C.; cycle 2: 1 min 94° C., 15 min 37° C., 15 min 65° C.; cycle 3: 1 min 94° C., 15 min 50° C., 15 min 65° C.; cycle 4: 1 min 94° C., 15 min 60° C., 15 min 65° C.; cycle 5: 1 min 94° C., 30 min 65° C.). Emulsions were pooled and disrupted with TBT2 (10 mM Tris.HCl pH 7.4, 20 mM NaCl, 0.1% v/v Tween20, 0.1 mg ml-1 BSA) and 1-hexanol (typically 100 µl TBT2 and 700 µl 1-hexanol for each 750 µl emulsion). HNA/DNA complexes were recovered from the aqueous phase by precipitation with isopropanol and resuspended in 100 µl TBT2. HNA-bound plasmid DNA was further purified by gel filtration (Illustra MicroSpin S400 gel-purification column, GE Life Sciences UK Ltd, UK) to remove excess primer and incubated with 100 µg of paramagnetic beads (Dynabeads® MyOnew Streptavidin C1 beads; Invitrogen Ltd. UK) in BWBS (10 mM Tris.HCl pH 7.4, 1 M NaCl, 0.1% v/v Tween20, 1 mM EDTA) at room temperature for at least 2 h to capture primer-HNA-plasmid complexes. Beads were washed in using a Kingfisher mL (Thermo Fisher Scientific, Massachusetts, USA) with 500 µl BWBS, TBT2 and TBT2 supplemented with 20% to 30% formamide (v/v) prior to being resuspended in 50 µl EB (10 mM Tris.HCl pH 8.5). Bead aliquots (5 µl) were used as template in PCR (carried out with primers Tgoba578Bsa and pAfo308Bsa (Table SI1)) to recover the selected polymerase genes and cloned into TgoT for subsequent selection rounds. PolC7 and PolD4 were isolated after a first round of selection from the motif 10A library (see FIG. S2) carried out with 50 pmol of the BC36N6 (biotin-C36-spacer-N6) primer (Table S11). Pol6G12 was isolated after a further selection round of the motif 10A library carried out with 10 pmol 6b (biotin-C36 spacer-CACCTA) primer (Table S1). PolD4K is a variant form of D4 harboring an additional mutation (D4K: D4 Q664K).

5. High Throughput Polymerase Activity Assay (PAA)

The principles of PAA are summarized in FIG. S3. Basically, biotinylated primers are extended against a known template by candidate polymerases under testing conditions (e.g. full-substitution of natural nucleotides by hNTPs). The extension reactions are captured onto solid phase and template removed by chemical denaturation. A sequence-specific DIG-labeled probe targeting the extension product is annealed to the extended primers and detection proceeds as in ELISA, using an anti-DIG HRP-conjugated antibody. A chromogenic HRP substrate is used to quantify antibody binding and thus primer extension.

Primer extension reactions were set up by adding equal volumes of annealed reaction mixture, additives (e.g. $MnCl_2$) and enzyme. Reaction mixtures were typically setup as 3 µM 2×BFITCfd primer, 6 µM template (TempN or RTtempHNA, Table S12) and 375 µM of each nucleotide in 2× ThermoPol buffer. Reaction mixtures were annealed by incubating them at 94° C. for 30 s before snap cooling them to 4° C. on ice. A number of additives were tested to investigate their effect in polymerase activity but, typically, the additive mixtures used were 1.5 mM $MnCl_2$ (for HNA synthesis) or water (for HNA RT). Cleared lysates (1× or 10×) in 1× Thermopol buffer were added undiluted while purified polymerases were generally diluted 4- to 10-fold in 1× Thermopol buffer. Typical primer extension final reaction volumes were 6 µl. Primer extension reaction conditions ranged from short single extensions (1 min 94° C., 1 min 50° C., 1 min 65° C.), used in screening for DNA-dependent DNA synthesis, to long multi-cycle extensions (2× (1 h 50° C., 1 h 65° C., 1 min 94° C.) used in screening for processive DNA-dependent HNA synthesis. Reactions were carried out in 96-well plates (Hard-Shell® Skirted low-profile PCR plates; Bio-Rad Laboratories Ltd., UK) prior to being transferred to streptavidin-coated 96-well microplates (StreptaWell; Roche Diagnostics GmbH, Germany) containing 150 µl PBST (125 mM NaCl, 16.6 mM $Na_2HPO_4$, 8.43 mM $NaH_2PO_4$, 0.2% (v/v) Tween20, at pH 7.2). Biotinylated extensions were allowed to bind to the streptavidin-coated wells at room temperature for 20 min and unbound products removed with PBST washes. Template was removed by incubating the plates in 100 mM NaOH for 30 s, and further PBST washes were carried out to remove the alkali and neutralize pH. 3 pmol of a Digoxigenin (DIG)-labeled DNA probe (Table S2) were added to each well in PBST and allowed to hybridize to the nascent strand for 20 min at room temperature. Excess unbound probe was removed by three PBST washes, and anti-DIG antibody-HRP (horse radish peroxidase) conjugate (Roche Diagnostics GmbH, Germany) added in PBST (at 1:3000 or 1:4000 dilution). The antibody was allowed to bind for 20 min at room temperature. Unbound anti-DIG antibody was removed with three PBST washes and the extent of bound anti-DIG antibody was measured by colorimetric development of a chromogenic peroxidase substrate (1-StepTM Ultra TMB-ELISA; Thermo Fisher Scientific, Massachusetts, USA). HNA synthesis was screened using template TempN and DIGN10 probe (Table S2). HNA RT activity was measured using template RTtempHNA and DIGN4 probe (Table S2).

6. HNA Synthesis and ssHNA Physicochemical Properties

Typical HNA syntheses were carried out with 12 µg (approximately 6U (DNA polymerase activity)) purified Pol6G12 in 100 µl reactions containing 1 µM primer, 2 µM template, 125 µM of each hNTP, 0.5 mM $MnCl_2$ in 1× ThermoPol buffer. Reactions were annealed as for PAA (see 5.) prior to Pol6G12 addition. RNasin® Plus RNase inhibitor (Promega UK, UK) was added, according to manufacturer's guidelines, to reactions using RNA primers. Reaction conditions were adjusted according to the length of the template used but were typically multi-cycle extensions (3× (90 min 50° C., 90 min 65° C., 1 min 94° C.)) to obtain a substantial fraction of the full-length product.

6.1 DNase Resistance:

HNA was initially synthesized as above from primer 2×BFITCfd on template TempNmis (Table S2) (extension conditions: 3× (1 min 40° C., 2 h 60° C., 30 s 94° C.). Products were separated by 20% urea-polyacrylamide gel electrophoresis (8 M urea, 20% acrylamide), and full-length HNA product isolated by gel purification (see 14.) followed by precipitation in isopropanol at −20° C. HNA was resuspended in EB and its concentration determined by measuring absorbance at 260 nm ($A_{260}$) with a Nanodrop ND1000 spectrophotometer (Thermo Fisher Scientific, Massachusetts, USA). DNA templates were digested with TurboDNase I (Ambion Inc., Texas, USA) (usually 10 U per 100 pmol of template) in DNase I buffer (New England Biolabs Inc., Massachusetts, USA), due to problems with HNA precipitation in TurboDNase buffer. DNA templates were typically completely degraded within 15 min of incubation at 37° C., while HNA showed no sign of degradation after more than 2 h, as estimated by SYBR Gold (Invitrogen Ltd., UK) staining. To completely remove template DNA, HNA synthesis reactions were therefore typically incubated with TurboDNase I for 2 h and isolated using QIAquick Nucleotide purification (Qiagen GmbH, Germany).

6.2 Acid Resistance (FIG. S17):

An aliquot of HNA (4 µl of 2 µM solution), synthesized using TempN (Table S2) and purified as described above, or DNA (Nproduct, Table S3) was added to 8 µl of pH 1 buffer (130 mM HCl, 50 mM KCl in water) and incubated at 40° C. for different lengths of time. After acid incubation, 2 µl bicarbonate buffer (900 mM $NaHCO_3$, 100 mM $Na_2CO_3$) were added to raise the reaction's pH to 9. The reaction was incubated for a further 30 min at 40° C. before addition of an equal volume of formamide gel-loading buffer (98% formamide (v/v), 10 mM EDTA) to stabilize the samples. Nucleic acids were separated by 20% urea-PAGE and visualized with SYBR Gold (found to stain both HNA and DNA) or Acridine Orange (found to stain only DNA) using a Typhoon TrioTM scanner (GE Healthcare UK Ltd., UK). Undegraded products were quantified using ImageQuant TL and the ratios of undegraded nucleic acids determined against the initial time point. To determine acid resistance of HNA aptamers, a similar protocol was used, but incubation in pH 1.0 buffer was performed for 3 h at 40° C., followed by 1 h at 40° C. at pH 9.2. Acid-treated aptamers, or untreated control aptamers, were gel purified (see 13) and target binding quantified by SPR (see FIG. S17).

6.3 Mass Spectrometry of HNA Oligos:

Substantially larger syntheses of HNA were required to obtain the required material for matrix-assisted laser desorption/ionization (MALDI) determination of HNA molecular weight and sequence. For the shorter HNA molecule (shown in FIG. S6), 10×100 µl reactions (as described above in (6.) using fdOme primer (Table S2) and TempNshort2 template (Table S3). Reactions were carried out for 1 h 50° C. and 2 h 65° C. and subsequently, DNaseI treated (as described in 6.1 and 14). Reactions were pooled and anhydrous butan-2-ol used to dehydrate the reaction reducing its overall volume to approximately 250 µl. Concentrated reactions were desalted (NAPTM-5 columns Sephadex™ G-25 DNA Grade, GE Healthcare UK Ltd., UK) following manufacturer's instructions and sample volume again reduced with anhydrous butanol to 200 µl. 1 ml of denaturing PAGE loading buffer (98% formamide 10 mM EDTA) were added to the samples and these were incubated at 99° C. for 15 min prior to urea-PAGE purification (as described in 14) with minor modifications. After passive diffusion and filtration, $NH_4OAc$ was added to 0.5 M final concentration and HNA precipitated with ethanol (without addition of glycogen). Precipitated samples were then vacuum dried to sublime the salt used in precipitation. Oligo samples were resuspended in 25 µl, 0.1 M TEAA (Triethylammonium acetate) and further desalted using zip-tip C18 (Millipore, Massachusetts, USA). The zip-tip C18 was washed 3 times with 10 µl, 0.1 M TEAA and then 3× in 10 µl water. Next, the oligo was eluted directly onto a MALDI target with 5 µl of 3-hydroxypicolinic acid. All mass spectrometric measurements were carried out in positive ion mode on an Ultraflex III ToF-ToF instrument (Bruker Daltonik, GmbH, Germany). After the oligo molecular weight measurements, MALDI-ISD (In Source Decay) experiments were performed on the same spot, to obtain the sequence of the 3'-end. Chemically-synthesized equivalent DNA and RNA oligos were used as control and are shown in FIG. S6.

The longer HNA molecule, shown in FIG. 2B, is the same HNA generated to determine the aggregate error of information transfer in the HNA system (see section 12) from TempNpuremis (Table S3). For the longer molecule, 20× 100 µl reaction using t4fdOme primer (Table S2) and TempNpuremis were required to synthesize sufficient HNA for MALDI analysis. Apart from the different extension conditions (1 h 50° C., 4 h 65° C.), the longer HNA molecule was prepared as described above for the HNA based on TempNshort2, and MALDI was carried out in similar conditions.

7. XNA Syntheses

CeNA:

CeNA syntheses were carried out with 10 µg (~10U) of purified PolC7 as 100 µl reactions containing 1 µM primer, 3 µM template, 125 µM of each ceNTP, 0.5 mM $MnCl_2$ in 1× ThermoPol buffer. Reactions were annealed as for PAA reaction mixtures prior to the addition of the polymerase and carried out as multi-cycle reactions (as for HNA) or as single cycle extensions of 15 min 40° C., 2 h 50° C., 2 h 65° C.

LNA: LNA syntheses were carried out with 20 µg (~20U) of purified PolC7 as 100 µl reactions containing 1 µM primer, 2 µM template, 125 µM of each lNTP, 0.5 mM $MnCl_2$ in 1× ThermoPol buffer supplemented with 3 µg of ET-SSB (Extreme thermostable single-stranded binding protein; New England Biolabs Inc., Massachusetts, USA). Reactions were annealed as for PAA reaction mixtures prior to the addition of the polymerase. Reactions were carried out as 2× (5 min 40° C., 1 h 50° C., 2 h 65° C., 2 min 95° C.). TNA: TNA reactions were carried out with 6.1 µg (~6U) of purified RT521 as 30 µl reactions containing 0.3 µM primer, 1.2 µM template, 50 µM of each tDTP, tCTP, tTTP, 10 µM of tGTP and 0.5 mM $MnCl_2$ in 1× ThermoPol buffer. Typical extension conditions used were 10 min 40° C., 10 min 50° C., 2 h 65° C. ANA/FANA: ANA and FANA syntheses were carried out in 10 µl reactions containing 1 µM biotinylated primer (bNAPfd, Table S3), 2 µM template (TempNpuremis, Table S3) and 250 µM of each a/faNTP in 1× ThermoPol buffer (New England Biolabs Inc., Massachusetts, USA). Reactions were annealed by heating to 94° C. for 5 min and cooling to 4° C. at 0.1° C. $s^{-1}$ prior to the addition of PolD4YK. For ANA, 0.27 µg of polymerase were added and reactions carried out as single cycle extensions of 30 min 50° C., 2 h 65° C. For FANA syntheses, 0.14 µg of polymerase were added and reactions carried out as single cycle extensions of 5 min 50° C., 5 min 65° C. After synthesis, ANA and FANA were incubated with 1 µl ExoI (New England Biolabs Inc., Massachusetts, USA) for 30 min at 37° C. and 5 min 80° C., prior to capture onto 100 µg paramagnetic beads (10 min, RT, Invitrogen Ltd., UK). The DNA template strands were eluted with 2× of 20 mM NaOH and the beads were then washed 1× in BWBS and 1× in EB. ANA and FANA attached to beads were resuspended in 10 µl EB.

8. Alkali Agarose Gel Electrophoresis (AAGE)

Alkali agarose gel electrophoresis was carried out as previously described (39, 40). Briefly, 4%-6% agarose gels (NGQT-1000, Thistle Scientific Ltd., UK) made in 50 mM NaCl supplemented with 1 mM EDTA were allowed to equilibrate in running buffer (50 mM NaOH, 1 mM EDTA) for 1 h at room temperature prior to being used. Nucleic acid samples were added to 2× loading buffer (100 mM NaOH, 20% (v/v) glycerol, 10 mM EDTA) and incubated at 80° C. for 5 min prior to being snap cooled (wet ice) and loaded onto the denaturing gel. AAGE was typically carried out at room temperature at 2 V $cm^{-1}$ for 2-5 h to limit excessive heating.

9. Statistical Coupling Analysis (SCA)

Sequence diversity within polB-family polymerases is too low within clades to encompass enough sequence variation to generate meaningful covariation for SCA. Between clades, sequence diversity is high but standard sequence search algorithms, such as BLAST, do not reliably detect all known polymerases. Structural conservation of polB-family polymerases is higher than sequence conservation and we exploited this to generate a multiple sequence alignment (MSA) to be used as input for SCA calculations as follows: available B-family polymerase structures from diverse clades (*P. furiosus* (2JGU(41)), RB69 (1WAJ(35), 11G9 (34), 1CLQ(42)), *E. coli* Pol II (1Q81(43), 3MAQ(44)), Herpes Simplex Virus DNA polymerase (2GV9(45)), Yeast Pol δ (3IAY(46)) and *Sulfolobus* PolB1 (1S5J(47))) were aligned to *T. gorgonarius* (1TGO(36), 2VWJ(48)) using the online DaliLite (v.3.1) server (49). This initial alignment was used as the starting point for a refined manually-curated alignment, matching individual Tgo structural elements to the available polymerases.

As the polymerases used in the structural alignment represent a number of different clades (archaeal (e.g. *T. gorgonarius*), viral, (e.g. Herpes) eukaryotic (e.g. *Sulfolobus* pol δ) and bacterial (e.g. *E. coli* Pol II)), each was used as a query sequence to search public protein databases, generating four datasets. Each dataset was aligned with MUSCLE (50) as previously described (51) and sequences not obviously of polymerase provenance (e.g. lacking the catalytic aspartates) were removed. The four datasets were then integrated, using the structural alignment to guide the resulting MSA, and duplicate entries were removed. The resulting dataset contained 671 polymerase sequences aligned to Tgo. Positions conserved to higher than 97% identity (34/773 residues in Tgo) were removed from SCA analysis as subalignments would contain fewer than 20 sequences and skew the distribution of correlation values. SCA was performed using the SCA toolbox 3.0, kindly provided by R. Ranganathan (U. of Texas, Dallas), in MATLAB R2009a (The Mathworks, Inc., Massachusetts, USA). The log-normal fit of the SCA correlations ($\mu=-1.749$ and $\sigma=0.808$) suggested a 99th quantile cut-off of $kT^*=1.964$, above which correlations were considered significant. The output correlation matrix was analyzed by two-dimensional clustering (as shown in FIG. S7) as previously described (52) as well as in Excel (Microsoft Corporation, Washington, USA). Residues showing significant covariation, as well as highly conserved residues (which were excluded from the analysis, see above), were mapped to the 1TGO, 4AIL and 3MAQ structures (FIG. S7).

10. Screening for HNA Reverse Transcriptase Activity

Residue L409 in Pfu (L408 in Tgo) had been implicated in RNA RT activity (22). We searched for SCA hits within a 5 Å-shell of L408 in 1TGO to discover potential allosteric interaction networks involved in template recognition, identifying 4 residues out of 13 within 5 Å as bona fide SCA hits. We partially randomized (NWC) each of these four positions by iPCR (as in 3) using primers described in Table S4. 36 transformants of each library were screened by PAA (FIG. S3) as in (5.) with 2 µM 2×BFITCfd (Table S2), 8 RTtempHNA (Table S2) and 0.5 mM of each dNTP in 1× ThermoPol buffer. Extensions were carried out as 3× (1 h 50° C., 1 h 65° C., 2 min 94° C., 2 min 40° C.). In view of the positive results obtained for I521, a second, more comprehensive, screen (188 clones) was carried out on a single-residue library generated from a fully-degenerate I521 codon. The fully randomized (NNS) library was generated by iPCR as described above with primers RT521baNNS and RT520fo (Table S4).

11. XNA Reverse Transcriptase Reactions

HNA:

HNA RT reactions were carried out with concentrated (10×) cleared lysates (prepared as in 2.) or with purified RT521 (0.4-6.1 µg per reaction) using HNA templates synthesized by Pol6G12 (as in 6.). RT reactions (50 µl) contained 0.2 µM primer, 0.16 µM template, 200 µM of each dNTP in 1× ThermoPol buffer with or without supplements: 2% TritonX-100 (v/v), 1.5 µg pH yeast tRNA and 1 mM $MgSO_4$. Reaction mixtures were annealed as in PAA (5.) prior to RT521 addition, and were incubated for 4 h 65° C. unless stated otherwise. Reactions with the cleared lysate, as shown in FIG. 2D, were carried out as 50 µl containing 0.04 µM CyRevfd primer (Table S3), 0.04 µM template (synthesized from YtRtemp4—Table S3), 200 µM of each dNTP in 1× ThermoPol buffer. Reactions were carried out for 4 h at 65° C. CeNA, TNA, LNA: Reverse transcription of TNA, LNA and CeNA were carried out as above for HNA in 20 µl containing 0.2 µg polymerase (RT521 in TNA, RT521K in CeNA and LNA), 0.1 µM primer, 0.2 µM template, 200 µM of each dNTP in 1× ThermoPol buffer supplemented with 1 mM $MgSO_4$. LNA RT reactions, as shown in FIG. S8, were also supplemented with 0.3 M trehalose. Reactions were carried out at 65° C. for 2 h (CeNA), 4 h (TNA) or 16 h (LNA). ANA, FANA: Reverse transcriptions of ANA and FANA were carried out as above except 10 μg of ANA- or FANA-coated paramagnetic beads (see above 7.1) were used as template in a 20 μl reverse transcription reaction containing 1 μM primer (LMB3+test7, Table S3) and 500 μM each dNTP in 1× ThermoPol buffer supplemented with 1 mM MgSO$_4$. Reactions were annealed as for forward syntheses (section 7.1), 0.2 μg RT521K were added and reactions were carried out for 2 h at 65° C.

12. Aggregate Fidelity of XNA Synthesis and Reverse Transcription

HNA was synthesized as above using NAPfd primer (RNA) and YtRtemp7 template (Table S3). Extension reactions were carried out as 3× (1 min 40° C., 1 h 50° C., 1 h 65° C., 1 min 94° C.), and DNA template was removed with 8U TurboDNase I (per 100 μl synthesis) for 1 h 37° C. HNA was purified using QIAquick PCR purification column, eluted in 50 μl EB, then used as the template in an HNA-RT reaction, as described above (see section 11.), using primer LMB3+tag3a (Table S3). For RT PCR, unextended primers and nucleotides were removed with ExoSAP-IT (USB® Affymetrix, Inc., California, USA), according to manufacturer's recommendations, and HNA/DNA hybrids purified with a QIAquick nucleotide purification column (Qiagen GmbH, Germany). HNA/DNA was eluted in 30-50 μl EB was and an aliquot was used as template for PCR with primers matching the outnesting tags (e.g. NAP and LMB3+ (Table S3, FIG. S10) using FastStart-Taq (Roche Diagnostics Ltd., UK) according to manufacturer's recommendation: 4 min 94° C., 30× (30 s 94° C., 30 s 52° C., 30 s 72° C.). Amplification products were resolved by agarose gel electrophoresis (see e.g. FIG. 3g and FIG. S11), isolated by gel purification (QIAquick gel purification kit, Qiagen GmbH, Germany) and cloned into pCR4.1 using a TOPO-TA Cloning® kit (Invitrogen Ltd., UK) for sequencing.

HNA aggregate fidelity (shown in FIG. S11 and summarized in Table S8) was also determined for the designed template TempNpuremis (Table S3). Briefly, HNA synthesis was carried out as described above using tag4fdOMe primer (all 2'O-methyl-DNA) (Table S3) in a single cycle of extension (1 min 40° C., 1 h 50° C., 1 h 65° C.). Template was removed with TurboDNase and the full-length HNA gel-purified (described above in 6 and 6.1). RT reactions were set up as described above (section 11) using biotinylated primer bLMB3+test7 (Table S3) for 4 h at 65° C. Reactions were treated with ExoSAP-IT and captured on paramagnetic beads (Dynabeads® MyOne™ Streptavidin C1 beads; Invitrogen Ltd., UK) (50 μg beads per 20 μl) in BWBS for 15 min at room temperature. They were washed once in BWBS and once in EB before being resuspended in 10 μl EB. The isolated DNA was amplified and cloned as above.

Aggregate fidelities of the synthesis and reverse transcription of the other 5 XNAs (CeNA, TNA, LNA, ANA and FANA) were determined as above with minor modifications. Briefly, forward extensions used a biotinylated primer bNAPfd (Table S3) that could be captured onto paramagenetic beads. DNA template was removed by successive 20 mM NaOH washes prior to RT directly on bead-captured 1st strand (as carried out for ANA and FANA purifications in 7.1). After RT, beads were isolated and washed twice in BWBS and once in EB prior to being resuspended in 10 μl EB. The isolated DNA was amplified as described above and the gel-purified fragment cloned.

13. Fidelity in an all DNA System

We also determined fidelity of HNA polymerase Pol6G12 and HNA-RT RT521 in a DNA-only system to deconvolute their contributions to aggregate fidelity and to allow benchmarking to commercially available polymerases of known error rate, e.g. VentR®(exo–) (New England Biolabs Inc., Massachusetts, USA). Determination of corresponding fidelity of polymerases (Pol6G12 and RT521) on DNA required a different strategy as DNase I treatment could not be used to remove template. We adapted a purification strategy based on paramagnetic beads (53) to isolate the correct DNA strands at each step of the experiment.

Forward syntheses (100 μl) using 1 μM bNAPfd primer, 2 μM YtRtemp7 template (Table S3), 200 μM of each dNTP in 1× ThermoPol buffer (New England Biolabs Inc., Massachusetts, USA) were carried out for 1 h at 55° C. with either Pol6G12 or Vent. Extensions were captured onto paramagnetic beads (Dynabeads® MyOne™ Streptavidin C1 beads; 250 μg beads/100 μl reaction) in BWBS at room temperature for 10 min. Captured syntheses were washed once in BWBS (to remove non-specifically bound products), twice in 100 mM NaOH at 37° C. (to denature and remove the non-biotinylated template) and once again in BWBS (to neutralize pH). Beads were resuspended in 25 EB for 2nd strand synthesis.

2nd strand syntheses, equivalent to the RT step in HNA, were carried out in 50 μl containing 0.2 μM primer, 5 μl bead suspension, 200 μM of each dNTP in 1× ThermoPol buffer. Reactions were carried out for 1 h at 55° C. with either Vent or RT521. Beads were captured after the reaction and washed in BWBS (as described above). The second strand products were eluted from the bound DNA templates with 80 μl 20 mM NaOH and quickly neutralized with 20 μl 80 mM HCl and 1 μl 1 M Tris.HCl (pH 7.4). Full-length second strands were enriched using paramagnetic beads pre-coated with 4 pmol μg$^{-1}$ of biotinylated NAPcapture (Table S3), complementary to the 3'-end of the second strand synthesis product. Captured products were eluted in 20 mM NaOH, neutralized with HCl and Tris.HCl as above, and used as template for PCR as in 11. Amplification was carried out with NAP and LMB3+ primers (Table S3) introduced by the double outnest strategy (shown in FIG. S10).

14. Aptamer Selection

For aptamer selections to HIV-TAR RNA motif (TAR), two libraries were designed based on the hairpin structure of previously described anti-TAR RNA and DNA aptamers (24) with either N6 (TARtemp5) or N12 (TARtemp4) (Table S5, FIG. S13) random positions. For selection of aptamers against Hen Egg Lysozyme (HEL), library ApLib4 was used, containing N40 random positions (Table S5, FIG. S15). For aptamer selection, screening and characterization, HNA was synthesised as 100 μl reactions using 1 μM primer, 2 μM template, 125 μM of each hNTP, 0.5 mM MnCl$_2$ in 1× ThermoPol buffer in a two-step extension (90 min 50° C., 90 min 65° C.). Synthesis used either a DNA primer (Cy3fd—Table S3), that could be removed by TurboDNase treatment (see below) during purification to generate all-HNA aptamers, or an RNA primer (fitcRNAfd—Table S3), which survives DNase treatment, to generate FITC-labeled RNA-HNA chimeric aptamers. FITC-labeled aptamers allowed detection by ELONA (using an anti-FITC antibody as in 5) and flow cytometry (using FITC fluorescence, see 18).

To remove DNA template, aptamer preparations were diluted into 1× DNase buffer (New England Biolabs Inc., Massachusetts, USA), incubated with 10U TurboDNase (Ambion Inc., Texas, USA) for 2 h at 37° C., then purified by urea-PAGE. HNA was extracted from a gel slice by maceration, freeze-thawing, passive diffusion (overnight at room temperature) and filtration though a 0.2 μm Spin-X column (Corning Life Sciences, Massachusetts, USA), then ethanol precipitated. Before use, HNA aptamers were resuspended in EB at 1 µM and annealed by rapid heating and cooling (2 min 94° C., 10 min 17° C.). Unless stated otherwise, aptamer experiments (e.g. ELONA, SPR, BLI, FACS) were performed in Buffer R (20 mM NaOAc, 140 mM KOAc, 3 mM Mg(OAc)$_2$, 0.1% (v/v) Tween20).

Aptamer selections (54) were performed as follows: 5-10 pmol HNA library was incubated with 500 µg MyOnew Streptavidin C1 Dynabeads® (Invitrogen Ltd., UK) for 1 h at room temperature and the beads discarded to deplete bead-binding sequences. The supernatant was then incubated with 500 µg beads pre-blocked with 1× Roti-Block (Carl Roth GmbH, Germany) for 30 min at room temperature and saturated with biotinylated sTAR, biotinylated ITAR or biotinylated HEL (bHEL; Sigma Aldrich L0289; Sigma-Aldrich Company Ltd., UK). Beads were washed 4× in 2 ml buffer and binders eluted with 100 mM NaOH for 1 min at 37° C. Eluted aptamers were neutralized with 1 M Tris.HCl pH 6.2 and ethanol precipitated. Selective pressure was increased over the course of subsequent selection cycles by incrementally lengthening the duration of washing steps (from 5 min in round 1 (R1) to 60 min in R5-R8) and, during the anti-TAR selections, by decreasing the Mg(OAc)$_2$ concentration from 10 mM (R1-4) to 3 mM (R5-R8) (55).

Eluted HNA sequences were reverse transcribed to DNA following addition of a DNA poly(dA) tail using Pol6G12 in 1× ThermoPol buffer with 100 µM dATP and 1 mM MnCl$_2$ for 10-20 h at 65° C. Primer LMB3polyT (Table S5) was annealed to the polydeoxyadenylated HNA and RT performed as described above (see 11.), but with higher dNTP concentrations (0.5 mM each) and supplemented with 2 mM MgSO$_4$. RT reactions were treated with ExoSAP-IT (USB® Affymetrix, Inc., California, US) to remove unextended primers. First strand cDNA was amplified by a two-step nested PCR strategy using hot-start GoTaq® polymerase (Promega UK, UK). Step 1: 20-25-cycle PCR from the RT product with primers LMB3+(Table S3) and tag3 (Table S5). Step 2, 10-15 cycle PCR, using in-nested primers (tag1 and fdtag3, Table S5) designed to reconstitute the HNA synthesis priming site, which had been lost through DNase I treatment. Fragments were isolated using agarose gel electrophoresis and a QIAquick gel extraction kit (Qiagen GmbH, Germany), and cloned into pCR4.1 using a TOPO TA kit (Invitrogen Ltd., UK). Alternatively, to generate ssDNA templates for HNA synthesis in preparation for subsequent selection cycles, they were used as templates in preparative (2 ml total) PCR reactions with primers biotinfd and tag 1 (Table S5) purified using a QIAquick gel extraction kit (Qiagen GmbH, Germany) and bound to paramagnetic streptavidin-coated beads (Dynabeads® MyOne™ Streptavidin C1 beads). Non-biotinylated antisense strand (i.e. the template for HNA synthesis) was eluted with 100 mM NaOH for 1 min at 37° C., neutralized with 1 M Tris.HCl at pH 6.2 and ethanol precipitated. Prior to HNA synthesis for further selection cycles, templates were again pre-incubated with paramagnetic beads to ensure complete removal of the biotinylated antisense strand.

15. Aptamer Screening and Aptamer-ELISA (ELONA)

We screened HNA aptamers both by sequencing (to identify emergent motifs) and binding activity using ELISA. For the anti-sTAR selections, 51 R8 aptamers were cloned, sequenced and grouped into clades by the Neighbor-Joining method based on ClustalW alignments using MacVector software (MacVector Inc., North Carolina, USA) (FIG. S13 and FIG. S15). DNA templates for a selection of clones representative of different clades were chemically synthesized, used for HNA synthesis, and tested in ELONA (see below). For the anti-ITAR and anti-HEL selections, templates were generated by colony PCR (25 cycles using fd and biontintag1 primers) from isolated cloned RT-PCR products, followed by streptavidin bead capture and NaOH denaturation as described above. Templates for hits were subsequently chemically synthesized for further characterization.

ELONA (Aptamer-ELISA) was carried out as described (56) with minor modifications. For screening and characterization, ssRNA-HNA chimeras were prepared as described above (13.) (using fitcRNAfd (Table S5)) and binding assayed by immunodetection of the FITC-tag on the bound aptamer. For ELONA, 10 pmol/well of antigen (STAR, scrambledTAR-1, -2, -3, -4, fragTAR-1, fragTAR-2, ITAR, bHEL) were captured on streptavidin-coated 96-well microplates (StreptaWell, Roche Diagnostics Ltd., UK) and 10 nM aptamers (for specificity experiments), or a serial dilution from 200 nM (for affinity determination on sTAR or bHEL), in 50 µl buffer R were bound for 1 h with or without blocking with excess free biotin. Alternatively, antigens at 5 mg ml$^{-1}$ in 7.5% sodium bicarbonate pH 9.4 (HEL (Sigma Aldrich L6876; Sigma-Aldrich Company Ltd., UK), Human Lysozyme (Sigma Aldrich L1667; Sigma-Aldrich Company Ltd., UK), BSA (First Link (UK) Ltd., UK) or Cytochrome C (Acros Organics, part of Thermo Fisher, New Jersey, USA) were directly coated onto hydrophobic 96-well microplates (Maxisorp, VWR International Ltd, UK), blocked with 2% Marvel (Premier International Foods, UK), then equilibrated in buffer R. Unbound aptamers were removed by 3×5 min washes of 200 µl buffer R, then incubated with 100 µl HRP-conjugated sheep anti-FITC (Southern Biotech, Alabama, USA) (1:5000 dilution) for 45 min before three additional washes (R buffer). Bound antibody was detected using a colorimetric substrate as described above (see PAA, 5)

16. Determining Aptamer Binding Affinity and Kinetics Using SPR

Surface Plasmon Resonance (SPR) measurements were made using a BIAcore 2000 instrument (GE Healthcare UK Ltd., UK) at a flow rate of 20 µl min$^{-1}$ in buffer R at 20° C. Label-free, all-HNA aptamers were prepared as described above (12). For all experiments, immobilized NeutrAvidin™ (Pierce, 31000; Thermo Fisher Scientific, Massachusetts, USA) surfaces (~3000 RU per flow cell) were prepared using an amine coupling kit (GE Life Sciences UK Ltd, UK) with CM4 sensor chips (GE Life Sciences UK Ltd, UK) in 5 mM NaOAc (sodium acetate), pH 5.5, then equilibrated in buffer R for capture of biotinylated ligands.

For anti-TAR aptamers, 1000RU sTAR was captured (or, as a reference flow cell, 1000RU scrambledTAR-1) before blocking with excess free biotin. Anti-TAR aptamers were injected for 150 s at a series of concentrations (125 nM, 62.5 nM, 31.3 nM, 15.6 nM, 7.8 nM and 3.9 nM) and dissociation monitored for 600 s, in buffer R (20 mM NaOAc, 140 mM KOAc, 3 mM Mg(OAc)$_2$, 0.1% (v/v) Tween20). After every aptamer injection, the sensor surface was regenerated using two 5 µl injections of 10% (v/v) formamide, 1 mM EDTA in water. Positive and negative control aptamers (RNA anti-TAR aptamer R06 (24) or HNA anti-HEL aptamer LYS-S8-10) or acid-treated aptamers (T5-S8-7) were injected at 100 nM.

For anti-hen egg lysozyme (HEL) aptamers, ~2000 RU bHEL was captured (or, as a reference cell, 2000RU biotinylated cytochrome C, prepared using a biotinylation kit (Pierce, 21343); Thermo Fisher Scientific, Massachusetts, USA) before blocking with excess free biotin. Anti-HEL aptamers were injected for 150 s at a series of concentrations (125 nM, 62.5 nM, 31.3 nM, 15.6 nM, 7.8 nM 3.9 nM and 2.0 nM) and dissociation monitored for 600 s, in buffer R. After every aptamer injection, the sensor surface was regenerated using two 5 µl injections of 50 mM NaOH and 1 M NaCl in water. Positive and negative control aptamers (RNA ant-HEL aptamer A2 (23) or HNA anti-TAR aptamer T5-S8-7) or acid-treated aptamers (LYS-S8-19) were injected at 100 nM in buffer R. As the RNA aptamer A2 was found to have very low affinity in buffer R, this aptamer was also injected at 10 µM.

To obtain optimal fits, SPR data was fitted to double-exponential model using KaleidaGraph (Synergy Software, Pennsylvania, USA) and Prism (GraphPad Software Inc., California, USA) (57). The rate constants of dissociation were measured by fitting dissociation data at time t ($R_{dissoc}$) using a double-exponential function:

$$R_{dissoc} = R_{o1} \exp^{-(k_{off1}t)} + R_{o2} \exp^{-(k_{off2}t)} + RI \quad (1)$$

where $k_{off}$ is the dissociation rate constant, $R_o$ is maximum change in resonance for each phase, RI is the bulk resonance change. The rate constants of association were obtained by fitting the observed change in resonance signal ($R_{assoc}$) at time t using the following equation:

$$R_{assoc} = \left(\frac{k_{on1} CR_{max1}}{k_{on1}C + k_{off1}}\right)\left[1 - \exp^{-(k_{on1}C + k_{off1})t}\right] + \left(\frac{k_{on2} CR_{max2}}{k_{on2}C + k_{off2}}\right)\left[1 - \exp^{-(k_{on2}C + k_{off2})t}\right] + RI \quad (2)$$

where $k_{on}$ is the association rate constant, C is the analyte concentration and $R_{max}$ is maximum change in resonance.

Deviation from pseudo-first order kinetics for nucleic acid-lysozyme interactions is well established with ligand heterogeneity arising from a strong multi-site electrostatic binding component ($pI_{HEL}=9.6$), which are diminished at higher ionic strength (23). Further complexity may arise from aptamer heterogeneity or conformational flexibility.

17. Determining Tamer Binding Affinity and Kinetics Using BLI

Bio-layer Interferometry (BLI) measurements were made using an Octet Red instrument (ForteBio Inc., California, USA). As in SPR (14), binding of label-free aptamers was detected using immobilized ligand (bHEL or 2xb-sTAR captured on streptavidin). SA tips (ForteBio Inc., California, USA) were equilibrated in buffer R (20 mM NaOAc, 140 mM KOAc, 3 mM Mg(OAc)$_2$, 0.1% (v/v) Tween20) and saturated with ligands at 0.2 µM (bHEL, biotinylated cytochrome C (see 16) or sTAR), or in buffer alone (i.e. no ligand) for 15 min, then blocked with excess free biotin. Tips were washed in buffer R, then incubated with serial dilutions of anti-TAR and anti-HEL HNA aptamers (and controls) as described for SPR experiments, except that all reagents were prepared on microtitre plates in 200 µl volumes, rather than injected. Association and dissociation phases were monitored for 600 s and 900 s respectively. The data were fit with a 1:1 binding model with drift:

$$R_{dissoc} = R_{max} \exp^{-(k_{off}t)} + Dt + RI \quad (3)$$

$$R_{assoc} = \left(\frac{k_{on} CR_{max}}{k_{on}C + k_{off}}\right)\left[1 - \exp^{-(k_{on}C + k_{off})t}\right] + Dt + RI \quad (4)$$

where $k_{on}$ and $k_{off}$ are the association and dissociation rate constants respectively, C is the analyte concentration, $R_{max}$ is maximum change in resonance and D is the linear drift and RI is the bulk interference change.

18. Aptamer Binding to Cells

RNA-HNA aptamer chimeras were prepared as described above (using fitcRNAfd (Table S5)). The binding of the FITC-labeled aptamers to J558L mouse myeloma cells stably transfected with a membrane-expressed construct of HEL (kindly provided by Dr. Facundo Batista, CRUK), or untransfected J558L cells, was determined by flow cytometry (FACS). Buffer R without Tween, supplemented with 30 mM NaCl and 0.1% BSA (New England Biolabs Inc., Massachusetts, USA) was used for all steps. Ten million cells per tube were washed three times then incubated with 10 nM anti-lysozyme aptamers (LYS-S8-19, LYS-S8-10, or as a control anti-TAR aptamers T5-S8-7), in 200 µl for 1 h at room temperature. Unbound aptamers were removed by 3×5 min washes (centrifugation at 1000×g). FITC fluorescence was detected using a FACSCalibur instrument with Cellquest software (BD Biosciences, UK).

19. Fluorescence Polarization (FP)

Anti-HEL aptamers were synthesized and purified as described above (6. and 6.3) from fdOme (Table S2) and chemically-synthesised DNA templates. Aptamers were resuspended in ddH$_2$O, sample concentration was determined (NanoDrop ND-1000; Thermo Fisher Scientific, Massachusetts, USA) and adjusted to 20 nM. Aptamers were incubated for 10 min 99° C. followed by 1 min at room temperature to allow for efficient aptamer folding.

Protein serial dilutions (fourteen 2-fold dilution steps) were set up in 2×R buffer (40 mM NaOAc, 280 mM KOAc, 6 mM Mg(OAc)$_2$, 0.2% (v/v) Tween20) together with a protein-free control also in 2×R buffer. 10 µl annealed aptamer were added to 10 µl of protein and allowed to equilibrate for 2 h before being transferred to 384-well polystyrene black microtiter plates (Greiner Bio One Ltd., UK) and FP measured. Experiments were carried out in triplicate.

Aptamer-protein interactions are measured in FP by the effect of binding on the tumbling rate of the fluorophore. To maximize the polarization shift due to binding, neutravidin-bound lysozyme was used as target. At the highest protein concentrations tested, lysozyme (bHEL; Sigma-Aldrich Company Ltd., UK) was at 13.3 µM and neutravidin (Thermo Fisher Scientific, Massachusetts, USA) at 3.3 µM. Experiments with neutravidin alone as well as neutravidin with an unrelated protein (BSA) were carried out as controls (FIG. S16D).

FP was measured on a PHERAstar microplate reader (BMG Biotech Ltd., UK) using module FP 485 520/520 to monitor the fluorescence of the FITC label at the 5'-end of the 2OMe-DNA primer used for aptamer synthesis. Control reactions without a target protein were used to adjust measurement gain (target 100 mP). Results were analysed using Prism (GraphPad Software Inc., California, USA) with data (Y) fit to the following equation:

$$Y = \frac{Min + (Max - Min) \times (b - \sqrt{(b \times b - (4 \times c))})}{(2 \times a)} \quad (5)$$

where Max refers to the FP saturation, Min is the free ligand polarization and a is the fixed aptamer concentration. c is aptamer concentration multiplied by the protein concentration (X) and b is aptamer+X+Kd.

Example 1: Compartmentalised Self-Tagging (CST)

To enable discovery of polymerases capable of processive XNA synthesis, we developed a selection strategy called compartmentalized self-tagging (CST) (FIG. S1). CST selections were performed on libraries of TgoT, a variant of the replicative polymerase of *Thermococcus gorgonarius* comprising mutations to the uracil-stalling (V93Q) (19) and 3-5' exonuclease (D141A, E143A) functions, as well as a "Terminator" mutation (A485L) (20). TgoT libraries were created from both random and phylogenetic diversity targeted to 22 short sequence motifs within a 10 Å-shell of the nascent strand (FIG. S2).

Example 2: D4K Polymerase

Figure 1:
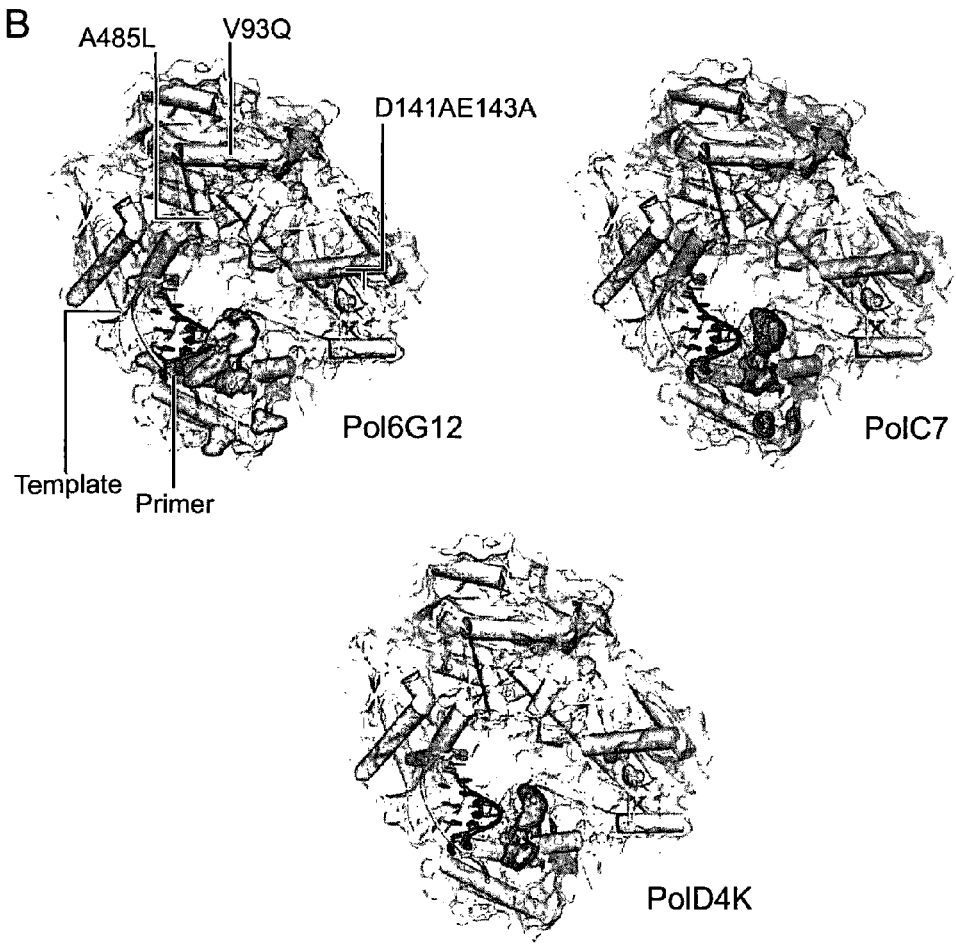
FIG. 1: Engineering XNA polymerases.

Next, we explored if other polymerases derived by CST and SCA might enable synthesis and reverse transcription of other synthetic genetic polymers. Screening identified PolD4K (L403P, P657T, E658Q, K659H, Y663H, E664K, D669A, K671N, T676I) (FIG. 1) as an efficient synthetase for ANA (D4K) and FANA (D4K) (FIG. 3A-C, E, F).

"Terminator" (9° N exo–: A485L) polymerase has previously been shown to support TNA synthesis (16), but TNA RTs were lacking. RT521 proved capable of both efficient TNA synthesis and reverse transcription (FIG. 3D).

In addition, RT521 is an efficient RT for both ANA and FANA (FIGS. 3B and 3C). An additional mutation (RT521: E664K) also present in D4K, was found to enhance CeNA-RT activity and enable reverse transcription of LNA (FIGS. 3A, 3E, S8). Together, these engineered polymerases support the synthesis and reverse transcription of six synthetic genetic polymers, and thus enable replication of the information encoded therein (FIG. 3G).

Example 3: XNA-Templated XNA Replication

Mutations enabling DNA-templated XNA synthesis were found to cluster at the periphery of the primer-template interaction interface in the polymerase thumb subdomain, >20 Å from the active site (FIG. 1B) and in one case allowed direct XNA-templated XNA replication (FANA, FIG. S9). In contrast, broad XNA RT activity was effected by just a single point mutation (I521L) in proximity to the catalytic aspartate (D542) and the polymerase active site. Its identification by SCA points to potential allosteric interaction networks involved in template recognition.

Example 4: Fidelity

As previously observed for TNA (16), non-cognate polymer synthesis can come at a cost of reduced fidelity as polymerase structures are poorly adapted to detect mismatches or aberrant geometry in the non-canonical XNA.DNA (or DNA.XNA) duplexes. We determined aggregate fidelities (as the probability of errors per position) of a full DNA→XNA→DNA replication cycle ranging from $4.3 \times 10^{-3}$ (CeNA) to $5.3 \times 10^{-2}$ (LNA), with HNA, CeNA, ANA and FANA superior to LNA and TNA (Table S8, FIGS. S11, S12).

Example 5: Evolution of Aptamers

Synthesis and reverse transcription establishes heredity (defined as the ability to encode and pass on genetic information) in all six XNAs. We next sought to explore the capacity of such genetic polymers for Darwinian evolution. As a stringent test for evolution and for acquisition of higher order functions such as folding and specific ligand binding, we initiated aptamer selections directly from diverse HNA sequence repertoires. We used a modification of the standard aptamer selection protocol comprising magnetic beads for capture and isolation of all-HNA aptamers against two targets that had been previously used to generate both DNA and RNA aptamers (23, 24): the HIV trans-activating response RNA (TAR) and hen egg lysozyme (HEL).

After eight rounds (R8) of selection using a biotinylated (27 nt) version of the TAR RNA motif (sTAR) as bait, clear consensus motifs emerged (FIG. S13) from which we identified an HNA aptamer (T5-S8-7) that bound specifically to sTAR with a dissociation constant ($K_D$) between 28-67 nM as determined by Surface Plasmon Resonance (SPR), Bio-Layer Interferometry (BLI) and ELONA titration (FIGS. 4C, S14 and Table S6). Other anti-TAR HNA aptamers, from the same selection experiment, displayed similar affinities but distinctive fine specificities with regards to binding TAR loop or bulge regions (FIGS. 4A and S14). We initiated selection against HEL from an $N_{40}$ random sequence repertoire and again observed emergence of a consensus motifs after R8 (FIG. S15). We identified specific HEL binders with $K_D$ of 107-141 nM as determined by SPR, BLI and Fluorescence Polarization (FP) (FIGS. 4C, S16 and Table S7). Anti-HEL HNA aptamers cross-reacted with human lysozyme and to a minor degree (<10%) with the highly-positively charged cytochrome C (pI=9.6), but did not show binding to unrelated proteins such as BSA and streptavidin (FIG. 4B). Fluorescently-labeled HNA aptamers allowed direct detection of surface HEL expression by flow cytometry (FACS) in a transfected cell line demonstrating specificity in a complex biological environment (FIG. 4D).

Example 6: Optimisation and Applications of Arabino Polymerases

We describe the optimisation of D4 as an ANA and FANA polymerase, the characterisation of RT-521K {Pinheiro, #1084} as an ANA and FANA reverse transcriptase and the combination of these activities to demonstrate ANA and FANA can store genetic information.

Engineering an ANA Polymerase

It was realised that D4 had activity as an ANA polymerase during screens for polymerase tolerance of a variety of 2' modified NTPs. These were carried out using D4 with various modified steric gate (Y409) residues as full substitution of ATP (e.g. for aATP) with BTP (CTP, GTP, UTP) against a template encoding an almost equimolar mix all four bases (TempN).

D4A (D4: Y409A), D4G (D4: Y409G) and D4S (D4: Y409S) all synthesised to the end of template TempN (+57 nt) with this mixture of aATP, CTP, GTP and UTP (FIG. 12) I then tested incorporation of the same mix (aATP, BTP) and with aNTPs (aATP, aCTP, aGTP, aUTP) comparing D4S, D4SK (D4: Y409S, Q664K) and TSK (TgoT: Y409S, E664K) following optimisation of position 664 for RNA synthesis. This demonstrated that both mutants with Lys664 (D4SK and TSK) outperformed the original D4S polymerase (FIG. 12). Furthermore, D4SK outperformed TSK, suggesting that either the additional thumb subdomain mutations or the active site mutation (L403P) in D4 improved incorporation of aATP. (We obtained aGTP from P. Herdewijn).

Following optimisation of the steric gate (Y409) for RNA synthesis, I screened the TxK (TgoT: Y490x E664K) lysates with diversified steric gates I had prepared for the NTP screen with aNTPs. This screen suggested Y409S is a remarkably suboptimal mutation and in fact a wild-type Tyr steric gate would be optimal (FIG. 12c). I confirmed this by comparing TYK with TSK (FIG. 12d) and then TYK against D4YK (D4: Q664K) (FIG. 12e). Further reverse engineering revealed that both the L403P that arose sporadically in D4 during CST and the Therminator {Gardner, 2002 #46} mutation (Tgo: A485L) improve ANA synthesis mutation (FIG. 13).

L403 is immediately N-terminal to D404, one of the catalytic triad aspartates in Tgo (D404, D540, D524) and is six residues N-terminal of the steric gate (Y409) on the same α-helix as both these key active site residues. Modelling a β-2'OH onto the incoming dNTP and 3' NMP of E. coli pol II (PDB: 3MAQ) suggests the β-2'OH of the 3' NMP will come within 3 Å of the sugar, base and bridging oxygen of the sugar-α phosphate of the incoming dNTP (FIG. 14). If disruption dNTP binding is the mechanism by which aNTPs chain terminate this would explain the observed phenotype that aCTP is incorporated efficiently but chain terminates at n+1 in vitro {Sanger, 1977 #549} and offers a possible explanation for the mechanism of L403P. Proline mutations are known to kink a helices by up to 30° {Richardson, 1981 #895} and a kink in the A-motif α helix of Tgo may shift its position sufficiently to reduce the steric clash generated between the aromatic ring of Y409 and an β-2'OH (NTP) or any interaction generated between the β-2'OH of a 3' aNMP and incoming dNTP, explaining the improvement seen with both these substrates (FIG. 12).

D4YK is also a FANA polymerase

D4YK is even more active as a FANA polymerase than as an ANA polymerase, presumably as the β-2'modification is smaller and so any steric clashes generated are reduced. Not only is FANA synthesis effective at relatively low FANA-NTP (faNTP) concentrations (less than 50 µM each, compared to 250 µM each for ANA synthesis) but synthesis of both a 97 nt incorporation tRNA and an N40 library is efficient in less than 5 minutes (FIG. 15). This rapid synthesis and toleration of a wide range of substrate concentrations is indicative of an efficient polymerase, but neither single incorporation kinetics nor processivity have been investigated for D4YK.

Properties of ANA and FANA

ANA is known to exhibit base-dependent differences in annealing to DNA {Noronha, 2000 #517} and this may impact RT efficiency due to weak binding of the DNA primer to ANA. To investigate the efficiency of primer binding I synthesized and gel-purified a stretch of purine-rich ANA (TestBind1) and a stretch of pyrimidine-rich ANA (TestBind3) and tested binding of complementary DNA oligonucleotides to these strands by annealing the ssANA oligonucleotide to ssANA in 1× Thermopol buffer at 2:1 DNA oligonucleotide excess. This showed purine-rich ANA binds complementary DNA substantially better than pyrimidine-rich ANA (FIG. 16).

This is expected as ANA usually hybridises with DNA less tightly (lower Tm) than a corresponding DNA:DNA duplex, especially when araU:dA base pairs are numerous {Giannaris, 1994 #666} {Noronha, 2000 #517} {Wilds, 2000 #729}. This holds when aU is replaced with aT {Noronha, 2000 #517}, but is substantially less pronounced when aU is in a homopolymeric strand {Giannaris, 1994 #666}.

The duplex destabilisation presumably derives from the β-2'OH, which projects into the major groove where it lies close to nucleobase immediately to its 3' and may interfere with stacking {Mikita, 1988 #545; Schweitzer, 1994 #573} {Gao, 1991 #553} {Noronha, 2000 #517}. More recent studies demonstrate a strong context dependency to Tm of both ANA and FANA hybrid duplexes due to the different properties of the beta-2' constituent, as a beta-2'OH clashes with the C—H8 of a purine nucleobase immediately 3', whereas a beta-2'F may be able to form a pseudohydrogen bond {Anzahaee, 2011 #519; Watts, 2010 #520}. Also of note are the multiple bands seen in the purine-rich ANA gel (FIG. 16b), suggesting that purine-rich ANA either folds into a range of secondary structures which retard electrophoresis or that purine-rich ANA concatamerises. This was not seen with FANA or HNA (V. Pinheiro, personal communication) and running the same ANA sample on a denaturing (8 M urea) gel results in a single band, suggesting all ANA present is the same length (FIG. 16c).

Indeed, all primers bind effectively to FANA using the same sequences, gel purified in the same manner, consistent with previous reports that FANA hybridises to DNA efficiently with no significant context bias (FIG. 16e) {Wilds, 2000 #729}. There is accumulating evidence that fluorine can serve as a hydrogen bond donor/acceptor {Wicki, 2007 #649} {Forconi, 2011 #650} and the □-2'F are within 3 Å of their proposed H-bond acceptors so it is plausible that pseudohydrogen bonds serve to stabilise FANA duplexes {Stryer, 1995 #861}. The weaker base pairing of pyrimdine-rich ANA to purine-rich DNA also affected synthesis, taking 24 h to synthesise a substantial quantity of full-length pyrimidine-rich ANA compared to only 2 h for purine rich ANA, suggesting weak affinity of the nascent strand for the template reduces synthesis efficiency substantially. This does not appear to be an inherent bias of the polymerase for incorporating purines more preferentially than pyrimidines as both polymers synthesised readily in FANA.

Testing various purification methods for ANA demonstrated that it partitions into the aqueous phase during phenol:chloroform extraction (FIG. 17a), is DNase sensitive and RNase resistant (FIG. 17b). The nuclease sensitivity of ANA and FANA were expected, as there was also no reason to expect the β-2'OH/F to protect from DNase I- or DNase II-mediated cleavage (as nucleophilic attack on the phosphate bond does not require interactions with the 2' position for either DNase I {Suck, 1986 #898} or II {Cheng, 2006 #896}) or to result in RNase sensitivity (as RNase cleavage proceeds via formation of an intermediate 2',3' cyclic phosphate, requiring an β-2'OH {Findlay, 1961 #899}). Although exonucleases are expected to degrade ANA, hybridisation to DNA is clearly sufficiently robust that exonucleases can be used for purification as ANA:DNA hybrid duplexes survive treatment with both 5'-3' (T5 exonuclease) and 3'-5' (Exonuclease I) exonucleases (FIG. 17c).

Screening for ANA and FANA Reverse Transcriptases

ANA and FANA were synthesised using D4YK from DNA primers against a biotinylated template. This was captured onto streptavidin-coated paramagnetic beads and the nascent ANA or FANA strand eluted using two washes in 30 mM NaOH. The single stranded products were neutralised, ethanol precipitated and used as a template to screen a panel of commercial polymerases as well as in-house engineered polymerases for RT activity.

No commercial reverse transcriptases polymerases displayed FANA RT activity, as judged by subsequent PCR from the cDNA (FIG. 18a). Amongst commercial DNA polymerases Therminator and Dpo4 showed weak RT activity with both 6G12 {Pinheiro, #1084} and RT-521K displaying robust activity, again judged by PCR from the cDNA (FIG. 18a). RT-521K is the promiscuous RT for unnatural nucleic acids recently described {Pinheiro, #1084}. RT-521 (bearing the same I521L mutation but lacking E664K, which enhances affinity for the nascent duplex, {Cozens, #1085}) is also an effective FANA reverse transcriptase but the nature of this experimental setup meant it did not show a PCR band.

We have learnt that RT-521 must be removed before PCR as even low concentrations of RT-521 inhibit PCR. In this case, the reverse transcription reactions were purified by ExoI (NEB) treatment to remove unextended primers and 0.05 volumes (1 µl out of 20 µl reaction) were used as template for 20 µl PCR with FastStart Taq (Roche). If the reactions had been purified by a method which removed RT-521 (e.g. silica column or phenol:chloroform extraction) the PCR for the RT-521 reaction would have been expected to be positive, as observed in other experiments (FIG. 19).

The experiment was repeated for ANA and no polymerases showed RT activity, (FIG. 18b) however this is most likely an artefact of the template used as the RT primer is not pyrimidine-rich and so binds poorly to ANA. As RT-521K is active as an ANA reverse transcriptase (FIG. 18a) this screen was not pursued.

Fidelity of ANA and FANA Synthesis

Synthesis of ANA and FANA molecules, reverse transcription, PCR amplification and TOPO-cloning allowed sequencing from colonies and hence an estimate of the aggregate fidelity of the system. The primers used for both forward synthesis and reverse transcription encode sites for outnesting primers and unique mismatches in their own template binding sites. This meant the PCR step could be carried out with outnesting primers which has the dual benefit of reducing background products and allowing unambiguous identification of sequences produced by enzymatic forward synthesis and reverse transcription due the presence of the primer encoded diagnostic mismatches.

D4YK has an apparent fidelity of $7.66 \times 10^{-3}$ with ANA and $9.45 \times 10^{-3}$ with FANA {Pinheiro, #1084}, both of which are comparable to the fidelity of TgoT with dNTPs ($8.3 \times 10^{-3}$) {Cozens, #1085}. These data not only demonstrate that D4YK is an enzyme of reasonable fidelity, but also establish ANA and FANA as synthetic genetic polymers.

Library Affinity

Having established that ANA and FANA are capable of acting as genetic polymers I next wanted to establish whether they had any potential as aptamer scaffolds. To this end, N40 libraries (with forward and reverse priming sites separated by 40 random incorporations, see 2.21 for sequence) were synthesised and gel purified and their affinity for hen egg lysozyme (HEL) was assayed by electrophoretic mobility shift assay (EMSA). While HEL has natural electrostatic affinity for nucleic acids {Potty, 2011 #901; Steinrauf, 1999 #902} aptamers exhibiting enhanced binding to HEL have nonetheless been selected from RNA {Cox, 2001 #906}, DNA {Tran, 2010 #903} and HNA {Pinheiro, #1084}.

EMSA analysis was used to assay binding as it is simple to set up and it was hoped EMSA would minimise non-specific (electrostatic) interactions as it does not measure equilibrium binding {Hellman, 2007 #907}. These data are rough but suggest both libraries have affinities of ~500 nM for lysozyme, judged by quantification of the unbound fraction (FIG. 20). There is no bound fraction apparent on the gel, presumably as it either is prevented from entering the gel as lysozyme is a globular protein or as the positive charge of lysozyme interferes with electrophoresis. Even though the library molecules had greater mass than lysozyme (~27 kD vs 14.6 kD) the globular protein would be expected to enter the pores of an agarose gel more slowly than a nucleic acid and, more importantly, the positive charge of lyzosyme would cause lysozyme to be electrophoresed in the opposite direction to DNA (which migrates towards the anode).

This experiment was not designed to provide a quantitative measure of affinity, but rather to provide a guide for initiating selections as characterisation of initial libraries should allow selections to be carried out under conditions where recovery can be predicted. Repeating this process over subsequent rounds should allow recovery of sufficient nucleic acid to ensure robust RT-PCR following each selection stop without risking either losing binding sequences through inefficient reverse transcription or introduction of excessive bias through tens of cycles of PCR. Furthermore, it allows the amount of ligand available for binding to be decreased in a controlled manner, thereby tightening selection without wasting libraries.

SELEX: Round One

Using the parameters suggested by the EMSA with the initial libraries, the first SELEX round was carried out with 30 nM ANA or FANA and 25 nM lysozyme in 500 µl 1× Hanks Balanced Salt Solution, supplemented with 0.1% Tween-20 to facilitate bead handling. ANA and FANA concentrations were increased 10-fold over the EMSA conditions to allow sampling of a large number of molecules (15 pmol, $9 \times 10^{12}$ molecules). This was to ensure a first round permissive for binding so as to not deplete the library of too many rare binders early on, while removing any non-binders. As 10-15% of the ANA and FANA libraries were expected to bind at 250 nM lysozyme according to the EMSA, lysozyme was used at 25 nM (actually 26.6 nM for ease of pipetting) to reflect the increased ANA and FANA concentration. Recovery of ~10% of ANA and FANA result in recovery of ~1.5 pmol, substantially more than is necessary for robust RT-PCR. Indeed, the initial double-outnested PCR was positive at only PCR 20 cycles using 0.1 volumes of the RT as template (FIG. 20).

Example 7: Comparative Data—D4 and D4K

In order to demonstrate the gain in activity conferred by the E664K mutation made to generate D4K (which has E664K) from D4 (which has E664Q), a polymerase dilution experiment was carried out. In this experiment, the concentration of buffer (1× Thermopol (NEB) buffer), arabinosyl-NTPs (0.25 mM each), primer (200 nM), template (400 nM), the reaction volume (5 ml) and extension conditions (1 min 94° C., 30 sec 50° C., 2 min 65° C.) were held constant.

The data are shown in FIG. 21.

The data show that D4 produces very little full-length (+57 nucleotide incorporations) product at 300 nM and no full-length product at 75 nM.

In contrast, full-length product (+57 nucleotide incorporations) is present even at only 18.8 nM using D4K.

These data demonstrate that D4K can synthesise full-length ANA product when less than 1/15 the polymerase concentration required for D4 to produce the same product is used, indicating a substantial gain in activity from the E664K mutation.

Example 8: Comparative Data—D4K and D4K521

The further mutation I521L adds further beneficial function, especially to D4K.

In order to demonstrate the gain in activity conferred by the I521L mutation in a D4K context, the mutant polymerase "D4K521" was generated. D4K521 bears the following mutations from wild type Tgo: V93Q, D141A, E143A, L403P, A485L, I521L, P657T, E658Q, K659H, Y663H, E664K, D669A, K671N, and I676T.

In order to demonstrate the gain in activity conferred by the I521L mutation made to generate D4K521 from D4K, a polymerase dilution experiment was carried out.

In this experiment, the concentration of buffer (1× Thermopol (NEB) buffer), arabinosyl-NTPs (0.125 mM each), primer (200 nM), template (400 nM), the reaction volume (4 ml) and extension conditions (1 min 94° C., 30 sec 50° C., 2 min 65° C.) were held constant.

The data are shown in FIG. 22.

The data show that, under these conditions, D4K produces full-length (+57 nucleotide incorporations) product at 18.8 nM, but less or no full-length product at lower polymerase concentrations. In contrast, full-length product (+57 nucleotide incorporations) is present even at only 2.3 nM using D4K521.

These data demonstrate that D4K521 can synthesise full-length ANA product when less than 1/8 the polymerase concentration required for D4K to produce the same product is used, indicating a further gain in activity from the I521L mutation.

Example 9: Processive Arabinonucleic Acid (ANA) and Fluoroarabinonucleic Acid (FANA) Synthesis by the Engineered DNA Polymerases D4K and D4K521

Both ANA and FANA triphosphates are potent chain terminators in vitro, yet are incorporated into genomic DNA in vivo. We engineer DNA polymerases to generate polymers consisting entirely of ANA or FANA. Described here is such a polymerase, D4K.

The enzyme D4 was derived from TgoT, a variant of the replicative polB from *Thermococcus gorgonarius*, which bears mutations to disable uracil stalling (V93Q), to disable exonuclease activity (A141A, E143A) and the Terminator mutation (A485L) to enhance incorporation of non-cognate substrates. Compartmentalised Self-Tagging (CST) selections were performed on a library based on TgoT, in which diversity was focussed at Motif 10A. This yielded D4, which bears, 8 mutations clustered in a region of the thumb domain ("motif 10A") (P657I, E658Q, K659H, Y663H, E664Q, D669A, K671N, T676I) and 1 in the A-motif (the sporadic mutation L403P).

D4 was then further modified in motif 10A, at residue 664 (referred to as the second gate residue), following work that showed mutation E664K of this residue was optimal for RNA synthesis activity. D4 with the mutation E664K gave rise to polymerase D4K, which is now used for ANA synthesis.

A typical synthesis reaction is shown in FIG. 25 and would consist of: 1× ThermoPol buffer (NEB), supplemented with 1 mM $MgSO_4$, 250 uM each ANA-NTP, 2 pmol fluorophore-labelled DNA primer, 4 pmol DNA template and 300 nM purified D4K for ANA and would be thermocycled for 4 cycles of: 30 sec 94° C., 5 min 50° C., 30 min 65° C. and products analysed by 8-15% denaturing (8 M urea) PAGE. FANA synthesis is typically carried out in a similar reaction except with 25 uM each FANA-NTP and 150 nM D4K for 30 sec 94° C., 5 min 50° C., 50 min 65° C.

Polymerases of the invention such as the exemplary D4K and/or D4K521 also have the beneficial property of synthesising arabino nucleic acids from arabino templates. For example, we demonstrate FANA templated ANA synthesis as well as ANA templated FANA and ANA synthesis. Results are shown in FIG. 29 and FIG. 30.

Example 10: Reverse Transcription of ANA, FANA, and Base-Modified Mixtures by RT-521K Both ANA and FANA inhibit polymerases as templating bases, and cannot be reverse transcribed back to DNA by reverse transcriptases or DNA polymerases.

Furthermore, reverse transcription of ANA and FANA allowed PCR amplification, cloning and sequencing of these nucleic acid synthesis reactions (FIG. 3). A typical reverse transcription reaction is shown in FIG. 26 and would consist of: 1× ThermoPol buffer (NEB), supplemented with 0.5 mM $MgSO_4$, 500 uM each dNTP with DNA primer pre-annealed to ANA or FANA templates. 0.01 ug/ul RT-521K is then added and incubated at 65° C. for 2-4 hours.

RT-521L can of reverse transcribe all-arabino and all-fluorarabino nucleic adds as well as the mixtures described consisting araC, araG, Floxuridine and either Cladribine or Fludarabine. FIG. 23 shows RT-PCR of (a) arabino nucleic acid (ANA), (b) fluoroarabino nucleic acid (FANA) and (c) a "tetra-antimetabolite" polymer consisting Cladribine, araC, araG and 5-fluorodeoxyuracil (Floxuradine). In all cases, forward synthesis was with D4YK from a biotinylated DNA primer, purification was by binding to streptavidin-coated paramagnetic beads and NaOH— eluting the template and reverse transcription with RT-521 followed by PCR with FastStart Taq (Roche). Expected product sizes are 179 bp for (a) and (b) and 160 bp for (c) as the template was shorter.

Example 11: Incorporation of Base-Modified NTPs by D4K and Use of "Tetra-Antimetabolite" Polymers as Prodrugs Arabino nucleosides are often used as antivirals or anti-cancer therapeutics, however their utility is limited by problems in delivery and targeting. Despite this, araC is one of numerous nucleoside analogue drugs licensed for use in the treatment of various proliferative diseases. Among these are Cladribine (2'-deoxy-beta-2'-chloro-adenosine), Fludarabine (9-beta-D-arabinofuranosyl-2-fluoroadenine) and Floxuridine (5-fluoro-2'-deoxyuridine), all of which are active as antineoplastic metabolites. D4K can synthesise polymers consisting of araC, araG, 5-Fluorodeoxyuracil and either Fludarabine or Cladribine from their respective 5'-triphosphates and RT-521K can reverse transcribe them (FIG. 27). Synthesis and reverse transcription are carried out as for ANA, except that Fludarabine incorporation is better at 50° C. and so any synthesis reactions containing Fludarabine 5'triphosphate are carried out at 50° C. (FIG. 27). D4K can also incorporate of 5' nucleotide triphosphates derivatives of 6'thio-deoxyguanosine and 5'aza-cytidine and presumably other nucleoside analogues (FIG. 28). It should now be possible to derive aptamers against cell surface proteins that will internalise with aptamers bound. This has been demonstrated in several cases (e.g. Prostate Specific Membrane Antigen, Transferrin receptor 7, protein tyrosine kinase 7, nucleolin). As these "tetra-antimetabolite" nucleic acids are susceptible to degradation by DNase I (TURBO DNase, Ambion) and DNase II (Sigma) but stable when treated with RNase (RNase Cocktail, Ambion), intracellular degradation and simultaneous release of 4 anti-proliferative drugs should occur at this point.

This is expected to have the benefits of:

Targeting the antimetabolite drugs to the cancer, thereby reducing both side-effects (by reducing serum levels) and enhancing potency.

Reducing the amount of drug which has to be administered, as targeting the drugs ought to reduce the proportion of drug that is excreted or degraded before having any clinical effect.

Further enhancement of drug activity as the tetra-antimetabolite polymers will degrade into cytotoxic nucleoside analogues that target different intracellular NTP metabolism pathways. Therefore it can be expected that synergy would be observed. For example, it is known that araC and GTI-2040 (siRNA against ribonucleotide reductase) exhibit synergy. As Fludarabine is an irreversible ribonucleotide reductase inhibitor, it is expected to exhibit synergy with araC.

Broadening the range of ailments that can be treated with antimetabolite drugs. Currently they are largely limited to leukaemias as the target cells have to be dependent on uptake of extracellular nucleosides to take up sufficient levels of nucleoside analog drug to have an effect. With this method, nucleoside analogs can be targeted to any cancerous or infected cell with specific extracellular markers.

It may result in release of 5' monophosphates within the cell, thereby sidestepping the rate-limiting step (the initial kinase of an imported nucleoside).

It may even be possible to give a sub-clinical dose of an antimetabolite drug (e.g. Gemcitabine) to potentiate the activity of the aptamers once delivered. Any degradation of polymers in serum would in only result in the presence of licensed drugs in the blood, and could be abrogated by capping the ends (e.g. with cyclic linkages, 2'O-methyl-DNA nucleotides, cholesterol) to protect against exonucleoase degradation.

Example 12: Manufacture of Polymers

We Demonstrate Manufacture of "Toxic Nucleic Acids" (txNA)

txNA can be synthesised and reverse transcribed, is potently cytotoxic when delivered to cells, is amenable to in vitro evolution (SELEX) and can form sufficiently complex and stable structures to bind specific target antigens with high affinity (ie—act as aptamers). We demonstrate that it is possible to synthesise and reverse transcribe a range of polymers consisting of different mixtures of the nucleotide triphosphates derivatives of the nucleosides in as described above without compromising fidelity and that these polymers are cytotoxic.

txNA polymers may be delivered e.g. by conjugation to known internalising aptamers e.g. the known CD30 aptamer (sequence: 5'-mGmAmU rUrCrG rUrArU rGrGrG rUrGrG rGrArU rCrGrG rGrArA rGrGrG rCrUrA rCrGrA rArCrA mCmCmG-3', where m=2'O-methyl-RNA and r=RNA, as described previously {Zhang, 2009 #1114}). This was done using conventional click chemistry. Conjugation to the 2'O-methyl/RNA chimeric CD30 aptamer was carried out with 50 uM 5'alkyne-CD30 aptamer, 250 uM 5' azide-FD, 2.5 mM CuBr, 7.5 mM TBTA, 0.5 mM sodium ascorbate in 70% 3:1 DMSO:tertiary butanol (final concentrations: 52.5% DMSO, 17.5% tertiary butanol) and resulted in recovery of 60% of the CD30 aptamer as an aptamer-primer conjugate after gel purification. The conjugate retained robust internalisation and was able to prime synthesis of txNA.

Primer extension reactions showing polymerase-directed synthesis of various txNAs (D=dNTPs. Other lanes Fludarabine-TP (F) or Cladribine-TP (C) and araCTP, araGTP, Floxuridine-TP). Multiple extension cycles (3 cycles of (15 sec 94° C., 5 min 50° C., 1 h 65° C.)) result in full-length txNA product. Single extension cycles (15 sec 94° C., 5 min 50° C., 14 h 42 min (overnight) 65° C.) demonstrate the relative efficiency of synthesis with different substrates. Results are shown in FIG. 31.

Example 13: Synthesis of Polymeric Prodrug Polymers

The template used for all polymeric prodrug syntheses was TempN:

```
Encoded molecule                          (SEQ ID NO: 18)
5'-CCCCTTATTAGCGTTTGCCAGATCGATTACCGAACAGCACTACG

TGGCTAAGTGCTTATCTGGTCCAGCATCGTGAG-3'

Template                                  (SEQ ID NO: 19)
5'-CTCACGATGCTGGACCAGATAAGCACTTAGCCACGTAGTGCTGT

TCGGTAATCGATCTGGCAAACGCTAATAAGGGG-3'
```

The underlined bases are the primer binding site and the final 57 are the encoded bases.

TempN encodes 14 A, 14 C, 15 G and 14 T nucleotide incorporations (57 nt total) comprising all possible dinucleotide combinations and synthesis is generally efficient.

Initially, Fludarabine-TP (in place of aATP) or Cladribine-TP (also in place of aATP) and Floxuridine-TP (in place of aUTP) were tested for incorporation with araC-TP and araG-TP. Arabinoslyadenine (araA) and arabinosyluridine (araU) have low therapeutic potential because they are not efficiently activated in vivo and they are easily degraded to non-toxic metabolites. Fludarabine and Cladribine are resistant to adenosine deaminase as a result of C2'-adenine modification and are more therapeutically effective than araA. Floxuridine is a widely-used and potent chemotherapeutic and removal of araU would hopefully improve the stability of intramolecular secondary structure as araU base pairs weakly.

Fludarabine, Cladribine and Floxuridine were all well-incorporated by D4YK, although with longer extension times compared to native aNTPs. Primer extension reactions with single extension cycles suggested Fludarabine-TP was better-tolerated than Cladribine-TP (FIG. 31), consistent with the larger C2'-adenine modification (Cl vs. F) and agrees with previous studies using natural DNA polymerases. Modifications to C2'-adenine are expected to project into the minor groove of the nascent strand and may prove disruptive to polymerase-directed synthesis as DNA polymerases hydrogen bond extensively to the minor groove.

This xNTP mixture (Fludarabine-TP, araC-TP, araG-TP and Floxuridine-TP) was used for synthesis optimisation. I investigated the effects of multiple extension cycles during primer extension reactions, varying synthesis temperature, changing template, and supplementing the reaction with a range of chemicals known to enhance PCR.

Extension cycles were investigated by running experiments with the same total extension at 65° C. but with various numbers of cycles, for example:

|  | Program 1 | Program 2 | Program 3 | Program 4 |
|---|---|---|---|---|
| 94° C. | 1 min | 1 min | 1 min | 1 min |
| 50° C. | 5 min | 5 min | 5 min | 5 min |
| 65° C. | 60 min | 30 min | 60 min | 30 min |
| Number of cycles | 2 | 4 | 4 | 8 |
| Total time at 65° C. | 2 hours | 2 hours | 4 hours | 4 hours |

Here, Programs 1 and 2 have the same total time (2 hours) at the extension temperature (65° C.) but over with 2×60 min or 4×30 min extension cycles. This experiment suggested that more cycles improve synthesis, even if the total extension time was not increased as Programs 2, 3 and 4 all resulted in better synthesis than Program 1.

Example 14: Synthesis of Alternative txNAs

Having established that synthesis of txNA is possible I tested polymer synthesis using commercially available triphosphates of alternative nucleoside antimetabolites: 6' thio-dG-TP, Gemcitabine-TP and Clofarabine-TP. These were chosen as they are either more toxic or are active against different cell types than the antimetabolites they would replace. 6' thio-dG is more toxic than araG and both Gemcitabine and Clofarabine have been reported to be active against solid tumours (unlike araC and Fludarabine). Clofarabine is also more stable than either Fludarabine or Cladribine as the β-2'F modification stabilises the nucleoside against enzymatic or acidic cleavage of the glycosidic bond linking the base to the sugar and Clofarabine 5' monophosphate is less sensitive to enzymatic dephosphorylation.

The alternative triphosphates were tested in various combinations in order to determine which variations could be synthesised without further polymerase engineering.

Synthesis was reduced by substitution of aATP for Fludarabine-TP, Cladribine-TP or Clofarabine-TP, with Clofarabine-TP in particular being poor (FIG. 32a). 6' thio-dGTP was tolerated substantially worse than aGTP in combination with Floxuridine-TP, aCTP and either Fludarabine-TP or Cladribine-TP at 50° C. (FIG. 32b).

Gemcitabine-TP was well incorporated in combination with aATP, aGTP and Floxuridine-TP (FIG. 32b). Substituting Gemcitabine-TP for aCTP and/or aGTP for 6' thio-dGTP is greatly inhibitory in combination with Floxuridine-TP and Fludarabine-TP, Cladribine-TP or Clofarabine-TP (FIG. 32b). Decitabine-TP was well incorporated although it was only tested in the presence of dDTP (dATP, dGTP and dTTP) (FIG. 32b).

Finally, it is evident that the C2'adenine modification in Fludarabine-TP, Cladribine-TP and Clofarabine-TP are inhibitory as primer extension reactions carried out with dATP, aCTP, dGTP and Floxuridine-TP show full-length product formation in only 5 mins (FIG. 32d). Clearly, this polymer also omits aGTP, however aGTP was not found to be an inhibitory factor for ANA synthesis. This may be because the halide (fluoride in Fludarabine, chloride in Cladribine and Clofarabine) polarises the base and distorts base pairing, because the halide obstructs hydrogen bonding to the polymerase thumb subdomain in the minor groove or a combination of these factors.

FIG. 32 shows Synthesis of txNAs of different compositions:
(a) Comparison of synthesis against template TempN with varying adenosine analogue. All reactions contained Gemcitabine-TP, araG-TP and Floxuridine-TP and one of aA-TP, Fludarabine-TP, Cladribine-TP or Clofarabine-TP. (b) Synthesis of polymeric prodrugs containing different mixtures of adenosine, cytidine and guanosine analogues. All reactions contained Floxuridine-TP as well as triphosphates of the indicated analogues. Gemc=gemcitabine. (c) Incorporation of decitabine-TP with dDTP (dATP, dGTP, dTTP). (d) Synthesis of a polymer consisting dATP, araCTP, dGTP and Floxuridine-TP.

FIG. 33 Shows Cytotxicity of txNA Polymeric Prodrugs (a) 10 nM untargeted polymers incubated with Jurkat cells for 2 hours in media+10% FBS at 37° C. prior to washing. (b) 20 nM targeted and untargeted polymers incubated with CCRF-CEM cells in DPBSM for 1 hour at 4° C. prior to washing. Data are averages of a single experiment carried out in triplicate and error bars represent SD. *fd=primer *fd only, CD30=CD30 aptamer only, CD30*fd=CD30 atpamer-primer *fd conjugate, *fd-txNA=primer *fd extended with txNA, CD30*fd-txNA=CD30 aptamer conjugated to *fd and extended with txNA, Nothing=no polymer (buffer only).

The most general optimum mix based on the nucleosides analysed here is likely to be Clofarabine, araC or Gemcitabine, αS-G and Floxuridine Example 15: Enhanced Synthesis of txNAs Using PolD4K521

Following the improved synthesis of ANA and FANA by PolD4K521 (FIG. 22) we tested synthesis of certain txNA polymers by D4K521.

The reactions were set up in the same manner as described above (1× Thermopol buffer, 0.25 mM each xNTP, 200 nM primer fd with 5'FITC, 400 nM template TempN and polymerase D4K521 at a range of concentrations from 300 nM to 18.8 nM.)

The reactions were incubated for 1 min 94° C., 30 min 50° C., 30 min 65° C. These syntheses were carried out using Clofarabine-triphosphate, araC-triphosphate, FANA-G-triphosphate and Floxuridine-triphosphate.

FIG. 34 demonstrates an increased level of full-length product with D4K521 as compared to D4 or D4K. FIG. 34 shows enhanced synthesis of txNA consisting Clofarabine, araC, FANA-G and Floxuridine by D4K521 (D4K I521L) compared to D4K or D4.

Example 16: Anti-Metabolite Polymer Synthesis

In this example we demonstrate the development of anti-metabolite polymer consisting of α-thio-2'deoxyadenosine, 2'2'difluorodeoxycytidine (Gemcitabine), FANA-G and 5-fluoro, 2'deoxyuridine (Floxuridine)

A range of various polymer combinations were tested before this polymer was chosen for SELEX for reasons of enhanced serum stability (α-thio-2'deoxyadenosine (αS-dA)), toxicity 2'2'difluorodeoxycytidine (Gemcitabine) and 5-fluoro, 2'deoxyuridine (Floxuridine) and ease of synthesis (FANA-G).

Typically, all syntheses were carried out using polymerase D4K (PolD4K) at 300 nM in 1× Thermopol buffer with 0.25 mM each nucleoside triphosphate, 100 nM primer fd with 5' FITC and 200 nM template TempN in 3-5 µl reactions.

These conditions were used for synthesis of polymers variously consisting of:
Adenosine analogues: Fludarabine, Cladribine, Clofarabine, αS-dA
Cytidine analogues: araC, Gemcitabine
Guanidine analogues: araG, α-thio-2'guanosine (αS-G), α-thio-2'deoxyguanosine (αS-dG)

Thymidine analogue: Floxuridine.

These data are shown in FIGS. 35-37.

FIG. 35 shows synthesis of txNA polymers by D4K, incubated for 2 h at 50° C. In this case, efficient synthesis against template TempN was observed using Fludarabine/araC/αS-G/Floxuridine, Cladribine/araC/αS-G/Floxuridine, Fludarabine/Gemcitabine/αS-G/Floxuridine, Cladribine/Gemcitabine/αS-G/Floxuridine, Fludarabine/araC/araG/Floxuridine, Cladribine/araC/araG/Floxuridine and to a lesser extent with Clofarabine/araC/araG/Floxuridine and Cladribine/gemcitabine/araG/Floxuridine although it is worth noting that, no synthesis failed. Optimisation may be possible.

FIG. 36 shows synthesis of txNA polymers by D4K, incubated for 15 min at 50° C. In this case, efficient synthesis against template TempN was observed using Fludarabine, Caldribine ofrClofarabine/araC/FANA-G/Floxuridine declining in the order Fludarabine>Cladribine>Clofarabine. Full-length extension was also observed for Cladribine/Gemcitabine/FANA-G/Floxuridine, Cladribine/araC/αS-G/Fluxoridine and Cladribine/araC/αS-G/Floxuridine. Again, no syntheses failed. Optimisation may be possible.

FIG. 37 shows syntheses of txNA polymers by D4K, incubated for 1 hour at 50° C. FIGS. 37 *a*) and 37 *b*) show the same polymers under test, except a) shows extension using template TempN (encoding 57 nucleotide incorporations of known sequence) and b) shows extension using template N40, encoding 40 random incorporations followed by a patch of 20 known nucleotides. Relative extension efficiency with either template is comparable, suggesting analyses with TempN or N40 will be general for other templates and that differences are due to differences between the relative synthetic ability. In this case, extension was efficient using FANA-A or αS-dA/Gemcitabine/FANA-G or αS-dG/Floxuridine. Good extension was also obtained with Cladribine/araC/FANA-G, αS-G or αS-dG/Floxuridine.

Following these tests we decided to work with a polymer consisting αS-dA, Gemcitabine, FANA-G and Floxuridine. Fidelity data suggested some xNTPs were incorporated more efficiently than others and so the xNTP concentrations were optimised to balance good incorporation against enhancing fidelity: for SELEX, this mix was used as 0.075 mM αS-dATP, 0.150 mM Gemcitabine-TP, 0.050 mM FANA-GTP and 0.025 mM Floxuridine-TP. This resulted in an improvement in misincorporation rate from $4.3 \times 10^{-2}$ (with 0.25 mM each xNTP) to $1.2 \times 10^{-2}$.

Example 17: Selection of Anti-Metabolite Aptamers

In this example the application of the invention to the selection of nucleic acid aptamers is demonstrated. In particular the invention finds application in synthesis of XNA aptamers for selection.

In this example, aptamer selection against CD30 and CD171 (L1-CAM) is demonstrated. Initial aptamer selections were carried out against CD30 and L1-CAM. CD30 is a TNF receptor family member that is expressed in activated lymphoid cells (Chiarle et al., 1999), Hodgkin's lymphoma, anaplastic large cell lymphomas (a type of non-Hodgkin's lymphoma) and is not expressed in healthy non-lymphoid tissues (Durkop et al., 2000, Chiarle et al., 1999). Furthermore, CD30 is robustly internalised via the endosomal/lysosomal pathway (Sutherland et al., 2006) and is known to be an effective target for antibody-drug complexes (Sutherland et al., 2006, Francisco et al., 2003).

L1-CAM (L1 cell adhesion molecule) is an L1 cell adhesion molecule family member, part of the immunoglobulin superfamily. L1-CAM is present in some neurons, Schwann cells, leucocytes and the kidney and is a target of beta-catenin signalling that confers enhanced motility, growth and transformation on cells when overexpressed (Shtutman et al., 2006, Gavert et al., 2005). Two studies in mice using anti-L1-CAM monoclonal antibodies observed significant reductions in tumour burdens in nude mice with induced tumours and did not observe hepatotoxicity (Wolterink et al., 2010, Arlt et al., 2006). L1-CAM promotes cell motility in vitro (Gavert et al., 2005, Shtutman et al., 2006, Hai et al., 2012, Li and Galileo, 2010, Gavert et al., 2007) and is associated with poor prognosis of invasive and metastasising cancers in vivo, including ovarian, uterine, lung and uterine (Tsutsumi et al., 2011, Raveh et al., 2009, Fogel et al., 2003). Furthermore, L1-CAM is most commonly expressed at the invasive front of cancers (Gavert et al., 2005, Raveh et al., 2009), meaning a cytotoxic aptamer against L1-CAM may be useful to target metastasising and invasive areas of tumours to halt the spread of disease in late-presenting patients and limit recurrence in surgery and radiotherapy patients.

In this example, selections were carried out against the extracellular domains of both CD30 and L1-CAM expressed as N-terminal Fc chimeras. Briefly, for each round libraries were annealed in 1×HBSSTT (Hanks' Balanced Salt Solution with 5 mM each TRIS pH 7.4 and 8.3 and 0.05% Tween-20) for 5 min 85° C. and cooled to 4° C. at 0.1° C./sec, exposed to either protein AG or streptavidin-coated paramagnetic beads (see below), filtered to remove the beads and then added to recombinant protein in 1×HBSST. These mixtures were incubated at room temperature on a rotator to allow aptamers to bind to the recombinant proteins in solution and binders were recovered via protein AG or streptavidin-coated paramagnetic beds. Rounds 1, 2 and 5 were carried out using native protein and Protein AG Magnetic Beads (Pierce). All other rounds were carried out using protein biotinylated with NHS-LC-LC-biotin (Pierce) and recovered from the binding incubation using NanoLink Streptavidin Magnetic beads (SoluLink). The beads were washed in 1×HBSSTT for 2 h-16 h at room temperature using a Thermo KingFisher and aptamers eluted from the proteins bound to the beads using 30 mM NaOH. Negative selections were carried out against free Fc from round 5 onwards.

The recovered aptamers were ethanol or isopropanol precipitated, reverse transcribed using RT-521K and PCR-amplified. A second, in-nested PCR was carried out to generate the template for the next selection round using one native DNA primer and one biotinylated primer. Following ExoI treatment, PCR products were bound to NanoLink Streptavidin Magnetic beads, non-biotinylated strands stripped with NaOH and the biotinylated strand eluted in water at 95° C. This strand was used as the template for XNA synthesis.

Following 7 rounds of selection for CD30 and 8 rounds for L1-CAM the libraries were deep-sequenced using an Illumina MiSeq sequencer. Analysis of the sequences revealed enrichment of a number of clones, the best of which bound their respective targets with good affinity when assayed by fluorescence polarisation (FIG. 38).

The sequences of these aptamers are:

```
CD30_I3:                                    (SEQ ID NO: 20)
TAGATGTGGTAGAAGTCGTCATTTGGCGAGAAAGCTCAGTCTCAGG

CD30_I30                                    (SEQ ID NO: 21)
TTTCATGGTATTGATAAAGCTGTTGCCGATACTTGGAACAATTTCT

L1CAM_I1:                                   (SEQ ID NO: 22)
GCGACGCCGTTCAACCAGATATTGAAGCAGAACGCAAAAGAGAGAT
GAGATTGAGGCT

L1-CAM_I6:                                  (SEQ ID NO: 23)
TAGATGTGGTAGAAGTCGTCATTTGGCGAGAAAGCTCAGTCTCAGG

L1-CAM_Icore:                               (SEQ ID NO: 24)
ACGACGCGACGCCGTTCAACCAGATATTGAAGCAGAACGCAAAAGA
```

An alternative version of L1-CAM_I6 lacking the 3' seven nucleotides was also enriched (L1-CAM_14) and has very similar characteristics. L1_Icore is the 40 nucleotide "core" of 3 of the most abundant clones which together represent 2.33% of the library. All aptamers have only been tested as the above sequences with 5'DNA primer fd.

The isolation of these sequences which bind their target antigen with affinities with sub-100 nM affinity (with the exception of CD30_I3) demonstrates that selection of txNA aptamers is possible.

It should be noted that CD30_13 does bind CD30 tightly and with good affinity, just not as good as the others. Regarding the nomenclature, CD30 is the target and 13 refers to the clone (the "I" is because the library was screened by Illumina sequencing). There is variation between CD30_13 and CD30_130. Without wishing to be bound by theory, it is believe that this is due to their different sequences—which gives them different structures and hence different binding properties.

FIG. 38 shows the affinity of selected aptamers. Aptamers selected against a) CD30 and b) L1-CAM were tested in fluorescence polarisation (FP) and affinities calculated as above (and/or Pinheiro et al (2012)). Affinities are inset into the graphs. Apart from CD30_I3, all aptamers have affinities tighter than 100 nM.

Example 18: Polymeric Prodrug Cytotoxicity

In order to test the toxicity of txNAs directly targeted to CCRF-CEM cells, we conjugated the CD30 aptamer to a DNA primer (primer "*fd") using CuAAC and used this conjugate to synthesise txNA consisting of Fludarabine, araC, araG and Floxuridine. After gel purification this polymer (CD30*fd-txNA) consisted of an aptamer that internalises via binding to CD30 and a txNA "tail" consisting 14 Fludarabine-MPs (monophosphates), 14 araC-MPs, 15 araG-MPs and 14 Floxuridine-MPs. The controls used were unconjugated primer (*fd) only, unconjugated aptamer (CD30) only, aptamer-primer conjugate (CD30*fd) only, unconjugated txNA (*fd-txNA) and no polymer.

Preliminary experiments with untargeted txNA on Jurkat cells had demonstrated that this txNA is cytotoxic when incubated with cells in RPMI-1640 supplemented with 10% FBS for 2 hours, washed, and cultured for 72 hours prior to viability assay by XTT (FIG. 38.10a). XTT is reduced by actively metabolising cells to a soluble, coloured formazan salt that can be easily detected by absorbance reading (Roehm et al., 1991). As only live cells reduce XTT, this provides a measure of cell viability with low $Abs_{475}$ readings indicating high toxicity as few cells are metabolising. The most likely explanation for this is degradation of txNA in serum (FIG. 38.9b) resulting in release of nucleotide-monophosphates that would be rapidly dephosphorylated and transported into cells, although some txNA may be taken up by pinocytosis.

In order to reduce this non-specific effect, the polymers were incubated with cells at 20 nM in Dulbecco's modified PBS with $Mg^{2+}$ and $Ca^{2+}$ supplemented with 1 mM $MgCl_2$ at 4° C. for 1 hour to allow the aptamer to bind to CD30 antigens and then washed three times in RPMI-1640 GlutaMAX medium supplemented with 10% FBS and 100 U/ml penicillin and 100 µg/ml streptomycin and incubated for 72 hours at 37° C., 5% CO2 prior to viability assay. For each wash, 90 µl (0.9 V) was removed after centrifugation and a fresh 90 µl added to each well. This experiment demonstrated that the CD30 aptamer-conjugated txNA (CD30*fd-txNA) was the only polymer to exhibit cytotoxicity.

While the CD30*fd-txNA polymer was only moderately cytotoxic, this experiment demonstrates that aptamer-polymeric prodrug conjugates are cytotoxic when experimental conditions are biased so that only molecules that bind to cell-surface antigens will be retained. Presumably, substantially greater quantities of polymer would be internalised if serum stability could be improved to the extent that an untargeted polymer in serum was not toxic. The inclusion of nucleotides that enhance stability (such as Clofarabine and αS-G) within the polymer and perhaps a phosphothiorate tail as well as aptamers selection under in vivo conditions (in serum at 37° C.) will hopefully increase stability.

FIG. 39 shows cytotoxicity of txNA polymeric prodrugs, in particular toxicity of targeted and untargeted polymers as measured by XTT assay. XTT is reduced to a coloured product by viable cells, meaning a lower Abs475 indicates a more toxic agent as fewer cells remain actively metabolising, which is used as a proxy for viability. (a) 10 nM untargeted polymers incubated with Jurkat cells for 2 hours in media+10% FBS at 37° C. prior to washing. (b) 20 nM targeted and untargeted polymers incubated with CCRF-CEM cells in DPBSM for 1 hour at 4° C. prior to washing. Data are averages of a single experiment carried out in triplicate and error bars represent SD. *fd=primer *fd only, CD30=CD30 aptamer only, CD30*fd=CD30 aptamer-primer *fd conjugate, *fd-txNA=primer *fd extended with txNA, CD30*fd-txNA=CD30 aptamer conjugated to *fd and extended with txNA, Nothing=no polymer (buffer only).

Example 19: Increased Toxicity by Targeted Polymer

In an alternative assay, we carried out the same conjugation reaction using the ssDNA anti-PTK7 aptamer "sgc8c" and generated a txNA consisting Fludarabine, araC, araG and Floxuridine. In this example, the nucleic acid polymer was incubated with Jurkat cells in RPMI-1640 with 10% FCS for 2 hours, prior to a single wash where 75% of the media was removed and replaced with fresh media. After this wash, the cells were incubated for 3 days prior to a viability assay.

The viability assay, shown in FIG. 40, shows that there is an increase in toxicity between an untargeted polymer ("txNA only", $IC_{50}$ 17 nM±1.4 nM) and the aptamer-targeted polymer ("sgc8c+txNA", $IC_{50}$ 6.4 nM±1.2 nM). The toxicity of the untargeted polymer (txNA only) is presumably explained by a combination of degradation in serum and a small amount or polymer remaining adhered to the cells despite the wash. The increased toxicity of the targeted polymer (sgc8c+txNA) suggests that the aptamer enhances the binding and/or uptake to cells of the polymer, signifying this strategy is a valid mechanism to deliver cytotoxic polymers to cells.

FIG. 40 shows increased toxicity by targeted polymer. While the txNA polymer shows substantial toxicity to Jurkat cells ($IC_{50}$ 17 nM±1.4 nM), the aptamer-conjugated polymer shows an almost 3-fold increase in toxicity ($IC_{50}$ 6.4 nM±1.2 nM).

Example 20: Targeted Cell Killing

In this example, we demonstrate targeted cell killing through specific internalization of a toxic nucleic acid polymer produced according to the present invention. The toxic polymer was synthesized using the polymerase D4K with the biotinylated FD primer on the TempN template and using the following nucleotides: ATP, GTP, 5FdU, AraC. Following primer extension for 1 h at 65° C. the reaction was desalted and purified via gel electrophoresis. The biotinylated extension product was mixed at a ratio of 1:1 (biotin to biotin-binding pockets) with either streptavidin or 1F5scFv-streptavidin, an anti-CD20 scFv-streptavidin fusion (FIG. 41). FIG. 41 shows a schematic of the materials used. Top: an anti-CD20 (1F5) scFv genetically fused to the streptavidin monomer results in a tetrameric protein complex, capable of binding up to four biotinylated oligonucleotides (two shown). 1F5-streptavidin: Pagel et al 2006 (doi: 10.1182/blood-2005-11-4327) Bottom: streptavidin bound to polymer. After 30 min incubation at room temperature the complexes were purified using an Akta micro.

The polymer linked to the targeting protein was then mixed with Nanocargo transfection reagent according to the manufacturer's instructions (Tecrea, UK), and added to Ramos cells at a final concentration of 40 nM (polymer concentration). After 96 hours incubation in a humidified atmosphere at 37° C. (5% CO2), WST-1 reagent (Roche, UK) was added to the cells to measure cell growth inhibition (FIG. 42). FIG. 42 shows that targeted polymer delivery leads to specific cell death. Only when the toxic polymer is targeted to the Ramos cells via CD20 is cell growth inhibited. Strong growth inhibition was observed when the polymer was targeted to CD20 and internalized with Nanocargo. The polymer attached to streptavidin did not reduce cell viability.

Primers and Materials
Table S1: Polymerase Library Primers and PCR Primers Used in CST Primers used to synthesize the mutagenesis libraries and for CST. Degenerate positions are shown using the standard IUPAC ambiguity code for nucleic acids. Mutation spikes, introduced either at 5% (e.g. 95% A, 5% C, G, T) (Motifs 1, 2, 3, 4, 5, 7 and 9) or 10% (Motifs A−, A, A+, B−, B, 6−, 6+, C, C+, 8, 10A, 10B, 10C, 11 and 12) are shown underlined in grey. BsaI recognition sites are in red. All primers used in making mutagenesis libraries were synthesized by Matthew Watson and Donna Williams in the MRC LMB oligonucleotide synthesis service.

| Name | Sequence |
|---|---|
| Motif1ba | 5'-GAGTCAGGTCTCTCCGAGCCGAAAATCCAGC GCATGGGCGATANNTTTGCGGTGGAGGTCAAGGG A-3' (SEQ ID NO: 25) |
| Motif1fo | 5'-GAGTCAGGTCTCCTCGGATCCWTCCCTTCCG AG-3' (SEQ ID NO: 26) |
| Motif2ba | 5'-GAGTCAGGTCTCACTTACACCCTTGAGGCAG TATATGAANYCNTCTTWGGAMAGNCGAAGGAG-3' (SEQ ID NO: 27) |
| Motif2fo | 5'-GAGTCAGGTCTCGTAAGTGGGGAGGTTAATC GTTCTCCTAATGACGGGGTAGAGGTCGAAGTGGA TCCTTCC-3' (SEQ ID NO: 28) |
| Motif3ba | 5'-GAGTCAGGTCTCGGATGTATCTCGCTCTAGT ACCGGAAACCTCGTCGAGTGGTWTTTGCTG-3' (SEQ ID NO: 29) |
| Motif3fo | 5'-GAGTCAGGTCTCACATCCCAAANAGNCTGGC CAABGAGWYKCGMGAGCTBGGCTTCCA-3' (SEQ ID NO: 30) |
| Motif4ba | 5'-GAGTCAGGTCTCAATGAWCTTGCACCAAACA AGCCGGACGAGCGTGAGCTGGCAAGAAG-3' (SEQ ID NO: 31) |
| Motif4fo | 5'-GAGTCAGGTCTCTTCATTCCTCTCGTAGGCT WYCBTCAGCAA-3' (SEQ ID NO: 32) |

TABLE

| | IC50 (Ramos, CCRF-CEM) in nM | | | | | | | |
|---|---|---|---|---|---|---|---|---|
| | Corresponding base | | | | | | | |
| | T/U | C | | A | | | G | |
| | | | | Drug | | | | |
| Cell line | 5FdU | AraC | GemC | Fludarabine | Cladribine | Clofarabine | AraG | TempN polymer (A, G, 5FdU, AraC) |
| Ramos | 10.1 | 22.7 | 1.6 | 1301 | 56.7 | 18 | ~100000 | 1.5 |
| CCRF-CEM | 8.8 | 12.9 | 11.7 | 864.2 | 86.7 | 20 | 883.9 | 0.8 |

Example 21: Improving Polymer Serum Stability

In order to make the polymer more serum stable, we replaced ATP and GTP with thio-ATP and thio-GTP. Over a period of 24 h at 37° C. in serum, the polymer containing the thio-nucleotides is significantly more stable (FIG. 43). FIG. 43 shows polymer serum stability. After 24 hours at 37° C. in complete serum most of the thio-modified polymer remains intact.

-continued

| Name | Sequence |
|---|---|
| MotifA-baW | 5'-GAGTCAGGTCTCGGTGGATACGTCAAGGAGC CCGAAAGGGGACTGTGGGAG-3' (SEQ ID NO: 33) |
| MotifA-fo | 5'-GAGTCAGGTCTCTCCACCSDBGTAWSYSBBT SYTCTTCTTGC-3' (SEQ ID NO: 34) |

| Name | Sequence |
|---|---|
| TgAmoba2 | 5'-GGAAAGGTCTCAGTGGRAMRRCMTSRYYTMT CTGGACTTCCGCTCCCTGTATCCTTCGATCATAR TCACCCATAACGTC-3' (SEQ ID NO: 35) |
| TgAmofo | 5'-GAGTAGGTCTCTCCACAGTCCCCTTTCGGGC TCCTTG-3' (SEQ ID NO: 36) |
| MotifA+ba | 5'-GAGTCAGGTCTCCACTCRAWMNWGAGGGTTG TRNRRAWTACGACRHRGCTCCTCAG-3' (SEQ ID NO: 37) |
| MotifA+fo | 5'-GAGTCAGGTCTCTGAGTGTATCAGGGGAGAC GTTATGGGTGAYTAT-3' (SEQ ID NO: 38) |
| Motif5ba | 5'-GAGTCAGGTCTCGAGGASAGACAGAAGGTAA AGAAGAAGATGAAGGCCACGATCGACCCA-3' (SEQ ID NO: 39) |
| Motif5fo | 5'-GAGTCAGGTCTCCTCCTCCANGAGWBBTYYG ANGAGGCT-3' (SEQ ID NO: 40) |
| MotifB-ba | 5'-GAGTCAGGTCTCCGAGAAGAAACTCCTCGAT TACAGGCAACGACTGATCAAAATC-3' (SEQ ID NO: 41) |
| MotifB-fo | 5'-GAGTCAGGTCTCTTCTCSANTGGGTC-3' (SEQ ID NO: 42) |
| TgTBmoba2 | 5'-GGAAAGGTCTCTGATCAAGATCCTTGCTAAT AGCTTCTACGGTTACTACGGCTATVCSAAGGCCC GC-3' (SEQ ID NO: 43) |
| TgTBmofo | 5'-GAGTAGGTCTCTGATCAGTCGTTGCCTGTAA TCGAGGAG-3' (SEQ ID NO: 44) |
| Motif6-ba | 5'-GAGTCAGGTCTCGCCGAGAGCG-3' (SEQ ID NO: 45) |
| Motif6-foW | 5'-GAGTCAGGTCTCCTCGGNGCACTCCTTGCAG TACCAGCGGGCCTTTGNATA-3' (SEQ ID NO: 46) |
| Motif6 + ba2 | 5'-GAGTCAGGTCTCTACATCRMSHYSRYSWKSA RSGAAMTAGAGRVSAAATTTGG-3' (SEQ ID NO: 47) |
| Motif6 + fo2 | 5'-GAGTCAGGTCTCGATGTACTBCCBGCCCCAA GCGGTAACGCTCTBGGCGCAC-3' (SEQ ID NO: 48) |
| TgCmoba | 5'-GGAAAGGTCTCAGGCTTTAAAGTCCTCTACG CGGACACAGATGGAYTYYWCGCAACGATCCCTG G-3' (SEQ ID NO: 49) |
| TgCmofo | 5'-GAGTAGGTCTCTAGCCAAATTTCTCCTCTAT TTCCC-3' (SEQ ID NO: 50) |
| MotifC+ba | 5'-GAGTCAGGTCTCTCAAARRSARGGCAMDSRA GTTCCTGRASTACATCAAC-3' (SEQ ID NO: 51) |
| MotifC+fo | 5'-GAGTCAGGTCTCTTTTGANGGTTTCGGCGTC CGCTCCAGGTATTGTTGC-3' (SEQ ID NO: 52) |
| Motif7ba3 | 5'-GAGTCAGGTCTCGGCCTGCTCVAACTCVAAT ACVAGGGCTTCTACVNSCGCGGCTTC-3' (SEQ ID NO: 53) |
| Motif7fo3 | 5'-GAGTCAGGTCTCCAGGCCGNGCNSTYTTGNG TTGATGTA-3' (SEQ ID NO: 54) |
| Motif8ba | 5'-GAGTCAGGTCTCTACGCGNTSNTSGACGAGG AGGAC-3' (SEQ ID NO: 55) |
| Motif8fo | 5'-GAGTCAGGTCTCCGCGTACTBCTBCTBCGTC ACGAAGAAGCCGCG-3' (SEQ ID NO: 56) |
| Motif9ba2 | 5'-GAGTCAGGTCTCAGATAAYAACGCGCGGGCT TVAAATAGTTVGGCGTGACTGGA-3' (SEQ ID NO: 57) |
| Motif9fo | 5'-GAGTCAGGTCTCTTATCYTSYCSYYCTCGT C-3' (SEQ ID NO: 58) |
| Motif10Aba | 5'-GAGTCAGGTCTCATAACCARASMSCTGMRSG ASTACARGGCCANSGGGCCGCATG-3' (SEQ ID NO: 59) |
| Motif10Afo | 5'-GAGTCAGGTCTCGGTTATCTBCTBGTAGATG ACCAGCTBCTBCGGTGGAACCTBGTACTTGCT-3' (SEQ ID NO: 60) |
| Motif10Bba | 5'-GAGTCAGGTCTCCTCGCCGCAARSGGGRTAA AARTCMRSCCCGGAACGG-3' (SEQ ID NO: 61) |
| Motif10Bfo | 5'-GAGTCAGGTCTCGGCGAGGCGVTTTGCAACA GCCACATGCGGCCCGGTGGC-3' (SEQ ID NO: 62) |
| Motif10Cba2 | 5'-GAGTCAGGTCTCATGCTCVRGGGCTBGGGGA GGATTRGGGACAGGGC-3' (SEQ ID NO: 63) |
| Motif10Cfo2a | 5'-GAGTCAGGTCTCGAGCACGRNGTAYYYTATG ANYRYTCCAGGCCGGA-3' (SEQ ID NO: 64) |
| Motif 11_fo3 | 5'-GAGTCAGGTCTCGTGCTTSBYTRSGTCAWAT TCSBYARNGRNTATARYCCTGTCCCCA-3' (SEQ ID NO: 65) |
| Motif 11ba3a | 5'-GAGTCAGGTCTCAAGCACAAGTACGATGCAV AATACTACATCVAGAACVAGGTTCTTCCAGCT-3' (SEQ ID NO: 66) |
| Motif12_fo | 5'-GAGTCAGGTCTCGTAACCAAAGGCCCTCAGA ATCCTCTBCACAGCTGGAAGAACCTGGTTCTC-3' (SEQ ID NO: 67) |
| Motif12_ba | 5'-GAGTCAGGTCTCGGTTACMRWARWGRWGATT TAARGTNSCAGARSASCMRWCAGRYSGGCTTG-3' (SEQ ID NO: 68) |
| Tgoba578Bsa | 5'-GAGTCAGGTCTCGCTTCCTCAAGGTCGTCAA G-3' (SEQ ID NO: 69) |
| Tgofo582Bsa | 5'-GAGTCAGGTCTCGGAAGCGCTTTATCATCTC CTTCTCG-3' (SEQ ID NO: 70) |
| pAfo308Bsa | 5'-GAGTCAGGTCTCCGCCATTTTTCACTTCACA G-3' (SEQ ID NO: 71) |
| pAba304Bsa | 5'-GAGTCAGGTCTCATGGCGCACATTGTGCGAC ATTTTTTTTGTCTGCC-3' (SEQ ID NO: 72) |
| BC36N6 | 5'-biotin-$C_{36}$ spacer- NNNNNN-3' |
| 6b | 5'-biotin-$C_{36}$ spacer-CACCTA-3' (SEQ ID NO: 73) |

Table S2: Primer, Templates and Screening Probes.

Primers, templates and probes used in PAA. DNA-dependent synthesis of XNAs was typically assessed by denaturing PAGE (primer extensions) or by PAA. Chemically synthesized templates harboring unnatural nucleic acid stretches were used to assess different candidate reverse transcriptases. HNA is shown in red, LNA in black and CeNA in blue. The primer fdOMe was synthesized as 2'-OMe DNA. Probes, labeled at their 5'-end with digoxigenin (DIG), were obtained from Eurogentec S.A. (Belgium). Templates RTtempHNA and RTtempNCeNA were synthesized by P. Herdewijn. Template RTtempNLNA4 was a kind gift from Exiqon A/S (Denmark).

| Name | Sequence |
| --- | --- |
| 2xBFITCfd | 5'-biotin-(dT-FITC)(dT-biotin)CCCCTTATTAGCGTTTGCCA-3' (SEQ ID NO: 74) |
| fd | 5'-CCCCTTATTAGCGTTTGCCA-3' (SEQ ID NO: 75) |
| NAPfd | 5'-biotin-(dT-FITC)CAGTATCGACAAAGGACCCCTTATTAGCGTTTGCCA-3' (SEQ ID NO: 76) |
| fdOMe | 5'-FITC-CCCCTTATTAGCGTTTGCCA-3' (SEQ ID NO: 77) |
| TempN | 5'-CTCACGATGCTGGACCAGATAAGCACTTAGCCACGTAGTGCTGTTCGGTAATCGATCTGGCAAACGCTAATAAGGGG-3' (SEQ ID NO: 78) |
| TempNpurine | 5'-CCTAGTTCTTCCTCTTCCCGATGCTGGACCAGATAAGCACTTAGCCACGTAGTGCTGTTCGGTAATCGATCTGGCAAACGCTAATAAGG-3' (SEQ ID NO: 79) |
| RTtempHNA | 5'-GTTCGGTAATCGATCTGGCAAACGCTAATAA-3' (SEQ ID NO: 80) |
| RTtempNLNA4 | 5'-GTAGTGCTGTTCGGTAATCGATCTGGCAAACGCTAATAA-3' (SEQ ID NO: 81) |
| RTtempNCeNA | 5'-AGCACTAGCCACGTAGTGCTGCTCGGTAATCGATCTGGCAAACGCTAATAAGGGG-3' (SEQ ID NO: 82) |
| DIGNmin3 | 5'-DIG-TTCGGTAATCGATCTGG-3' (SEQ ID NO: 83) |
| DIGN4 | 5'-DIG-GCTGTTCGGTAATCG-3' (SEQ ID NO: 84) |
| DIGN10 | 5'-DIG-GTAGTGCTGTTCG-3' (SEQ ID NO: 85) |
| DIGN25 | 5'-DIG-GATAAGCACTTAGCC-3' (SEQ ID NO: 86) |

Table S3: Primers and Templates Used in XNA Synthesis, Reverse Transcription and Fidelity Experiments Primers and templates used in HNA, CeNA, TNA and LNA syntheses and respective RT reactions. Previously described 2xBFITCfd primer and TempN template were also used. YtRtemp4, YtRtemp5 and YtRtemp7 are variants of YtRtemp with additional tags and modifications at the 3'-end and/or 5'-end to improve synthesis, RT and its detection. 2'-OMe DNA, present in tag4fd-based primers, is shown in green.

| Name | Sequence |
| --- | --- |
| YtRtemp | 5'-GGTGGGGTTCCCGAGCGGCCAAAGGGAGCAGACTCTAAATCTGCCGTCATCGACTTCGAAGGTTCGAATCCTTCCCCCACCACCA-3' (SEQ ID NO: 87) |
| AtRtemp | 5'-GGGGCTATAGCTCAGCTGGGAGAGCGCCTGCTTTGCACGCAGGAGGTCTGCGGTTCGATCCCGCATAGCTCCACCA-3' (SEQ ID NO: 88) |
| FtRtemp | 5'-GCGGATTTAGCTCAGTTGGGAGAGCGCCAGACTGAAGATCTGGAGGTCCTGTGTTGATCCACAGAATTCGCACCA-3' (SEQ ID NO: 89) |
| YtRtemp4 | 5'-TGGCAAACGCTAATAAGGGGTGGGGTTCCCGAGCGGCCAAAGGGAGCAGACTCTAAATCTGCCGTCATCGACTTCGAAGGTTCGAATCCTTCCCCCACCTCCA-biotin-3' (SEQ ID NO: 90) |
| YtRtemp5 | 5'-CAAAGTAGTGCTGTTCGTGGGGTTCCCGAGCGGCCAAAGGGAGCAGACTCTAAATCTGCCGTCATCGACTTCGAAGGTTCGAATCCTTCCCCCACCACCAGATCGATTACCGAAGGTGGCAAACGCTAATGAGGG(ddC)-3' (SEQ ID NO: 91) |
| YtRtemp7 | 5'-CAAAGTAGTGCTGTTCGTGGGGTTCCCGAGCGGCCAAAGGGAGCAGACTCTAAATCTGCCGTCATCGACTTCGAAGGTTCGAATCCTTCCCCCACCACCAGATCGATTACCGAAGGTGGCAAACGCTAATGAGGGAAAAAAAA-3' (SEQ ID NO: 92) |
| TempNmis | 5'-CTCGCGATGCTGGACCAGATAAGCACTTAGCCACGTAGTGCTGTTCGGTAATCGATCTGGCAAACGCTAATAAGTGGAAAAAAAA-3' (SEQ ID NO: 93) |
| TempNpuremis (T1) | 5'-CCTAATTCTTCCTCTTCCCGATGCTGGACCAGATAAGCACTTAGCCACGTAGTGCTGTTCGGTAATCGATCTGGCAAACGCTAATATGGAAAAAA-3' (SEQ ID NO: 94) |
| Nproduct | 5'-GATCGATTACCGAACAGCACTACGTGGCTAAGTGCTTATCTGGTCCAGCATCGTGAG-3' (SEQ ID NO: 95) |
| AtRNA2HNA | 5'-Cy3-CAGGAAACAGCTATGACAAATGGTGGAGCTATG-3' (SEQ ID NO: 96) |
| YtRNA2HNA | 5'-Cy3-CAGGAAACAGCTATGACAAATGGTGGTGGGG-3' (SEQ ID NO: 97) |
| FtRNA2HNA | 5'-Cy3-CAGGAAACAGCTATGACAAATGGTGCGAATTCTGTGG-3' (SEQ ID NO: 98) |
| NAPfd (DNA or RNA) | 5'-FITC-CAGTATCGACAAAGGACCCCTTATTAGCGTTTGCCA-3' (SEQ ID NO: 99) |
| bNAPfd | 5'-biotin-(dT-FITC)CAGTATCGACAAAGGACCCCTTATTAGCGTTTGCCA-3' (SEQ ID NO: 100) |
| NAP | 5'-CAGTATCGACAAAGGA-3' (SEQ ID NO: 101) |
| NAPcapture | 5'-Biotin-$C_{18}$ spacer-$C_{18}$ spacer-CAGTATCGACAAAGGA-3' (SEQ ID NO: 102) |
| Tag4 | 5'-GTCGGATCCGTTTAAGCTAGG-3' (SEQ ID NO: 103) |
| Tag4fdOMe (P) | 5'-FITC-GTCGGATCCGTTTAAGCTAGGCCCCTTATTAGCGTTTGCCA-3' (SEQ ID NO: 104) |
| fitcRNAfd | 5'-FITC-CCCCUUAUUAGCGUUUGCCA-3' (SEQ ID NO: 105) |
| Cy3fd | 5'-Cy3-CCCCTTATTAGCGTTTGCCA-3' (SEQ ID NO: 106) |
| LMB3 + tag3a | 5'-Cy5-CAGGAAACAGCTATGACAAACAAGGTAGTGCTGTTCGTGGGG-3' (SEQ ID NO: 107) |

-continued

| Name | Sequence |
|---|---|
| LMB3 + N40 | 5'-Cy5-CAGGAAACAGCTATGACAAACTAACGATGCTGGACCA-3' (SEQ ID NO: 108) |
| LMB3+ | 5'-CAGGAAACAGCTATGACAAA-3' (SEQ ID NO: 109) |
| Test7 | 5'-Cy5-CCCTAGTTCTTCCTCTTCCC-3' (SEQ ID NO: 110) |
| LMB3 + test7 ($P_{RT}$) | 5'-CAGGAAACAGCTATGACAAACCCTAGTTCTTCCTCTTCCC-3' (SEQ ID NO: 111) |
| bLMB3 + test7 | 5'-Cy5-CAGGAAACAGCTATGACAAACCCTAGTTCTTCCTCTTCCC-3' (SEQ ID NO: 112) |
| CyRevfd | 5'-Cy5-TGGCAAACGCTAATAAGGG-3' (SEQ ID NO: 113) |
| Cytag4fdOMe | 5'-Cy5-GTCGGATCCGTTTAAGCTAGGCCCCTTATTAGCGTTTGCCA-3' (SEQ ID NO: 114) |
| TempNshort2 (T2) | 5'-ACCAGTAGTGCTGTTCGGTAATCGATCTGGCAAACGCTAATAAGGGG-3' (SEQ ID NO: 115) |

Table S4: iPCR Primers Used to Generate the Single Residue Degenerate Libraries for RT Activity Screening Primers used in iPCR to generate single-residue libraries used to screen for HNA RT activity by PAA. As all SCA-identified residues around L408 were hydrophobic residues, the initial screen was carried out in their coding vicinity (NWC degeneracy generates mutants coding N, I, H, L, D, V, Y and F at the targeted residue). Given the positive results obtained with the initial screen on residue 521, a second more through screen was carried out (NNS). The BsaI site introduced in the primers to allow seamless cloning is highlighted in red.

| Name | Sequence |
|---|---|
| RT405ba | 5'-GAGTCAGGTCTCCGCTCCCTGTATCCTTCGATAATAATC-3' (SEQ ID NO: 116) |
| RT405fo | 5'-GAGTCAGGTCTCGGAGCGGSNGTCCAGATACACG-3' (SEQ ID NO: 117) |
| RT408ba | 5'-GAGTCAGGTCTCCGCTCCNWCTATCCTTCGATAATAATC-3' (SEQ ID NO: 118) |
| RT408fo | 5'-GAGTCAGGTCTCGGAGCGGAAGTCCAGATACACG-3' (SEQ ID NO: 119) |
| RT520ba | 5'-GAGTCAGGTCTCAGGCAGNWCATCGAGACTACGATAAGGG-3' (SEQ ID NO: 120) |
| RT521ba | 5'-GAGTCAGGTCTCAGGCAGTACNWCGAGACTACGATAAGGG-3' (SEQ ID NO: 121) |
| RT521baNNS | 5'-GAGTCAGGTCTCAGGCAGTACNNSGAGACTACGATAAGGG-3' (SEQ ID NO: 122) |
| RT520fo | 5'-GAGTCAGGTCTCCTGCCTGCCCCAAGCGGTAACGCTC-3' (SEQ ID NO: 123) |
| RT575ba | 5'-GAGTCAGGTCTCGGCCTGNWCGAACTCGAATACGAGGGC-3' (SEQ ID NO: 124) |
| RT575fo | 5'-GAGTCAGGTCTCCAGGCCGGGCAGTTTGGCGTTGATGTAG-3' (SEQ ID NO: 125) |

Table S8: Aggregate Error Rates of XNA Synthesis and Reverse Transcription.

Total error rates are the measured errors from sequencing which include the error contribution from Taq amplification, the aggregate contribution to misincorporations and the aggregate contribution to insertions and deletions (indel). Results obtained from the enzyme deconvolution (FIG. S11) are also given. Error rates below $1 \times 10^{-3}$ could not be accurately detected and are shown in grey.

| XNA | Synthesis | Reverse Transcription | Bases read (kb) | Indel error ($\times 10^{-3}$) | Misincorporation error ($\times 10^{-3}$) | Total Error ($\times 10^{-3}$) |
|---|---|---|---|---|---|---|
| HNA | Pol6G12 | RT521 | 3.67 | 19.7 | 6.80 | 29.0 |
| CeNA | PolC7 | RT521K | 1.76 | 2.84 | 4.31 | 9.64 |
| ANA | PolD4K | RT521K | 1.38 | 5.81 | 7.66 | 16.0 |
| FANA | PolD4K | RT521K | 1.59 | 5.03 | 9.45 | 17.0 |
| TNA | RT521 | RT521 | 1.43 | 17.5 | 48.5 | 68.5 |
| LNA | PolC7 | RT521K | 1.63 | 6.76 | 52.8 | 62.0 |
| DNA | Vent | Vent | 1.24 | 3.28 | <1 | 5.74 |
| DNA | Vent | RT521 | 1.52 | <1 | 3.48 | 5.98 |
| DNA | Pol6G12 | Vent | 1.14 | 3.58 | 15.4 | 21.5 |
| DNA | Pol6G12 | RT521 | 1.52 | 9.06 | 20.8 | 32.3 |

REFERENCES

1. A. Eschenmoser, *Science* 284, 2118 (1999).
2. A. M. Leconte et al., *J Am Chem Soc* 130, 2336 (2008).
3. P. E. Nielsen, *Annu Rev Biophys Biomol Struct* 24, 167 (1995).
4. K. U. Schoning et al., *Science* 290, 1347 (2000).
5. P. Herdewijn, *Chem Biodivers* 7, 1 (2010).
6. M. A. Campbell, J. Wengel, *Chem Soc Rev* 40, 5680 (2011).
7. D. Loakes, P. Holliger, *Chem Commun (Camb)*, 4619 (2009).
8. D. Loakes, *Nucleic Acids Res* 29, 2437 (2001).
9. C. Boiziau, J. J. Toulme, *Antisense Nucleic Acid Drug Dev* 11, 379 (2001).
10. J. P. Schrum, A. Ricardo, M. Krishnamurthy, J. C. Blain, J. W. Szostak, *Journal of the American Chemical Society* 131, 14560 (2009).
11. X. Li, Z. Y. Zhan, R. Knipe, D. G. Lynn, *J Am Chem Soc* 124, 746 (2002).
12. D. M. Rosenbaum, D. R. Liu, *J Am Chem Soc* 125, 13924 (2003).
13. Y. Brudno, M. E. Birnbaum, R. E. Kleiner, D. R. Liu, *Nat Chem Biol* 6, 148 (2010).
14. P. E. Burmeister et al., *Chem Biol* 12, 25 (2005).
15. H. Yu, S. Zhang, J. C. Chaput, *Nat Chem* doi:10.1038/nchem. 1241, (2012).
16. J. K. Ichida, A. Horhota, K. Zou, L. W. McLaughlin, J. W. Szostak, *Nucleic Acids Res* 33, 5219 (2005).
17. C. J. Wilds, M. J. Damha, *Nucleic Acids Res* 28, 3625 (2000).

18. A. M. Noronha et al., *Biochemistry* 39, 7050 (2000).
19. M. J. Fogg, L. H. Pearl, B. A. Connolly, *Nat Struct Biol* 9, 922 (2002).
20. A. F. Gardner, W. E. Jack, *Nucleic Acids Res* 30, 605 (2002).
21. S. W. Lockless, R. Ranganathan, *Science* 286, 295 (1999).
22. B. Arezi, H. Hogrefe, J. A. Sorge, C. J. Hansen, Stratagene, US 2003/0228616 A1, United States of America (2003).
23. A. S. Potty, K. Kourentzi, H. Fang, P. Schuck, R. C. Willson, *Int J Biol Macromol* 48, 392 (2011).
24. F. Duconge, J. J. Toulme, *RNA* 5, 1605 (1999).
25. S. A. Benner, *Science* 306, 625 (2004).
26. Materials and methods are available as supporting material on *Science Online*.
27. I. M. Lagoja, A. Marchand, A. Van Aerschot, P. Herdewijn, *Curr Protoc Nucleic Acid Chem* Chapter 1, Unit 1 9 (2003).
28. F. W. Liu, A. Di Salvo, P. Herdewijn, *Curr Protoc Nucleic Acid Chem* Chapter 1, Unit 1 20 (2008).
29. R. N. Veedu, B. Vester, J. Wengel, *Chembiochem* 8, 490 (2007).
30. K. Zou, A. Horhota, B. Yu, J. W. Szostak, L. W. McLaughlin, *Org Lett* 7, 1485 (2005).
31. J. Ludwig, *Acta Biochim Biophys Acad Sci Hung* 16, 131 (1981).
32. A. Skerra, *Gene* 151, 131 (1994).
33. N. Ramsay et al., *J Am Chem Soc* 132, 5096 (2010).
34. M. C. Franklin, J. Wang, T. A. Steitz, *Cell* 105, 657 (2001).
35. J. Wang et al., *Cell* 89, 1087 (1997).
36. K. P. Hopfner et al., *Proc Acad Sci USA* 96, 3600 (1999).
37. W. P. Stemmer, S. K. Morris, *Biotechniques* 13, 214 (1992).
38. F. Diehl et al., *Nat Methods* 3, 551 (2006).
39. J. Sambrook, E. F. Fritsch, T. Maniatis, *Molecular Cloning—A Laboratory Manual.* (Cold Spring Harbour Laboratory Press, New York, ed. Second Edition, 1989), vol. 1.
40. M. W. McDonell, M. N. Simon, F. W. Studier, *J Mol Biol* 110, 119 (1977).
41. S. W. Kim, D. U. Kim, J. K. Kim, L. W. Kang, H. S. Cho, *Int J Biol Macromol* 42, 356 (2008).
42. Y. Shamoo, T. A. Steitz, *Cell* 99, 155 (1999).
43. J. S. Brunzelle et al. (2003).
44. F. Wang, W. Yang, *Cell* 139, 1279 (2009).
45. S. Liu et al., *J Biol Chem* 281, 18193 (2006).
46. M. K. Swan, R. E. Johnson, L. Prakash, S. Prakash, A. K. Aggarwal, *Nat Struct Mol Biol* 16, 979 (2009).
47. C. Savino et al., *Structure* 12, 2001 (2004).
48. S. J. Firbank, J. Wardle, P. Heslop, R. J. Lewis, B. A. Connolly, *J Mol Biol* 381, 529 (2008).
49. H. Hasegawa, L. Holm, *Curr Opin Struct Biol* 19, 341 (2009).
50. R. C. Edgar, *BMC Bioinformatics* 5, 113 (2004).
51. D. Loakes, J. Gallego, V. B. Pinheiro, E. T. Kool, P. Holliger, *J Am Chem Soc* 131, 14827 (2009).
52. G. M. Suel, S. W. Lockless, M. A. Wall, R. Ranganathan, *Nat Struct Biol* 10, 59 (2003).
53. J. D. Vaught et al., *J Am Chem Soc* 132, 4141 (2010).
54. A. D. Ellington, J. W. Szostak, *Nature* 346, 818 (1990).
55. F. Darfeuille et al., *Comb Chem High Throughput Screen* 5, 313 (2002).
56. D. W. Drolet, L. Moon-McDermott, T. S. Romig, *Nat Biotechnol* 14, 1021 (1996).
57. D. J. O'Shannessy, D. J. Winzor, *Anal Biochem* 236, 275 (1996).
58. D. S. Tawfik, A. D. Griffiths, *Nat Biotechnol* 16, 652 (1998).
59. M. Zuker, *Nucleic Acids Res* 31, 3406 (2003).
60. G. Kolb et al., *Biochemistry* 44, 2926 (2005).
61. R. Kirby et al., *Anal Chem* 76, 4066 (2004).
62. L. K. Steinrauf, D. Shivan, W. J. Yang, M. Y. Chiang, *Biochem Biophys Res Commun* 266, 366 (1999).
63. F. Darfeuille, J. B. Hansen, H. Orum, C. Di Primo, J. J. Toulme, *Nucleic Acids Res* 32, 3101 (2004).

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A recombinant nucleic acid polymerase capable of producing an arabino nucleic acid polymer from a deoxyribonucleic acid (DNA) template,
    wherein said polymerase comprises (i) an amino acid sequence having at least 80% identity to the amino acid sequence shown in SEQ ID NO:1; and (ii) substitutions at the following residues relative to the amino acid sequence shown in SEQ ID NO:1: L403P, P657T, E658Q, K659H, Y663H, D669A, K671N, T676I, and E664K,
    wherein said polymerase has arabino nucleic acid polymerase activity and a wild type Y residue at position 409 (Y409) relative to the amino acid sequence shown in SEQ ID NO:1.

2. The recombinant nucleic acid polymerase of claim 1, wherein said polymerase further comprises substitutions D141A and E143A.

3. The recombinant nucleic acid polymerase of claim 1, wherein said polymerase further comprises at least one substitution selected from the group consisting of V93Q and A485L.

4. The recombinant nucleic acid polymerase of claim 1, wherein said polymerase further comprises substitutions V93Q, A485L, D141A, and E143A.

5. The recombinant nucleic acid polymerase of claim 1, wherein said polymerase further comprises substitution I521L.

6. The recombinant nucleic acid polymerase of claim 1, wherein said arabino nucleic acid polymer is an arabinonucleic acid (ANA) or a 2'-fluoro-arabinonucleic acid (FANA) nucleic acid polymer.

7. The recombinant nucleic acid polymerase of claim 1, wherein said polymerase is capable of producing an arabinonucleic acid (ANA) or a 2'-fluoro-arabinonucleic acid (FANA) nucleic acid polymer from a deoxyribonucleic acid (DNA) template, wherein said polymerase includes the amino acid sequence consisting of the amino acids represented at 651 to 679 (patch 10A) of SEQ ID NO:5.

8. The recombinant nucleic acid polymerase of claim 1, capable of producing an ANA or FANA from a DNA template, wherein said polymerase has the amino acid sequence shown in SEQ ID NO:5.

9. A method of making an arabino nucleic acid polymer, comprising contacting a nucleic acid template with the nucleic acid polymerase of claim 1, and incubating to allow polymerization.

10. The method of claim 9, wherein said arabino nucleic acid polymer is an arabinonucleic acid (ANA) or a 2'-fluoro-arabinonucleic acid (FANA) nucleic acid polymer.

11. A method of making a 2'-fluoro-arabinonucleic acid (FANA) nucleic acid polymer comprising contacting a FANA template with a recombinant nucleic acid polymerase and incubating to allow polymerization, wherein said recombinant nucleic acid polymerase comprises (a) an amino acid sequence having at least 80% identity to the amino acid sequence shown in SEQ ID NO:1; (b) substitutions at the following residues relative to the amino acid sequence shown in SEQ ID NO:1: L403P, P657T, E658Q, K659H, Y663H, D669A, K671N, T676I, and E664K; and (c) a wild type Y residue at position 409 (Y409) relative to the amino acid sequence shown in SEQ ID NO:1.

* * * * *